(12) United States Patent
Subramanian et al.

(10) Patent No.: US 9,683,033 B2
(45) Date of Patent: *Jun. 20, 2017

(54) CELL CULTURE METHODS TO REDUCE ACIDIC SPECIES

(71) Applicant: AbbVie Inc., North Chicago, IL (US)

(72) Inventors: Kartik Subramanian, Northborough, MA (US); Xiaobei Zeng, Carolina, PR (US); Diane D. Dong, Shrewsbury, MA (US); Wen Chung Lim, Worcester, MA (US); Kathreen A. Gifford, Marlborough, MA (US); Christopher Chumsae, North Andover, MA (US)

(73) Assignee: ABBVIE, INC., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/008,895

(22) Filed: Jan. 28, 2016

(65) Prior Publication Data

US 2016/0145331 A1  May 26, 2016

Related U.S. Application Data

(60) Division of application No. 14/842,933, filed on Sep. 2, 2015, now Pat. No. 9,359,434, which is a
(Continued)

(51) Int. Cl.
  *C07K 16/00* (2006.01)
  *C07K 1/00* (2006.01)
(Continued)

(52) U.S. Cl.
  CPC ...... *C07K 16/241* (2013.01); *A61K 39/39591* (2013.01); *C07K 1/165* (2013.01);
(Continued)

(58) Field of Classification Search
  CPC ............ A61K 39/39595; C07K 16/241; C07K 1/165; C07K 1/18; C07K 1/20; C07K 1/22; C07K 16/00; C12P 21/00
  See application file for complete search history.

(56) References Cited

U.S. PATENT DOCUMENTS 3,887,430 A    6/1975  Torney et al.
RE30,985 E     6/1982  Cartaya
(Continued)

FOREIGN PATENT DOCUMENTS

CN       1563090 A     1/2005
CN     105777895 A     7/2016
(Continued)

OTHER PUBLICATIONS

Khawli et al., (MAbs. Nov.-Dec. 2010;2(6):613-624).*
(Continued)

*Primary Examiner* — Cherie M Stanfield
(74) *Attorney, Agent, or Firm* — McCarter & ENglish, LLP; Maria Laccotripe Zacharakis; Lisa Tyner

(57) ABSTRACT

The instant invention relates to the field of protein production and purification, and in particular to compositions and processes for controlling the amount of acidic species expressed by host cells, as well as to compositions and processes for controlling the amount of acidic species present in purified preparations.

30 Claims, 78 Drawing Sheets

Related U.S. Application Data continuation of application No. 13/830,583, filed on Mar. 14, 2013, now Pat. No. 9,150,645.

(60) Provisional application No. 61/636,493, filed on Apr. 20, 2012.

(51) Int. Cl.

| | | |
|---|---|---|
| *C07K 16/24* | (2006.01) | |
| *C07K 1/16* | (2006.01) | |
| *C07K 1/18* | (2006.01) | |
| *A61K 39/395* | (2006.01) | |
| *C12P 21/00* | (2006.01) | |
| *C07K 1/20* | (2006.01) | |
| *C07K 1/22* | (2006.01) | |

(52) U.S. Cl.
CPC .................. *C07K 1/18* (2013.01); *C07K 1/20* (2013.01); *C07K 1/22* (2013.01); *C07K 16/00* (2013.01); *C12P 21/00* (2013.01); *C07K 2317/14* (2013.01); *C07K 2317/21* (2013.01)

(56) References Cited

U.S. PATENT DOCUMENTS

| | | |
|---|---|---|
| 4,399,216 A | 8/1983 | Axel et al. |
| 4,510,245 A | 4/1985 | Cousens et al. |
| 4,560,655 A | 12/1985 | Baker |
| 4,634,665 A | 1/1987 | Axel et al. |
| 4,657,866 A | 4/1987 | Kumar |
| 4,767,704 A | 8/1988 | Cleveland et al. |
| 4,801,687 A | 1/1989 | Ngo |
| 4,816,397 A | 3/1989 | Boss et al. |
| 4,877,608 A | 10/1989 | Lee et al. |
| 4,925,796 A | 5/1990 | Bergh et al. |
| 4,927,762 A | 5/1990 | Darfler |
| 4,933,435 A | 6/1990 | Ngo |
| 4,968,615 A | 11/1990 | Koszinowski et al. |
| 5,045,468 A | 9/1991 | Darfler |
| 5,047,335 A | 9/1991 | Paulson et al. |
| 5,096,816 A | 3/1992 | Maiorella |
| 5,110,913 A | 5/1992 | Coan et al. |
| 5,112,469 A | 5/1992 | Kempf et al. |
| 5,118,796 A | 6/1992 | Prior et al. |
| 5,122,469 A | 6/1992 | Mather et al. |
| 5,126,250 A | 6/1992 | McDonough et al. |
| 5,168,062 A | 12/1992 | Stinski |
| 5,169,936 A | 12/1992 | Staples et al. |
| 5,179,017 A | 1/1993 | Axel et al. |
| 5,231,024 A | 7/1993 | Moeller et al. |
| 5,328,985 A | 7/1994 | Sano et al. |
| 5,378,612 A | 1/1995 | Nakashima et al. |
| 5,429,746 A | 7/1995 | Shadle et al. |
| 5,530,101 A | 6/1996 | Queen et al. |
| 5,545,403 A | 8/1996 | Page |
| 5,545,806 A | 8/1996 | Lonberg et al. |
| 5,545,807 A | 8/1996 | Surani et al. |
| 5,561,053 A | 10/1996 | Crowley |
| 5,569,825 A | 10/1996 | Lonberg et al. |
| 5,605,923 A | 2/1997 | Christensen, IV et al. |
| 5,616,487 A | 4/1997 | Palsson et al. |
| 5,625,126 A | 4/1997 | Lonberg et al. |
| 5,633,162 A | 5/1997 | Keen et al. |
| 5,633,425 A | 5/1997 | Lonberg et al. |
| 5,644,036 A | 7/1997 | Ramage et al. |
| 5,654,407 A | 8/1997 | Boyle et al. |
| 5,656,272 A | 8/1997 | Le et al. |
| 5,661,016 A | 8/1997 | Lonberg et al. |
| 5,672,347 A | 9/1997 | Aggarwal et al. |
| 5,672,502 A | 9/1997 | Birch et al. |
| 5,698,195 A | 12/1997 | Le et al. |
| 5,705,364 A | 1/1998 | Etcheverry et al. |
| 5,721,121 A | 2/1998 | Etcheverry et al. |
| 5,730,975 A | 3/1998 | Hotamisligil et al. |
| 5,770,429 A | 6/1998 | Lonberg et al. |
| 5,789,650 A | 8/1998 | Lonberg et al. |
| 5,795,967 A | 8/1998 | Aggarwal et al. |
| 5,811,299 A | 9/1998 | Renner et al. |
| 5,859,205 A | 1/1999 | Adair et al. |
| 5,876,961 A | 3/1999 | Crowe et al. |
| 5,877,293 A | 3/1999 | Adair et al. |
| 5,929,212 A | 7/1999 | Jolliffe et al. |
| 5,945,098 A | 8/1999 | Sarno et al. |
| 5,945,311 A | 8/1999 | Lindhofer et al. |
| 5,976,833 A | 11/1999 | Furukawa et al. |
| 5,989,830 A | 11/1999 | Davis et al. |
| 5,994,510 A | 11/1999 | Adair et al. |
| 6,005,082 A | 12/1999 | Smeds |
| 6,015,558 A | 1/2000 | Hotamisligil et al. |
| 6,024,938 A | 2/2000 | Corbo et al. |
| 6,036,978 A | 3/2000 | Gombotz et al. |
| 6,048,728 A | 4/2000 | Inlow et al. |
| 6,066,719 A | 5/2000 | Zapata |
| 6,075,181 A | 6/2000 | Kucherlapati et al. |
| 6,090,382 A | 7/2000 | Salfeld et al. |
| 6,093,324 A | 7/2000 | Bertolini et al. |
| 6,113,898 A | 9/2000 | Anderson et al. |
| 6,150,584 A | 11/2000 | Kucherlapati et al. |
| 6,171,586 B1 | 1/2001 | Lam et al. |
| 6,171,825 B1 | 1/2001 | Chan et al. |
| 6,235,281 B1 | 5/2001 | Stenzel et al. |
| 6,255,458 B1 | 7/2001 | Lonberg et al. |
| 6,258,562 B1 | 7/2001 | Salfeld et al. |
| 6,270,766 B1 | 8/2001 | Feldman et al. |
| 6,300,129 B1 | 10/2001 | Lonberg et al. |
| 6,303,626 B1 | 10/2001 | Abramovici et al. |
| 6,339,142 B1 | 1/2002 | Basey et al. |
| 6,399,381 B1 | 6/2002 | Blum et al. |
| 6,406,909 B1 | 6/2002 | Shibuya et al. |
| 6,410,270 B1 | 6/2002 | Strittmatter et al. |
| 6,413,746 B1 | 7/2002 | Field |
| 6,436,397 B1 | 8/2002 | Baker et al. |
| 6,448,380 B2 | 9/2002 | Rathjen et al. |
| 6,451,983 B2 | 9/2002 | Rathjen et al. |
| 6,489,447 B1 | 12/2002 | Basey et al. |
| 6,498,237 B2 | 12/2002 | Rathjen et al. |
| 6,506,598 B1 | 1/2003 | Andersen et al. |
| 6,509,015 B1 | 1/2003 | Salfeld et al. |
| 6,528,286 B1 | 3/2003 | Ryll |
| 6,593,458 B1 | 7/2003 | Rathjen et al. |
| 6,656,466 B1 | 12/2003 | Etcheverry et al. |
| 6,673,575 B1 | 1/2004 | Franze et al. |
| 6,673,986 B1 | 1/2004 | Kucherlapati et al. |
| 6,680,181 B2 | 1/2004 | Castan |
| 6,870,034 B2 | 3/2005 | Breece et al. |
| 6,872,549 B2 | 3/2005 | Van Ness et al. |
| 6,890,736 B1 | 5/2005 | Reddy et al. |
| 6,900,056 B2 | 5/2005 | Lee et al. |
| 6,914,128 B1 | 7/2005 | Salfeld et al. |
| 6,924,124 B1 | 8/2005 | Singh |
| 6,936,441 B2 | 8/2005 | Reiter et al. |
| 6,974,681 B1 | 12/2005 | McGrew |
| 7,029,872 B2 | 4/2006 | Gerngross |
| 7,070,775 B2 | 7/2006 | Le et al. |
| 7,084,260 B1 | 8/2006 | Lonberg et al. |
| 7,122,641 B2 | 10/2006 | Vedantham et al. |
| 7,189,820 B2 | 3/2007 | Ruben |
| 7,192,584 B2 | 3/2007 | Le et al. |
| 7,223,394 B2 | 5/2007 | Salfeld et al. |
| 7,229,432 B2 | 6/2007 | Marshall et al. |
| 7,250,165 B2 | 7/2007 | Heavner et al. |
| 7,276,239 B2 | 10/2007 | Le et al. |
| 7,297,680 B2 | 11/2007 | Opstelten et al. |
| 7,323,553 B2 | 1/2008 | Fahrner et al. |
| 7,326,681 B2 | 2/2008 | Gerngross |
| 7,332,303 B2 | 2/2008 | Schilling et al. |
| 7,390,660 B2 | 6/2008 | Behrendt et al. |
| 7,427,659 B2 | 9/2008 | Shukla et al. |
| 7,429,491 B2 | 9/2008 | Luan et al. |
| 7,449,308 B2 | 11/2008 | Gerngross et al. |
| 7,473,680 B2 | 1/2009 | DeFrees et al. |
| 7,504,485 B2 | 3/2009 | Salfeld et al. |
| 7,517,670 B2 | 4/2009 | Umana et al. |
| 7,521,206 B2 | 4/2009 | Heavner et al. |

(56) References Cited

U.S. PATENT DOCUMENTS

| | | |
|---|---|---|
| 7,521,210 B2 | 4/2009 | Knudsen |
| 7,541,031 B2 | 6/2009 | Salfeld et al. |
| 7,588,761 B2 | 9/2009 | Salfeld et al. |
| 7,612,181 B2 | 11/2009 | Wu et al. |
| 7,645,609 B2 | 1/2010 | Follstad |
| 7,714,112 B2 | 5/2010 | Engstrand et al. |
| 7,750,129 B2 | 7/2010 | Johansson et al. |
| 7,767,207 B2 | 8/2010 | Ghayer et al. |
| 7,863,426 B2 | 1/2011 | Wan et al. |
| 7,883,704 B2 | 2/2011 | Salfeld et al. |
| 7,906,329 B2 | 3/2011 | Umana et al. |
| 7,919,264 B2 | 4/2011 | Maksymowych et al. |
| 7,947,471 B2 | 5/2011 | Knudsen |
| 7,972,810 B2 | 7/2011 | Crowell et al. |
| 8,034,906 B2 | 10/2011 | Borhani et al. |
| 8,043,863 B2 | 10/2011 | Bosques et al. |
| 8,053,236 B2 | 11/2011 | Morris et al. |
| 8,067,182 B2 | 11/2011 | Kelley et al. |
| 8,093,045 B2 | 1/2012 | Pla et al. |
| 8,192,951 B2 | 6/2012 | Wang et al. |
| 8,197,813 B2 | 6/2012 | Salfeld et al. |
| 8,206,714 B2 | 6/2012 | Salfeld et al. |
| 8,209,132 B2 | 6/2012 | Bosques et al. |
| 8,216,583 B2 | 7/2012 | Kruase et al. |
| 8,216,851 B2 | 7/2012 | Parsons et al. |
| 8,231,876 B2 | 7/2012 | Wan et al. |
| 8,304,250 B2 | 11/2012 | Parsons et al. |
| 8,313,925 B2 | 11/2012 | Gregory et al. |
| 8,338,088 B2 | 12/2012 | Collins et al. |
| 8,361,705 B2 | 1/2013 | Parsons et al. |
| 8,361,797 B2 | 1/2013 | Osborne et al. |
| 8,372,400 B2 | 2/2013 | Salfeld et al. |
| 8,372,401 B2 | 2/2013 | Salfeld et al. |
| 8,388,965 B2 | 3/2013 | Rao et al. |
| 8,399,627 B2 | 3/2013 | Votsmeier et al. |
| 8,414,894 B2 | 4/2013 | Salfeld et al. |
| 8,420,081 B2 | 4/2013 | Fraunhofer et al. |
| 8,436,149 B2 | 5/2013 | Borhani et al. |
| 8,470,318 B2 | 6/2013 | Ravetch et al. |
| 8,470,552 B2 | 6/2013 | Croughan et al. |
| 8,512,983 B2 | 8/2013 | Gawlitzek et al. |
| 8,530,192 B2 | 9/2013 | Knudsen |
| 8,586,356 B2 | 11/2013 | Bosques et al. |
| 8,623,644 B2 | 1/2014 | Umana et al. |
| 8,629,248 B2 | 1/2014 | Umana et al. |
| 8,632,773 B2 | 1/2014 | Kasermann et al. |
| 8,652,487 B2 | 2/2014 | Maldonado |
| 8,663,945 B2 | 3/2014 | Pla et al. |
| 8,663,999 B2 | 3/2014 | Parsons et al. |
| 8,703,498 B2 | 4/2014 | Parsons et al. |
| 8,729,241 B2 | 5/2014 | Liu et al. |
| 8,753,633 B2 | 6/2014 | Salfeld et al. |
| 8,821,865 B2 | 9/2014 | Neu et al. |
| 8,852,889 B2 | 10/2014 | Prentice |
| 8,883,146 B2 | 11/2014 | Fraunhofer et al. |
| 8,883,156 B2 | 11/2014 | Wan et al. |
| 8,895,009 B2 | 11/2014 | Wan et al. |
| 8,895,709 B2 | 11/2014 | Hickman et al. |
| 8,906,372 B2 | 12/2014 | Wan et al. |
| 8,906,646 B2 | 12/2014 | Pla et al. |
| 8,911,964 B2 | 12/2014 | Pla et al. |
| 8,916,153 B2 | 12/2014 | Wan et al. |
| 8,921,526 B2 | 12/2014 | Chumsae et al. |
| 8,946,395 B1 | 2/2015 | Herigstad et al. |
| 8,969,024 B2 | 3/2015 | Kaymakcalan et al. |
| 9,017,687 B1 | 4/2015 | Wang et al. |
| 9,018,361 B2 | 4/2015 | Hickman et al. |
| 9,023,992 B2 | 5/2015 | Rasmussen et al. |
| 9,035,027 B2 | 5/2015 | Ghayur et al. |
| 9,062,106 B2 | 6/2015 | Bengea et al. |
| 9,067,990 B2 | 6/2015 | Wang et al. |
| 9,073,988 B2 | 7/2015 | Pla et al. |
| 9,085,618 B2 * | 7/2015 | Ramasubramanyan .................. C07K 16/241 |
| 9,085,619 B2 | 7/2015 | Fraunhofer et al. |
| 9,090,688 B2 | 7/2015 | Bengea et al. |
| 9,090,867 B2 | 7/2015 | Pla et al. |
| 9,096,666 B2 | 8/2015 | Wan et al. |
| 9,096,879 B2 | 8/2015 | Khetan et al. |
| 9,102,723 B2 | 8/2015 | Wan et al. |
| 9,103,821 B2 | 8/2015 | Bosques et al. |
| 9,109,010 B2 | 8/2015 | Hickman et al. |
| 9,144,755 B2 | 9/2015 | Brown et al. |
| 9,145,546 B2 | 9/2015 | Nurcombe et al. |
| 9,150,645 B2 | 10/2015 | Subramanian et al. |
| 9,181,337 B2 | 11/2015 | Subramanian et al. |
| 9,181,572 B2 | 11/2015 | Subramanian et al. |
| 9,182,467 B2 | 11/2015 | Parsons et al. |
| 9,200,069 B2 | 12/2015 | Ramasubramanyan et al. |
| 9,200,070 B2 * | 12/2015 | Ramasubramanyan .................. C07K 16/241 |
| 9,206,390 B2 | 12/2015 | Rives et al. |
| 9,234,032 B2 | 1/2016 | Pla et al. |
| 9,234,033 B2 | 1/2016 | Rives et al. |
| 9,249,182 B2 | 2/2016 | Ramasubramanyan et al. |
| 9,255,143 B2 | 2/2016 | Bengea et al. |
| 9,265,815 B2 | 2/2016 | Fraser et al. |
| 9,266,949 B2 | 2/2016 | Ramasubramanyan et al. |
| 9,273,132 B2 | 3/2016 | Wan et al. |
| 9,284,371 B2 | 3/2016 | Pla et al. |
| 9,290,568 B2 | 3/2016 | Rives et al. |
| 9,315,574 B2 | 4/2016 | Ramasubramanyan et al. |
| 9,328,165 B2 | 5/2016 | Wan et al. |
| 9,334,319 B2 * | 5/2016 | Ramasubramanyan .................. C07K 1/165 |
| 9,346,879 B2 | 5/2016 | Ramasubramanyan et al. |
| 9,359,434 B2 | 6/2016 | Subramanian et al. |
| 9,365,645 B1 | 6/2016 | Bengea et al. |
| 9,499,614 B2 | 11/2016 | Pfrengle et al. |
| 9,505,834 B2 | 11/2016 | Bengea et al. |
| 9,512,214 B2 | 12/2016 | Rives et al. |
| 9,522,953 B2 | 12/2016 | Ramasubramanyan et al. |
| 2001/0021525 A1 | 9/2001 | Hirai et al. |
| 2002/0045207 A1 | 4/2002 | Krummen et al. |
| 2002/0119530 A1 | 8/2002 | Maiorella et al. |
| 2002/0132299 A1 | 9/2002 | Field |
| 2002/0137673 A1 | 9/2002 | Pingel et al. |
| 2002/0187526 A1 | 12/2002 | Ruben et al. |
| 2003/0012786 A1 | 1/2003 | Teoh et al. |
| 2003/0049725 A1 | 3/2003 | Heavner et al. |
| 2003/0096414 A1 | 5/2003 | Ciccarone et al. |
| 2003/0125247 A1 | 7/2003 | Rosen et al. |
| 2003/0153735 A1 | 8/2003 | Breece et al. |
| 2003/0157108 A1 | 8/2003 | Presta |
| 2003/0161828 A1 | 8/2003 | Abdelghany et al. |
| 2003/0166869 A1 | 9/2003 | Vedantham et al. |
| 2003/0170813 A1 | 9/2003 | Suga et al. |
| 2003/0175884 A1 | 9/2003 | Umana et al. |
| 2003/0178368 A1 | 9/2003 | van Reis |
| 2003/0203448 A1 | 10/2003 | Reiter et al. |
| 2003/0206898 A1 | 11/2003 | Fischkoff et al. |
| 2003/0211573 A1 | 11/2003 | Ryll |
| 2003/0219438 A1 | 11/2003 | Salfeld et al. |
| 2003/0229212 A1 | 12/2003 | Fahrner et al. |
| 2003/0235585 A1 | 12/2003 | Fischkoff et al. |
| 2004/0009172 A1 | 1/2004 | Fischkoff et al. |
| 2004/0029229 A1 | 2/2004 | Reeves et al. |
| 2004/0033228 A1 | 2/2004 | Krause et al. |
| 2004/0033535 A1 | 2/2004 | Boyle et al. |
| 2004/0038878 A1 | 2/2004 | Tanikawa et al. |
| 2004/0043446 A1 | 3/2004 | DeFrees et al. |
| 2004/0101939 A1 | 5/2004 | Santora et al. |
| 2004/0120952 A1 | 6/2004 | Knight et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0132140 A1 | 7/2004 | Satoh et al. |
| 2004/0136986 A1 | 7/2004 | Raju |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0162414 A1 | 8/2004 | Santora et al. |
| 2004/0166111 A1 | 8/2004 | Kaymakcalan et al. |

(56) References Cited

U.S. PATENT DOCUMENTS

| | | |
|---|---|---|
| 2004/0171152 A1 | 9/2004 | Price et al. |
| 2004/0191243 A1 | 9/2004 | Chen et al. |
| 2004/0191256 A1 | 9/2004 | Raju |
| 2004/0214289 A1 | 10/2004 | deVries et al. |
| 2004/0219142 A1 | 11/2004 | Banerjee et al. |
| 2005/0004354 A1 | 1/2005 | Salfeld et al. |
| 2005/0084969 A1 | 4/2005 | Schorgendorfer et al. |
| 2005/0100965 A1 | 5/2005 | Ghayur et al. |
| 2005/0123541 A1 | 6/2005 | Heavner et al. |
| 2005/0175611 A1 | 8/2005 | Mahler et al. |
| 2005/0249735 A1 | 11/2005 | Le et al. |
| 2005/0271654 A1 | 12/2005 | Rinderknecht et al. |
| 2005/0272124 A1 | 12/2005 | Chen et al. |
| 2006/0009385 A1 | 1/2006 | Hoffman et al. |
| 2006/0018907 A1 | 1/2006 | Le et al. |
| 2006/0024293 A1 | 2/2006 | Salfeld et al. |
| 2006/0057638 A1 | 3/2006 | Bosques et al. |
| 2006/0083741 A1 | 4/2006 | Hoffman et al. |
| 2006/0127950 A1 | 6/2006 | Bosques et al. |
| 2006/0149042 A1 | 7/2006 | Konstantinov et al. |
| 2006/0223147 A1 | 10/2006 | Nishiya et al. |
| 2006/0246073 A1 | 11/2006 | Knight et al. |
| 2006/0252672 A1 | 11/2006 | Betenbaugh et al. |
| 2006/0269479 A1 | 11/2006 | Colton et al. |
| 2006/0275867 A1 | 12/2006 | Chotteau et al. |
| 2006/0287432 A1 | 12/2006 | Christensen et al. |
| 2007/0003548 A1 | 1/2007 | Heavner et al. |
| 2007/0004009 A1 | 1/2007 | Dixit et al. |
| 2007/0015239 A1 | 1/2007 | Bihoreau et al. |
| 2007/0020260 A1 | 1/2007 | Presta |
| 2007/0041905 A1 | 2/2007 | Hoffman et al. |
| 2007/0054390 A1 | 3/2007 | Kelley et al. |
| 2007/0060741 A1 | 3/2007 | Kelley et al. |
| 2007/0071747 A1 | 3/2007 | Hoffman et al. |
| 2007/0081996 A1 | 4/2007 | Hoffman et al. |
| 2007/0110743 A1 | 5/2007 | Drapeau et al. |
| 2007/0111284 A1 | 5/2007 | Ryll |
| 2007/0134256 A1 | 6/2007 | Lai et al. |
| 2007/0161084 A1 | 7/2007 | Crowell et al. |
| 2007/0172475 A1 | 7/2007 | Matheus et al. |
| 2007/0172897 A1 | 7/2007 | Maksymowych et al. |
| 2007/0184045 A1 | 8/2007 | Doctor et al. |
| 2007/0184529 A1 | 8/2007 | Etcheverry et al. |
| 2007/0190057 A1 | 8/2007 | Wu et al. |
| 2007/0196373 A1 | 8/2007 | Le et al. |
| 2007/0202051 A1 | 8/2007 | Schuschnig |
| 2007/0202104 A1 | 8/2007 | Banerjee et al. |
| 2007/0212770 A1 | 9/2007 | Grillberger et al. |
| 2007/0248600 A1 | 10/2007 | Hansen et al. |
| 2007/0269463 A1 | 11/2007 | Donovan |
| 2007/0292442 A1 | 12/2007 | Wan et al. |
| 2007/0298040 A1 | 12/2007 | Le et al. |
| 2008/0009040 A1 | 1/2008 | Grillberger et al. |
| 2008/0025976 A1 | 1/2008 | Le et al. |
| 2008/0058507 A1 | 3/2008 | Liu et al. |
| 2008/0095762 A1 | 4/2008 | Presta |
| 2008/0112953 A1 | 5/2008 | McAuley et al. |
| 2008/0118496 A1 | 5/2008 | Medich et al. |
| 2008/0131374 A1 | 6/2008 | Medich et al. |
| 2008/0160577 A1 | 7/2008 | Dell'Orco et al. |
| 2008/0166348 A1 | 7/2008 | Kupper et al. |
| 2008/0193466 A1 | 8/2008 | Banerjee et al. |
| 2008/0206246 A1 | 8/2008 | Ravetch et al. |
| 2008/0219952 A1 | 9/2008 | Fischer et al. |
| 2008/0226635 A1 | 9/2008 | Koll et al. |
| 2008/0227136 A1 | 9/2008 | Pla et al. |
| 2008/0254514 A1 | 10/2008 | Knudsen |
| 2008/0269132 A1 | 10/2008 | Gomes et al. |
| 2008/0269468 A1 | 10/2008 | Vogel et al. |
| 2008/0274507 A1 | 11/2008 | Gomes et al. |
| 2008/0292642 A1 | 11/2008 | Borhani et al. |
| 2008/0305114 A1 | 12/2008 | Salfeld et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0053786 A1 | 2/2009 | Kao et al. |
| 2009/0060910 A1 | 3/2009 | Johnson et al. |
| 2009/0068172 A1 | 3/2009 | Kaymakcalan et al. |
| 2009/0068705 A1 | 3/2009 | Drapeau et al. |
| 2009/0069232 A1 | 3/2009 | Callewaert et al. |
| 2009/0110679 A1 | 4/2009 | Li et al. |
| 2009/0123378 A1 | 5/2009 | Wong et al. |
| 2009/0136525 A1 | 5/2009 | Gerngross et al. |
| 2009/0142828 A1 | 6/2009 | Bucciarelli et al. |
| 2009/0148513 A1 | 6/2009 | Fraunhofer et al. |
| 2009/0151023 A1 | 6/2009 | Kuvshinov et al. |
| 2009/0155205 A1 | 6/2009 | Salfeld et al. |
| 2009/0175857 A1 | 7/2009 | Salfeld et al. |
| 2009/0202546 A1 | 8/2009 | Harris et al. |
| 2009/0202557 A1 | 8/2009 | Argiriadi et al. |
| 2009/0203055 A1 | 8/2009 | Ngantung et al. |
| 2009/0208500 A1 | 8/2009 | Joly et al. |
| 2009/0226530 A1 | 9/2009 | Lassner et al. |
| 2009/0239259 A1 | 9/2009 | Hsieh |
| 2009/0253174 A1 | 10/2009 | Serber et al. |
| 2009/0258018 A1 | 10/2009 | Medich et al. |
| 2009/0269302 A1 | 10/2009 | Salfeld et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0004907 A1 | 1/2010 | Kidal et al. |
| 2010/0016557 A1 | 1/2010 | Salfeld et al. |
| 2010/0021451 A1 | 1/2010 | Wong |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0069617 A1 | 3/2010 | Gagnon |
| 2010/0113294 A1 | 5/2010 | Venkataraman et al. |
| 2010/0120094 A1 | 5/2010 | Johnsen et al. |
| 2010/0135987 A1 | 6/2010 | Hickman et al. |
| 2010/0136025 A1 | 6/2010 | Hickman et al. |
| 2010/0145029 A1 | 6/2010 | Gagnon |
| 2010/0151499 A1 | 6/2010 | Collins et al. |
| 2010/0160894 A1 | 6/2010 | Julian et al. |
| 2010/0167313 A1 | 7/2010 | Essig et al. |
| 2010/0172911 A1 | 7/2010 | Naso et al. |
| 2010/0189717 A1 | 7/2010 | Kim et al. |
| 2010/0221823 A1 | 9/2010 | McCoy et al. |
| 2010/0255013 A1 | 10/2010 | Presta |
| 2010/0256336 A1 | 10/2010 | Yuk et al. |
| 2010/0278808 A1 | 11/2010 | Ravetch et al. |
| 2010/0278822 A1 | 11/2010 | Fraunhofer et al. |
| 2010/0279306 A1 | 11/2010 | Bosques et al. |
| 2010/0291624 A1 | 11/2010 | Zhang et al. |
| 2010/0292443 A1 | 11/2010 | Sabbadini et al. |
| 2010/0297609 A1 | 11/2010 | Wells et al. |
| 2010/0297697 A1 | 11/2010 | Ambrosius et al. |
| 2011/0002935 A1 | 1/2011 | Wan et al. |
| 2011/0003338 A1 | 1/2011 | Bayer et al. |
| 2011/0039300 A1 | 2/2011 | Bayer et al. |
| 2011/0039729 A1 | 2/2011 | Delisa et al. |
| 2011/0053223 A1 | 3/2011 | Bayer et al. |
| 2011/0053265 A1 | 3/2011 | Follstad et al. |
| 2011/0054414 A1 | 3/2011 | Shang et al. |
| 2011/0081679 A1 | 4/2011 | Jing et al. |
| 2011/0081700 A1 | 4/2011 | Hasslacher et al. |
| 2011/0086050 A1 | 4/2011 | Presta |
| 2011/0086798 A1 | 4/2011 | Sethuraman et al. |
| 2011/0097336 A1 | 4/2011 | Wu et al. |
| 2011/0117601 A1 | 5/2011 | Haberger et al. |
| 2011/0123544 A1 | 5/2011 | Salfeld et al. |
| 2011/0124024 A1 | 5/2011 | Raju et al. |
| 2011/0129468 A1 | 6/2011 | Mccue et al. |
| 2011/0130544 A1 | 6/2011 | Ram et al. |
| 2011/0136682 A1 | 6/2011 | Bosques et al. |
| 2011/0171227 A1 | 7/2011 | Okun et al. |
| 2011/0207676 A1 | 8/2011 | Callewaert et al. |
| 2011/0213137 A1 | 9/2011 | Bosques et al. |
| 2011/0263828 A1 | 10/2011 | Wong et al. |
| 2011/0300151 A1 | 12/2011 | Okun et al. |
| 2011/0318340 A1 | 12/2011 | Collin et al. |

(56) References Cited

U.S. PATENT DOCUMENTS

| | | |
|---|---|---|
| 2012/0014956 A1 | 1/2012 | Kupper et al. |
| 2012/0015438 A1 | 1/2012 | Schilling et al. |
| 2012/0039900 A1 | 2/2012 | Stuhlmuller et al. |
| 2012/0039908 A1 | 2/2012 | Combs et al. |
| 2012/0077213 A1 | 3/2012 | Pla et al. |
| 2012/0093810 A1 | 4/2012 | Takada et al. |
| 2012/0107783 A1 | 5/2012 | Julian et al. |
| 2012/0107874 A1 | 5/2012 | Liu et al. |
| 2012/0122076 A1 | 5/2012 | Lau et al. |
| 2012/0122759 A1 | 5/2012 | Brown et al. |
| 2012/0123688 A1 | 5/2012 | Ramasubramanyan et al. |
| 2012/0129185 A1 | 5/2012 | Maksymowych et al. |
| 2012/0134988 A1 | 5/2012 | Ravetch et al. |
| 2012/0171123 A1 | 7/2012 | Medich et al. |
| 2012/0177596 A1 | 7/2012 | Fischkoff et al. |
| 2012/0177640 A1 | 7/2012 | Burg et al. |
| 2012/0178107 A1 | 7/2012 | Salfeld et al. |
| 2012/0183997 A1 | 7/2012 | Alley et al. |
| 2012/0190005 A1 | 7/2012 | Schaub et al. |
| 2012/0195885 A1 | 8/2012 | Correia et al. |
| 2012/0201831 A1 | 8/2012 | Salfeld et al. |
| 2012/0202974 A1 | 8/2012 | Eon-Duval et al. |
| 2012/0213792 A1 | 8/2012 | Salfeld et al. |
| 2012/0219564 A1 | 8/2012 | Salfeld et al. |
| 2012/0230913 A1 | 9/2012 | Johnston et al. |
| 2012/0238730 A1 | 9/2012 | Dong et al. |
| 2012/0244168 A1 | 9/2012 | Salfeld et al. |
| 2012/0251541 A1 | 10/2012 | Baurin et al. |
| 2012/0251550 A1 | 10/2012 | Borhani et al. |
| 2012/0258114 A1 | 10/2012 | Salfeld et al. |
| 2012/0258496 A1 | 10/2012 | Ellwanger et al. |
| 2012/0263731 A1 | 10/2012 | Fraunhofer et al. |
| 2012/0264920 A1 | 10/2012 | Wang et al. |
| 2012/0264927 A1 | 10/2012 | Parsons et al. |
| 2012/0271041 A1 | 10/2012 | Ficko Trcek |
| 2012/0276109 A1 | 11/2012 | Fraser et al. |
| 2012/0276134 A1 | 11/2012 | Fraser et al. |
| 2012/0276155 A1 | 11/2012 | Kishimoto et al. |
| 2012/0276157 A1 | 11/2012 | Fraser et al. |
| 2012/0276158 A1 | 11/2012 | Fraser et al. |
| 2012/0276160 A1 | 11/2012 | Maldonado |
| 2012/0276631 A1 | 11/2012 | Bengea et al. |
| 2012/0277165 A1 | 11/2012 | Collins et al. |
| 2012/0282262 A1 | 11/2012 | Okun et al. |
| 2012/0282270 A1 | 11/2012 | Krause et al. |
| 2012/0288494 A1 | 11/2012 | Borhani et al. |
| 2012/0294888 A1 | 11/2012 | Kishimoto et al. |
| 2012/0301498 A1 | 11/2012 | Altreuter et al. |
| 2012/0301510 A1 | 11/2012 | Kishimoto et al. |
| 2012/0308514 A1 | 12/2012 | Salfeld et al. |
| 2012/0309056 A1 | 12/2012 | Leon et al. |
| 2012/0329709 A1 | 12/2012 | Collins et al. |
| 2013/0004507 A1 | 1/2013 | Fischkoff et al. |
| 2013/0028903 A1 | 1/2013 | Wan et al. |
| 2013/0065219 A1 | 3/2013 | Tsang et al. |
| 2013/0084605 A1 | 4/2013 | Zhou et al. |
| 2013/0096283 A1 | 4/2013 | Khetan et al. |
| 2013/0115224 A1 | 5/2013 | Salfeld et al. |
| 2013/0122011 A1 | 5/2013 | Hoffman et al. |
| 2013/0122018 A1 | 5/2013 | Salfeld et al. |
| 2013/0149300 A1 | 6/2013 | Hiatt et al. |
| 2013/0156760 A1 | 6/2013 | Fraunhofer et al. |
| 2013/0189737 A1 | 7/2013 | Kang et al. |
| 2013/0195888 A1 | 8/2013 | Wang et al. |
| 2013/0205604 A1 | 8/2013 | Esenwein et al. |
| 2013/0231255 A1 | 9/2013 | Collins et al. |
| 2013/0243786 A1 | 9/2013 | Banerjee et al. |
| 2013/0244280 A1 | 9/2013 | Parikh et al. |
| 2013/0245139 A1 | 9/2013 | Kozlov et al. |
| 2013/0273059 A1 | 10/2013 | Wan et al. |
| 2013/0280267 A1 | 10/2013 | Wan et al. |
| 2013/0280274 A1 | 10/2013 | Subramanian et al. |
| 2013/0281355 A1 | 10/2013 | Vijayasankaran et al. |
| 2013/0309242 A1 | 11/2013 | Wan et al. |
| 2013/0323261 A1 | 12/2013 | Wan et al. |
| 2013/0330356 A1 | 12/2013 | Salfeld et al. |
| 2013/0330357 A1 | 12/2013 | Salfeld et al. |
| 2013/0336957 A1 | 12/2013 | Wang et al. |
| 2013/0338344 A1 | 12/2013 | Ramasubramanyan et al. |
| 2013/0344084 A1 | 12/2013 | Subramanian et al. |
| 2014/0010820 A1 | 1/2014 | Wang et al. |
| 2014/0045212 A1 | 2/2014 | Bosques et al. |
| 2014/0046032 A1 | 2/2014 | Blanche et al. |
| 2014/0065710 A1 | 3/2014 | Rives et al. |
| 2014/0072585 A1 | 3/2014 | Herigstad et al. |
| 2014/0087423 A1 | 3/2014 | Koncilja et al. |
| 2014/0120583 A1 | 5/2014 | Prentice |
| 2014/0134674 A1 | 5/2014 | Pla et al. |
| 2014/0134675 A1 | 5/2014 | Pla et al. |
| 2014/0141007 A1 | 5/2014 | Fraunhofer et al. |
| 2014/0141008 A1 | 5/2014 | Fraunhofer et al. |
| 2014/0142286 A1 | 5/2014 | Prentice |
| 2014/0154270 A1 | 6/2014 | Wang et al. |
| 2014/0178984 A1 | 6/2014 | Jerums et al. |
| 2014/0199340 A1 | 7/2014 | Maldonado |
| 2014/0199729 A1 | 7/2014 | Srivastava et al. |
| 2014/0206038 A1 | 7/2014 | Pla et al. |
| 2014/0234905 A1 | 8/2014 | Pla et al. |
| 2014/0255423 A1 | 9/2014 | Hickman et al. |
| 2014/0271622 A1 | 9/2014 | Prentice |
| 2014/0271623 A1 | 9/2014 | Parren et al. |
| 2014/0271626 A1 | 9/2014 | Chumsae et al. |
| 2014/0271632 A1 | 9/2014 | Hossler et al. |
| 2014/0271633 A1 | 9/2014 | Hossler |
| 2014/0273057 A1 | 9/2014 | Prentice et al. |
| 2014/0274911 A1 | 9/2014 | Collins et al. |
| 2014/0274912 A1 | 9/2014 | Prentice |
| 2014/0275494 A1 | 9/2014 | Wang et al. |
| 2014/0288272 A1 | 9/2014 | Allison et al. |
| 2014/0288278 A1 | 9/2014 | Nti-gyabaah et al. |
| 2014/0296490 A1 | 10/2014 | Faid et al. |
| 2014/0301977 A1 | 10/2014 | Nadarajah et al. |
| 2014/0314745 A1 | 10/2014 | Rives et al. |
| 2014/0363845 A1 | 12/2014 | Sinacore et al. |
| 2014/0377275 A1 | 12/2014 | Neu et al. |
| 2015/0023977 A1 | 1/2015 | Fraunhofer et al. |
| 2015/0110775 A1 | 4/2015 | Subramanian et al. |
| 2015/0110799 A1 | 4/2015 | Ramasubramanyan et al. |
| 2015/0125905 A1 | 5/2015 | Pla et al. |
| 2015/0132320 A1 | 5/2015 | Chumsae et al. |
| 2015/0132801 A1 | 5/2015 | Ramasubramanyan et al. |
| 2015/0133639 A1 | 5/2015 | Wentz et al. |
| 2015/0139988 A1 | 5/2015 | Labkovsky et al. |
| 2015/0140006 A1 | 5/2015 | Ramasubramanyan et al. |
| 2015/0141632 A1 | 5/2015 | Markosyan |
| 2015/0158944 A1 | 6/2015 | Bengea et al. |
| 2015/0166650 A1 | 6/2015 | Ramasubramanyan et al. |
| 2015/0166653 A1 | 6/2015 | Wang et al. |
| 2015/0183865 A1 | 7/2015 | Rives et al. |
| 2015/0183866 A1 | 7/2015 | Rives et al. |
| 2015/0197579 A1 | 7/2015 | Stefan et al. |
| 2015/0210735 A1 | 7/2015 | Hickman et al. |
| 2015/0259410 A1 | 9/2015 | Ramasubramanyan et al. |
| 2015/0299249 A1 | 10/2015 | Herigstad et al. |
| 2015/0320728 A1 | 11/2015 | Fraser et al. |
| 2015/0320856 A1 | 11/2015 | Altreuter et al. |
| 2015/0320870 A1 | 11/2015 | Maldonado |
| 2015/0320884 A1 | 11/2015 | Fraser et al. |
| 2015/0328333 A1 | 11/2015 | Fraser et al. |
| 2015/0329588 A1 | 11/2015 | Wang et al. |
| 2015/0335762 A1 | 11/2015 | Fraser et al. |
| 2015/0344564 A1 | 12/2015 | Hickman et al. |
| 2015/0361169 A1 | 12/2015 | Wan et al. |
| 2015/0361170 A1 | 12/2015 | Fraunhofer et al. |
| 2016/0017030 A1 | 1/2016 | Neu et al. |
| 2016/0017281 A1 | 1/2016 | Sunstrom |
| 2016/0022650 A1 | 1/2016 | Fraser et al. |
| 2016/0030554 A1 | 2/2016 | Kishimoto et al. |
| 2016/0030555 A1 | 2/2016 | Kishimoto et al. |
| 2016/0039924 A1 | 2/2016 | Zeng |
| 2016/0039925 A1 | 2/2016 | Subramanian et al. |
| 2016/0046708 A1 | 2/2016 | Subramanian et al. |
| 2016/0068881 A1 | 3/2016 | Prentice |
| 2016/0083452 A1 | 3/2016 | Hickman et al. |

(56) References Cited

U.S. PATENT DOCUMENTS

| | | |
|---|---|---|
| 2016/0115193 A1 | 4/2016 | Herigstad et al. |
| 2016/0115195 A1 | 4/2016 | Mendiratta et al. |
| 2016/0122384 A1 | 5/2016 | Kim et al. |
| 2016/0138064 A1 | 5/2016 | Rives et al. |
| 2016/0145331 A1 | 5/2016 | Subramanian et al. |
| 2016/0159897 A1 | 6/2016 | Zeng |
| 2016/0185848 A1 | 6/2016 | Hossler et al. |
| 2016/0186130 A1 | 6/2016 | Pla et al. |
| 2016/0194390 A1 | 7/2016 | Ramasubramanyan et al. |
| 2016/0201028 A1 | 7/2016 | Trcek |
| 2016/0207922 A1 | 7/2016 | Tang et al. |
| 2016/0207992 A1 | 7/2016 | Bengea et al. |
| 2016/0215319 A1 | 7/2016 | Mendiratta et al. |
| 2016/0222101 A1 | 8/2016 | Fraunhofer et al. |
| 2016/0227381 A1 | 8/2016 | Bargetzi et al. |
| 2016/0237149 A1 | 8/2016 | Flikweert et al. |
| 2016/0237150 A1 | 8/2016 | Subramanian et al. |
| 2016/0280767 A1 | 9/2016 | Beri et al. |

FOREIGN PATENT DOCUMENTS

| | | |
|---|---|---|
| CN | 105777896 A | 7/2016 |
| CN | 105777904 A | 7/2016 |
| DE | 3631229 | 3/1988 |
| EP | 0101681 A1 | 3/1984 |
| EP | 0173177 A1 | 3/1986 |
| EP | 0186833 A2 | 7/1986 |
| EP | 0212489 A2 | 3/1987 |
| EP | 230584 A1 | 8/1987 |
| EP | 0351789 A2 | 1/1990 |
| EP | 0366043 A1 | 5/1990 |
| EP | 374510 A1 | 6/1990 |
| EP | 453898 A2 | 10/1991 |
| EP | 0460426 B1 | 12/1991 |
| EP | 0481791 A2 | 4/1992 |
| EP | 0492448 A1 | 7/1992 |
| EP | 0523949 A1 | 1/1993 |
| EP | 585705 A1 | 3/1994 |
| EP | 0612251 A1 | 8/1994 |
| EP | 0614984 A2 | 9/1994 |
| EP | 0659766 A1 | 6/1995 |
| EP | 0746398 A1 | 12/1996 |
| EP | 0764719 A2 | 3/1997 |
| EP | 0956873 A2 | 11/1999 |
| EP | 0956875 A2 | 11/1999 |
| EP | 1075488 A1 | 2/2001 |
| EP | 1174148 A1 | 1/2002 |
| EP | 1176195 A1 | 1/2002 |
| EP | 1221476 A2 | 7/2002 |
| EP | 1254666 A1 | 11/2002 |
| EP | 1308455 A2 | 5/2003 |
| EP | 1308456 A2 | 5/2003 |
| EP | 1418967 A2 | 5/2004 |
| EP | 1568388 A1 | 8/2005 |
| EP | 1745141 A1 | 1/2007 |
| EP | 1849862 A2 | 10/2007 |
| EP | 1851305 A1 | 11/2007 |
| EP | 2080809 A1 | 7/2009 |
| EP | 2144929 A1 | 1/2010 |
| EP | 2152856 A1 | 2/2010 |
| EP | 2213726 A1 | 8/2010 |
| EP | 2305712 A1 | 4/2011 |
| EP | 2357250 A2 | 8/2011 |
| EP | 2495307 A1 | 9/2012 |
| EP | 2500414 A1 | 9/2012 |
| EP | 2528002 A2 | 11/2012 |
| EP | 2574677 A1 | 4/2013 |
| EP | 3036254 A1 | 6/2016 |
| EP | 3036320 A1 | 6/2016 |
| EP | 3072957 A1 | 9/2016 |
| GB | 2160530 A | 12/1985 |
| GB | 2279077 A | 12/1994 |
| IN | 2285/MUM/2013 * | 7/2013 |
| IN | 2285/MUM/2013 A1 | 1/2015 |
| JP | 6-292592 | 10/1994 |
| JP | 7289288 A | 11/1995 |
| WO | WO-87/00195 A1 | 1/1987 |
| WO | WO-90/03430 A1 | 4/1990 |
| WO | WO-90/05144 A1 | 5/1990 |
| WO | WO-91/02078 A1 | 2/1991 |
| WO | WO-91/04054 A1 | 4/1991 |
| WO | WO-91/09967 A1 | 7/1991 |
| WO | WO-92/01047 A1 | 1/1992 |
| WO | WO-92/11383 A1 | 7/1992 |
| WO | WO-92/16221 A1 | 10/1992 |
| WO | WO-92/16553 A1 | 10/1992 |
| WO | WO-92/17583 A1 | 10/1992 |
| WO | WO-93/06213 A1 | 4/1993 |
| WO | WO-93/11793 A1 | 6/1993 |
| WO | WO-94/02602 A1 | 2/1994 |
| WO | WO-94/08619 A1 | 4/1994 |
| WO | WO-94/20139 A1 | 9/1994 |
| WO | WO-94/25585 A1 | 11/1994 |
| WO | WO-94/26910 A1 | 11/1994 |
| WO | WO-94/29347 A1 | 12/1994 |
| WO | WO-9511317 A1 | 4/1995 |
| WO | WO-95/23813 A1 | 9/1995 |
| WO | WO-96/33208 A1 | 10/1996 |
| WO | WO-96/33735 A1 | 10/1996 |
| WO | WO-96/34096 A1 | 10/1996 |
| WO | WO-97/04801 A1 | 2/1997 |
| WO | WO-97/13852 A1 | 4/1997 |
| WO | WO-97/29131 A1 | 8/1997 |
| WO | WO-98-08934 A1 | 3/1998 |
| WO | WO-98/23645 A1 | 6/1998 |
| WO | WO-98/24883 A2 | 6/1998 |
| WO | WO-98/24884 A1 | 6/1998 |
| WO | WO-98/24893 A2 | 6/1998 |
| WO | WO-98/50433 A2 | 11/1998 |
| WO | WO-98/56418 A1 | 12/1998 |
| WO | WO-98/58964 A1 | 12/1998 |
| WO | WO-99/22764 A1 | 5/1999 |
| WO | WO-99/32605 A1 | 7/1999 |
| WO | WO-99/54342 A1 | 10/1999 |
| WO | WO-99/57134 A1 | 11/1999 |
| WO | WO-99/57246 A1 | 11/1999 |
| WO | WO-0003000 A2 | 1/2000 |
| WO | WO-01-44442 A1 | 6/2001 |
| WO | WO-0147554 A1 | 7/2001 |
| WO | WO-01-59069 A1 | 8/2001 |
| WO | WO-0177362 A1 | 10/2001 |
| WO | WO-02/12502 A2 | 2/2002 |
| WO | WO-0212501 A2 | 2/2002 |
| WO | WO-02/076578 A1 | 10/2002 |
| WO | WO-02/094192 A2 | 11/2002 |
| WO | WO-02/101019 A2 | 12/2002 |
| WO | WO-03/046162 | 6/2003 |
| WO | WO-03045995 A2 | 6/2003 |
| WO | WO-03/059935 A2 | 7/2003 |
| WO | WO-03/066662 A2 | 8/2003 |
| WO | WO-03/102132 A2 | 12/2003 |
| WO | WO-2004008100 A2 | 1/2004 |
| WO | WO-2004009776 A2 | 1/2004 |
| WO | WO-2004/026891 A2 | 4/2004 |
| WO | WO-2004/058944 A2 | 7/2004 |
| WO | WO-2004058800 A2 | 7/2004 |
| WO | WO-2004/076485 A2 | 9/2004 |
| WO | WO-2004/097006 A1 | 11/2004 |
| WO | WO-2005042569 A1 | 5/2005 |
| WO | WO-2005-062967 A2 | 7/2005 |
| WO | WO-2005/063813 A2 | 7/2005 |
| WO | WO-2005/082483 A1 | 9/2005 |
| WO | WO-2005100584 A2 | 10/2005 |
| WO | WO-2006/014683 A2 | 2/2006 |
| WO | WO-2006/026445 A1 | 3/2006 |
| WO | WO-2006/043895 A1 | 4/2006 |
| WO | WO-2006045438 A1 | 5/2006 |
| WO | WO-2006/099308 A2 | 9/2006 |
| WO | WO-2006/110277 A1 | 10/2006 |
| WO | WO-2007-005786 A2 | 1/2007 |
| WO | WO-2007/024743 A2 | 3/2007 |
| WO | WO-2007/055916 A2 | 5/2007 |
| WO | WO-2007/070315 A2 | 6/2007 |
| WO | WO-2007-077217 A2 | 7/2007 |

(56) References Cited

FOREIGN PATENT DOCUMENTS

| | | |
|---|---|---|
| WO | WO-2007/087384 A2 | 8/2007 |
| WO | WO-2007/117490 A2 | 10/2007 |
| WO | WO-2007/117505 A2 | 10/2007 |
| WO | WO 2007117490 A2 * | 10/2007 |
| WO | WO-2008/008360 A1 | 1/2008 |
| WO | WO-2008/028686 A2 | 3/2008 |
| WO | WO-2008/033517 A2 | 3/2008 |
| WO | WO-2008-057240 A2 | 5/2008 |
| WO | WO-2008/057634 A2 | 5/2008 |
| WO | WO-2008068879 A1 | 6/2008 |
| WO | WO-2008/077545 A1 | 7/2008 |
| WO | WO-2008087184 A2 | 7/2008 |
| WO | WO-2008/128230 A1 | 10/2008 |
| WO | WO-2008121616 A2 | 10/2008 |
| WO | WO-2008135498 A2 | 11/2008 |
| WO | WO-2009/027041 A1 | 1/2009 |
| WO | WO-2009/017491 A1 | 2/2009 |
| WO | WO-2009023562 A2 | 2/2009 |
| WO | WO-2009058769 A1 | 5/2009 |
| WO | WO-2009/073569 A2 | 6/2009 |
| WO | WO-2009/079382 A1 | 6/2009 |
| WO | WO-2009135656 A1 | 11/2009 |
| WO | WO-2010-048183 A1 | 4/2010 |
| WO | WO-2010036443 A1 | 4/2010 |
| WO | WO-2010043703 A1 | 4/2010 |
| WO | WO-2010/080062 A1 | 7/2010 |
| WO | WO-2010/102114 A1 | 9/2010 |
| WO | WO-2010/111633 A2 | 9/2010 |
| WO | WO-2010122460 A1 | 10/2010 |
| WO | WO-2010/129469 A1 | 11/2010 |
| WO | WO-2010127069 A1 | 11/2010 |
| WO | WO-2010/136209 A1 | 12/2010 |
| WO | WO-2010/138502 A2 | 12/2010 |
| WO | WO-2010/141039 A1 | 12/2010 |
| WO | WO-2011005773 A2 | 1/2011 |
| WO | WO-2011009623 A1 | 1/2011 |
| WO | WO-2011-019619 A1 | 2/2011 |
| WO | WO-2011015926 A1 | 2/2011 |
| WO | WO-2011024025 A1 | 3/2011 |
| WO | WO-2011044180 A1 | 4/2011 |
| WO | WO-2011/073235 A1 | 6/2011 |
| WO | WO-2011069056 A2 | 6/2011 |
| WO | WO-2011098526 A1 | 8/2011 |
| WO | WO-2011110598 A1 | 9/2011 |
| WO | WO-2011/133886 A2 | 10/2011 |
| WO | WO-2011127322 A1 | 10/2011 |
| WO | WO-2011133902 A2 | 10/2011 |
| WO | WO-2011134919 A2 | 11/2011 |
| WO | WO-2011134920 A1 | 11/2011 |
| WO | WO-2012/014183 A1 | 2/2012 |
| WO | WO-2012019160 A1 | 2/2012 |
| WO | WO-2012030512 A1 | 3/2012 |
| WO | WO-2012/046255 A2 | 4/2012 |
| WO | WO-2012050175 A1 | 4/2012 |
| WO | WO-2012051147 A1 | 4/2012 |
| WO | WO-2012/065072 A2 | 5/2012 |
| WO | WO-2012/068134 A1 | 5/2012 |
| WO | WO-2012062810 A2 | 5/2012 |
| WO | WO-2012/078276 A1 | 6/2012 |
| WO | WO-2012120500 A2 | 9/2012 |
| WO | WO-2012140138 A1 | 10/2012 |
| WO | WO-2012145682 A1 | 10/2012 |
| WO | WO-2012/149197 A2 | 11/2012 |
| WO | WO-2012147048 A2 | 11/2012 |
| WO | WO-2012147053 A1 | 11/2012 |
| WO | WO-2012158551 A1 | 11/2012 |
| WO | WO-2013-011076 A2 | 1/2013 |
| WO | WO-2013006461 A1 | 1/2013 |
| WO | WO-2013006479 A2 | 1/2013 |
| WO | WO-2013009648 A2 | 1/2013 |
| WO | WO-2013013013 A2 | 1/2013 |
| WO | WO-2013/021279 A2 | 2/2013 |
| WO | WO-2013-066707 A1 | 5/2013 |
| WO | WO-2013-067301 A1 | 5/2013 |
| WO | WO-2013/095966 A1 | 6/2013 |
| WO | WO-2013-158273 A1 | 10/2013 |
| WO | WO-2013-158279 A1 | 10/2013 |
| WO | WO-2013158275 A1 | 10/2013 |
| WO | WO-2013-164837 A1 | 11/2013 |
| WO | WO-2013-176754 A1 | 11/2013 |
| WO | WO-2013-177115 A2 | 11/2013 |
| WO | WO-2013-177118 A2 | 11/2013 |
| WO | WO-2013-181585 A2 | 12/2013 |
| WO | WO-2013-186230 A1 | 12/2013 |
| WO | WO-2014/018747 A2 | 1/2014 |
| WO | WO-2014/039903 A2 | 3/2014 |
| WO | WO-2014/052360 A2 | 4/2014 |
| WO | WO-2014/096672 A1 | 6/2014 |
| WO | WO-2014/099636 A1 | 6/2014 |
| WO | WO-2014/125374 A2 | 8/2014 |
| WO | WO-2014/143184 A1 | 9/2014 |
| WO | WO-2014-149935 A1 | 9/2014 |
| WO | WO-2014/150655 A1 | 9/2014 |
| WO | WO-2014/151878 A2 | 9/2014 |
| WO | WO-2014/158231 A1 | 10/2014 |
| WO | WO-2014/159488 A1 | 10/2014 |
| WO | WO-2014/159494 A1 | 10/2014 |
| WO | WO-2014/159499 A1 | 10/2014 |
| WO | WO-2014/179601 A2 | 11/2014 |
| WO | WO-2014-196780 A1 | 12/2014 |
| WO | WO-2014/207763 A1 | 12/2014 |
| WO | WO-2015/004679 A1 | 1/2015 |
| WO | WO-2015/007912 A1 | 1/2015 |
| WO | WO-2015/051293 A2 | 4/2015 |
| WO | WO-2015/073884 A2 | 5/2015 |
| WO | WO-2015/115849 A1 | 8/2015 |
| WO | WO-2016/007764 A1 | 1/2016 |
| WO | WO-2016/102383 A1 | 6/2016 |

OTHER PUBLICATIONS

DIONEX Application Note 125 (Monitoring Protein Deamidation by Cation-Exchange Chromatography. 2009; pp. 1-7).*
Du et al., (MAbs Sep.-Oct. 2012;4(5):578-85. doi: 10.4161/mabs. 21328. Epub Jul. 23, 2012).*
Santora et al., (Anal Biochem. Nov. 1, 1999;275(1):98-108).*
Claims of Mar. 2, 2015 for U.S. Appl. No. 14/635,505.*
Claims of Jul. 14, 2016 for U.S. Appl. No. 15/009,286.*
"Genentech unveils production capacity hikes," in-Pharma Technologist.com Jun. 28, 2005, pp. 1-2.
"Memorandum in Support of Centocor's Motion for Summary Judgment No. 1 that All Asserted Claims Are Invalid for Lack of Written Description", dated Aug. 1, 2013 and submitted by defendant in Civil Action No. 09-40089-FDS, 28 pages.
"Memorandum in Support of Centocor's Motion for Summary Judgment No. 2 that All Asserted Claims Are Invalid for Lack of Enablement", dated Aug. 1, 2013 and submitted by defendant in Civil Action No. 09-40089-FDS, 22 pages.
"Memorandum in Support of Centocor's Motion for Summary Judgment No. 4 that Claims Encompassing Non-recombinant Human Antibodies Are Invalid for Failing to Meet the Requirements of 35 U.S.C. §112", dated Aug. 1, 2013 and submitted by defendant in Civil Action No. 09-40089-FDS, 21 pages.
"Memorandum in Support of Centocor's Motion No. 3 for Summary Judgment that the 394 and 031 Patents Are Invalid under 35 U.S.C. §102(f) for Failing to Name the Proper Inventors", dated Aug. 1, 2013 and submitted by defendant in Civil Action No. 09-40089-FDS,13 pages.
"Memorandum in Support of Centocor's Motion No. 6 for Summary Judgment that References Dated Before Feb. 10, 1997 Qualify as Prior Art to the 394 and 031 Patents", dated Aug. 1, 2013 and submitted by defendant in Civil Action No. 09-40089-FDS, 16 pages.
"Plaintiffs' Memorandum in Support of Their Motion for Partial Summary Judgment", dated Aug. 1, 2013 and submitted by plaintiff in Civil Action No. 09-40089-FDS, 49 pages.
"Plaintiffs' Rule 56.1 Statement of Undisputed Material Facts in Support of Their Motion for Partial Summary Judgment", dated Aug. 1, 2013 and submitted by plaintiff in Civil Action No. 09-40089-FDS, 13 pages.

(56) References Cited

OTHER PUBLICATIONS

Abbott Laboratories Press Release, "Abbott Laboratories Receives FDA Approval Earlier Than Expected for HUMIRA (adalimumab) for the Treatment of Rheumatoid Arthritis," Dec. 31, 2002, pp. 1-4.
Abraham, E., et al., "Efficacy and Safety of Monoclonal Antibody to Human Tumor Necrosis Factor α in Patients with Sepsis Syndrome," *JAMA*, vol. 273(12):934-941 (1995).
Adams. et al., "Aggressive cutaneous T-cell lymphomas after TNFα blockade," J. Am. Acad. Dermatol 2004;51 :660-2.
Ahmed, M. U.et al.; N-(Carboxyethyl)lysine, a product of the chemical modification of proteins by methylglyoxal, increases with age in human lens proteins; Biochem. J. 1997, 324, 565-570.
Ahmed, N. & Thornalley, P. J.; Peptide Mapping of Human Serum Albumin Modified Minimally by Methylglyoxal in Vitro and in Vivo; Ann. N.Y. Acad. Sci. 2005, 1043,260-266.
Ahmed, N. et al.; Peptide Mapping Identifies Hotspot Site of Modification in Human Serum Albumin by Methylglyoxal Involved in Ligand Binding and Esterase Activity; J. Biol. Chem. 2005, 280, 5724-5732.
Ahmed, N.; Thornalley, P. J.; Advanced glycation endproducts: what is their relevance to diabetic complications?; Diabetes, Obes. Metab. 2007, 9, 233-245.
Alfaro, J. F.; Chemo-Enzymatic Detection of Protein Isoaspartate Using Protein Isoaspartate Methyltransferase and Hydrazine Trapping; Anal. Chem. 2008, 80, 3882-3889.
Alfaro, J. F.; Synthesis of LuxS Inhibitors Targeting Bacterial Cell-Cell Communication; Org. Lett. 2004, 6, 3043-3046.
Altamirano, C., et al., "Strategies for fed batch cultivation of t-PA producing CHO cells: substitution of glucose and glutamine and rational design of culture medium", *J. Biotechn.* 110:171-179, 2004.
Andersen DC, The effect of cell-culture conditions on the oligosaccharide structures of secreted glycoproteins. Curr Opin Biotechnol. Oct. 1994;5(5):546-9.
Anonymous, "SACHEM Displacement Chromatography," Aug. 29, 2012, Retrieved from the internet: www.displacementchromatography.com, retrieved on Jul. 30, 2014.
Antes et al. "Analysis of lysine clipping of a humanized Lewis-Y specific IgG antibody and its relation to Fc-mediated effector function" Journal of Chromatography B:Biomedical Sciences and Applications, Elsevier, Amsterdam, NL, vol. 852, No. 1-2, May 31, 2007, 250-256.
Averginos, Gab '04 Abstracts—GE Healthcare Life Sciences, "HUMIRA manufacturing: challenges and the path taken", France, Oct. 3-5, 2004, published 2005, pp. 14-16.
Avgerinos et al. (GAb '04 Abstracts—GE Healthcare Life Sciences, France Oct. 3-5, 2004, pp. 15-16 published 2005).
Awdeh, Z.L., A.R. Williamson, and B.A. Askonas, One cell-one immunoglobulin. Origin of limited heterogeneity of myeloma proteins. Biochem J, 1970. 116(2): p. 241-8.
Azevedo et al., "Integrated Process for the Purification of Antibodies Combining Aqueous Two-Phase Extraction, Hydrophobic Interaction Chromatography and Size-Exclusion Chromatography", *Journal of Chromatography* (2008) 1213(2): 154-161.
Babcock, James et al., "Partial Replacement of Chemically Defined Media with Plant-Derived Protein Hydrolysates," *BioPharm International*, vol. 23: 6. Jun. 2010, 6 pages.
Ballez, J.S. et al., "Plant protein hydrolysates support CHO-320 cells proliferation and recombinant IFN-[gamma] production in suspension and inside microcarriers in protein-free media", *Cytotechnology* 44:3, 103-114, 2004.
Bandyopadhyay S., et al. Physicochemical and functional characterization of a biosimilar adalimumab ZRC-3197, Biosimilars, 2015;5, pp. 1-18.
Barbuto, J. et al. "Production of Neutralizing Antibodies to Tumor Necrosis Factor by Human Tumor-Infiltrating B Lymphocytes" *Proc. Am. Assoc. Cancer Res,*. 34:487, Abstr. 2904 (1993).
Barnes et al., "Stability of Protein Production from Recombinant Mammalian Cells," Biotechnology and Bioengineering, 81:6, Mar. 20, 2003, pp. 631-639.

BD Bioscience Product Description for BBL Phytone Peptone (Advanced Processing, Third Edition) (Sep. 23, 2010) (www.bdbiosciences.com/external_files/Doc_Recon_2.0/ab/others/Phytone_Soytone.pdf www.bdbiosciences.com/external_files/Doc_Recon_2.0/ab/others/Phytone_Soytone.pdf>), (last accessed Jan. 8, 2015), 4 pages.
Bendtzen, K. et al. "Auto-antibodies to IL-1α and TNFα in Normal Individuals and in Infectious and Immunoinflammatory Disorders" *The Physiological and Pathological Effects of Cytokines*, 447-52 (1990).
Biblia, T.A. et al., "In Pursuit of the Optimal Fed-Batch Process for Monoclonal Antibody Production", Biotechnol. Prog 11(1):1-13, Jan.-Feb. 1995.
Birch, JR. et al., "Antibody production", Adv. Drug Delivery Reviews 58:671-685, 2006.
Blaker, GJ, et al., "The Glucose, Insulin and Glutamine Requirements of Suspension Cultures of HeLa Cells in a Defined Culture Medium", J. Cell Sci. 9:529-537, 1971.
Biastoff, S.; et al.; Colorimetric Activity Measurement of a Recombinant Putrescine N-Methyltransferase from *Datura stramonium*; Planta Med. 2006, 72, 1136.
Boekstegers, P., et al., "Repeated administration of a F(ab')2 fragment of an anti-tumor necrosis factor alpha monoclonal antibody in patients with severe sepsis: effects on the cardiovascular system and cytokine levels," *Shock*, vol. 1(4):237-245 (1994).
Bollati-Fogolin M., et al., "Temperature Reduction in Cultures of hGM-CSF-expressing CHO Cells: Effects on Productivity and Product Quantity", Biotechnol. Prog. 21:17-21, 2005.
Bonafede et al. "Cost per treated patient for etanercept, adalimumab, and infliximab across adult indications: a claims analysis" Advances in Therapy, Springer Healthcare Communications, Heidelberg, vol. 29, No. 3, Mar. 9, 2012, 234-249.
Boswell et al. "Effects of Charge on Antibody Tissue Distribution and Pharmacokinetics" Bioconjugate Chem.(21) 2153-2163 (2010).
Boyle, P. et al. "A Novel Monoclonal Human IgM Autoantibody which Binds Recombinant Human and Mouse Tumor Necrosis Factor-α" *Cell. Immunol.*, 152:556-68 (1993).
Boyle, P. et al. "The B5 Monoclonal Human Autoantibody Binds to Cell Surface TNFα on Human Lymphoid Cells and Cell Lines and Appears to Recognize a Novel Epitope" *Cell. Immunol.*, 152:569-81 (1993).
Brekke, O. et al., "Therapeutic Antibodies for Human Diseases at the Dawn of the Twenty-first Century," *Nature*, vol. 2:52-62 (2002).
Brock, Jonathan et al., "Detection and identification of arginine modifications on methylglyoxal-modified ribonuclease by mass spectrometric analysis," Journal of Mass Spectrometry, 2007; 42: 89-100.
Brorson et al., "Bracketed Generic Inactivation of Rodent Retroviruses by Low pH Treatment; for Monoclonal Antibodies and Recombinant Proteins," Biotechnology and Bioengineering,; vol. 82(3): 321-329 (2003).
Bruggemann et al., "Production of human antibody repertoires in transgenic mice" Cur. Op. Biotechnol. ;455-458 (1997).
Bruggemann, M., Neuberger, M.S., "Strategies for expressing human antibody repertoires in transgenic mice," *Immunol. Today* 17:391-397 (1996).
Burteau et al. (In Vitro Cell Dev Biol—Animal, Jul. / Aug. 2003. 39-291-296).
Byun, et al. Archives of Biochemistry and Biophysics, "Transport of anti-IL-6 binding fragments into cartilage and the effects of injury," 532 (2013), pp. 15-22.
Cai B, et al. "C-Terminal Lysine Processing of Human Immunoglobulin G2 Heavy Chain In Vivo" Biotechnol. Bioeng. 2011;108: 404-412.
Cambridge Antibody Technology, advertisement of phage display services, Science vol. 253, No. 5018 (1991).
Carter et al.,"Humanization of an anti-p185HER2 antibody for human cancer therapy," *Proc. Nat. Acad. Sci*89:4285-4289 (1992).
Chang KH, et al., "N-Acetylcysteine Increases the Biosynthesis of Recombinant EPO in Apoptotic Chinese Hamster Ovary Cells", Free Radic Res. 30(2):85-91, 1999.
Chang, T. & Wu, L., Methylglyoxal, oxidative street, and hypertension, Can. J. Physiol.Pharmacol. 84: 1229-1238 (2006).

(56) References Cited

OTHER PUBLICATIONS

Chaplen, F.W.R., et al., Effect of endogenous methylgiyoxal on Chinese hamster ovary celis grown in culture Cytotechnology 1996, vol. 22, Issue 1-3, Abstract and references, 6 pages.

Chaplen, F.W.R., Incidence and potential implications of the toxic metabolite methylglyoxal in cell culture: A review, Cytotechnology 26: 173-183, 1998.

Chaplen, FWR; A dissertation entitled Analysis of Methylglyoxal Metabolism in Mammalian Cell Culture; Univ. of Wisconsin-Madison 1996, 218 pages.

Charter, Edward A., "A New Process for the Separation and Purification of Egg Yolk; Antibodies," BASc., The University of British Columbia; A Thesis; Apr. 1993, 163 pages.

Chelius, D. et al.; Identification and Characterization of Deamidation Sites in the Conserved Regions of Human Immunoglobulin Gamma Antibodies, Anal. Chem. 2005, 77,6004-6011.

Choo et al. "High-level production of a monoclonal antibody in murine myeloma cells by perfusion culture using a gravity settler" Biotechnology Progress, vol. 23, No. 1, Jan. 1, 2007, 225-231.

Chow, A. et al. "Effect of monoclonal antibody on human tumor necrosis factor (TNF MAb) on TNFα, IL-1β, and IL-6 levels in patients with sepsis syndrome" *Clinical Research*, 42:2 299A (1994).

Chua, FKF et al., "Hyper-stimulation of monoclonal antibody production by high osmolarity stress in eRDF medium", J. Biotechnology 37(3):265-275, Nov. 15, 1994.

Chumsae, C., et al., Comparison of methionine oxidation in thermal stability and chemically stressed samples of a fully human monoclonal antibody. Journal of Chromatography B, 2007. 850(1-2): p. 285-294.

Chumsae, C., Gaza-Bulseco, G., & Liu, H., Identification and localization of unpaired cysteine residues in monoclonal antibodies by fluorescence labeling and mass spectrometry. Anal Chem, 2009. 81(15): p. 6449-57.

Chumsae, Chris et al.: "Arginine modifications by methylglyoxal: discovery in a recombinant monoclonal antibody and contribution to acidic species.", Analytical Chemistry Dec. 3, 2013, vol. 85, No. 23, Dec. 3, 2013(Dec. 3, 2013), pp. 11401-11409.

Chung et al., "Utilization of Lysozyme Charge Ladders to Examine the Effects of Protein Surface; Charge Distribution on Binding Affinity in Ion Exchange Systems," Langmuir 26(2): 759-768 (2010).

Chung et al. "Cetuximab-induced anaphylaxis and IgE specific for galactose-a-1,3-galactose" NEJM 358:11, 1109-1117 (2008).

Cleland, J. et al., "A Specific Molar Ratio of Stabilizer to Protein is Required for Storage Stability of a Lyophilized Monoclonal Antibody," *Journal of Pharmaceutical Sciences*, vol. 90(3):310-321 (2001).

Clincke, M. et al., "Effect of surfactant pluronic F-68 on CHO cell growth, metabolism, production, and glycosylation of human recombinant IFN-γ in mild operating conditions," Biotechnol. Prog. 27(1): 181-190, 2011.

Cohen, J., et al., "Intersept: An international, multicenter, placebo-controlled trial of monoclonal anitbody to human tumor necrosis factor-α in patients with sepsis," Crit Care Med, vol. 24(9):1431-1440 (1996).

Cordoba, A.J., et al., Non-enzymatic hinge region fragmentation of antibodies in solution. Journal of Chromatography B, 2005. 818(2): p. 115-121.

Cox, J. et al. "A directory of human germ-line Vκ segments reveals a strong bias in their usage" *Eur. J. Immunol.*, 24(2):827-36 (1994).

Cromwell (GAB'04 Abstracts—GE Healthcare Life Sciences, Franc Oct. 3-5, 2004, pp. 17-18 published 2005).

Crowell, C.K., et al., Amino acid and manganese supplementation modulates the glycosylation state of erythropoietin in a CHO culture system. Biotechnology and bioengineering, Feb. 15, 2007; 96(3):538-549.

Dai, S.; An Integrated Proteomic Analysis of Major Isoaspartyl-Containing Proteins in the Urine of Wild Type and Protein Llsoaspartate O-Methyltransferase-Deficient Mice; Anal. Chem. 2013, 85, 2423-2430.

Daugherty, et al. Formulation and Delivery Issues for Monoclonal Antibody Therapeutics. Advanced Drug Delivery Reviews, 2006. vol. 58, pp. 686-706.

Davies et al., "Antibody VH domains as small recognition units." *Biotechnology*, 13:475-479 (1995).

Department of Surgery, University of Toronto, Annual Report (1998-1999)(348 pages).

DePhillips et al., "Determinants of protein retention characteristics on cation-exchange adsorbents,"; Journal of Chromatograph A, 933:57-72 (2001).

DeZongotita et al., "Phosphate feeding improves high-cell-concentration NS0 myeloma cell culture performance for monoclonal antibody production" Biotechnology and Bioengineering. 2000, 69: 566-576.

Dick et al: "C-terminal lysine variants in fully human monoclonal antibodies: Investigation of test methods; and possible causes", Biotechnology and Bioengineering, vol. 100, No. 6, Aug. 15, 2008, pp. 1132-1143.

Dobo, A. & Kaltashov, I. A.; Detection of Multiple Protein Conformational Ensembles in Solution via Deconvolution of Charge-State Distributions in ESI MS; Anal. Chem. 2001,73, 4763-4773.

Dolezal, et al., "*Escherichia coli* Expression of a Bifunctional Fab-peptide Epitope Reagent for the Rapid Diagnosis of HIV-1 and HIV-2", *Immunotechnology*, 1:197-209 (1995).

Doring, E., "Identification and Characterization of a TNFa Antagonist Derived from a Monoclonal Antibody" (1994) *Mol. Immunol*. 31(14): 1059-1067.

Drew, Berry et al., "The Effects of Media Formulations on the Biochemical Profile of IgG Expressed in Sp2/0 Cells as Measured by Cation Exchange HPLC," European Society of Animal Cell Technology Meeting Jan. 2007, Poster #1115, 1 page.

Du et al., "Chromatographic analysis of the acidic and basic species of recombinant monoclonal antibodies" *MAbs*, Sep.-Oct. 2012; 4(5):578-85.

Elliot et al., "Repeated therapy with monoclonal antibody to tumour necrosis factor α (cA2) in patients with rheumatoid arthritis" (1994) *Lancet*, 344:1125-1127.

Elliot, "Treatment of rheumatoid arthritis with chimeric monoclonal antibodies to tumor necrosis factor α" (1993) *Arthritis & Rheumatism*, 36(12):1681-1690.

Ellison, Jay W. et al., "The Nucleotide Sequence of a Human Immunoglobulin Cγ1 Gene," Nucleic Acids Research, vol. 10, No. 13 (1982), 9 pages.

Emery, P. "Adalimumab therapy: Clinical findings and implications for integration into clinical guidelines for rheumatoid arthritis." *Drugs of Today*, 41(3): p. 155-163. (2005).

Erbitux (cetuximab) label, *Revised* Aug. 2013, 8 pages.

European Medicines Agency (EMA Europe), "2004 Report on Scientific Discussion for the Approval of Humira™ (adalimumab)," Last accessed Nov. 12, 2014 at www.ema.europa.eu/docs/en_GB/document_library/EPAR_Scientific_Discussion/human/000481/WC500050867.pdf; 25 pages.

Ewert et al., "Biophysical Properties of Human Antibody Variable Domains," J. Mol. Biol. 324: 531-; 553 (2003).

Exhibit dated Aug. 1, 2013 and cited by defendant in Civil Action No. 09-40089-FDS providing the Jun. 23, 2009 trial transcript of the PM session in the matter of *Centocor, et al.* v. *Abbott Laboratories*, 50 pages.

Exhibit dated Aug. 1, 2013 and cited by defendant in Civil Action No. 09-40089-FDS providing the trial transcript in the matter of *Abbott Laboratories, et al.* v. *The Mathilda and Terrance Kennedy Institute*, S.D.N.Y., 90 pages.

Exhibit dated Aug. 1, 2013 and cited by plaintiff in Civil Action No. 09-40089-FDS providing excerpts from the File History of U.S. Appl. No. 12/578,487, 5 pages.

(56) References Cited

OTHER PUBLICATIONS

Exhibit dated Aug. 1, 2013 and cited by defendant in Civil Action No. 09-40089-FDS providing the Jun. 24, 2009 trial transcript of the AM session in the matter of Centocor, et al. v. Abbott Laboratories, E.D. TX., 42 pages.
Exhibit dated Aug. 1, 2013 and cited by defendant in Civil Action No. 09-40089-FDS providing the Sep. 20, 2012 Day 8 trial transcript in the matter of Abbott v. Centocor Ortho Biotech Inc., D. MA., 71 pages.
Exhibit dated Aug. 1, 2013 and cited by plaintiff in Civil Action No. 09-40089-FDS providing Declaration by Jochen Salfeld, dated Jan. 17, 2013, 40 pages.
Extended European Search Report for Application No. 13877986.3. Dated Aug. 4, 2014, 11 pages.
Fahrner et al., "Industrial purification of pharmaceutical antibodies: development, operation, and validation of chromatography processes" Biotechnology and Genetic Engineering Reviews, 18, 2001, pp. 301-327.
FDA Package insert for Adalimumab, Sep. 26, 2003, pp. 1-16.
Feldmann, "Anti-TNF-alpha Therapy of Rheumatoid Arthritis: What Have We Learned?" (2001) *Annu. Rev. Immunol.*, 19:163-196.
Figini, "In Vitro assembly of Repertoires of Antibody Chains on the Surface of Phage by Renaturation" (1994) *J. Mol. Biol.*, 239:68-78.
Fishwild et al., "High-avidity human IgG kappa monoclonal antibodies from a novel strain of minilocus transgenic mice" (1996) *Nature Biotechnology*, 14:845-851.
Fleisher B., Mechanism of glycosylation in the Golgi apparatus. J Histochem Cytochem, Aug. 1983; 31(8):1033-1040.
Folk et al., "Carboxypeptidase B, Purification and Characterization of the Porcine Enzyme," J. Biological Chem, 1960, 235:2272-2277.
Fomsgaard, "Auto-antibodies to Tumor Necrosis Factor α in Healthy Humans and Patients with Inflammatory Diseases and Gram-Negative Bacterial Infections" (1989) *Scand. J. Immunol.* 30:219-23.
Foote, J., "Antibody framework residues affecting the conformation of the hypervariable loops" (1992) *J. Mol .Biol.*, 224(2):487-499.
Freitag et al., "Displacement chromatography in biotechnological downstream processing," J. Chromatography, (1995) 691(1):101-112.
Gagnon et al., "A Systematic Approach to the Purification of Monoclonal Antibodies," *LC-GC* 11 (1):26-34 (1993).
Gagnon, P., "Polishing methods for monoclonal IgG purification" Chapter 17, Taylor & Francis Group, LLC, pp. 491-505, 2007.
Gao et al. "Site-selective modifications of arginine residues in human hemoglobin induced by methylglyoxal." Biochemistry, 2006; pp. 15654-15660.
Gatto, B. "Biologics targeted at TNF: design, production and challenges", Reumatismo 58(2):94-103, 2006.
Gauthier, M. A.& Klok, H.-A. Arginine-Specific Modification of Proteins with Polyethylene Glycol Biomacromolecules; 2011, 12, 482-493.
Gaza-Bulseco, G., et al., Characterization of the glycosylation state of a recombinant monoclonal antibody using weak cation exchange chromatography and mass spectrometry. J Chromatogr B Analyt Technol Biomed Life Sci, 2008. 862(1-2): p. 155-60. Epub Dec. 8, 2007.
Genbank Entry for CHO Cathepsin L., EGW13555, Aug. 25, 2011, pp. 1-2.
Ghaderi, et al., "Implications of the Presence of N-glycolylneuraminic acid in Recombinant Therapeutic Glycoproteins", *Nature Biotechnology*, 28(8):863-868 (2010).
Ghaderi, et al., "Production platforms for biotherapeutic glycoproteins. Occurrence, impact, and challenges of non-human sialylation", *Biotechnology and Genetic Engineering Reviews*, 28:147-176 (2012).
Gonzalez et al. "Purification of Lactic Acid from Fermentation Broths by Ion-Exchange Resins" Ind. Eng. Chem. Res. 45:3243 (2006).
Goochee CF The Oligosaccharides of Glycoproteins: Bioprocess Factors Affecting Oligosaccharide Structure and their Effect on Glycoprotein Properties. Nature Biotechnology Dec. 1991 1346-1355.
Goochee, C.F. "Bioprocess Factors Affecting Glycoprotein Oligosaccharide Structure." *Develop. Biol. Standard*, vol. 76 (1992). 95-104.
Goswami et al., "Developments and Challenges for mAb-Based Therapeutics," *Antibodies*, 2:452-500, 2013.
Graf et al., "Ion exchange resins for the purification of monoclonal antibodies from animal cell culture" Bioseparation 4 (1) :7-20 (Feb. 1994). ;4 (1) :7-20 (Feb. 1994).
Gram et al., "In vitro selection and affinity maturation of antibodies from a naive combinatorial immunoglobulin library" (1992) *PNAS*, 89:3576-3580.
Gramer et al., "Glycosidase Activities of the 293 and NS0 Cell Lines, and of an Antibody-Producing Hybridoma Cell Line", *Biotechnology and Bioengineering*, 43:423-428 (1994).
Gramer M Jet Al: "Modulation of Antibody Galactosylation Through Feeding of Uridine, Manganese Chloride, and Galactose",Biotechnology and Bioengineering, Wiley & Sons, Hoboken, NJ, US,vol. 108, No. 7, Jul. 1, 2011, pp. 1591-1682.
Gramer, M.J., et al., "Manipulation of Antibody Glycoforms in a High-Yield GS-CHO Process to Meet Comparability Requirements", *Biotechnology and Bioengineering*, vol. 108, No. 7, Jul. 2011, pp. 1591-1602.
Green et al., "Antigen-specific human monoclonal antibodies from mice engineered with human Ig heavy and light chain YACs" (1994) *Nature Genetics*, 7:13-21.
Griffiths et al., "Isolation of high affinity human antibodies directly from large synthetic repertoires" (1994) *EMBO J.*, 13:3245-3260.
Griffiths, "Human anti-self antibodies with high specificity from phage display libraries" (1993) *The EMBO J.* 12(2):725-34.
Grosvenor, Sally, "A New Era in Cell Culture Media Development," *BioPharm International*, Jul. 2012 vol. 25: 7, 7 pages.
Grunberg, J. et al., "High-Yield Production of Recombinant Antibody Fragments in HEK-293 Cells Using Sodium Butyrate", BioTechniques 34(5):968-972, May 2003.
Gu, X. et al: "Improvement of interferon-gamma sialylation in Chinese hamster ovary cell culture by feeding of N-acetylmannosamine",Biotechnology and Bioengineering, Wiley & Sons, Hoboken, NJ, US, vol. 58, No. 6, Jun. 20, 1998, pp. 642-648.
Harding et al., "Class switching in human immunoglobulin transgenic mice" (1995) *Ann. NY Acad. Sci.*, 764:536-547.
Harlow and Lane, Antibodies A Laboratory Manual, Purification of Antibodies by using a; Deae-matrix (Batch), Storing and Purifying Antibodies; Chapter 8: 302-303 (1988).
Harlow et al., Eds ("Antibodies: A Laboratory Manual" 1988. Cold Spring Harbor Laboratory Press, Chapter 7, pp. 245, 247,and 253).
Harris, "Processing of C-terminal lysine and arginine residues of proteins isolated from mammalian cell culture" Journal of Chromatography, (1995) 705; 129-134.
Harris, R.J., et al., Identification of multiple sources of charge heterogeneity in a recombinant antibody. Journal of Chromatography B: Biomedical Sciences and Applications, 2001. 752(2): p. 233-245.
Harris, Reed J. et al., "Structural Characterization of a Recombinant CD4-IgG Hybrid Molecule," Eur. J. Biochem. 194:611-620 (1990).
Harrison et al., "Protein N-Glycosylation in the Baculovirus-Insect Cell Expression System and; Engineering of Insect Cells to Produce "Mammalianized" Recombinant Glycoproteins," Advances in; Virus Research, 68:159-191 (2006).
Hawkins, "Selection of Phage Antibodies by Binding Affinity Mimicking Affinity Maturation" (1992) *J. Mol. Biol.*, 226:889-896.
Heidemann, R. et al., "The use of peptones as medium additives for the production of a recombinant therapeutic protein in high density perfusion cultures of mammalian cells", Cytotechnology 32:157-167, 2000.
Helms et al., "Destabilizing loop swaps in the CDRs of an immunoglobulin VL domain," Protein; Science 4:2073-2081 (1995).
Hiatt et al., "Characterization and Applications of Antibodies Produced in Plants", *Intern. Rev. Immunol.*, 10:139-152 (1993).

(56) References Cited

OTHER PUBLICATIONS

Hiatt et al., "Production of Antibodies in Transgenic Plants", *Nature,* 342:76-78 (1989).
Hillgren, A. et al., "Protection mechanism of Tween 80 during freeze-thawing of a model protein LDH," *International Journal of Pharmaceutics,* vol. 237:57-69 (2002).
Hills, A.E. et al., Metabolic control of recombinant monoclonal antibody N-glycosylation in GS-NS0 cells, Biotechnology and Bioengineering, Oct. 20, 2001; 75(2):239-251.
Hipkiss, A.; Can the beneficial effects of methionine restriction in rats be explained in part by decreased methylglyoxal generation resulting from suppressed carbohydrate metabolism?; Biogerontology 2012, 13, 633-636.
Hokke et al., "Sialylated Carbohydrate Chains of Recombinant Human Glycoproteins Expressed in Chinese Hamster Ovary Cells Contain Traces of $N$-glycolylneuraminic acid", *FEBS,* 275:9-14 (1990).
Holler, "Modulation of Acute Graft-Versus-Host Disease After Allogeneic Bone Marrow Transplantation by Tumor Necrosis Factor-alpha (TNF-alpha) Release in the Course of Pretransplant Conditioning: Role of Conditioning Regimens and Prophylactic Application of a Monoclonal Antibody Neutralizing Human TNF-alpha (MAK 195F)" (1995) *Blood,* 86(3):890-899.
Holt, L. et al., "Domain antibodies: proteins for therapy," Trends in Biotechnology, vol. 21(11):484-490 (2003).
Hoogenboom et al., "By-passing immunisation : Human antibodies from synthetic repertoires of germline VH gene segments rearranged in vitro" (1992) *J. Mol. Biol.,* 227:381-388.
Hoogenboom, "Converting rodent into human antibodies by guided selection" (1996) *Antibody Engineering,* Oxford University Press, pp. 169-185.
Horvath et al: "Characterization of a Monoclonal Antibody Cell Culture Production Process Using a Quality by; Design Approach", Molecular Biotechnology, vol. 45, No. 3, Jul. 1, 2010, pp. 203-206.
Hossler et al., "Optimal and consistent protein glycosylation in mammalian cell culture", Glycobiology; (2009), 19(9):936-949.
Hossler et al.; "Improvement of mammalian cell culture performance through surfactant enabled concentrated feed media"; Biotechnology Progress; 29(4):1023-1033 (2013).
Hossler, Patrick et al., "Targeted Shifting of Protein Glycosylation Profiles in Mammalian Cell Culture through Media Supplementation of Cobalt." *J. Glycobiol* vol. 3; 1.(2014). 9 pages.
Huang et al. "Effects of anti-TNF monoclonal antibody infusion in patients with hairy cell leukaemia" (1992) *Br. J. Haematol.,* 81(2):231-234.
Huang, L., et al., In Vivo Deamidation Characterization of Monoclonal Antibody by LC/MS/MS. Analytical Chemistry, 2005. 77(5): p. 1432-1439.
Humira (adalimumab) label, *Revised* Sep. 2013, 87 pages.
Humira (adalimumab) prescribing information, Dec. 20, 2002, pp. 1-16.
Huse, "Generation of a large combinatorial library of the immunoglobulin repertoire in phage lambda" (1989) *Science,* 246:1275-81.
HyClone™ CDM4CHO Catalog listing (last accessed Nov. 17, 2014).
ICH Topic Q6B "Specifications:Test Procedures and Acceptance Criteria for Biotechnological/Biological Products," Sep. 1999, pp. 1-17.
Indian Patent Office—IPAIRS application status for 2285/MUM/2013—Application not yet published. Document found on internet at ipindiaonline.gov/in/patentsearch/search/index.aspx. Last accessed Apr. 13, 2015.
International Preliminary Report on Patentability for Application No. PCT/US07/08359, dated Dec. 12, 2011, 5 pages.
International Preliminary Report on Patentability for Application No. PCT/US2011/060388, dated May 30, 2012, 9 pages.
International Preliminary Report on Patentability for Application No. PCT/US2013/031352 dated Nov. 25, 2014, pp. 1-10.
International Preliminary Report on Patentability for Application No. PCT/US2013/031365, dated Mar. 3, 2015, 9 pages.
International Preliminary Report on Patentability for Application No. PCT/US2013/031380, dated Sep. 15, 2015, 13 pages.
International Preliminary Report on Patentability for Application No. PCT/US2013/031389, dated Oct. 21, 2014, pp. 1-10.
International Preliminary Report on Patentability for Application No. PCT/US2013/031485, dated Oct. 21, 2014, pp. 1-8.
International Preliminary Report on Patentability for Application No. PCT/US2013/031681, dated Oct. 21, 2014, pp. 1-8.
International Preliminary Report on Patentability for Application No. PCT/US2013/041954, dated Nov. 25, 2014, pp. 1-14.
International Preliminary Report on Patentability for Application No. PCT/US2013/041958, dated Dec. 4, 2014, pp. 1-2.
International Preliminary Report on Patentability for Application No. PCT/US2013/065720, dated Sep. 24, 2015, 8 pages.
International Preliminary Report on Patentability for Application No. PCT/US2013/065749 dated Sep. 15, 2015, 10 pages.
International Preliminary Report on Patentability for Application No. PCT/US2013/065797, dated Sep. 24, 2015, 8 pages.
International Preliminary Report on Patentability for Application No. PCT/US2013/069702, dated Sep. 15, 2015, 8 pages.
International Preliminary Report on Patentability for Application No. PCT/US2014/024151, dated Sep. 15, 2015, 9 pages.
International Preliminary Report on Patentability for Application No. PCT/US2014/024256, dated Sep. 15, 2015, pp. 1-9.
International Preliminary Report on Patentability for Application No. PCT/US2014/026606, dated Sep. 15, 2015, 13 pages.
International Preliminary Report on Patentability for Application No. PCT/US2014/026636, dated Sep. 15, 2015, 9 pages.
International Search Report and Written Opinion for Application No. PCT/US2008/085066, dated May 12, 2009, 5 pages.
International Search Report and Written Opinion for Application No. PCT/US2010/033387, dated Aug. 7, 2012, 10 pages.
International Search Report and Written Opinion for Application No. PCT/US2013/031380, dated Feb. 5, 2014, 162 pages.
International Search Report and Written Opinion for Application No. PCT/US2013/041954, dated Dec. 17, 2013, 21 pages.
International Search Report and Written Opinion for Application No. PCT/US2013/041958, dated Dec. 17, 2013, 21 pages.
International Search Report and Written Opinion for Application No. PCT/US2013/065720, dated Dec. 16, 2013, 14 pages.
International Search Report and Written Opinion for Application No. PCT/US2013/065797, dated Nov. 26, 2013, 14 pages.
International Search Report and Written Opinion for PCT/US2012/035266, dated Feb. 7, 2013 (corresponds to U.S. Appl. No. 13/547,020), 4 pages.
International Search Report and Written Opinion from PCT/US2013/065749 dated Mar. 18, 2014, 18 pages.
International Search Report and Written Opinion from PCT/US2014/024151 dated Aug. 7, 2014, pp. 1-16.
International Search Report and Written Opinion from PCT/US2015/039773 dated Sep. 25, 2015, pp. 1-14.
International Search Report for Application No. PCT/IB03/04502, dated May 26, 2004, 6 pages.
International Search Report for Application No. PCT/US2011/060388 dated May 30, 2012, 6 pages.
International Search Report for Application No. PCT/US2013/031352, Dated Apr. 25, 2013, 6 pages.
International Search Report for Application No. PCT/US2013/031389, Dated Jun. 3, 2013, 4 pages.
International Search Report for Application No. PCT/US2013/031485, Dated Jun. 25, 2013, 4 pages.
International Search Report for Application No. PCT/US2013/031681, Dated Jun. 14, 2013, 6 pages.
International Search Report for Application No. PCT/US2014/026606, Dated Dec. 8, 2014, 8 pages.
International Search Report for Application No. PCT/US2014/026636, Dated Jul. 29, 2014, 5 pages.
International Search Report for Application No. PCT/US2015/038819 Dated Sep. 2, 2015, 12 pages.
International Search Report from PCT/US2014/024256 dated Jul. 30, 2014, pp. 1-15.
Invitation to Pay Additional Fees for International Application No. PCT/US2013/031380, Dated Nov. 28, 2013, 5 pages.

(56) References Cited

OTHER PUBLICATIONS

Invitation to Pay Additional Fees for International Application No. PCT/US2013/065749, Dated May 27, 2014, pp. 1-8.
Invitation to Pay Additional Fees for International Application No. PCT/US2014/026606, Dated Jul. 8, 2014, pp. 1-8.
Jack, M.; Wright, D.; The Role of Advanced Glycation Endproducts and Glyoxalase 1 in Diabetic Peripheral Sensory Neuropathy; Transl. Res. 2012, 159, 355-365.
Jakobovits, A., "Production of fully human antibodies by transgenic mice" (1995) Curr. Op. Biotechnol., 6:561-566.
Jakubowski, H., Protein N-homocysteinylation: implications for atherosclerosis. Biomedicine; Pharmacotherapy, 2001. 55(8): p. 443-447.
Jayapal, Karthik P., et al., "Recombinant Protein Therapeutics from CHO Cells—20 Years and Counting," CHO Consortium, SBE Special Section, 40-47 (2007).
Jayme et al.; "Media formulation options and manufacturing process controls to safeguard against introduction of animal origin contaminants in animal cell culture"; Cytotechnology; 33:27-36 (2000).
Jefferis, R., Glycosylation of Recombinant Antibody Therapeutics. Biotechnology Progress, 2005.21(1): p. 11-16.
Jespers, "Guiding the Selection of Human Antibodies from Phage Display Repertoires to a Single Epitope of an Antigen" (1994) Bio/Technology, 12:899-903.
Johnson et al., "Characterization of cathepsin L secreted by Sf21 insect cells", Archives of Biochemistry and Biophysics (2005), 444:7-14.
Johnson, K.A., et al., Cation exchange HPLC and mass spectrometry reveal C-terminal amidation of an IqG1 heavy chain. Analytical Biochemistry, 2007. 360(1): p. 75-83.
Kalyanpur, M., "Downstream Processing in the Biotechnology Industry" Molecular Biotechnology, vol. 22:87-98 (2002).
Kanda, et al.: "Comparison of biological activity among nonfucosylated therapeutic IgG1 antibodies with three different N-linked Fc oligosaccharides: the high-mannose, hybrid, and complex types", Glycobiology, Oxford University Press, US, vol. 17, No. 1, Sep. 2006, pp. 104-118.
Karampetsou et al., "TNF-α antagonists beyond approved indications: stories of success and prospects for the future", Q J Med (2010) 103:917-928.
Kaschak et al: "Characterization of the basic charge variants of a human IgGI: Effect of copper concentration in cell culture media", MABS, vol. 3, No. 6, Nov. 1, 2011, pp. 577-583.
Kazuaki F et al "Enhancment of productivity of recombinant a-amidating enzyme by low temperature culture" Cytotechnology 31:85-94, 1999.
Kempeni, "Update on D2E7: a fully human anti-tumour necrosis factor -alpha monoclonal antibody" (2000) Ann. Rheum. Dis., 59(Suppl. I):144-145.
Kempeni, J, "Preliminary results of early clinical trials with the fully human anti-TNFα monoclonal antibody D2E7", Ann. Rheum. Dis., 1999, pp. 170-172, vol. 58, (Suppl. I).
Kempf, C, et al. "Virus inactivation during production of intravenous immunoglobulin." Transfusion 1991; vol. 31: p. 423-427.
Khawli et al, "Charge variants in IgGI: Isolation, characterization, in vitro binding properties and pharmacokinetics in rats", MABS, vol. 2, No. 6, Nov. 1, 2010, pp. 613-624;.
Kim et al.: "Development of serum-free medium supplemented with hydrolysates for the production of therapeutic antibodies in CHO cell cultures using design of experiments", Applied Microbiology and Biotechnology, Springer, Berlin, DE, vol. 83, No. 4, Mar. 6, 2009 (Mar. 6, 2009), pp. 639-648.
Kim, NS. et al., "Inhibition of sodium butyrate-induced apoptosis in recombinant Chinese hamster ovary cells by constitutively expressing antisense RNA of caspase-3", Biotechn. & Bioengin. 78(2):217-228, 2002.
Kingkeohoi, S., Analysis of methylglyoxal metabolism in CHO celis grown in culture, Cytotechnology (2005) 48:1-13.
Knight et al., "Construction and initial characterization of a mouse-human chimeric anti-TNF antibody" (1993) Mol. Immunol., 30(16):1443-1453.
Kopaciewicz et al., "Retention Model for High-Performance Ion-Exchange Chromatography,"; Journal of Chromatography, 266:3-21 (1983).
Kunkel, Jeremy P., et al., "Dissolved oxygen concentration in serum-free continuous culture affects N-linked glycosylation of a monoclonal antibody," Journal of Biotechnology, 62 (1998), 55-71.
Kwon et al., "Production of lactic acid by Lactobacillus rhamnosus with vitamin-suppremented soybean hydrolysate", Enzyme Microb Technol. (2000), 26:209-215.
Lerner, "Antibodies without immunization" (1992) Science, 258:1313-1314.
Leusch, "Failure to demonstrate TNFα-specific autoantibodies in human sera by ELISA and Western blot" (1991) J. Immunol. Methods, 139:145-47.
Lewis, "Use of alanine scanning mutagenesis to improve the affinity of an anti gp120 (HIV) antibody" (1994) J. Cell. Biochem., 18D:215.
Li, F. et al., "Current Therapeutic Antibody Production and Process Optimization" BioProcessing Journal, vol. 4(5):23-30 (2005).
Li, Feng, et al., "Cell Culture Processes for Monoclonal Antibody Production," mAbs 2:5, 466-479 (Sep.-Oct. 2010).
Lifely et al., "Glycosylation and Biological Activity of CAMPATH-1H Expressed in Different Cell Lines and Grown Under Different Culture Conditions", Glycobiology, 5(8):813-822 (1995).
Liu et al. "Recovery and purificaiton process development for monoclonal antibody production" MABS, 2(5), pp. 480-499 (2010).
Liu, H., Assessment of antibody fragmentation by reversed-phase liquid chromatography and mass spectrometry. J Chromatogr B Analyt Technol Biomed Life Sci, 2008. 876(1): p. 13-23. Epub Oct. 15, 2008.
Liu, H., et al., Heterogeneity of monoclonal antibodies. Journal of Pharmaceutical Sciences, 2008. 97(7): p. 2426-2447.
Liu, M, et al.; Discovery of Undefined Protein Cross-Linking Chemistry: A Comprehensive Methodology Utilizing 18O-Labeling and Mass Spectrometry; Anal. Chem. 2013, 5900-5908.
Liu, M.et al.; Protein Isoaspartate Methyltransferase-Mediated 18O-Labeling of Isoaspartic Acid for Mass Spectrometry Analysis; Anal. Chem. 2011, 84, 1056-1062.
Lo, T.W. et al., Binding and modification of proteins by methylglyoxal under physiological conditions. A kinetic and mechanistic study with N alpha-acetylarginine, N alpha-acetyilysine, and N alpha-acetyllysine, and bovine serum albumin, Dec. 23, 1994, The Journal of Biological Chemistrv, 269, 32299-32305.
Logan, John S. "Transgenic Animals: Beyond 'Funny Milk'", Current Opinion in Biotechnology, 4:591-595 (1993).
Lonberg et al., "Antigen-specific human antibodies from mice comprising four distinct genetic modifications" (1994) Nature, 368:856-859.
Lonberg et al., "Human Antibodies from Transgenic Mice" (1995) Int. Rev. Immunol., 13:65-93.
Low et al., "Mimicking Somatic Hypermutation: Affinity Maturation of Antibodies Displayed on Bacteriophage Using a Bacterial Mutator Strain" (1996) J. Mol. Biol., 260:359-368.
Low, Nigel: thesis extract (1996) Cambridge University.
Lu et al.: "A T-flask based screening platform for evaluating and identifying plant hydrolysates for a fed-batch cell culture process", Cytotechnology, Kluwer Academic Publishers, DO, vol. 55, No. 1, Aug. 18, 2007 (Aug. 18, 2007), pp. 15-29.
Luo et al., "Understanding of C-terminal lysine variants in antibody production using mammalian cells" Abstract of papers, ACS, Anaheim, CA, US, Mar. 2011, 1 page.
Luo et al: "Probing of C-terminal lysine variation in a recombinant monoclonal antibody production using Chinese hamster ovary cells with chemically defined media", Biotechnology and Bioengineering, vol. 109, No. 9, Apr. 11, 2012, pp. 2306-2315.
Luo, Ying et al.: "Development toward rapid and efficient screening for high performance hydrolysate lots in a recombinant monoclonal antibody manufacturing process.", Biotechnology Progress Jul. 2012, vol. 28, No. 4, Jul. 2012 (Jul. 2012), pp. 1061-1068.

(56) References Cited

OTHER PUBLICATIONS

Ma, et al., "Generation and Assembly of Secretory Antibodies in Plants", *Science*, 268:716-719 (1995).

Maeda, et al., "Analysis of Nonhuman N-Glycans as the Minor Constituents in Recombinant Monoclonal Antibody Pharmaceuticals", *Anal. Chem.*, 84:2373-2379 (2012).

Mahler, et al. Induction and analysis of aggregates in a liquid IgG1-antibody formulation. Eur J Pharm Biopharm. 2005, 59(3):407-17; p. 408; col. 1-2; p. 409; col. 2, "2.2.2 Stirring stress".

Manning, M., et al., *Stability of Protein Pharmaceuticals: An Update*. Pharmaceutical Research, 2010.27(4): p. 544-575.

Marks et al., "Human antibody fragments specific for human blood group antigens from a phage display library" (1993) *Bio/Technology*, 11:1145-1150.

Marks et al., "Molecular evolution of proteins on filamentous phage. Mimicking the strategy of the immune system" (1992) *J. Biol. Chem.* 267:16007-16010.

Marks, "By-passing immunization: Human antibodies from V-gene libraries displayed on phage" (1991) *J. Mol. Biol.*, 222:581-597.

Marks, "Human Monoclonal Antibodies from V-gene Repertoires Expressed on Bacteriophage." In *Antibody Engineering*, Second Edition, edited by Carl A.K. Borrebaeck (1995), pp. 53-88. New York: Oxford Univ. Press.

Marks, JD., "By-Passing Immunization: Building High Affinity Human Antibodies by Chain Shuffling" (1992) *Biotechnology*, 10:779-783.

Martin, A.C.R. "Accessing the Kabat antibody sequence database by computer" (1996) *Proteins: Structure, Function and Genetics*, 25:130-133.

Martinelle, K. et al., "Effect of different cell culture medium surfactants on cell growth and viability", Cells and Culture, Proceedings of the 20th ESACT Meeting v4 819-822, Jun. 17-20, 2007.

Matthews, R. G.; et al.; Cobalamin-Dependent and Cobalamin-Independent Methionine Synthases: Are There Two Solutions to the Same Chemical Problem?; Helv. Chim. Acta 2003, 86, 3939-3954.

McAtee et al., "Isolation of monoclonal antibody charge variants by displacement chromatography," Current Protocols in Protein Science, 8.10-8.10.13, 2012.

Medynski, "Phage Display: All Dressed Up and Ready to Role" (1994) *Bio/Technology*, 12:1134-1136.

Mehta, et al. "Purifying therapeutic monoclonal antibodies," Chemical Engineering Progress; May 2008, 104, 5; pp. S14-S20.

Mendez et al., "Functional transplant of megabase human immunoglobulin loci recapitulates human antibody response in mice" (1997) *Nature Genetics*, 15:146-156.

Meuwly, F. et al., "Conversion of a CHO cell culture process from perfusion to fed-batch technology without altering product quality", J.Biotechn. 123:106-116, 2006.

Miller et al., "Characterization of site-specific glycation during process development of a human therapeutic monoclonal antibody" Journal of Pharmaceutical Sciences, vol. 100, No. 7, Jul. 2011, 2543-2550.

Millipore, "Pellicon 2 Filters and Holders," 2003, pp. 1-8.

Mizuochi, T., et al., Structural and numerical variations of the carbohydrate moiety of immunoglobulin G. J Immunol, 1982. 129(5): p. 2016-20.

Moore, A., et al., "Effects of temperature shift on cell cycle, apoptosis and nucleotide pools in CHO cell batch cultures", Cytotechnology, 23:47-54, 1997.

Moorhouse, K.G., et al., Validation of an HPLC method for the analysis of the charge heterogeneity of the recombinant monoclonal antibody IDEC-C2B8 after papain digestion. Journal of Pharmaceutical and Biomedical Analysis, 1997. 16(4): p. 593-603.

Mostafa, A et al.; Plasma protein advanced glycation end products, carboxymethyl cysteine, and carboxyethyl cysteine, are elevated and related to nephropathy in patients with diabetes Mol. Cell. Biochem. 2007, 302, 35-42.

Muller-Spath, et al., "Chromatographic Separation of Three Monoclonal Antibody Variants Using Multicolumn Countercurrent Solvent Gradient Purification (MCSGP)" Biotechnology and Bioengineering, vol. 100. No. 6 (2008), pp. 1166-1177.

Möller, Monoclonal antibodies to human tumor necrosis factor α: in vitro and vivo application (1990) *Cytokine*, 2(3):162-69.

Neuberger M. et al., "Mice perform a human repertoire" (1997) *Nature*, 386:25-26.

Ngo et al., "Kosmotropes enhance the yield of antibody purified by affinity chromatography using immobilized bacterial immunoglobulin binding proteins," Journal of Immunoassay & Immunochemistry, (2008) 29(1):105-115.

Ni, W.; Analysis of Isoaspartic Acid by Selective Proteolysis with Asp-N and Electron Transfer Dissociation Mass Spectrometry; Anal. Chem. 2010, 82,7485-7491.

Nilsson, "Antibody engineering" (1995) *Current Opinion in Structural Biology*, 5:450-456.

Nogal, B., Chhiba, K. and Emery, J. C. (2012), Select host cell proteins coelute with monoclonal antibodies in protein a chromatography. Biotechnol Progress, 28: 454-458.

Noguchi et al., "Failure of Human Immunoresponse to N-Glycolylneuraminic Acid Epitope Contained in Recombinant Human Erythropoietin", *Nephron*, 72:599-603 (1996).

Noguchi et al., "Immunogenicity of N-Glycolylneuraminic Acid-Containing Carbohydrate Chains of Recombinant Human Erythropoietin Expressed in Chinese Hamster Ovary Cells", *J. Biochem.*, 117:59-62 (1995).

Oh, D-K. et al., "Increased erythritol production in fed-batch cultures of *Torula* sp. by controlling glucose concentration", J. Industrial Microb. & Biotechn. 26(4): 248-252, 2001.

Oh, et al., "Effect of N-Acetylcystein on Butyrate-Treated Chinese Hamster Ovary Cells to Improve the Production of Recombinant Human Interferon-β-1a", Biotechnol. Prog. 21(4):1154-1164, 2005.

Oh, SKW, et al., "Substantial Overproduction of Antibodies by Applying Osmotic Pressure and Sodium Butyrate", Biotechn. Bioengin. 42(5):601-610, 1993.

Osbourn, "From rodent reagents to human therapeutics using antibody guided selection" (2005) *Methods*, 36(1):61-68.

Ouellette, D.; Studies in serum support rapid formation of disulfide bond between unpaired cysteine residues in the VH domain of an immunoglobulin G1 molecule; Anal. Biochem. 2010, 397, 37.

Oya, T. et al. Methylglyoxal Modification of Protein: Chemical and Immunochemical Characterization of Methylglyoxal-Arginine Adducts. J. Bioi Chem. Jun. 25, 1999; vol. 274, No. 26, pp. 18492-19502.

Pacis, et al.: "Effects of cell culture conditions on antibody N-linked glycosylation—what affect high mannose 5 glycoform", Biotechnology and Bioengineering vol. 108, No. 10 Oct. 2011, pp. 2348-2358.

Paoli, T. et al., A Study of D-Lactate and Extracellular Methylglyoxal Production in Lactate ReUtilizing CHO Cultures, Biotechnology and Bioengineering, vol. 107, No. 1, Sep. 1, 2010, pp. 182-189.

Parekh RB N-glycosylation and the production of recombinant glycoproteins vol. 7, Issue 5, p. 117-122, May 1989 Trends in Biotechnology.

Parekh, R.B., et al., Association of rheumatoid arthritis and primary osteoarthritis with changes in the glycosylation pattern of total serum IgG. Nature, 1985. 316(6027): p. 452-7.

Patel, T. P. et al.: "Different culture methods lead to differences in glycosylation of a murine IgG monoclonal antibody", Biochemical journal, The Biochemical Society, London, GB, vol. 285, No. 3, Jan. 1, 1992 (Jan. 1, 1992), pp. 839-845.

PCT/US2013/069702 International Search Report & Written Opinion mailed Jan. 31, 2014, 13 pages.

Perchiacca et al., "Aggregation-resistance domain antibodies engineered with charged mutations; near the edges of the complementarity-determining regions," Protein Engineering Design & Selection, 25: 10 (591-601) 2012.

Perkins, M.; et. Al. Determination of the Origin of Charge Heterogeneity in a Murine Monoclonal Antibody; M. Pharm. Res. 2000, 17, 1110-1117.

(56) References Cited

OTHER PUBLICATIONS

Pietersz et al., "In vitro and in vivo Antitumor Activity of a Chimeric anti-CD19 Antibody", Cancer Immunol. Immunother., 41:53-60 (1995).

Pink, T. et al.: "Regulation of S-layer protein synthesis of bacillus stearothermophilus PV72 through variation of continuous cultivation conditions", Journal of Biotechnology, Elsevier Science Publishers, Amsterdam, NL, vol. 50, No. 2, Oct. 1, 1996 (Oct. 1, 1996), pp. 189-200.

Potter et al., "Antibody Production in the Baculovirus Expression System", Intern. Rev. Immunol., 10:103-112 (1993).

Poul et al., "Design of Cassette Baculovirus Vectors for the Production of Therapeutic Antibodies in Insect Cells", Immunotechnology, 1:189-196 (1995).

Quan, C., et al., A study in glycation of a therapeutic recombinant humanized monoclonal antibody: Where it is, how it got there, and how it affects charge-based behavior. Analytical Biochemistry, 2008.373(2): p. 179-191.

Queen, C., "A humanized antibody that binds to the interleukin 2 receptor" (1989) Proc. Natl. Acad. Sci. USA, 86(24):10029-10033.

Rabbani, N.; Thornalley, P. J.; Glyoxalase in diabetes, obesity and related disorders; Semin. Cell Dev. Biol. 2011, 22, 309-317.

Rader et al. "A phage display approach to rapid antibody humanization: Designed combinatorial V gene libraries" (1998) Proc Natl Acad Sci USA, 95:8910-8915.

Raju, TS. "Glycosylation Variations with Expression Systems and Their Impact on Biological Activity of Therapeutic Immunoglobulins", BioProcess International., 44-53 (2003).

Rau "Adalimumab (a fully human anti-tumour necrosis factor alpha monoclonal antibody) in the treatment of active rheumatoid arthritis: the initial results of five trials" Ann Rheum Dis 2002,61 (Suppl II): ii70-ii73.

Rea, J. C. et al.: "Validation of a pH gradient-based ion-exchange chromatography method for high-resolution monoclonal antibody charge variant separations", Journal of Pharmaceutical and Biomedical Analysis, New York, NY, US, vol. 54, No. 2, Jan. 25, 2011 (Jan. 25, 2011), pp. 317-323.

Reichert JM., et al., "Monoclonal antibody successes in the clinic", Nature Biotech. 23(9):1073-1078, 2005.

Reinhart, "Assessment of the safety and efficacy of the monoclonal anti-tumor necrosis factor antibody-fragment, MAK 195F, in patients with sepsis and septic shock: a multicenter, randomized, placebo-controlled, dose-ranging study" (1996) Crit. Care Med., 24(5):733-742.

Ren, D., et al., Reversed-phase liquid chromatography-mass spectrometry of site-specific chemical modifications in intact immunoglobulin molecules and their fragments. Journal of Chromatography A, 2008. 1179(2): p. 198-204.

Restelli, Veronica, et al., "The Effect of Dissolved Oxygen on the Production and the Glycosylation Profile of Recombinant Human Erythropoietin Produced From CHO Cells," Biotechnology and Bioengineering, vol. 94, No. 3, (2006) 481-494.

Rheinwald JG, et al., "Growth of Cultured Mammalian Cells on Secondary Glucose Sources", Cell, 287-293, 1974.

Ridder et al., "Generation of Rabbit Monoclonal Antibody Fragments from a Combinatorial Phage Display Library and Their Production in Yeast Pichia pastoris", Biotechnology, 13:255-260 (1995).

Riechmann, "Phage display and selection of a site-directed randomized single-chain antibody Fv fragment for its affinity improvement" (1993) Biochemistry, 32(34):8848-8855.

Roe, S. "Separation Based on Structure" Chapter 4, § 5.2, In, Protein Purification Methods; A Practical Approach, Harries, et al. Sep. 1989, p. 203.

Routier, F. H. et al.: "The glycosylation pattern of a humanized IgGI antibody(D1.3) expressed in CHO cells", Glycoconjugate Journal, Chapman & Hall, GB, vol. 14, No. 2, Jan. 1, 1997 (Jan. 1, 1997), pp. 201-207.

Roy, B.M., et al., Toxic concentrations of exogenously supplied methylglyoxal in hybridoma cell culture, Cytotechnology (2004) 46:97-107.

Roy, Samar N. et al., "Secretion of Biologically Active Recombinant Fibrinogen by Yeast." The Journal of Biological Chemistry, vol. 270; 40 (1995). 23761-23767.

Rube et al., "Ewing's sarcoma and peripheral primitive neuroectodermal tumor cells produce large quantities of bioactive tumor necrosis factor-α (TNF-α) after radiation exposure", Int. J. Radiation Oncology Biol. Phys., (2003), vol. 56, No. 5, pp. 1414-1425.

Rudikoff et al., "Single amino acid substitution altering antigen-binding specificity" (1982) Proc. Natl. Acad. Sci. USA, 70:1979-1983.

Sakai et al.; "Use of nonionic surfactants for effective supply of phosphatidic acid in serum-free culture of Chinese hamster ovary cells"; Journal of Bioscience and Bioengineering; 92(3):256-261 (2001).

Salfeld, "Development of a Fully Human Antibody to TNF by Phage Display Technology," IBC Conference, Antibody Engineering, San Diego (Dec. 1996), pp. 1-36.

Sandadi, S. et al., "Heuristic Optimization of Antibody Production by Chinese Hamster Ovary Cells", Biotech. Progress, American Institute of Chem. Engineers: 21(5): 1537-1542, 2005.

Sandhu, J. "Protein engineering of antibodies" (1992) Critical Reviews in Biotechnology, 12:437-462.

Santora et al., "Characterization of recombinant human monoclonal tissue necrosis factor-alpha antibody using cation exchange HPLC and capillary isoelectric focusing," Analytical Biochemistry, (1999) 275:98-108.

Santora, "Characterization of Noncovalent Complexes of Recombinant Human Monoclonal Antibody and Antigen Using Cation Exchange, Size Exclusion Chromatography, and BIAcore" (2001) Analytical Biochemistry, 299:119-129.

Sargent (pp. 1-3, Internet Archive captured Aug. 28, 2013, www.cellculturedish.com/2012/01 /cho-cells-the-top-expressionsystem-of-best-selling-biologic-drugs/).

Sato et al, "Stimulation of monoclonal antibody production by human-human hybridoma cells with an elevated concentration of potassium or sodium phosphate in serum-free medium," Cytotechnology 2:63-67, 1989.

Satoh, Mitsuo et al.: "Non-Fucosylated therapeutic antibodies as next-generation therapeutic antibodies", Expert opinion on biological therapy, Ashley, London, GB, vol. 6, No. 11, Nov. 1, 2006 (Nov. 1, 2006), pp. 1161-1173.

Saxena, R. K. et al.; Microbial production and applications of 1,2-propanediol; Indian J. Microbiol. 2010,50,2-11.

Schiestl et al. "Acceptable changes in quality attributes of glycosylated biopharmaceuticals" Nature Biotechnology, 29(4), 310-312 (2011).

Schwieterman, "Immunosuppression in Combination with Monoclonal Antibodies" in Biologic Agents in Autoimmune Disease (Mar. 2-4, 1995), 9 pages.

Scientific Discussion. Retrieved from the Internet: www.ema.europa.eu/dics/en_GB/document_library/EPAR_Sceintific_Discussion/human/00481/WC500050867.pdf [retrieved on Jun. 29, 2015], EMEA, 2004, 25 pages.

Senczuk et al. "Hydrophobic interaction chromatography in dual salt system increases protein binding capacity" Biotechnology and Bioengineering, 103(5), 930-935 (2009).

Seo, Jin Seok, et al., "Effect of culture pH on recombinant antibody production by a new human cell line, F2N78, grown in suspension at 33.0° C. and 37.0° C.," Appl. Microbiol Biotechnol., vol. 97 (2013). 5283-5291.

Seresht et al., "The impact of phosphate scarcity on pharmaceutical protein production in S. cerevisiae: linking transcriptomic insights to phenotypic responses" Microbial Cell Factories. 2011, 10: 104.

Sheeley et al., "Characterization of Monoclonal Antibody Glycosylation: Comparison of Expression Systems and Identification of Terminal α-Linked Galactose", Anal. Biochem., 247(1):102-110 (1997).

(56) References Cited

OTHER PUBLICATIONS

Sheikh et al., "Studies of the digestion of bradykinin, lysyl bradykinin, and kinin-degradation products by carboxypeptidases A, B, and N;". Biochemical Pharmacology. 1986, 35: 1957-1963.

Shen, Amy Y. et al., "Recombinant DNA Technology and Cell Line Development," from "Cell Culture Technology for Pharmaceutical and Cell-Based Therapies," CRC Press, 1995, 15-40.

Shih, "Effects of Anions on the Deamidation of Soy Protein". Journal of Food Science. 1991, 56: 452-454.

Shirato, Ken et al., "Hypoxic regulation of glycosylation via the N-acetylglucosamine cycle." J. Clin. Biochem. Nutr. vol. 48; 1 (2011). 20-25.

Shubert et al. "Comparison of ceramic hydroxy- and fluoroapatite versus Protein A/G-based resins in the isolation of a recombinant human antibody from cell culture supernatant" J. Chromatography A, 114 (2007) 106-113.

Shukla et al., "Host cell protein clearance during protein A chromatography: development of an improved column wash step," Biotechnology Progress, (2008) 24(5):1115-1121.

Shukla et al., "Recent advances in large-scale production of monoclonal antibodies and related proteins," Trends in Biotechnology, (2010) 28(5):253-261.

Sigma Catalog "RPMI1640" (last accessed Jan. 22, 2015), 3 pages.

Sigma MSDS for RMPI1640 (last accessed Jan. 22, 2015), 6 pages.

Sioud et al., "Characterization of naturally occurring autoantibodies against tumour necrosis factor-alpha (TNF-α): in vitro function and precise epitope mapping by phage epitope library" (1994) Clin. Exp. Immunol., 98:520-525.

Sundaram et al., "An innovative approach for the characterization of the isoforms of a monoclonal antibody product," Mabs, 3(6):505-512, 2011.

Sung, Y.H. et al., "Yeast hydrolysate as a low-cost additive to serum-free medium for the production of human thrombpoietin in suspension cultures of Chinese hamster ovary cells", *Applied Microbilolgy and Biotechnology* 63:5, 527-536, 2004.

Takagi, M. et al., "The effect of osmolarity on metabolism and morphology in adhesion and suspension chinese hamster ovary cells producing tissue plasminogen activator", Cytochnology 32:171-179, 2000.

Tamura et al., "Structural correlates of an anticarcinoma antibody: identification of specificity-determining residues (SDRs) and development of a minimally immunogenic antibody variant by retention of SDFs only," J. Immun. (2000) 164:1432-1441.

Tan et al., "Expression and purification of a secreted functional mouse/human chimaeric antibody against bacterial endotoxin in baculovirus-infected insect cells", Biotechnol. Appl. Biochem. (1999), 30:59-64.

Taylor et al.,"Human immunoglobulin transgenes undergo rearrangement, somatic mutation and class switching in mice that lack endogenous IgM" (1994) *Int. Immunol.*, 6:579-591.

Tebbey, Paul W., et al., "Consistency of quality for the glycosylated monoclonal antibody Humira (adalimumab)," MAbs, Sep. 3, 2015;7(5); 805-11.

Teichmann, S. Declaration dated Dec. 17, 2010 from opposition proceedings in EP 0929578, 6 pages.

TESS database "HYCLONE" Trademark #76244963. Filing date Apr. 23, 2001. Live mark. Last accessed Jan. 21, 2015.

TESS database "HYCLONE" Trademark #85769283. Filing date Sep. 30, 2012. Live mark. Last accessed Jan. 21, 2015.

Tharmalingam et al.; "Pluronic Enhances the Robustness and Reduces the Cell Attachment of Mammalian Cells"; Molecular Biotechnology; 39(2):167-177 (2008).

The Kennedy Institute of Rheumatology, 1995 Annual Scientific Report, "Anti-TNF trials and studies of mechanisms of action".

The MW Calculator available at the Sequence Manipulation Suite (see www.bioinformatics.org/sms2/index.html), downloaded Feb. 25, 2014, 2 pages.

The pI Calculator available at the Sequence Manipulation Suite (see www.bioinformatics.org/sms2/index.html, downloaded Feb. 25, 2014, p. 1.

The Statement on a Nonproprietary Name Adopted by the USAN Council for Adalimumab, p. 1, downloaded on May 19, 2011 from www.ama-assn.org/resources/doc/usan/adalimumab.doc. 1 page.

Thompson, "Affinity maturation of a high-affinity human monoclonal antibody against the third hypervariable loop of human immunodeficiency virus: use of phage display to improve affinity and broaden strain reactivity" (1996) J. Mol. Biol., 256(1):77-88.

Thorp, "Tumour Necrosis Factor Induction of ELAM-1 and ICAM-1 on Human Umbilical Vein Endothelial Cells—Analysis of Tumour Necrosis Factor Receptor Interaction" (1992) Cytokine, 4(4): 313-319.

Tomiya et al., "Comparing N-glycan processing in mammalian cell lines to native and engineered; lepidopteran insect cell lines," Glycoconjuqate Journal 21 :343-360 (2004).

Tomlinson, "The repertoire of human germline VH sequences reveals about fifty groups of VH segments with different hypervariable loops" (1992) J. Mol. Biol., 227:776-98.

Tomlinson, "The structural repertoire of the human Vk domain" (1995) The EMBO J., 14(18):4628-38.

Tracey, "Tumor necrosis factor: A pleiotropic cytokine and therapeutic target" (1994) Annu. Rev. Med., 45:491-503.

Tsuchiyama et al., "Comparison of anti-TNF alpha autoantibodies in plasma and from EBV transformed lymphocytes of autoimmune and normal individuals" (1995) Hum. Antibod. Hybridomas, 6(2):73-76.

United States Food and Drug Administration (FDA) Biological Licensing Application File No. 125057 (Adalimumab) (Dec. 31, 2002) (Last Accessed Mar. 4, 2015 at www.fda.gov/Drugs/DevelopmentApprovalProcess/HowDrugsareDevelopedandApproved/ApprovalApplications/TherapeuticBiologicApplications/ucm080610.htm, 1 page.

Vallee B et al. "The role of zinc in carboxypeptidase" The Journal of Biological Chemistry, (1960) 235, 1; 64-69.

Valliere-Douglass et al., "Glutamine-linked and Non-consensus Asparagine-linked Oligosaccharides Present in Human Recombinant Antibodies Define Novel Protein Glycosylation Motifs", J. Biol. Chem., 285:16012-16022 (2010).

Van Der Poll, "Effect of postponed treatment with an anti-tumour necrosis factor (TNF) F(ab')2 fragment on endotoxin-induced cytokine and neutrophil responses in chimpanzees" (1995) Clin. Exp. Immunol., 100:21-25.

Van Herreweghe, et al.; Tumor necrosis factor-induced modulation of glyoxalase I activities through phosphorylation by PKA results in cell death and is accompanied by the formation of a specific methylglyoxal-derived AGE; Proc. Natl. Acad. Sci. 2002, 99, 949-954.

Van Lent PL, et al. "The impact of protein size and charge on its retention in articular cartilage" J Rheumatol. Aug. 1987;14(4):798-805.

Varasteh et al. Optimization of Anti-Rh D Immunoglobulin Stability in the Lyphiliization Process. Iranian Journal of Basic Medical Sciences, Spring 2008, vol. 11, No. 1. pp. 55-61.

Vasilli, P. et al., The Pathophysiology of Tumor Necrosis Factors, Annu. Rev. Immunol. 10:411-452 (1992).

Vaughan, "Human antibodies by design" (1998) *Nature Biotechnology*, 16:535-539.

Vlasak, J. & Ionescu, R., *Heterogeneity of Monoclonal Antibodies Revealed by Charge-Sensitive Methods.* Current Pharmaceutical Biotechnology, 2008. 9(6): p. 468-481.

Wagner et al., "Antibodies generated from human immunoglobulin miniloci in transgenic mice" (1994) *Nucl. Acids Res.* 22:1389-1393.

Wagner et al., "The diversity of antigen-specific monoclonal antibodies from transgenic mice bearing human immunoglobulin gene miniloci" (1994) *Eur. J. Immunol.*, 24:2672-2681.

Walsh, et al.: "Post-translational modifications in the context of therapeutic proteins", Nature Biotechnology, vol. 24, No. 10, Oct. 2006, pp. 1241-1252.

Wang, Tina et al., "Exploring Post-translational Arginine Modification Using Chemically Synthesized Methylglyoxal Hydroimidazolones," J. Am. Chem. Soc., 2012, 134, pp. 8958-8967.

Wang, Z.; et al. Desulfurization of Cysteine-Containing Peptides Resulting from Sample Preparation for Protein Characterization by MS; Rapid Commun. Mass Spectrom. 2010, 24, 267-275.

(56) References Cited

OTHER PUBLICATIONS

Ward, "Binding activities of a repertoire of single immunoglobulin variable domains secreted from *Escherichia coli*" (1989) *Nature*, 341:544-546.
Watt, S.; et al.; Effect of Protein Stabilization on Charge State Distribution in Positive- and Negative-Ion Electrospray Ionization Mass Spectra; J. Am. Soc. Mass. Spectrom. 2007, 18, 1605-1611.
Wedemayer et al., "Structural insights into the evolution of an antibody combining site" (1997) *Science*, 276:1665-1669.
Wiendl et al., "Therapeutic Approaches in Multiple Sclerosis. Lessons from failed and interrupted treatment trials", BioDrugs. (2002), 16(3):183-200.
Williams et al., "Kinetic analysis by stopped-flow radiationless energy transfer studies: effect of anions on the activity of carboxypeptidase A". Biochemistry. 1986, 25, 94-100.
Williams, A. et al., Ion-Exchange Chromatography, Oct. 1998, Supplement 44, pp. 10-10-1-10-10-30.
Winter, "Humanized antibodies" (1993) *Immunol. Today*, 14(6):243-246.
Winter, "Making antibodies by phage display technology" (1994) *Annu. Rev. Immunol.*, 12:433-455.
Wolff et al., "The Kinetics of Carboxypeptidase B Activity," J. Biological Chem, 1962, 237:3094-3099.
Wong N.S.C. et al: "An investigation of intracellular glycosylation activities in CHO cells: Effects of nucleotide sugar precursor feeding" Biotechnology and Bioengineering, vol. 187, No. 2,Oct. 1, 2010, pp. 321-336.
Worthington Biochemical Corporation, porcine pancreas carboxypeptidase B, one page, Feb. 25, 2012.
Wurm, FM, "Production of recombinant protein therapeutics in cultivated mammalian cells", Nature Biotechnology 22(11):1393-1398, 2004.
www.cygnustechnologies.com/product_detail/host-cell-protein-antibodies/anti-cho-h . . . CYGNUS Technologies, Anti-CHO HCP (Apr. 18, 2012), 1 page.
Xiang, T., Chumsae, C. & Liu, H., Localization and Quantitation of Free Sulfhydryl in Recombinant Monoclonal Antibodies by Differential Labeling with 12C and 13C Iodoacetic Acid and LC-MS Analysis. Analytical Chemistry, 2009. 81(19): p. 8101-8108.
Yigzaw et al., "Exploitation of the adsorptive properties of depth filters for host cell protein removal during monoclonal antibody purification," Biotechnology Progress, (2006) 22(1):288-296.
Yuk, I.H. et al., Controlling Glycation of Recombinant Antibody in Fed Batch Cell Cultures, Nov. 2011 , Biotechnology and Bioengineering, vol. 108, No. 11 pp. 2600-2610.
Yumioka et al., "Screening of effective column rinse solvent for Protein-A chromatography," Protein Expression and Purification, (2010) 70(2): 218-223.
Zang, T.; et al.; Chemical Methods for the Detection of Protein N-Homocysteinylation via Selective Reactions with Aldehydes; Anal. Chem. 2009, 81, 9065-9071.
Zatarain-Rios E and Mannik M, "Charge-charge interactions between articular cartilage and cationic antibodies, antigens, and immune complexes," Arthritis Rheum. Nov. 1987;30(11):1265-73.
Zhang et al., "Isolation and characterization of charge variants using cation exchange displacement chromatography," 1218(31): 5079-5086, 2011.
Zhang, B., et al., Unveiling a Glycation Hot Spot in a Recombinant Humanized Monoclonal Antibody. Analytical Chemistry, 2008. 80(7): p. 2379-2390.
Zhang, T.; Identification and Characterization of Buried Unpaired Cysteines in a Recombinant Monoclonal IgG1 Antibody; Anal. Chem. 2012, 84, 7112-7123.
Zhang, W. and Czupryn, M.J., Free Sulfhydryl in Recombinant Monoclonal Antibodies. Biotechnology Progress, 2002. 18(3): p. 509-513.
Zhang, Y. et al., "Specificity and Mechanism of Metal Ion Activation in UDP-galactose: β-Galactoside-α-1,3-galactosyltransferase." *J. Biological Chemistry* vol. 276; 15 (2001). 11567-11574.

Zhao, G.; Chemical Synthesis of S-Ribosyl-L-homocysteine and Activity Assay as a LuxS Substrate; Bioorg. Med. Chem. Lett. 2003,13,3897-3900.
Zhou, Z. et al.; An Antibody-Catalyzed Allylic Sulfoxide-Sulfenate Rearrangement; J. Org. Chem. 1999,64,8334-8341.
Zhou, Z. S. et al. An Antibody-Catalyzed Selenoxide Elimination; J. Am. Chem. Soc. 1997, 119, 3623-3624.
Zou et al., "Dominant expression of a 1.3 Mb human Ig kappa locus replacing mouse light chain production" (1996) *FASEB J.*, 10:1227-1232.
Alessandri, L. et al., "Increased serum clearance of oligomannose species present on a human IgG1 molecule." *mAbs*, (2012), 4(4); 509-520.
An, Zhiqiang editor, "Therapeutic Monoclonal Antibodies: From Bench to Clinic," 2009 edition, John Wiley & Sons, Hoboken, NJ, US, pp. 73-76, section 3.4.3.
Anumula et al., "Quantitative glycan profiling of normal human plasma derived immunoglobulin and its fragments Fab and FcO" (2012) J. Immunol. Methods, 382:167-176.
Arakawa et al., *Biotechnology applications of amino acids in protein purification and formulations*, Amino Acids, vol. 33, pp. 587-605 (2007).
Arend et al., "Inhibition of the production and effects of interleukins-1 and tumor necrosis factor α in rheumatoid arthritis" (1995) Arth. Rheum., 38(2):151-160.
Ashkenazi et al., "Immunoadhesins: An alternative to human monoclonal antibodies" (1995) Methods, 8(2): 104-115.
Avgerinos, *HUMIRA manufacturing: challenges and the path taken*, Extended Reports from the 3rd International Symposium on Downstream Processing of Genetically Engineered Antibodies and Related Molecules (Oct. 3-5, 2004).
Babcock et al., *Partial Replacement of Chemically Defined CHO Media with Plant-Derived Protein Hydrolysates*, in Proceedings of the 21st Annual Meeting of the European Society for Animal Cell Technology (ESACT), Dublin, Ireland, Jun. 7-10, 2009, pp. 295-298 (Springer Netherlands).
Barb et al., "Branch-specific sialylation of IgG-Fc glycans by ST6Gal-I" Biochemistry, (2009) 48:9705-9707.
Bartelds et al., "Development of antidrug antibodies against adalimumab and association with disease activity and treatment failure during long-term follow-up" (2011) JAMA, 305(14):1460-1468.
Baynes et al., *Role of Arginine in the Stabilization of Proteins against Aggregation*, Biochemistry, vol. 44, pp. 4919-4925 (2005).
Bertolini et al., Stimulation of bone resorption and inhibition of bone formation in vitro by human tumour necrosis factors, (1986) Nature 319:516-518.
Bibila & Robinson, *In Pursuit of the Optimal Fed-Batch Process for Monoclonal Antibody Production*, Biotechnol. Prog., 11:1-13 (1995).
Bird et al. "Single-chain antigen-binding proteins." Science. (1988) 242:423-426.
Borys et al., *Ammonia Affects the Glycosylation Patterns of Recombinant Mouse Placental Lactogen-I by Chinese Hamster Ovary Cells in a pH-Dependent Manner*, Biotechnology and Bioengineering, 43:505-514 (1994).
Braun (2002), Anti-tumor necrosis factor a therapy for ankylosing spondylitis: international experience, Ann. Rheum. Dis. 61(Suppl. III):iii51-iii60.
Butler, *Animal cell cultures: recent achievements and perspectives in the production of biopharmaceuticals*, Appl. Microbiol. Biotechnol., 68: 283-291 (2005).
Butler, *Optimisation of the Cellular Metabolism of Glycosylation for Recombinant Proteins Produced by Mammalian Cell Systems*, Cytotechnology, 50:57-76 (2006).
Carpenter et al., Rational Design of Stable Protein Formulations: Theory and Practice, 101 pages, (2002).
Champion et al., *Defining Your Product Profile and Maintaining Control Over It, Part 2*, BioProcess Technical, vol. 3, pp. 52-57 (Sep. 2005).
Chen et al., *Effects of Elevated Ammonium on Glycosylation Gene Expression in CHO Cells*, Metabolic Engineering, 8:123-132 (2006).

(56) References Cited

OTHER PUBLICATIONS

Chun et al., *Usability of size-excluded fractions of soy protein hydrolysates for growth and viability of Chinese hamster ovary cells in protein-free suspension culture*, Bioresource Technology, 98:1000-1005 (2007).

Clincke et al. "Effect of iron sources on the glycosylation macroheterogeneity of human recombinant IFN-y produced by CHO cells during batch processes," BMC Proceedings (Nov. 22, 2011) 5(Suppl 8):PI14, pp. 1-2.

Clincke et al. "Characterization of metalloprotease and serine protease activities in batch CHO cell cultures: control of human recombinant IFN-γ proteolysis by addition of iron citrate," BMC Proceedings (Nov. 22, 2011) 5(Suppl 8):P115, pp. 1-3.

Clinical trial No. NCT00085644 "Human Anti-tumor Necrosis Factor (TNF) Monoclonal Antibody Adalimumab in Subjects With Active Ankylosing Spondylitis (ATLAS)" (2004).

Clinical trial No. NCT00235105 "Adalimumab in Early Axial Spondyloarthritis (Without Radiological Sacroiliitis): Placebo Controlled Phase Over 3 Months Followed by a 9 Months Open Extension Phase" (2005).

Coffman et al., *High-Throughput Screening of Chromatographic Separations: 1. Method Development and Column Modeling*, Biotechnology & Bioengineering, 100:605-618 (2008).

Commercially Available HUMIRA product, approved by the FDA in Dec. 2002 and available in Jan. 2003.

CPMP Policy Statement on DNA and Host Cell Proteins (HCP) Impurities, Routine Testing versus Validation Studies, EMEA, Jun. 10, 1997.

Cromwell, *Avastin: highlights from development*, Extended Reports from the 3rd International Symposium on Downstream Processing of Genetically Engineered Antibodies and Related Molecules (Oct. 3-5, 2004).

Cruz et al., *Process development of a recombinant antibody/interleukin-2 fusion protein expressed in protein-free medium by BHK cells*, Journal of Biotechnology, 96:169-183 (2002).

Cumming, *Glycosylation of recombinant protein therapeutics: control and functional implications*, Glycobiology, 1(2):115-130 (1991).

Das et al., "Delivery of rapamycin-loaded nanoparticle down regulates ICAM-1 expression and maintains an immunosuppressive profile in human CD34+ progenitor-derived dendritic cells" (2008) J Biomed Mater Res A., 85(4):983-92.

Davis et al., Recombinant Human Tumor Necrosis Factor Receptor (Etanercept) for Treating Ankylosing Spondylitis, Arthritis & Rheumatism 48:3230-3236 (2003).

Del Val et al., *Towards the Implementation of Quality by Design to the Production of Therapeutic Monoclonal Antibodies with Desired Glycosylation Patterns*, American Institute of Chemical Engineers, Biotechnol. Prog., 26(6):1505-1527 (2010).

Eason et al., "Inhibition of the effects of Tnf in renal allograft recipients using recombinant human dimeric tumor necrosis factor receptors" (1995) Transplantation, 59(2):300-305.

Ebersbach et al., "Affilin-novel binding molecules based on human gamma-B-crystallin, an all beta-sheet protein" (2007) J. Mol. Biol., 372 (1): 172-85.

Elliot et al., "Randomised double-blind comparison of chimeric monoclonal antibody to tumour necrosis factor alpha (cA2) versus placebo in rheumatoid arthritis" (1994) Lancet, 344(8930):1105-1110.

Endres, *Soy Protein Products Characteristics, Nutritional Aspects, and Utilization*, 2001 (AOCS Press, Champaign, Illinois).

Ertani et al., *Biostimulant activity of two protein hydrolyzates in the growth and nitrogen metabolism of maize seedlings*, J. Plant Nutr. Soil Sci., 000:1-8 (2009).

Espinosa-Gonzalez, *Hydrothermal treatment of oleaginous yeast for the recovery of free fatty acids for use in advanced biofuel production*, Journal of Biotechnology, 187:10-15 (2014).

Falconer et al., *Stabilization of a monoclonal antibody during purification and formulation by addition of basic amino acid excipients*, vol. 86, pp. 942-948 (2011).

Farnan et al., Multiproduct High-Resolution Monoclonal Antibody Charge Variant Separations by pH Gradient Ion-Exchange Chromatography, Analytical Chem., vol. 81, No. 21, pp. 8846-8857 (2009).

Fauchère et al., *Amino acid side chain parameters for correlation studies in biology and pharmacology*, Int. J. Peptide Res., vol. 32, pp. 269-278 (1988).

Fava et al., "Critical role of peripheral blood phagocytes and the involvement of complement in tumour necrosis factor enhancement of passive collagen-arthritis" (1993) Clin. Exp. Immunol., 94(2):261-266.

Felver et al., "Plasma tumor necrosis factor α predicts decreased long-term survival in severe alcoholic hepatitis" (1990) Alcohol. Clin. Exp. Res. 14(2):255-259.

Fernandes, "Demonstrating Comparability of Antibody Glycosylation during Biomanufacturing," European Biopharmaceutical Review. (2005) pp. 106-110.

Fietze et al., "Cytomegalovirus infection in transplant recipients the role of tumor necrosis factor" (1994) Transplantation, 58(6):675-680.

Follmam et al., Factorial screening of antibody purification processes using three chromatography steps without protein A, J. Chromatography A, vol. 1024, pp. 79-85 (2004).

Foong et al., *Anti-tumor necrosis factor-alpha-loaded microspheres as a prospective novel treatment for Crohn's disease fistulae*, Tissue Engineering, Part C: Methods, 16(5):855-64 (2010).

Franek et al., Plant Protein Hydrolysates: Preparation of Defined Peptide Fractions Promoting Growth and Production in Animal Cells Cultures, Biotech. Progress, 16:688-692 (2000).

FrieslandCampina Domo. *Product Data Sheet: Proyield Pea PCE80B*. Paramus, NJ: Aug. 2011.

FrieslandCampina Domo. *Product Data Sheet: Proyield Soy SE70M-UF*. Paramus, NJ: Apr. 2011.

FrieslandCampina Domo. *Product Data Sheet: Proyield Wheat WGE80M-UF*. Paramus, NJ: Apr. 2011.

FrieslandCampina Domo. *Product Information Sheet: CNE50M-UF*. Zwolfe, NL: Jun. 2010.

Gagnon et al., *Technology trends in antibody purification*, J. Chromatography A., vol. 1221, pp. 57-70 (available online Oct. 2011).

Gawlitzek et al., *Ammonium Alters N-Glycan Structures of Recombinant TNFR-IgG: Degradative Versus Biosynthetic Mechanisms*, Biotechnology and Bioengineering, 68(6):637-646 (2000).

Gawlitzek et al., *Identification of Cell Culture Conditions to Control N-Glycosylation Site-Occupancy of Recombinant Glycoproteins Expressed in CHO cells*, 103:1164-1175 (2009).

Gibbs, *Production and Characterization of Bioactive Peptides from Soy Fermented Foods and Their Hydrolysates*, Food Research International 27 (2004) pp. 123-131.

Gilar et al., "Characterization of glycoprotein digests with hydrophilic interaction chromatography and mass spectrometry" (2011) Analytical Biochem., 417:80-88.

Giroir et al., "Inhibition of tumor necrosis factor prevents myocardial dysfunction during burn shock" (1994) Am. J. Physiol., 267(1 Pt 2):H118-24.

Goetze, A. et al., "High-mannose glycans on the Fc region of therapeutic IgG antibodies increase serum clearance in humans." *Glycobiology* (2011), 21(7); 949-959.

Gong et al., *Fed-Batch Culture Optimization of a Growth-Associated Hybridoma Cell Line in Chemically Defined Protein-Free Media*, Cytotechnology, 52:25-38 (2006).

Goochee et al., *Environmental Effects on Protein Glycosylation*, Biotechnology, 8:421-427 (1990).

Gorfien et al., *Optimized Nutrient Additives for Fed-Batch Cultures*, BioPharm International, 16:34-40 (2003).

Grabulovski et al., "A Novel, Non-immunogenic Fyn SH3-derived Binding Protein with Tumor Vascular Targeting Properties" (2007) J Biol Chem 282, (5): 3196-3204.

Gramer et al. "Modulation of antibody galactosylation through feeding of uridine, manganese chloride, and galactose," Biotechnology and Bioengineering. (Jul. 1, 2011) 108(7):1591-1602.

Gross et al. "Involvement of various organs in the initial plasma clearance of differently glycosylated rat liver secretory proteins," Eur. J. Biochem. (1988) 173(3):653-659.

(56) References Cited

OTHER PUBLICATIONS

Gu et al., *Influence of Primatone RL Supplementation on Sialylation of Recombinant Human Interferon-γ Produced by Chinese Hamster Ovary Cell Culture Using Serum-Free Media*, Biotechnology and Bioengineering, 56(4):353-360 (1997).
Guidance for Industry—Q6B Specifications: Test Procedures and Acceptance Criteria for Biotechnological / Biological Products, Aug. 1999.
Guile et al., "A rapid high-resolution high-performance liquid chromatographic method for separating glycan mixtures and analyzing oligosaccharide profiles" (1996) Anal Biochem., 240(2):210-26.
Guse et al., *Purification and analytical characterization of an anti-CD4 monoclonal antibody for human therapy*, J. of Chromatography A, 661:13-23 (1994).
Haddadi et al., "Delivery of rapamycin by PLGA nanoparticles enhances its suppressive activity on dendritic cells" (2008) J Biomed Mater Res A., 84A(4):885-98.
Haibel (2005) *Arthritis and Rheumatism* 64(Suppl. III):316.
Haibel et al. (2004) *Arthritis and Rheumatism* 50(9):S217-18.
Hansen et al., "The role of tumor necrosis factor-alpha in acute endotoxin-induced hepatotoxicity in ethanol-fed rats" (1994) Hepatology, 20(2):461-474.
Hansen et al., *Extra- and intracellular amino acid concentrations in continuous Chinese hamster ovary cell culture*, Appl. Microbiol. Biotechnol., 41:560-564 (1994).
Harris et al., *Current Trends in Monoclonal Antibody Development and Manufacturing*, Chapter 12, pp. 193-205 (2010).
Hayter et al, *Chinese hamster ovary cell growth and interferon production kinetics in stirred batch culture*, Applied Microbiol. Biotech., 34:559-564 (1991).
Heeneman et al., *The concentrations of glutamine and ammonia in commercially available cell culture media*, J. Immunological Methods, 166:85-91(1993).
Hober, et al. "Protein A chromatography for antibody purification", J. Chromatography B, vol. 848 (2007) pp. 40-47.
Hong et al., *Substitution of glutamine by glutamate enhances production and galactosylation of recombinant IgG in Chinese hamster ovary cells*, Applied Microbiol. Biotech., 88:869-876 (2010).
Huang et al., *Nitrogen metabolism of asparagine and glutamate in Vero cells studied by 1H/15N NMR spectroscopy*, Applied Microbiol. Biotech., 77:427-436 (2007).
Hussain et al., "Hepatic expression of tumour necrosis factor-alpha in chronic hepatitis B virus infection" (1994) J. Clin. Pathol., 47:1112-1115.
Huston et al. "Protein engineering of antibody binding sites: recovery of specific activity in an anti-digoxin single-chain Fv analogue produced in *Escherichia coli*," Proc. Natl. Acad. Sci. USA(1988) 85:5879-5883.
International Conference on Harmonisation of Technical Requirements for Registration of Pharmaceuticals for Human Use, *Specifications: Test Procedures and Acceptance Criteria for Biotechnological / Biological Products Q6B*, Mar. 10, 1999.
International Preliminary Report on Patentability for Application No. PCT/US2014/059127, dated Apr. 14, 2016, 15 pages.
International Preliminary Report on Patentability for Application No. PCT/US2014/065793, dated May 17, 2016, 13 pages.
International Search Report and Written Opinion for Application No. PCT/US2014/058991, completed Dec. 18, 2014, 15 pages.
International Search Report and Written Opinion for Application No. PCT/US2014/065793, dated Jul. 27,2015, 20 pages.
International Search Report and Written Opinion from PCT/US2015/042846 dated Feb. 2, 2016, pp. 1-22.
International Search Report with Written Opinion corresponding to International Patent Application No. PCT/US2014/059127, mailed May 7, 2015, 21 pages.
Invitation to Pay Additional Fees for International Application No. PCT/US2014/058991, mailed Jan. 15, 2015, 6 pages.
Invitation to Pay Additional Fees for International Application No. PCT/US2014/059127, dated Jan. 15, 2015, 6 pages.
Invitation to Pay Additional Fees for International Application No. PCT/US2014/065793, dated May 4, 2015, 15 pages.
Jacob et al., Scale-up of Antibody Purification, Antibodies, vol. 1: Production & Purification, (2004).
Karnoup et al., *O-Linked glycosylation in maize-expressed human IgA1*, Glycobiology, 15(10):965-981 (2005).
Kaufman et al., "Amplification and expression of sequences cotransfected with a modular dihydrofolate reductase complementary dna gene" (1982) Mol. Biol., 159(4):601-621.
Kaufman et al., *Depletion of manganese within the secretory pathway inhibits O-linked glycosylation in mammalian cells*, Biochemistry, 33(33):9813-9 (1994).
Kelley et al., *Downstream Processing of Monoclonal Antibodies: Current Practices and Future Opportunities*, Process Scale Purification of Antibodies (2009).
Kim et al., *Glycosylation pattern of humanized IgG-like bispecific antibody produced by recombinant CHO cells*, Applied Microbiol. Biotech., 85:535-542 (2010).
Kipriyanov et al. "Recombinant single-chain Fv fragments carrying C-terminal cysteine residues: production of bivalent and biotinylated miniantibodies," Molecular Immunology, (1994) 31(14):1047-1058 F.
Kipriyanov et al., "Single-chain antibody streptavidin fusions: tetrameric bifunctional scFv-complexes with biotin binding activity and enhanced affinity to antigen," Human Antibodies and Hybridomas. (1995) 6(3):93-101.
Kobak, Osteonecrosis and monoarticular rheumatoid arthritis treated with intra-articular adalimumab, *S. Mod Rheumatol*, 18, 290-292, Feb. 20, 2008.
Koide et al., "Monobodies: antibody mimics based on the scaffold of the fibronectin type III domain" (2007), Methods Mol. Biol., 352: 95-109.
Konig et al., "Tumor necrosis factor α and interleukin-1 stimulate bone resorption in vivo as measured by urinary [3H] tetracycline excretion from prelabeled mice" (1988) J. Bone Miner. Res., 3(6):621-627.
Kramarczyk et al., *High-Throughput Screening of Chromatographic Separations: II. Hydrophobic Interaction*, 100: 708-720 (2008).
Krehenbrink et al., "Artificial Binding Proteins (Affitins) as Probes for Conformational Changes in Secretin PulD" (2008) J. Mol. Biol., 383 (5): 1058-68.
Kunkel et al., "Comparisons of the Glycosylation of a Monoclonal Antibody Produced under Nominally Identical Cell Culture Conditions in Two Different Bioreactors" (2000) Biotechnol. Prog., 16(3): 462-470.
Kurano et al., *Growth behavior of Chinese hamster ovary cells in a compact loop bioreactor. 2. Effects of medium components and waste products*, J. Biotechnol., 15(1-2):113-128 (1990).
Lain et al., *Development of a High-Capacity MAb Capture Step Based on Cation-Exchange Chromatography*, BioProcess Int'l, vol. 7, pp. 26-34 (May 2009).
Lazar et al., *Matrix-assisted laser desorption/ionization mass spectrometry for the evaluation of the C-terminal lysine distributon of a recombinant monoclonal antibody*, Rapid Communications in Mass Spectrometry, vol. 18, pp. 239-244 (2004).
Leader et al., *Agalactosyl IgG in Aggregates from the Rheumatoid Joint*, Br. J. Rheumatol., 35:335-341 (1996).
Leavitt et al. "Impaired Intracellular Migration and Altered Solubility of Nonglycosylated Glycoproteins of Vesicular Stomatitis Virus and Sindbis Virus," J. Biol. Chem. (1977) 252(24):9018-9023.
Lerner et al., "Tumor necrosis factors α and β can stimulate bone resorption in cultured mouse calvariae by a Prostaglandin-independent mechanism" (1993) J. Bone Miner. Res., 8(2):147-155.
Lienqueo et al., *Mathematical correlations for predicating protein retention times in hydrophobic interaction chromatography*, 978:71-79 (2002).
Ling et al., *Analysis of Monoclonal Antibody Charge Heterogeneity Using Ion-Exchange Chromatography on a Fully Biocompatible HPLC System*, Dionex (2009).

(56) References Cited

OTHER PUBLICATIONS

Liu et al., "The significance of changes in serum tumour necrosis factor (TNF) activity in severely burned patients" (1994) Burns, 20(1):40-44.

Lobo-Alfonso et al., *Benefits and Limitations of Protein Hydrolysates as Components of Serum-Free Media for Animal Cell Culture Applications, Protein Hydrolysates in Serum Free Media,* GIBCO Cell Culture, Invitrogen Corporation, Grand Island, New York, Chapter 4:55-78 (2010).

Lowe et al. "A Genetic Approach to Mammalian Glycan Function," Annu. Rev. Biochem. (2003) 72:643-691.

Lu et al., *Recent Advancement in Application of Hydrophobic Interaction Chromatography for Aggregate Removal in Industrial Purification Process,* 10:427-433 (2009).

Lubinieki et al., *Comparability assessments of process and product changes made during development of two different monoclonal antibodies,* Biologicals, vol. 39, pp. 9-22 (2011).

Luksa et al., *Purification of human tumor necrosis factor by membrane chromatography,* J. Chromatography A, 661:161-168 (1994).

Lund et al., *Control of IgG/Fc Glycosylation: A Comparison of Oligosaccharides from Chimeric Human/Mouse and Mouse Subclass Immunoglobulin Gs,* Molecular Immunology, 30(8):741-748 (1993).

MacDonald et al., "Tumour necrosis factor-alpha and interferon-gamma production measured at the single cell level in normal and inflamed human intestine" (1990) Clin. Exp. Immunol, 81(2):301-305.

Matsumoto et al., *Autoantibody Activity of IgG Rheumatoid Factor Increases with Decreasing Levels of Galactosylation and Sialylation,* J. Biochemistry, 128:621-628 (2000).

McCauley et al., "Altered cytokine production in black patients with keloids" (1992) J. Clin. Immunol., 12(4):300-308.

McClain et al., "Increased tumor necrosis factor production by monocytes in alcoholic hepatitis" (1989) Hepatology, 9(3):349-351.

McCue et al., *Effect of phenyl sepharose ligand density on protein monomer/aggregate purification and separation using hydrophobic interaction chromatography,* J. of Chromatography A, 1216:209-909 (2009).

McLeod, "Adalimumab, etanercept and infliximab for the treatment of ankylosing spondylitis: a systematic review and economic evaluation," Health Technol. Assess. 11(28):1-158 (2006).

Meert et al., *Characterization of Antibody Charge Heterogeneity Resolved by Preparative Immobilized pH Gradients,* Analytical Chem., vol. 82, pp. 3510-3518 (2010).

Melter et al., *Adsorption of monoclonal antibody variants on analytical cation-exchange resin,* J. Chromatography A, vol. 1154, pp. 121-131 (2007).

Millward et al. "Effect of constant and variable domain glycosylation on pharmacokinetics of therapeutic antibodies in mice," Biologicals.(2008) 36(1):41-47.

Mizrahi, *Primatone RL in mammalian cell culture media,* Biotechnol. Bioeng., 19:1557-1561 (1977).

Moller et al., "Monoclonal antibodies to human tumor necrosis factor α: In vitro and in vivo application" (1990) Cytokine 2(3):162-169.

Moloney and Haltiwanger, *The O-linked fucose glycosylation pathway: indentification and characterization of a uridien diphosphoglucose: fucose-β1,3-glucosyltransferase activity from Chinese hamster ovary cells,* Glycobiology, 9:679-87 (1999).

Morgan et al. "Designing Biobetter Monoclonal Antibody Therapeutics by Glycoengineering," International Pharmaceutical Industry. (2011) pp. 38-44.

Nixon et al., "Engineered protein inhibitors of proteases" (2006) Curr Opin Drug Discov Devel, 9(2): 261-8.

Nyberg et al., *Metabolic Effects on Recombinant Interferon-γ Glycosylation in Continuous Culture of Chinese Hamster Ovary Cells,* Biotech. Bioeng., 62(3):336-347 (1999).

Nygren et al., "Alternative binding proteins: affibody binding proteins developed from a small three-helix bundle scaffold" (2008) FEBS J., 275 (11): 2668-76.

Onda et al., *Reduction of the Nonspecific Animal Toxicity of Anti-Tac (Fv)-PE38 by Mutations in the Framework Regions of the Fv Which Lower the Isoelectric Point,* J. Immunology, vol. 163, pp. 6072-6077 (1999).

Pacesetter, Beckman Coulter Newsletter, vol. 3, Issue 1 (Apr. 1999).

Packer et al., "A general approach to desalting oligosaccharides released from glycoproteins" (1998) Glycoconj J., 15(8):737-47.

Proteus, "Protein A Antibody Purification Handbook," Pro-Chem Inc., 2005, pp. 1-52.

Raju et al. "Galactosylation variations in marketed therapeutic antibodies," MABS. (May 1, 2012) 4(3):385-391.

Raju et al., "Glycoengineering of Therapeutic Glycoproteins: In Vitro Galactosylation and Sialylation of Glycoproteins with Terminal N-Acetylglucosamine and Galactose Residues" (2001) Biochemistry, 40(30):8868-8876.

Raju, *Terminal sugars of Fc glycans influence antibody effector functions of IgGs,* Current Opinion in Immunology, 20:471-478 (2008).

Rankin et al., "The therapeutic effects of an engineered human anti-tumour necrosis factor alpha antibody(CDP571) in rheumatoid arthritis" (1995) Br. J. Rheumatol., 34:334-342.

Rao et al., *mAb Heterogeneity Characterization: MabPac Strong Cation-Exchanger Columns Designed to Extend Capabilities of mAb Analysis,* Tutorials (Mar. 15, 2011).

Rao et al., *Separation of Monoclonal Antibodies by Weak Cation-Exchange Chromatography Using ProPac and ProSwift Columns,* Dionex (available online 2010).

Remy et al., "Zinc-finger nucleases: A powerful tool for genetic engineering of animals" (2010) Transgenic Res., 19(3): 363-71.

Rivinoja et al, *Elevated Golgi pH Impairs Terminal N Glycosylation by Inducing Mislocalization of Golgi Glycosyltransferases,* J. Cell. Physiol., 220:144-154 (2009).

Robinson et al., *Characterization of a Recombinant Antibody Produced in the Course of a High Yield Fed-Batch Process,* Biotech. Bioeng., 44:727-735 (1994).

Rodriguez et al., *Enhanced Production of Monomeric Interferon-â by CHO Cells through the Control of Culture Conditions,* Biotechnol. Prog., 21:22-30 (2005).

Rosolem et al., *Manganese uptake and redistribution in soybean as affected by glyphosate,* Rev. Bras. Ciênc. Solo, 34:1915-1922 (2010).

Rouiller et al. "Effect of hydrocortisone on the production and glycosylation of an Fc-Fusion protein in CHO cell cultures," Biotechnology Progress.(May 2012) 28(3):803-813.

Rudd et al. "Glycosylation and the Immune System," Science. (2001) 291(5512):2370-2376.

Rudwaleit et al., Adalimumab is effective and well tolerated in treating patients with ankylosing spondylitis who have advanced spinal fusion, Rhematology; 48; 551-557 (2009).

Russell et al., "Targets for sepsis therapies: Tumor necrosis factor versus interleukin-1" (1993) Curr. Opin. Biotech., 4:714-721.

Santiago et al., "Targeted gene knockout in mammalian cells by using engineered zinc-finger nucleases" (2008) Proc. Natl. Acad. Sci. USA., 105(15):5809-14.

Santora et al., *Determination of Recombinant Monoclonal Antibodies and Noncovalent Antigen TNFα Trimer Using Q-TOF Mass Spectrometry,* Spectroscopy, 17(5):50-57 (2002).

Scales et al., "Hepatic ischemia/reperfusion injury: importance of oxidant/tumor necrosis factor interactions" (1994) Am. J. Physiol., 267 (6 Pt 1):G1122-1127.

Schenerman et al., *CMC Strategy Forum Report,* BioProcess Technical (2004).

Schlaeger E.-J., *The protein hydrolysate, Primatone RL, is a cost-effective multiple growth promoter of mammalian cell culture in serum-containing and serum-free media and displays anti-apoptosis properties,* J. Immunol. Meth., 194:191-199 (1996).

Serrick et al., "The early release of interleukin-2, tumor necrosis factor-alpha and interferon-gamma after ischemia reperfusion injury in the lung allograft" (1994) Transplantation, 58(11):1158-1162.

(56) References Cited

OTHER PUBLICATIONS

Shankar et al., "Evaluation of the role of second messenger systems in tumor necrosis factor-stimulated resorption of fetal rat limb bones" (1993) Bone, 14(6):871-876.
Sheffield Bioscience, Bio-Science Technical Manual: Supplements for cell culture, fermentation, and diagnostic media, 43 pages (2011).
Shen et al., Characterization of yeastolate fractions that promote insect cell growth and recombinant protein production, Cytotechnology, 54:25-34 (2007).
Sheron et al., "Increased production of tumour necrosis factor alpha in chronic hepatitis B virus infection" (1991) J. Hepatol., 12(2):241-245.
Shi et al., Real Time Quantitative PCR as a Method to Evaluate Xenotropic Murine Leukemia Virus Removal During Pharmaceutical Protein Purification, Biotechnology & Bioengineering, vol. 87, No. 7, pp. 884-896 (Sep. 2004).
Shibuya et al., "The elderberry (Sambucus nigra L.) bark lectin recognizes the Neu5Ac(alpha 2-6)Gal/GalNAc sequence"(1987) J. Biol. Chem., 262(4): 1596-1601.
Shields et al. "Lack of Fucose on Human IgGI N-Linked Oligosaccharide Improves Binding to Human FcyRlll and Antibody-dependent Cellular Toxicity," J. Biol. Chem. (2002) 277(30) :26733-26740.
Shim, H., "One target, different effects: a comparison of distinct therapeutic antibodies against the same targets." Experimental and Molecular Medicine, vol. 43, p. 539-549, Oct. 2011.
Shukla et al., Downstream processing of monoclonal antibodies—Application of platform approaches, J. of Chromatography B, 848:28-39 (2007).
Shukla et al., eds., Process Scale Bioseparations for the Biopharmaceutical Industry, (Taylor & Francis Group, Boca Raton FL) (2006).
Shukla et al., Recent advances in large-scale production of monoclonal antibodies and related proteins, Trends in Biotechnology, 28(5):253-261 (2010).
Shukla et al., Strategies to Address Aggregation During Protein a Chromatography, BioProcess International, 3:36-44 (2005).
Siemensma et al., Towards an Understanding of How Protein Hydrolysates Stimulate More Efficient Biosynthesis in Cultured Cells: Protein Hydrolysates in Biotechnology,Bio-Science, 36 pages (2010).
Silverman et al., "Multivalent avimer proteins evolved by exon shuffling of a family of human receptor domains" (2005) Nat. Biotechnol., 23 (12): 1556-61.
Skerra et al., "Alternative binding proteins: Anticalins—harnessing the structural plasticity of the lipocalin ligand pocket to engineer novel binding activities kerra" (2008) FEBS J., 275 (11): 2677-83.
Stumpp et al., "DARPins: A new generation of protein therapeutics" (2008) Drug Discov. Today, 13 (15-16): 695-701.
Sun et al., "Bowel necrosis induced by tumor necrosis factor in rats is mediated by platelet-activating factor" (1988) J. Clin. Invest., 81(5):1328-1331.
Suthanthiran et al., "Renal transplantation" (1994) New Engl. J. Med., 331(6):365-376.
Takashima et al., "Characterization of Mouse Sialyltransferase Genes: Their Evolution and Diversity" (2008) Biosci. Biotechnol. Biochem., 72(5):1155-1167.
Tang et al., Conformational characterization of the charge variants of a human IgG1 monoclonal antibody using H/D exchange mass spectrometry, mAbs, vol. 5, pp. 114-125 (2013).
Taylor et al. "A transgenic mouse that expresses a diversity of human sequence heavy and light chain immunoglobulins," Nucleic Acids Research,(1992) 20(23):6287-6295.
Thiansilakul et al., Compositions, functional properties and antioxidative activity of protein hydrolysates prepared from round scad (Decapterus maruadsi), Food Chemistry, 103:1385-1394 (2007).

Tian et al., Spectroscopic evaluation of the stabilization of humanized monoclonal antibodies in amino acid formulations, Int'l J. of Pharmaceutics, vol. 335, pp. 20-31 (2007).
To , et al., Hydrophobic interaction chromatography of proteins: I. The effects of protein and adsorbent properties on retention and recovery, J. of Chromatography A, 1141:191-205 (2007).
Tracey et al., "Shock and tissue injury induced by recombinant human cachectin" (1986) Science, 234(4775):470-474.
Tritsch et al., Spontaneous decomposition of glutamine in cell culture media, Experimental Cell Research, 28:360-364 (1962).
Tsubaki et al., C-terminal modification of monoclonal antibody drugs: Amidated species as a general product0related substance, Int'l J. Biological Macromolecules, vol. 52, pp. 139-147 (2013).
Tugcu et al., Maximizing Productivity of Chromatography Steps for Purification of Monoclonal Antibodies, vol. 99, No. 3, pp. 599-613 (available online Aug. 2007).
Urech, D.M. et al., Anti-inflammatory and cartilage-protecting effects of an intra-articularly injected anti-TNFa single-chain Fv antibody (ESBA105) designed for local therapeutic use, Ann Rheum Dis, 69, 443-449, Mar. 16, 2009.
Urlaub et al., "Isolation of Chinese hamster cell mutants deficient in dihydrofolate reductase activity" (1980) Proc. Natl. Acad. Sci. USA, 77:4216-4220.
Van der Heijde et al., Adalimumab effectively reduces the signs and symptoms of active ankylosing spondylitis in patients with total spinal ankylosis, Arthritis & Rheumatism 67:1218-1221 (2008).
Van der Heijde et al., Efficacy and Safety of Adalimumab in Patients with Ankylosing Spondylitis, Arthritis & Rheumatism 54:2136-46 (2006).
Van der Heijde et al., Efficacy and Safety of Infliximab in Patients with Ankylosing Spondylitis, Arthritis & Rheumatism 52:582-591 (2005).
Van Der Poll et al., "Activation of coagulation after administration of tumor necrosis factor to normal subjects" (1990) N. Engl. J. Med., 322(23):1622-1627.
Van Der Poll et al., "Comparison of the early dynamics of coagulation activation after injection of endotoxin and tumor necrosis factor in healthy humans" (1991) Prog. Clin. Biol. Res., 367:55-60.
Van Dulleman et al., "Treatment of Crohn's disease with anti-tumor necrosis factor chimeric monoclonal antibody (cA2)" (1995) Gastroenterology, 109(1):129-135.
Varki et al. Essentials of Glycobiology, 2nd edition, (1999) CSHL, Retrieved from the internet: ncbi.nlm.nih.gov/books/NBK1908/, 4 pages.
Wallick et al. "Glycosylation of a VH residue of a monoclonal antibody against alpha (1- ---6) dextran increases its affinity for antigen," J. Exp. Med.(1988) 168(3):1099-1109.
Walsh et al. "Effect of the carbohydrate moiety on the secondary structure of ?2-glycoprotein. I. Implications for the biosynthesis and folding of glycoproteins," Biochemistry. (1990).
Wang et al., "The immobilized leukoagglutinin from the seeds of Maackia amurensis binds with high affinity to complex-type Asn-linked oligosaccharides containing terminal sialic acid-linked alpha-2,3 to penultimate galactose residues" (1988) J Biol. Chem., 263(10): 4576-4585.
Wang et al., Antibody Structure, Instability and Formulation, J. Pharm. Sci., vol. 96, No. 1, pp. 1-26 (2007).
Warnock et al., "In vitro galactosylation of human IgG at 1 kg scale using recombinant galactosyltransferase" (2005) Biotechnol. Bioeng., 92(7):831-842.
Wei et al., Glyco-engineering of human IgG1-Fc through combined yeast expression and in vitro chemoenzymatic glycosylation, National Institute of Health Public Access Author Manuscript, Biochemistry, 47(39):10294-10304 (2008).
Weikert et al., "Engineering Chinese hamster ovary cells to maximize sialic acid content of recombinant glycoproteins" (1999) Nature Biotechnology, 17(11): 1116-1121.
Weinstein et al., "Primary structure of beta-galactoside alpha 2,6-sialyltransferase. Conversion of membrane-bound enzyme to soluble forms by cleavage of the NH2-terminal signal anchor" (1987) J. Biol. Chem. 262(36):17735-17743.

(56) References Cited

OTHER PUBLICATIONS

Weitzhandler et al., *Protein variant separations by cation-exchange chromatography on tentacle-type polymeric stationary phases,* Proteomics, vol. 1, pp. 179-185 (2001).

Wong et al., *Impact of Dynamic Online Fed-Batch Strategies on Metabolism, Productivity and N-Glycosylation Quality in CHO Cell Cultures,* Biotechnol. Bioeng., 89(2):164-177 (2005).

Wyss, et al. "The structural role of sugars in glycoproteins," Curr. Opin. Biotechnol. (1996), 7(4); 409-416.

Xie et al., *High Cell Density and High Monoclonal Antibody Production Through Medium Design and Rational Control in a Bioreactor,* Biotechnol. Bioeng., 51:725-729 (1996).

Yang et al., *Effect of Ammonia on the Glycosylation of Human Recombinant Erythropoietin in Culture,* Biotech. Progress, 16:751-759 (2000).

Yao et al., "The potential etiologic role of tumor necrosis factor in mediating multiple organ dysfunction in rats following intestinal ischemia-reperfusion injury" (1995) Resuscitation, 29(2):157-168.

Zhang et al. "A novel function for selenium in biological system: Selenite as a highly effective iron carrier for Chinese hamster ovarey cell growth and monoclonal antibody production," Biotechnology and Bioengineering. (2006) 95(6):1188-1197.

Zhang et al., "CHO glycosylation mutants as potential host cells to produce therapeutic proteins with enhanced efficacy" (2013) Advances in Biochemical Engineering/Biotechnology, 131:63-87.

Zhang et al., *Mass Spectrometry for Structural Characterization of Therapeutic Antibodies, Mass Spectrometry Reviews,* 28:147-176 (2009).

Zhang, F. et al., "The Effect of Dissolved Oxygen (DO) Concentration on the Glycosylation of Recombinant Protein Produced by the Insect Cell-Baculovirus Expression System." *Biotechnology and Bioengineering,* (2002), 77(2); 219-224.

Zhang, Y. et al., *Effects of peptone on hybridoma growth and monoclonal antibody formation,* Cytotechnology, 16:147-150 (1994).

Zhou, *Implementation of Advanced Technologies in Commercial MonoclonalAntibody Production,* Biotech. J., 3:1185-1200 (2008).

Zhu, *Mammalian cell protein expression for biopharmaceutical production,* Biotech.Adv., 30:1158-1170 (2012).

"Preliminary Data From Two Clinical Trials Demonstrate Abbott Laboratories' Humira Improved Symptoms of Psoriatic Arthritis and Ankylosing Spondylitis" *PR Newswire.* Jun. 14, 2004, pp. 1-6.

*Abbott Laboratories Announces Positive Results of Phase ll Humira (R) (adalimumab) Study in Psoriasis,* P.R. Newswire. Feb. 9, 2004, pp. 1-4.

Amersham Biosciences, *Antibody Purification Handbook* (2002), pp. 1-112.

Andersen et al., *Protein Glycosylation: Analysis, Characterization, and Engineering,* Encyclopedia of Industrial Biotechnology: Bioprocess, Bioseparation, and Cell Technology, Edited by Michael C. Flickinger, (2009), pp. 1-49.

EMEA, *Avastin Scientific Discussion* (2005), pp. 1-61.

Exposure Factors Handbook, U.S. Environmental Protection Agency, National Center for Environmental Assessment, Office of Res. And Dev. (Aug. 1997), pp. 1-50.

\* cited by examiner

Histidine sample preparation scheme

Lysine sample preparation scheme

Methionine sample preparation scheme

FIG. 111 Amino acid sample preparation scheme

CDM clarified harvest sample preparation scheme

Acid-type pH study sample preparation scheme

Effect of acid concentration on acid variant content

Effect of acid concentration on acid variant content

Effect of neutralization on acid variant content

Effect of neutralization on acid variant content

CELL CULTURE METHODS TO REDUCE ACIDIC SPECIES

CROSS REFERENCE TO RELATED APPLICATIONS

This application is a divisional application of U.S. patent application Ser. No. 14/842,933, filed on Sep. 2, 2015, pending, which is a continuation application of U.S. patent application Ser. No. 13/830,583, now U.S. Pat. No. 9,150,645, filed on Mar. 14, 2013, which claims priority to U.S. Provisional Application No. 61/636,493, filed on Apr. 20, 2012. The entire contents of each of the foregoing applications is incorporated herein by reference.

1. INTRODUCTION

The instant invention relates to the field of protein production, and in particular to compositions and processes for controlling the amount of acidic species generated during expression of a protein of interest by host cells, as well as the reduction of acidic species present in the clarified cell culture broth. In certain aspects of the invention, controlling the amount of acidic species generated during expression of a protein of interest is achieved by modifying the culture media of the cells. In certain aspects of the invention, controlling the amount of acidic species generated during expression of a protein of interest is achieved by modifying the culture process parameters. In certain aspects of the invention, controlling the amount of acidic species of a protein of interest is achieved by modifying a cell culture clarified harvest comprising the protein of interest.

2. BACKGROUND OF THE INVENTION

The production of proteins for biopharmaceutical applications typically involves the use of cell cultures that are known to produce proteins exhibiting varying levels of product-related substance heterogeneity. Such heterogeneity includes, but is not limited to, the presence of acidic species. For example, in monoclonal antibody (mAb) preparations, such acidic species heterogeneities can be detected by various methods, such as WCX-10 HPLC (a weak cation exchange chromatography) or IEF (isoelectric focusing). In certain embodiments, the acidic species identified using such techniques comprise a range of product-related impurities such as antibody product fragments (e.g., Fc and Fab fragments), and/or post-translation modifications of the antibody product, such as, deamidated and/or glycoslyated antibodies. However, because of their similar chemical characteristics to the antibody product molecules, reduction of acidic species is a challenge in monoclonal antibody purification. Control of acidic species heterogeneity is particularly advantageous in the context of cell culture processes used for commercially produced recombinant biotherapeutics as such heterogeneity has the potential to impact stability.

3. SUMMARY OF THE INVENTION

The present invention is directed to compositions and methods that control (modulate or limit) acidic species heterogeneity in a population of proteins. The presence of such acidic species corresponds to heterogeneity of the distribution of charged impurities, e.g., a mixture of protein fragments (e.g., Fc and Fab fragments of antibodies), and/or post-translation modifications of the proteins, such as, deamidated and/or glycoslyated proteins, in the population of proteins, and such heterogeneity particularly of interest when it arises in the context of recombinant protein production.

In certain embodiments, the acidic species heterogeneity arises from differences in the amount and/or type of acidic species in a population of proteins.

In certain embodiments, the acidic species heterogeneity is present in a population of proteins produced by cell culture. In certain embodiments, control is exerted over the amount of acidic species of protein produced by cell culture. In certain embodiments, the control is exerted over the amount of acidic species formed while the protein is present in a cell culture broth, while the culture is actively maintained or while the cells are removed. In certain embodiments, the protein is an antibody.

In certain embodiments, control over the amount of acidic species produced by cell culture is exerted by employing certain media components during production of a protein, for example, an antibody, of interest. In certain embodiments, control over the amount of acidic species of protein produced by cell culture is exerted by supplementing the media of cells expressing the protein of interest with one or more amino acids. In certain embodiments, the one or more amino acids are arginine, lysine, ornithine, histidine or combinations thereof.

In certain embodiments, control over the amount of acidic species of protein produced by cell culture is exerted by supplementing the media of cells expressing the protein of interest with calcium, for example, by supplementing the media with calcium chloride dihydrate.

In certain embodiments, control over the amount of acidic species of protein produced by cell culture is exerted by supplementing the media of cells expressing the protein of interest with vitamin niacinamide.

In certain embodiments, control over the amount of acidic species of protein produced by cell culture is exerted by supplementing the media of cells expressing the protein of interest with suitable combinations of arginine, lysine, calcium chloride and niacinamide.

In certain embodiments, control over the amount of acidic species produced by cell culture is exerted by ensuring that the production of a protein, for example, an antibody, of interest occurs under specific conditions, including specific pH.

In certain embodiments, control over the amount of acidic species of protein produced by cell culture is exerted by supplementing the media of cells expressing the protein of interest with arginine and lysine and by controlling the pH of the cell culture. In certain embodiments, the pH of the cell culture is adjusted to a pH of about 6.9. In certain embodiments, the pH of the cell culture is adjusted to a lower pH of about 6.8.

In certain embodiments, control over the amount of acidic species of protein produced by cell culture is exerted by supplementing the media of cells expressing the protein of interest with arginine and lysine and by choice of cell culture harvest criteria. In certain embodiments, the harvest criterion is a particular culture day. In certain embodiments, the harvest criterion is based on harvest viability.

In certain embodiments, control over the amount of acidic species produced by cell culture is exerted by supplementing a cell culture clarified harvest comprising a protein or antibody of interest with one or more amino acids. In certain embodiments, the one or more amino acids is arginine, histidine, or combinations thereof.

In certain embodiments, control over the amount of acidic species produced by cell culture is exerted by adjusting the pH of a cell culture clarified harvest comprising a protein or antibody of interest. In certain embodiments, the pH of the cell culture clarified harvest is adjusted to a pH of about 5. In certain embodiments, the pH of the cell culture clarified harvest is adjusted to a pH of about 6.

In certain embodiments, control over the amount of acidic species produced by cell culture is exerted by the use of a continuous or perfusion technology. In certain embodiments, this may be attained through choice of medium exchange rate. In certain, non-limiting, embodiments, maintenance of the medium exchange rates (working volumes/day) of a cell culture run between 0 and 20, or between 0.5 and 12 or between 1 and 8 or between 1.5 and 6 can be used to achieve the desired reduction in acidic species. In certain embodiments, the choice of cell culture methodology that allows for control of acidic species heterogeneity can also include, for example, but not by way of limitation, employment of an intermittent harvest strategy or through use of cell retention device technology.

In certain embodiments, the methods of culturing cells expressing a protein of interest, such as an antibody or antigen-binding portion thereof, reduces the amount of acidic species present in the resulting composition. In certain embodiments, the resulting composition is substantially free of acidic species. In one aspect, the sample comprises a cell culture harvest wherein the cell culture is employed to produce specific proteins of the present invention. In a particular aspect, the sample matrix is prepared from a cell line used to produce anti-TNF-α antibodies.

The purity of the proteins of interest in the resultant sample product can be analyzed using methods well known to those skilled in the art, e.g., weak cation exchange chromatography (WCX), capillary isoelectric focusing (cIEF), size-exclusion chromatography, Poros™ A HPLC Assay, HCP ELISA, Protein A ELISA, and western blot analysis.

In yet another embodiment, the invention is directed to one or more pharmaceutical compositions comprising an isolated protein, such as an antibody or antigen-binding portion thereof, and an acceptable carrier. In another aspect, the compositions further comprise one or more pharmaceutical agents.

4. BRIEF DESCRIPTION OF THE DRAWINGS

Figure 4:
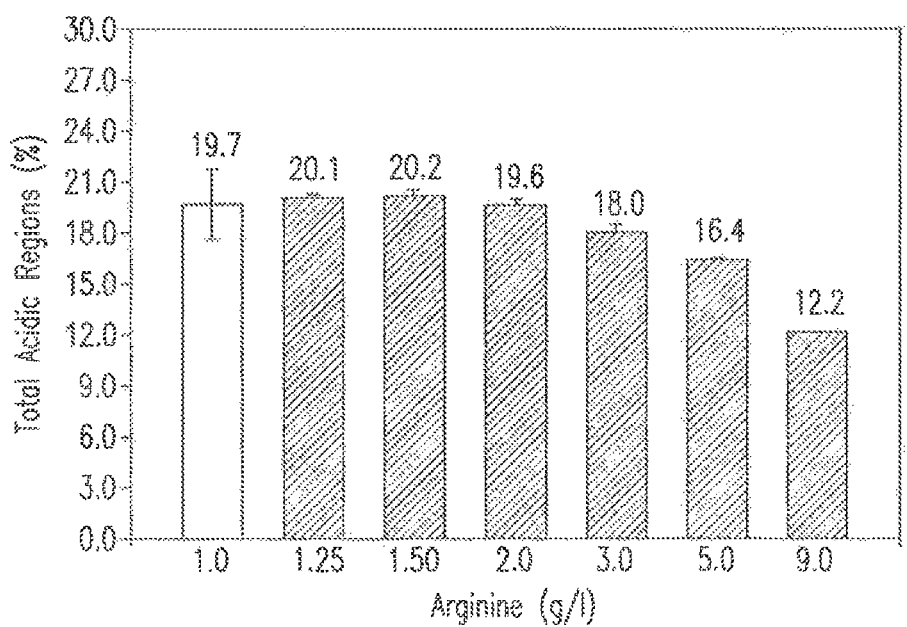

FIG. 4 depicts the effect of total arginine concentration in adalimumab producing cell line 2, media 1 on day 10 WCX 10 profile total acidic regions (n=2).

Figure 5:
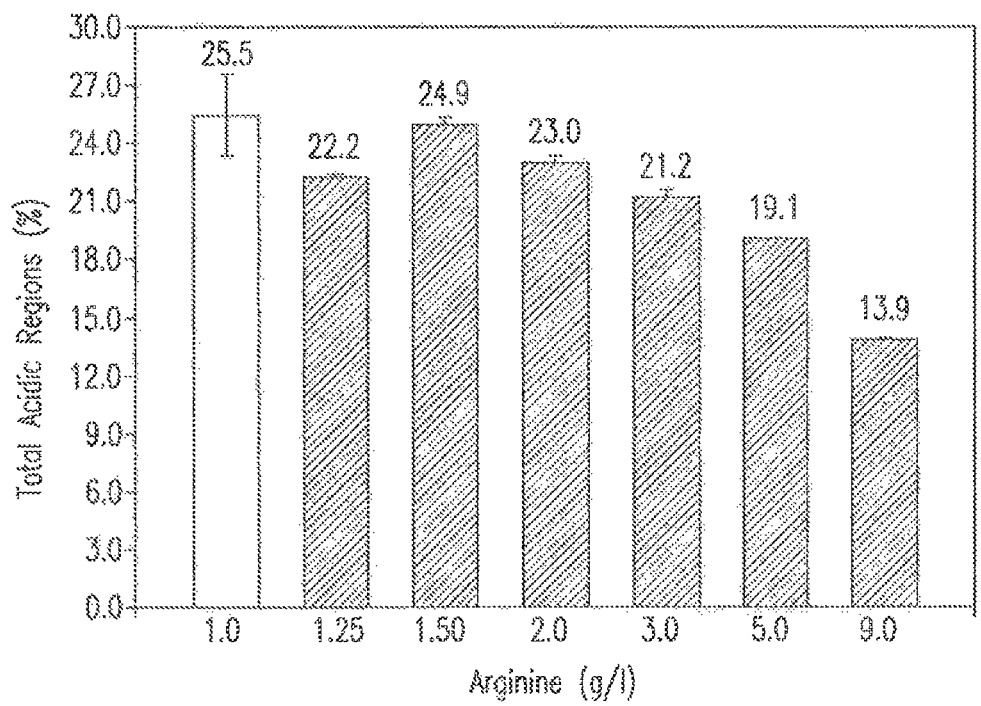

FIG. 5 depicts the effect of total arginine concentration in adalimumab producing cell line 2, media 1 on day 12 WCX 10 profile total acidic regions (n=2).

Figure 6:
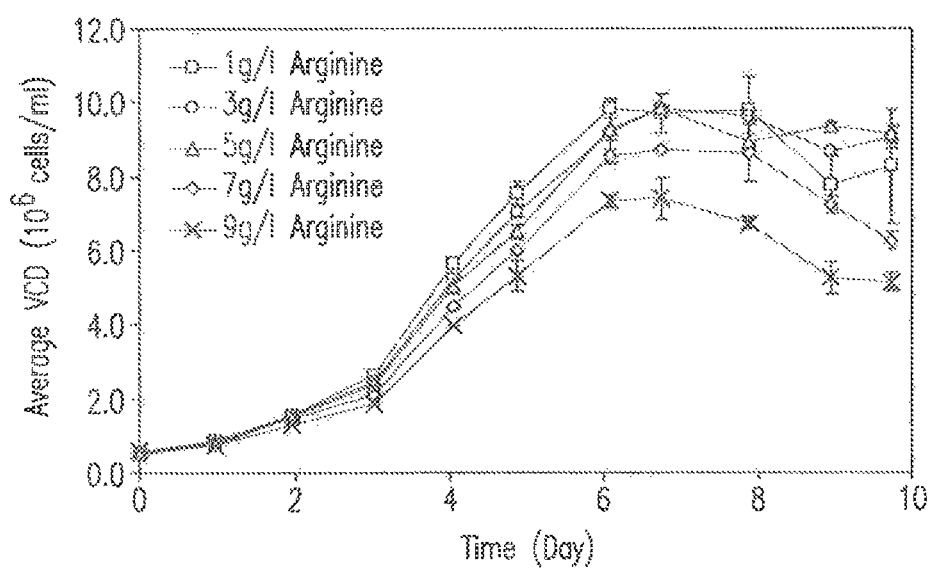

FIG. 6 depicts the effect of total arginine concentration in adalimumab producing cell line 3, media 1 on viable cell density (n=2).

Figure 7:
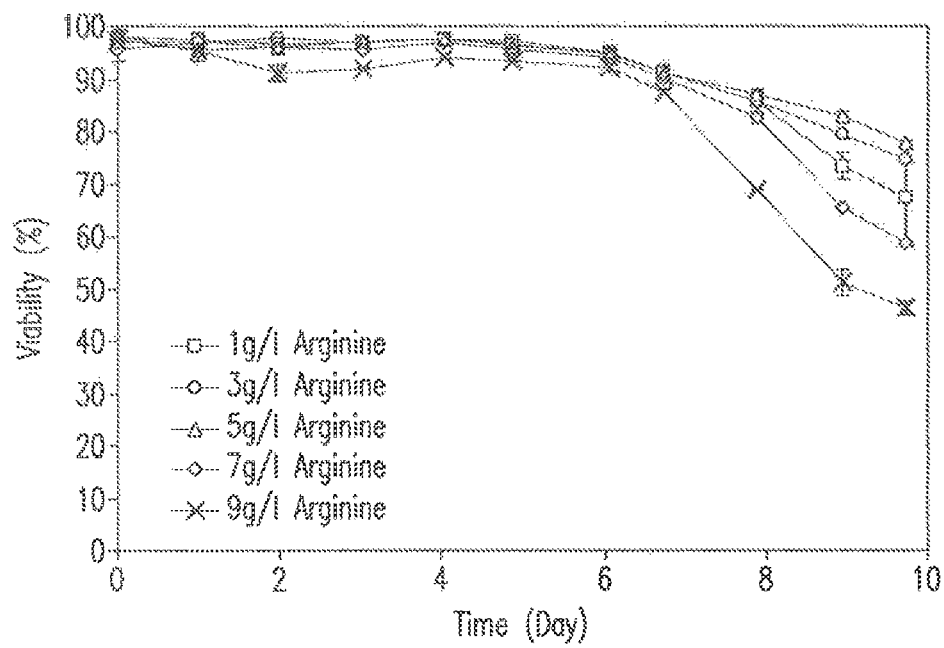

FIG. 7 depicts the effect of total arginine concentration in adalimumab producing cell line 3, media 1 on viability (n=2).

Figure 8:
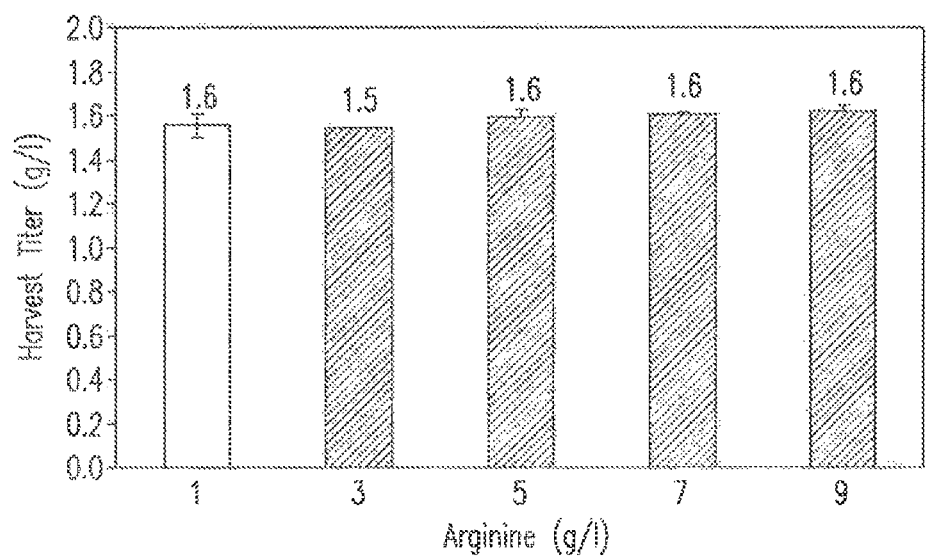

FIG. 8 depicts the effect of total arginine concentration in adalimumab producing cell line 3, media 1 on harvest titer (n=2).

Figure 9:
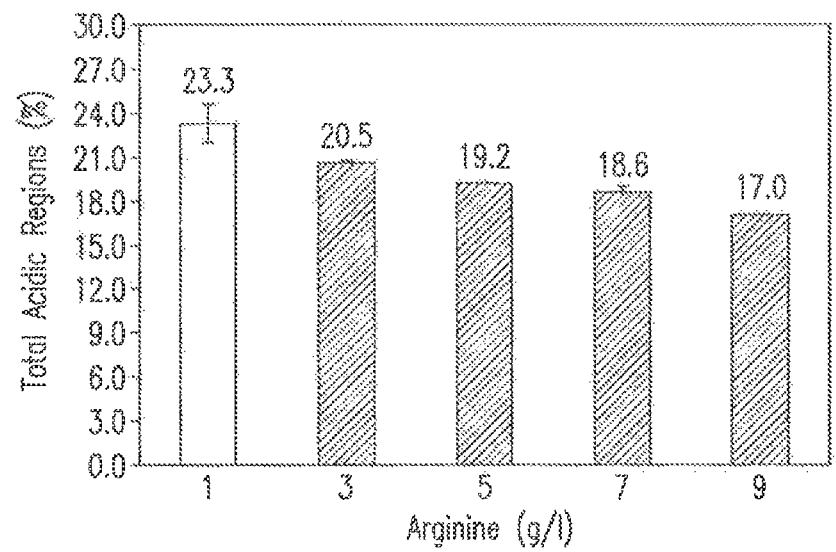

FIG. 9 depicts the effect of total arginine concentration in adalimumab producing cell line 3, media 1 on WCX 10 profile total acidic regions (n=2).

Figure 10:
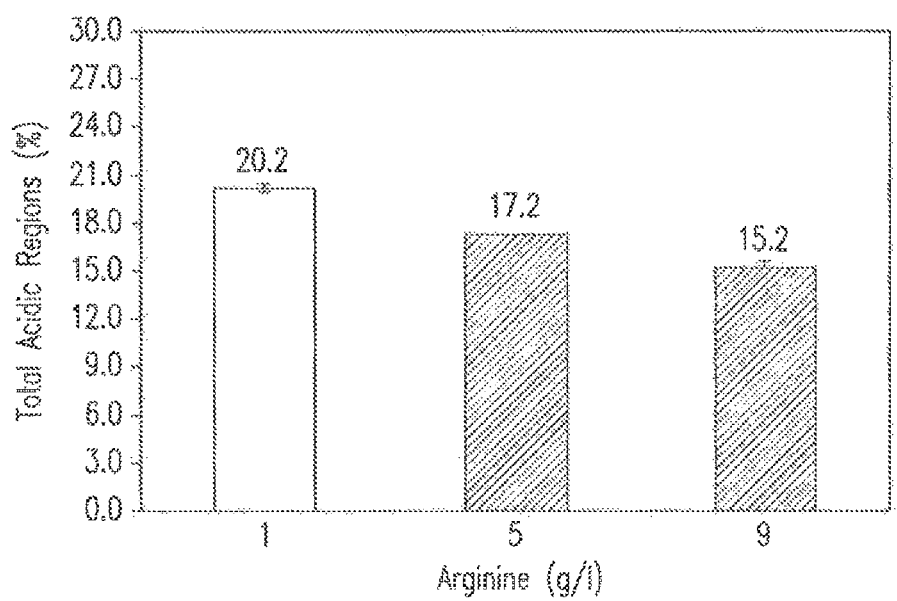

FIG. 10 depicts the effect of total arginine concentration in adalimumab producing cell line 1, media 1 on WCX 10 profile total acidic regions (n=2).

Figure 11:
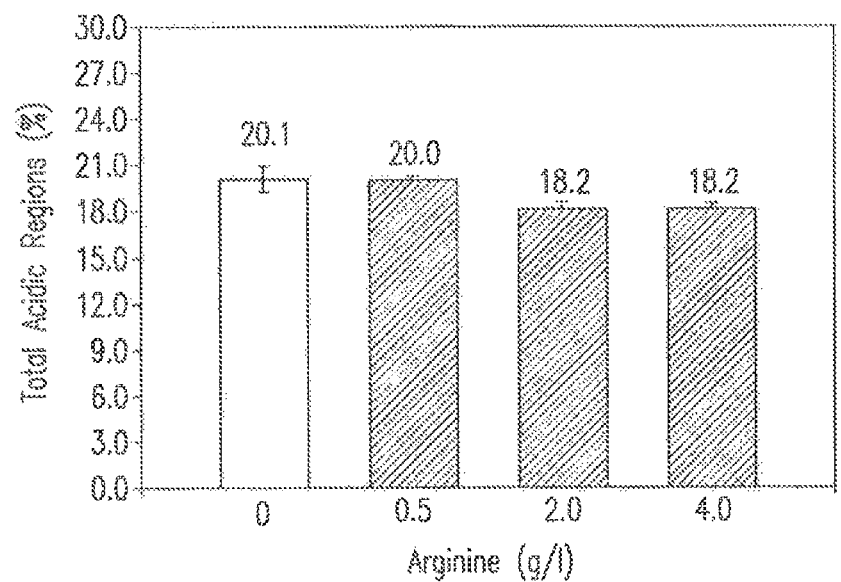

FIG. 11 depicts the effect of arginine addition to adalimumab producing cell line 1, media 2 on day 11 on WCX-10 profile total acidic regions (n=2).

Figure 12:
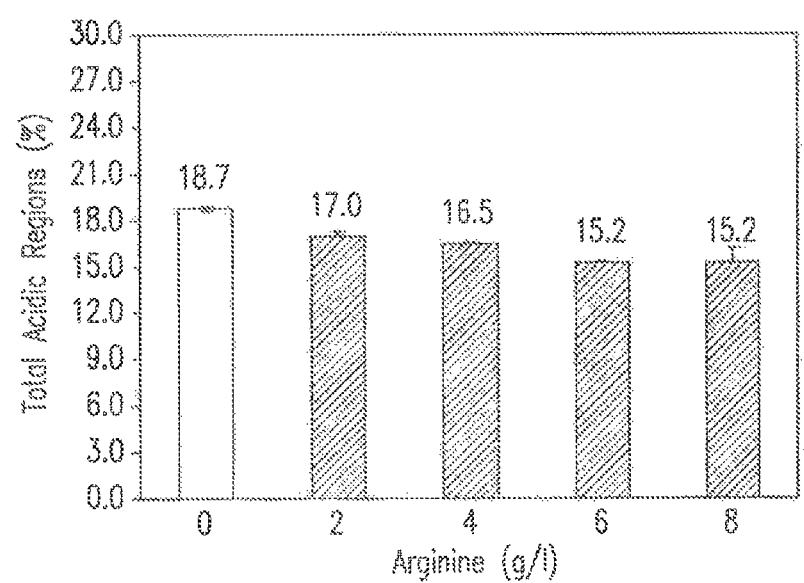

FIG. 12 depicts the effect of arginine addition to adalimumab producing cell line 2, media 3 on WCX-10 profile total acidic regions (n=2).

Figure 13:
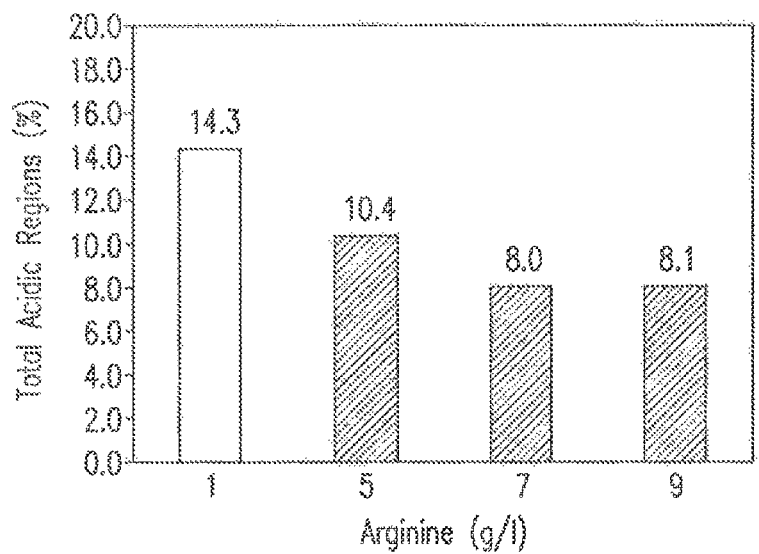

FIG. 13 depicts the effect of total arginine concentration in mAB1 producing cell line on WCX-10 profile total acidic regions (n=1).

Figure 14:
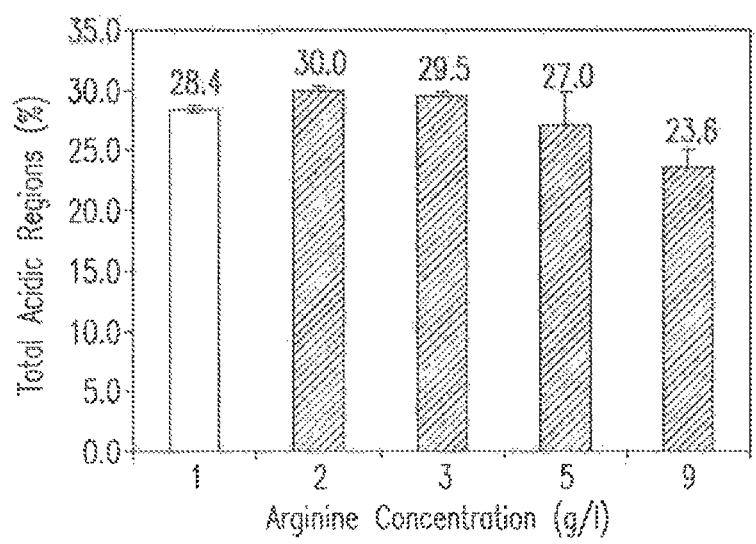

FIG. 14 depicts the effect of total arginine concentration in mAB2 producing cell line on WCX-10 profile total acidic regions (n=2)

Figure 15:
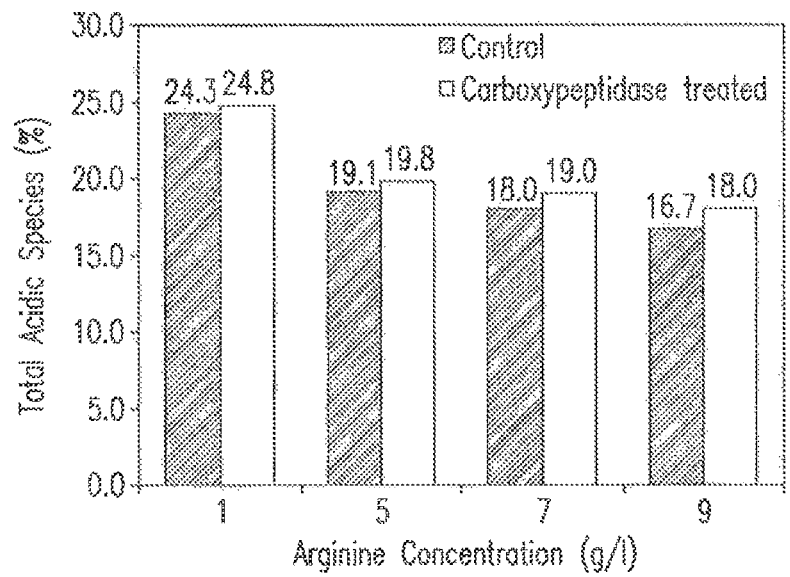

FIG. 15 depicts the effect of carboxypeptidase digestion of product from adalimumab producing cell line 3, media 1 experiment on WCX-10 profile total acidic regions (n=1).

Figure 16:
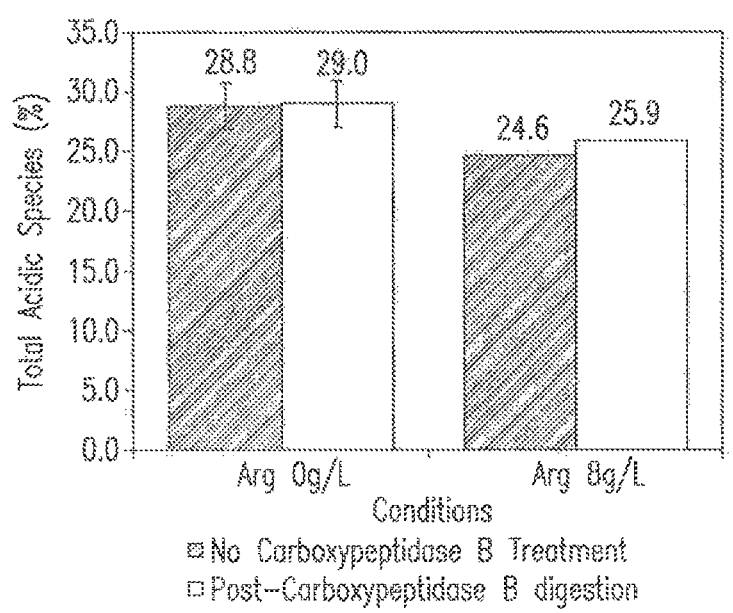

FIG. 16 depicts the effect of carboxypeptidase digestions of product from mAB2 producing cell line on WCX-10 profile total acidic regions (n=2).

Figure 17:
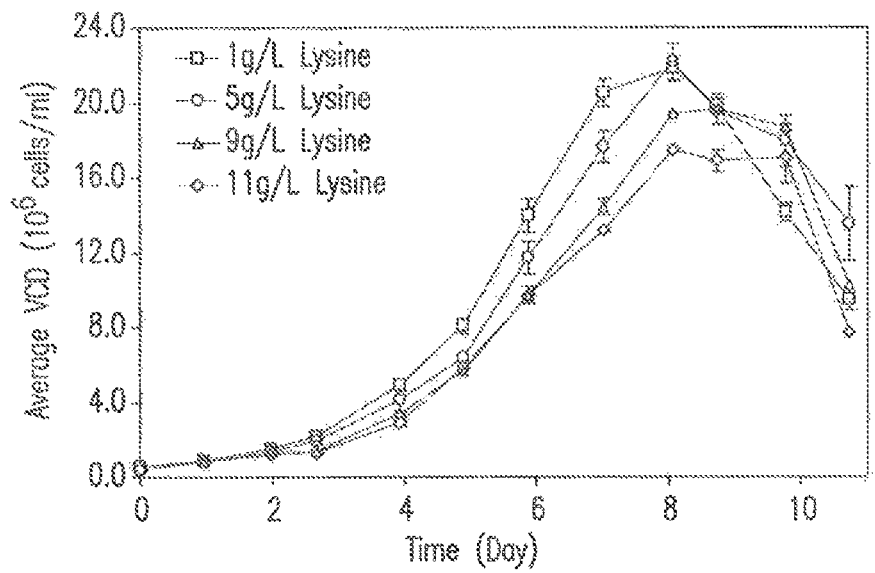

FIG. 17 depicts the effect of total lysine concentration in adalimumab producing cell line 2, media 1 on viable cell density (n=2).

Figure 18:
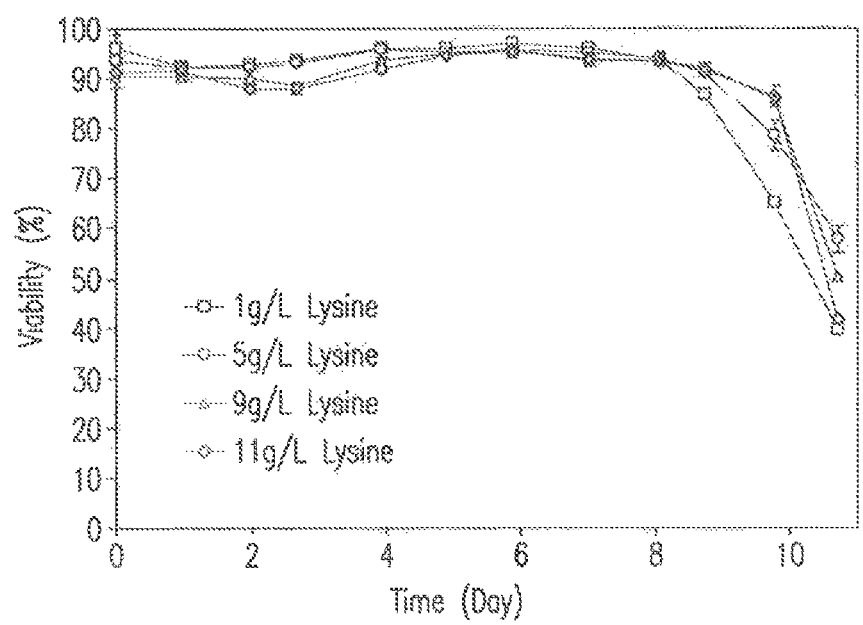

FIG. 18 depicts the effect of total lysine concentration in adalimumab producing cell line 2, media 1 on viability (n=2).

Figure 19:
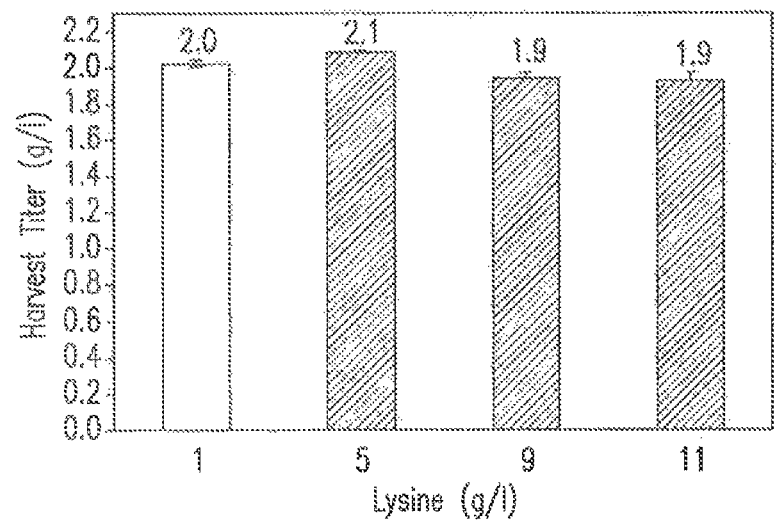

FIG. 19 depicts the effect of total lysine concentration in adalimumab producing cell line 2, media 1 on harvest titer (n=2).

Figure 20:
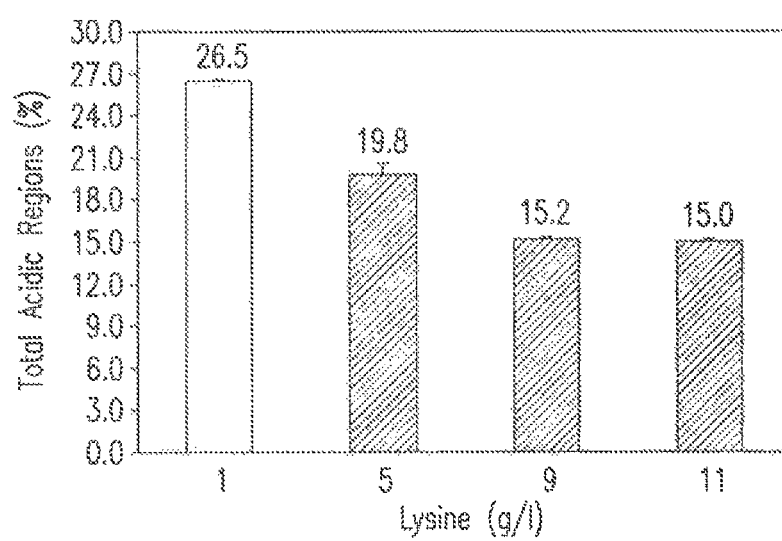

FIG. 20 depicts the effect of total lysine concentration in adalimumab producing cell line 2, media 1 on WCX 10 profile total acidic regions (n=2).

Figure 21:
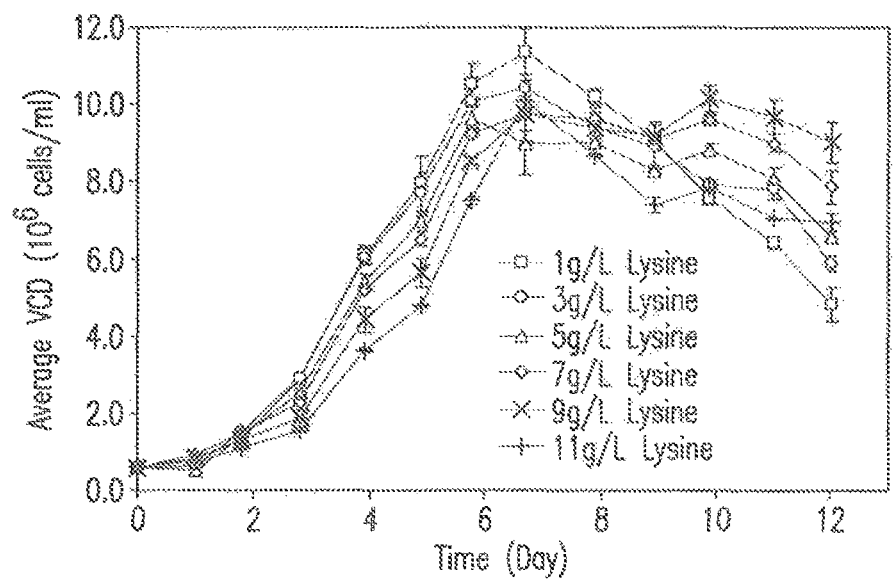

FIG. 21 depicts the effect of total lysine concentration in adalimumab producing cell line 3, media 1 on viable cell density (n=2).

Figure 22:
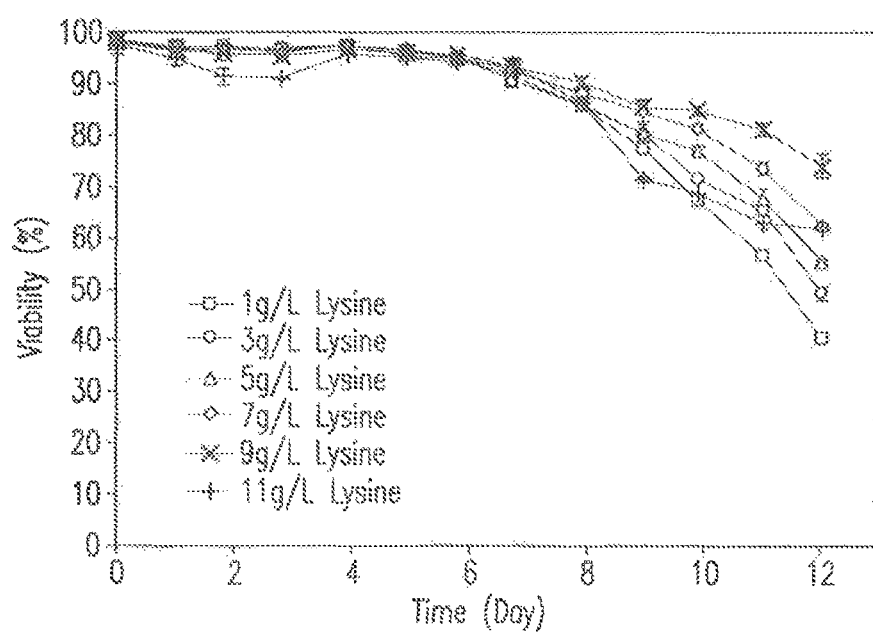

FIG. 22 depicts the effect of total lysine concentration in adalimumab producing cell line 3, media 1 on viability (n=2).

Figure 23:
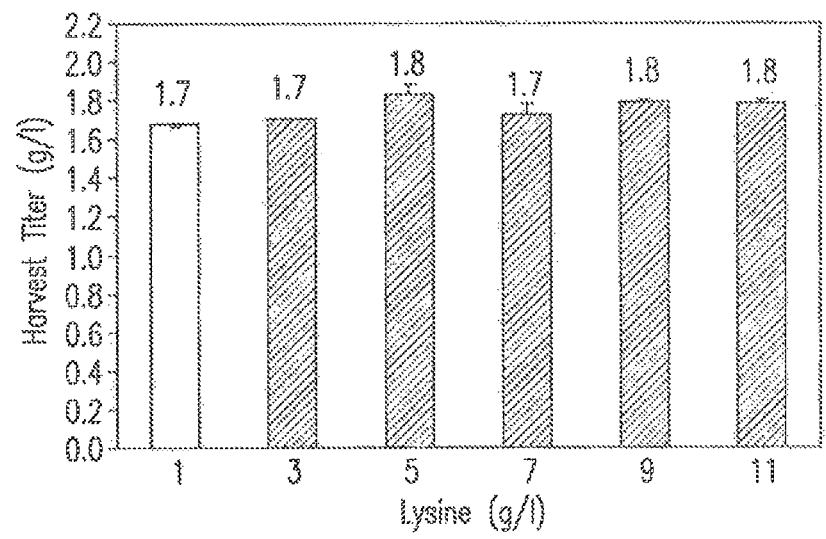

FIG. 23 depicts the effect of total lysine concentration in adalimumab producing cell line 3, media 1 on harvest titer (n=2).

Figure 24:
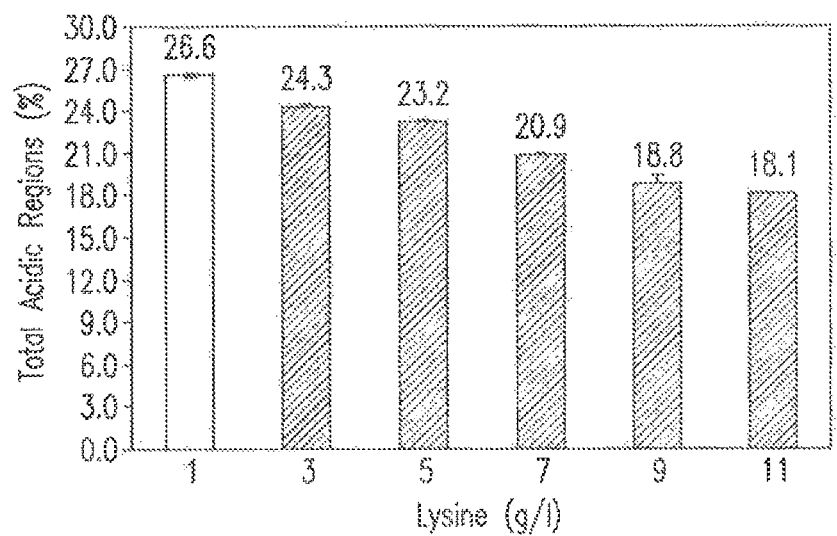

FIG. 24 depicts the effect of total lysine concentration in adalimumab producing cell line 3, media 1 on WCX 10 profile total acidic regions (n=2).

Figure 25:
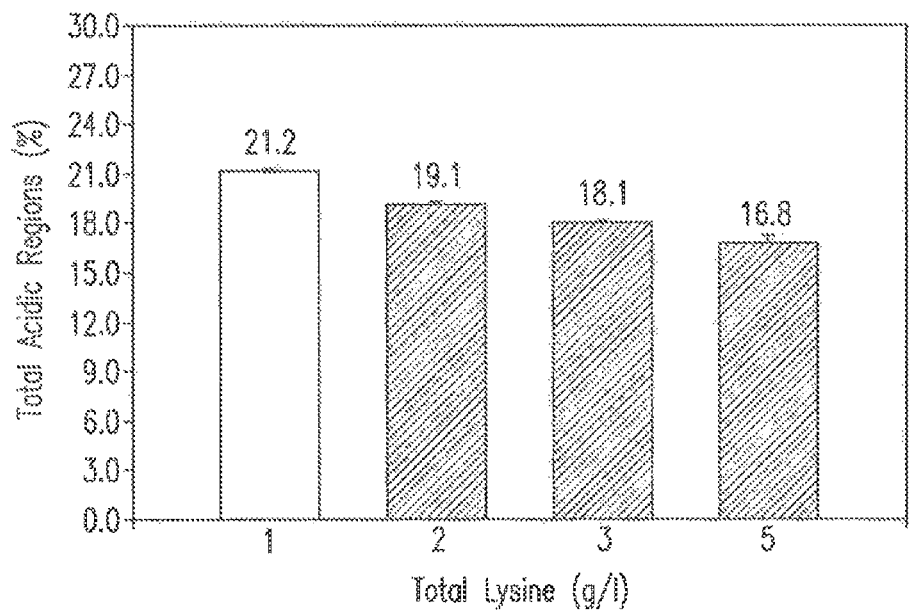

FIG. 25 depicts the effect of total lysine concentration in adalimumab producing cell line 1, media 1 on WCX 10 profile total acidic regions (n=2).

Figure 26:
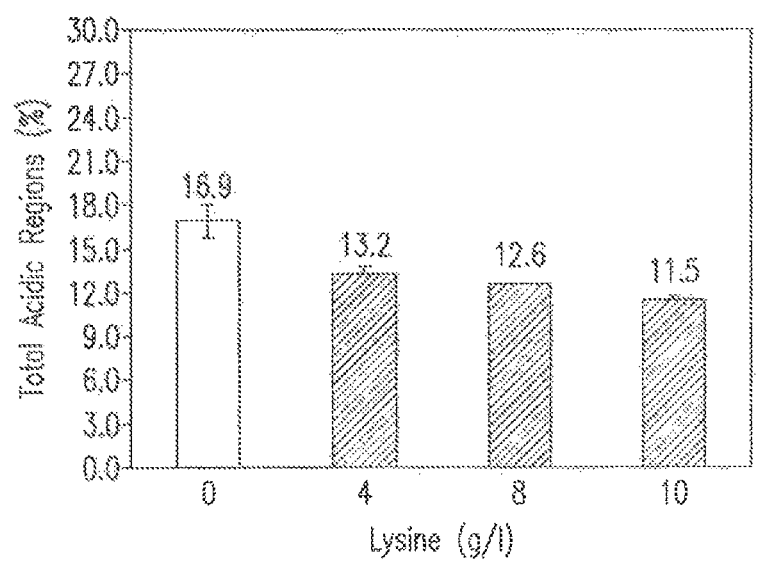

FIG. 26 depicts the effect of lysine addition to adalimumab producing cell line 1, media 2 on WCX-10 profile total acidic regions (n=2).

Figure 27:
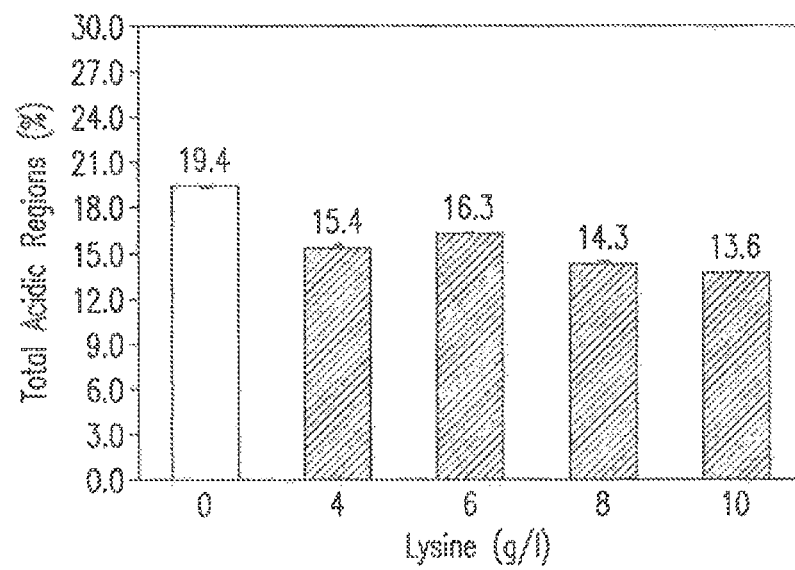

FIG. 27 depicts the effect of lysine addition to adalimumab producing cell line 2, media 3 on WCX-10 profile total acidic regions (n=2).

Figure 28:
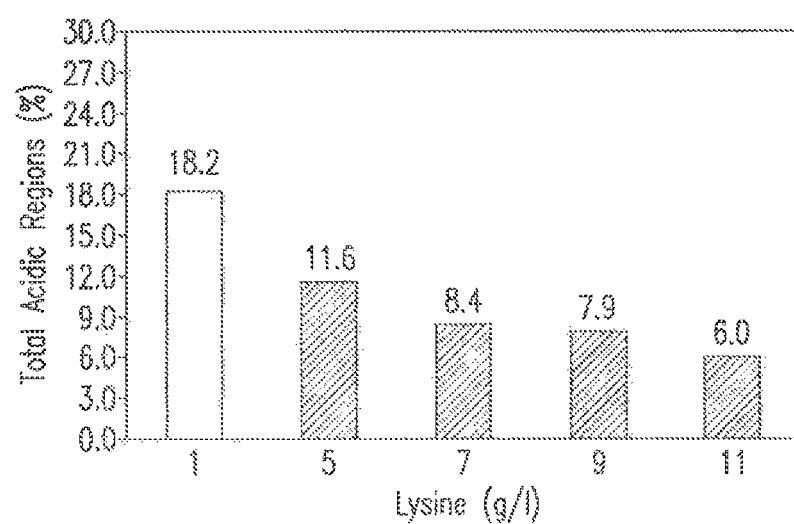

FIG. 28 depicts the effect of total lysine concentration in mAB1 producing cell line on WCX-10 profile total acidic regions (n=1).

Figure 29:
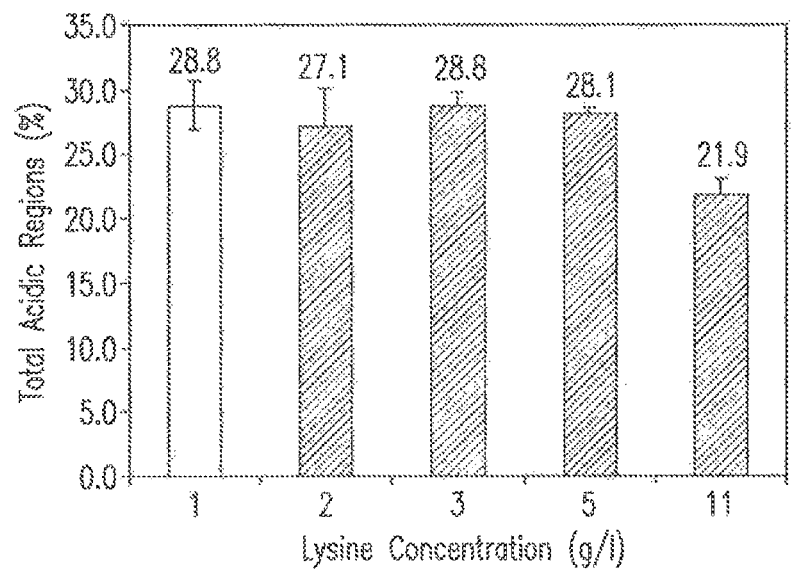

FIG. 29 depicts the effect of total lysine concentration in mAB2 producing cell line on WCX-10 profile total acidic regions (n=2).

Figure 30:
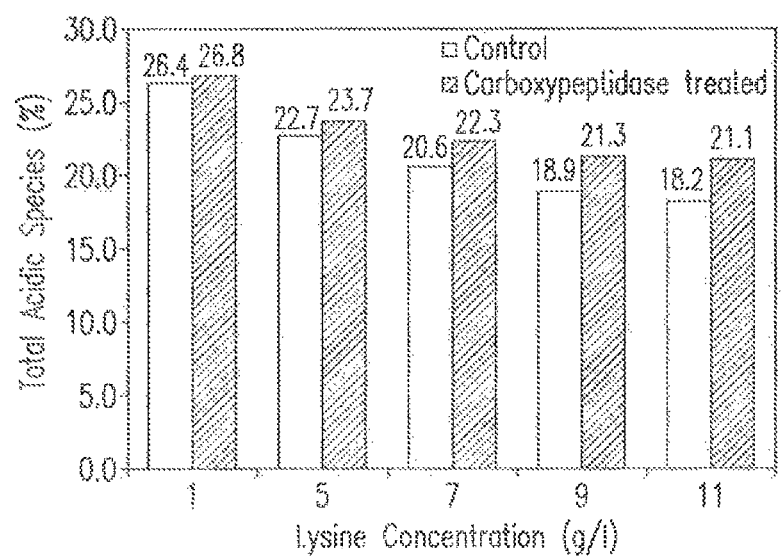

FIG. 30 depicts the effect of carboxypeptidase digestion of product from cell line 3, media 1 experiment on WCX-10 profile total acidic regions (n=1).

Figure 31:
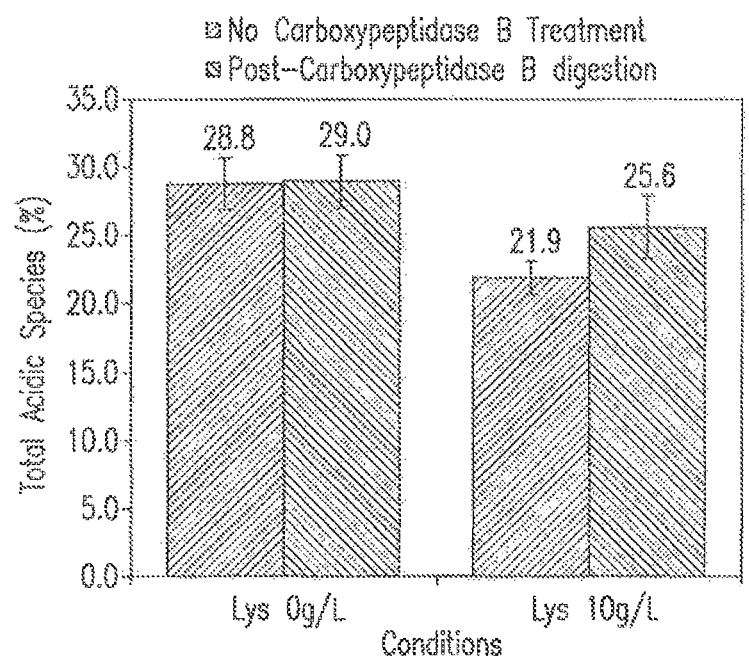

FIG. 31 depicts the effect of carboxypeptidase digestions of product from mAB2 producing cell line on WCX-10 profile total acidic regions (n=2).

Figure 32:
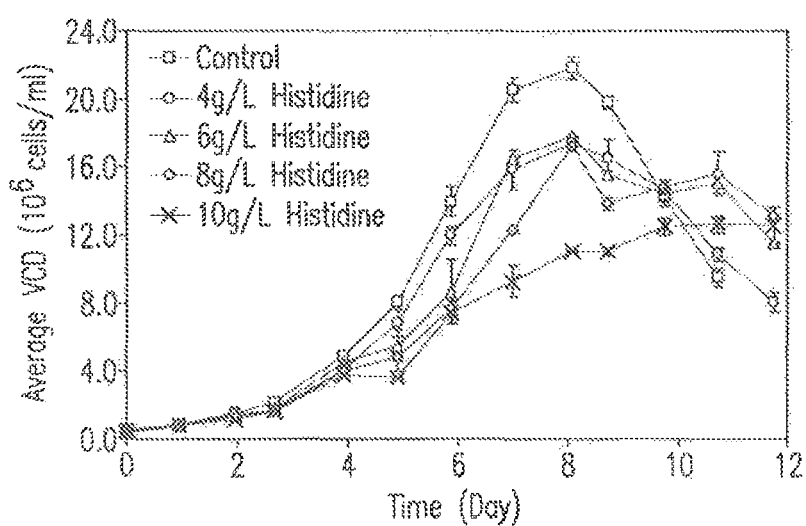

FIG. 32 depicts the effect of total histidine concentration in adalimumab producing cell line 2, media 1 on viable cell density (n=2).

Figure 33:
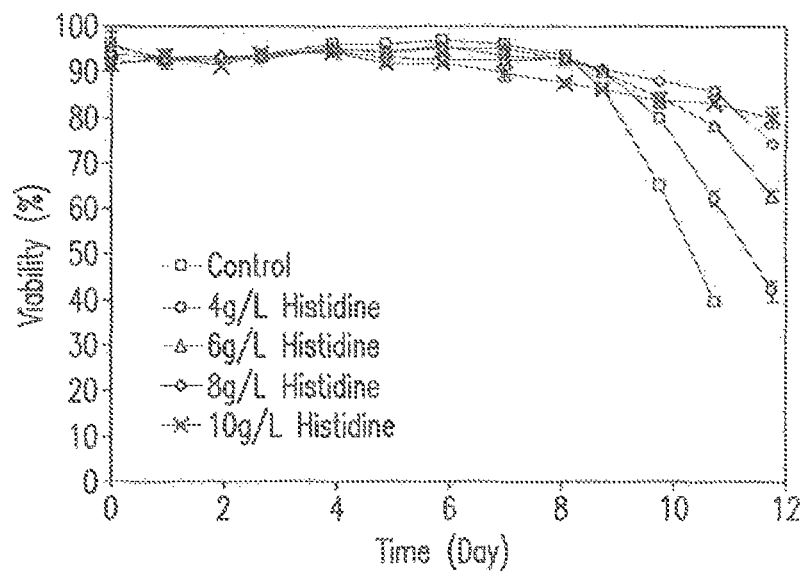

FIG. 33 depicts the effect of total histidine concentration in adalimumab producing cell line 2, media 1 on viability (n=2).

Figure 34:
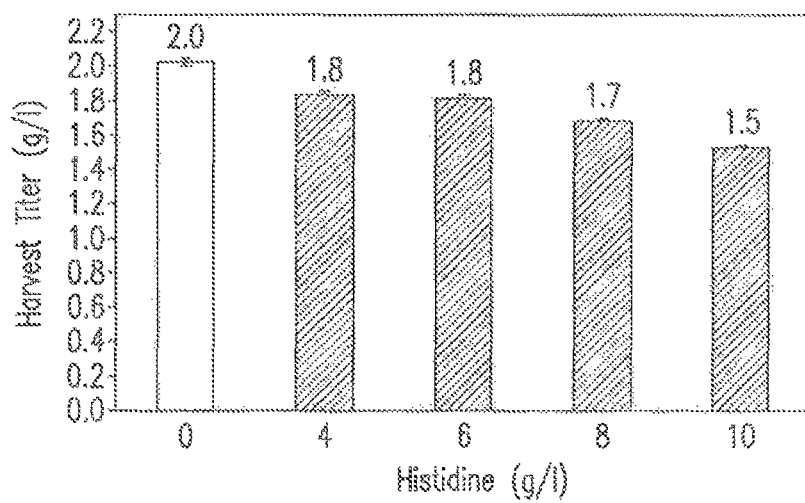

FIG. 34 depicts the effect of total histidine concentration in adalimumab producing cell line 2, media 1 on harvest titer (n=2).

Figure 35:
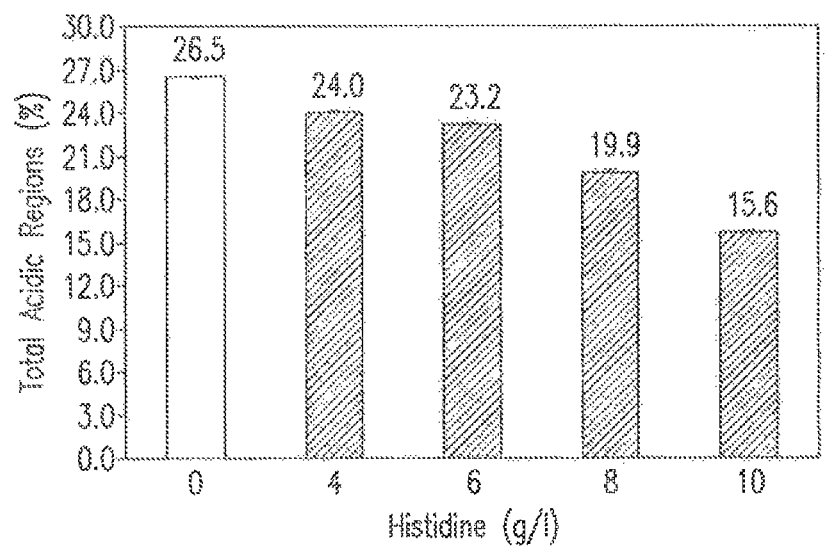

FIG. 35 depicts the effect of total histidine concentration in adalimumab producing cell line 2, media 1 on WCX 10 profile total acidic regions (n=2).

Figure 36:
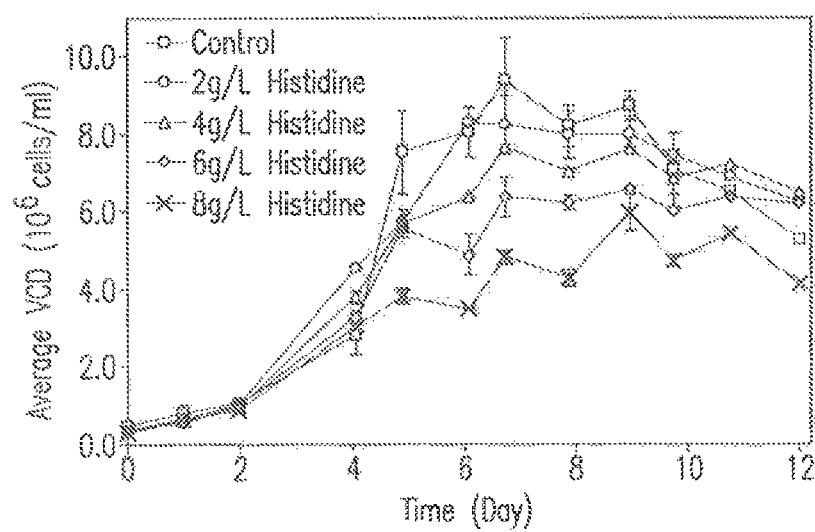

FIG. 36 depicts the effect of total histidine concentration in adalimumab producing cell line 3, media 1 on viable cell density (n=2).

Figure 37:
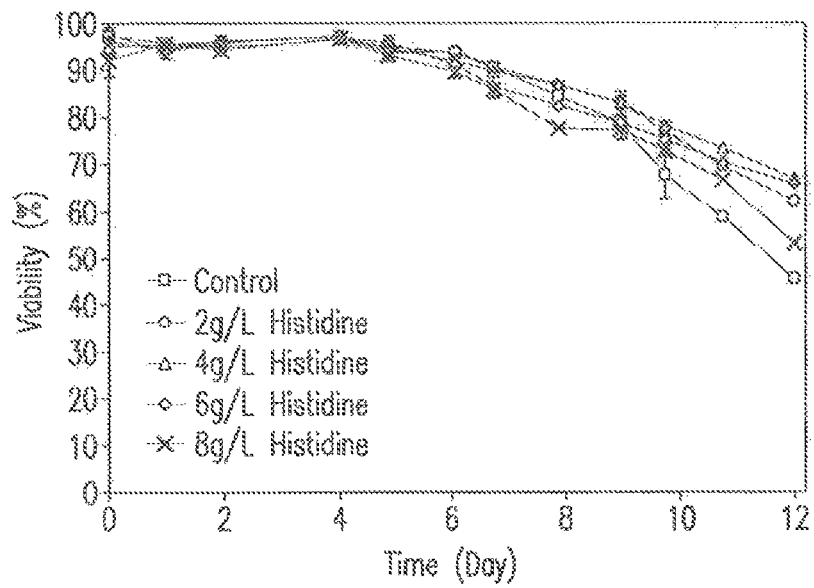

FIG. 37 depicts the effect of total histidine concentration in adalimumab producing cell line 3, media 1 on viability (n=2).

Figure 38:
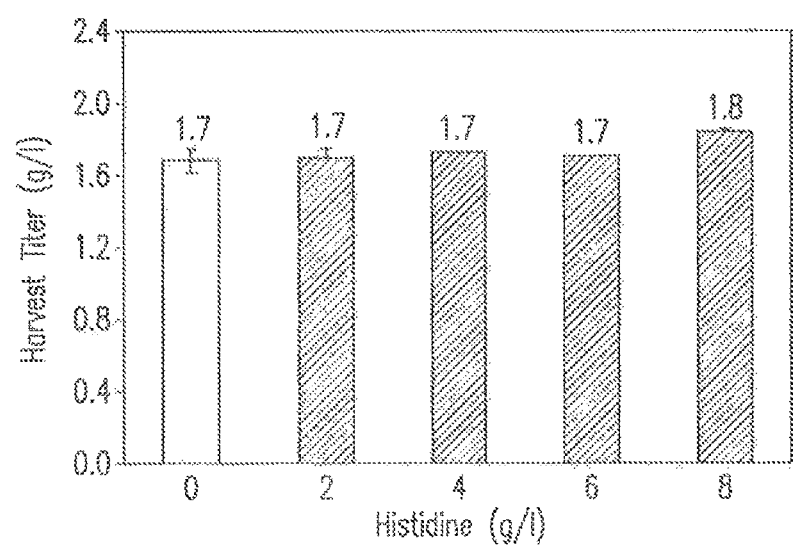

FIG. 38 depicts the effect of total histidine concentration in adalimumab producing cell line 3, media 1 on harvest titer (n=2).

Figure 39:
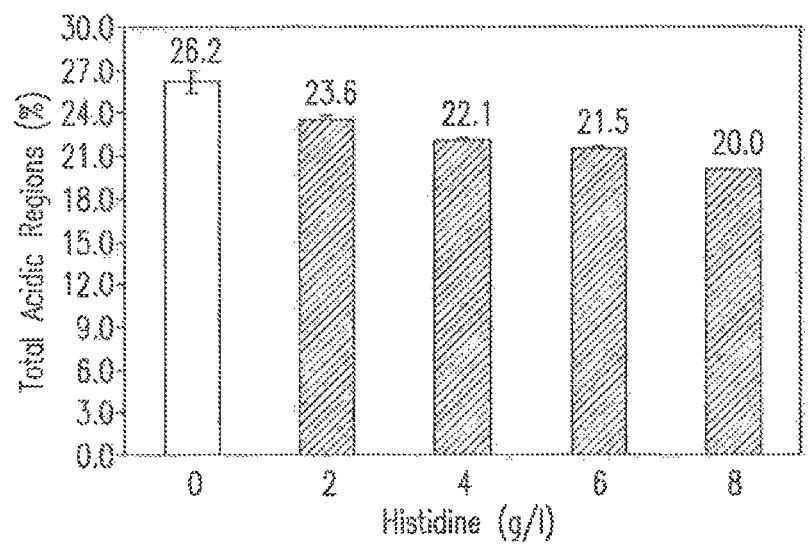

FIG. 39 depicts the effect of total histidine concentration in adalimumab producing cell line 3, media 1 on WCX 10 profile total acidic regions (n=2).

Figure 40:
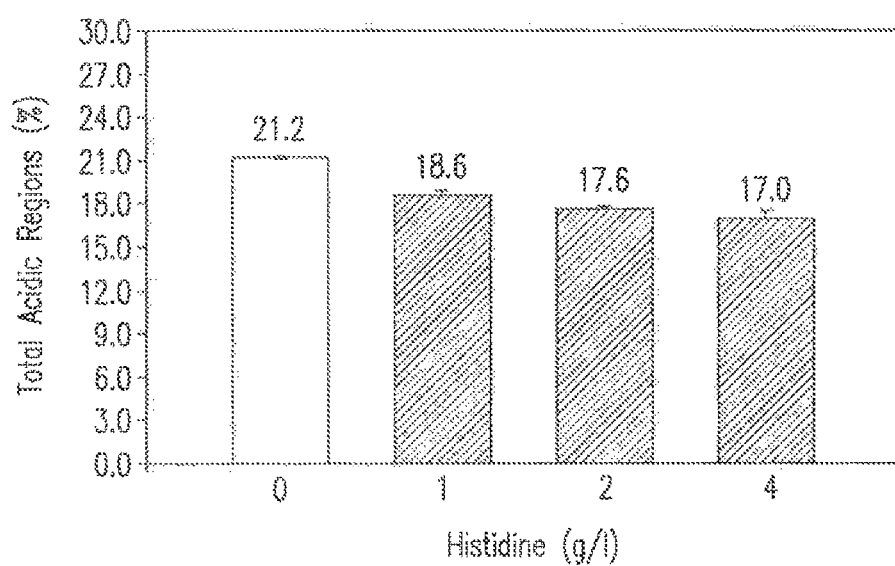

FIG. 40 depicts the effect of total histidine concentration in adalimumab producing cell line 1, media 1 on WCX 10 profile total acidic regions (n=2).

Figure 41:
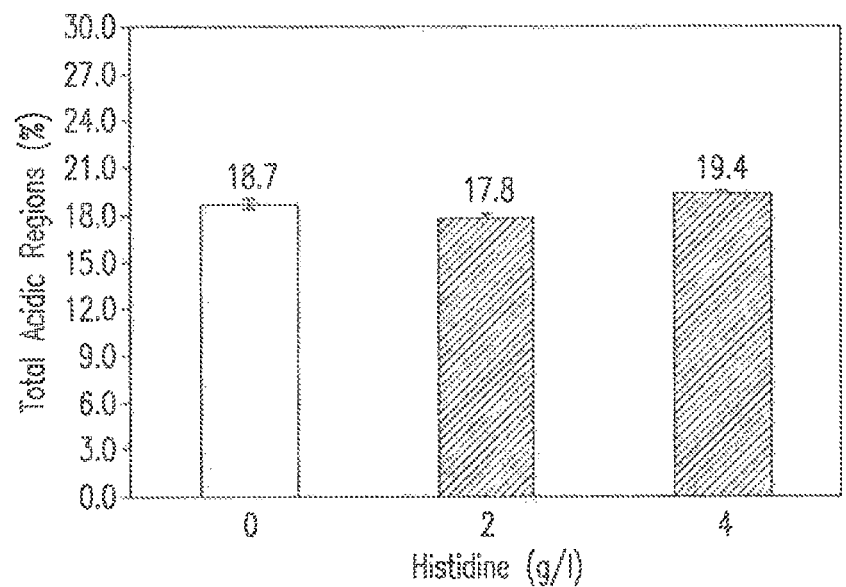

FIG. 41 depicts the effect of histidine addition to adalimumab producing cell line 1, media 2 on WCX-10 profile total acidic regions (n=2).

Figure 42:
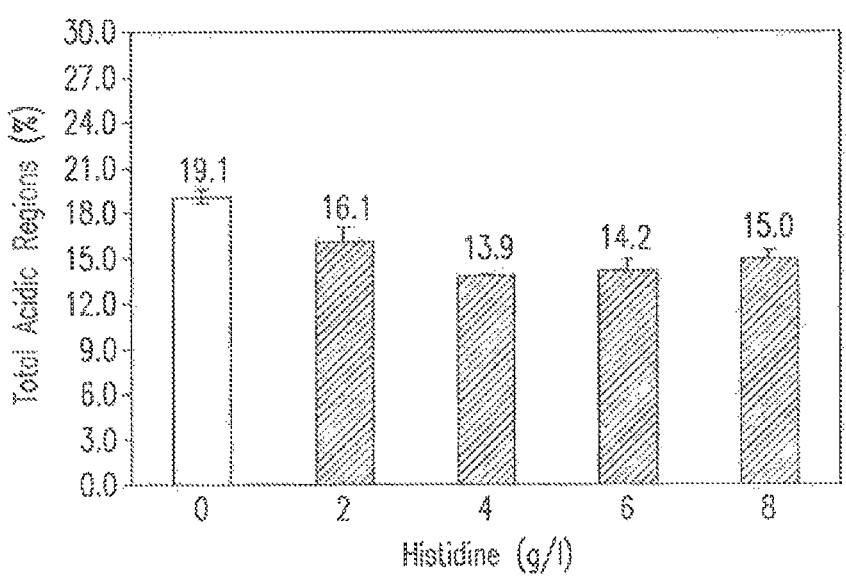

FIG. 42 depicts the effect of histidine addition to adalimumab producing cell line 2, media 3 on WCX-10 profile total acidic regions (n=2).

Figure 43:
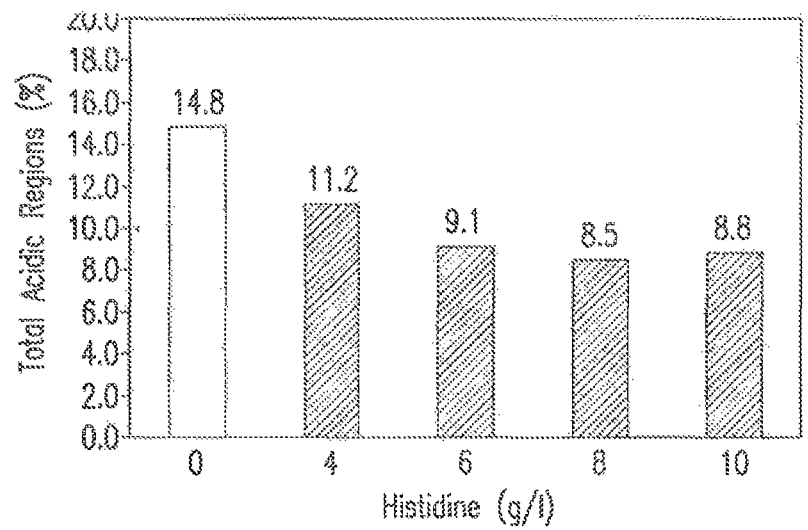

FIG. 43 depicts the effect of total histidine concentration in mAB1 producing cell line on WCX-10 profile total acidic regions (n=1).

Figure 44:
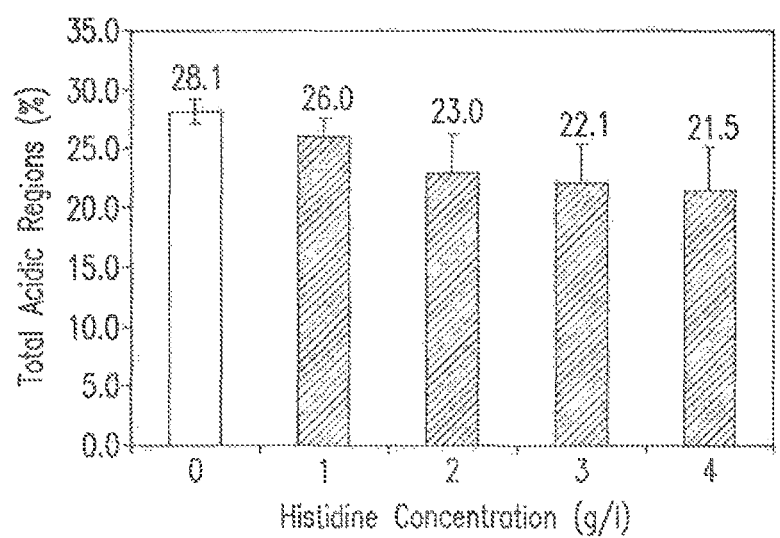

FIG. 44 depicts the effect of total histidine concentration in mAB2 producing cell line on WCX-10 profile total acidic regions (n=2).

Figure 45:
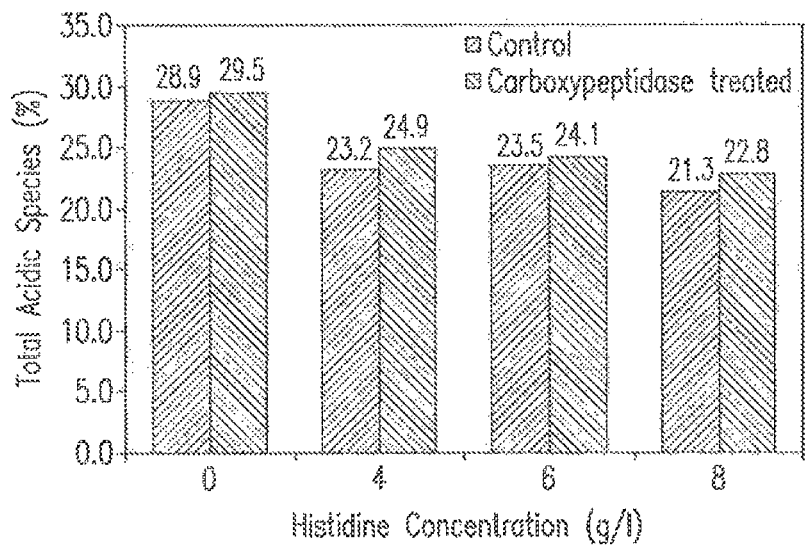

FIG. 45 depicts the effect of carboxypeptidase digestion of product from cell line 3, media 1 experiment on WCX-10 profile total acidic regions (n=1).

Figure 46:
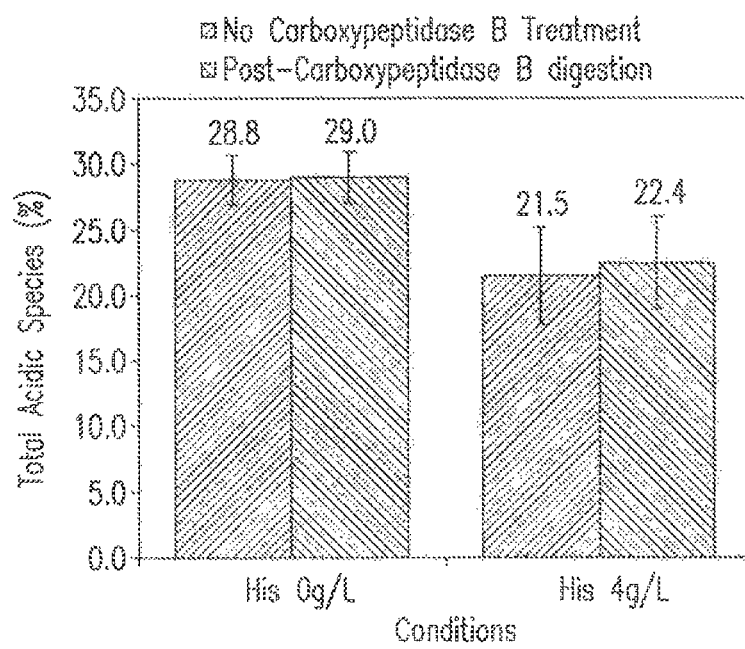

FIG. 46 depicts the effect of carboxypeptidase digestions of product from mAB2 producing cell line on WCX-10 profile total acidic regions (n=2).

Figure 47:
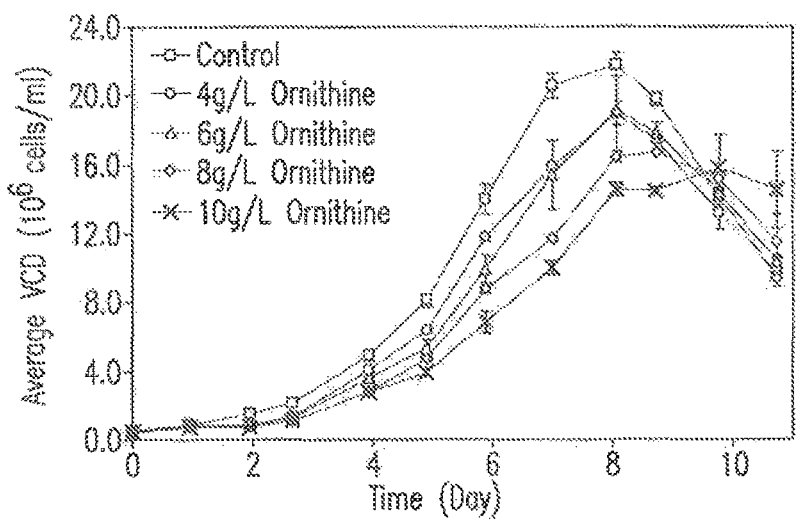

FIG. 47 depicts the effect of total ornithine concentration in adalimumab producing cell line 2, media 1 on viable cell density (n=2).

Figure 48:
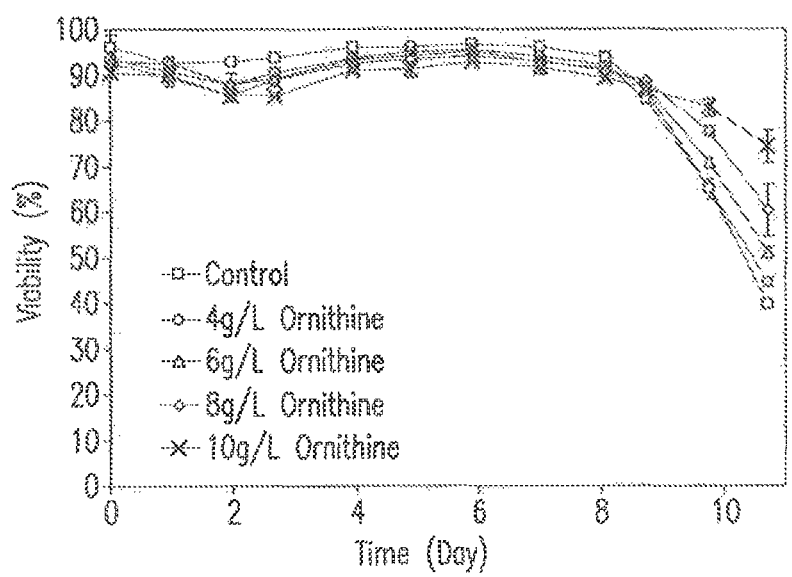

FIG. 48 depicts the effect of total ornithine concentration in adalimumab producing cell line 2, media 1 on viability (n=2).

Figure 49:
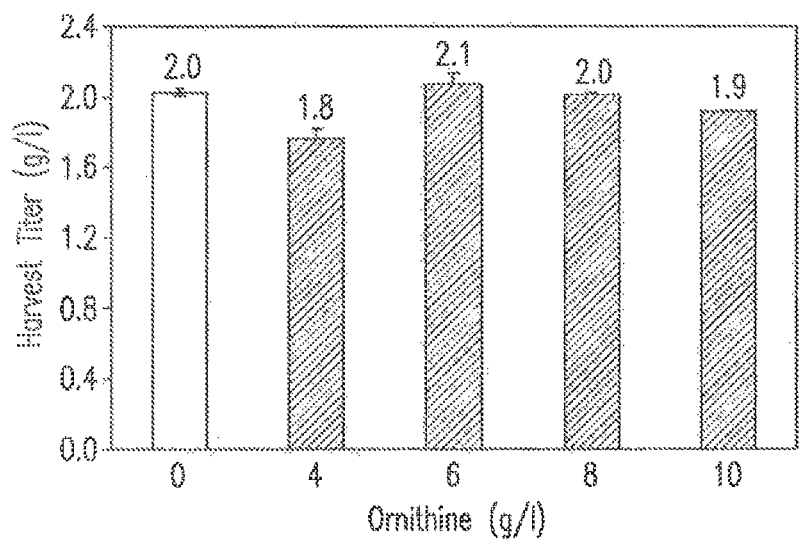

FIG. 49 depicts the effect of total ornithine concentration in adalimumab producing cell line 2, media 1 on harvest titer (n=2).

Figure 50:
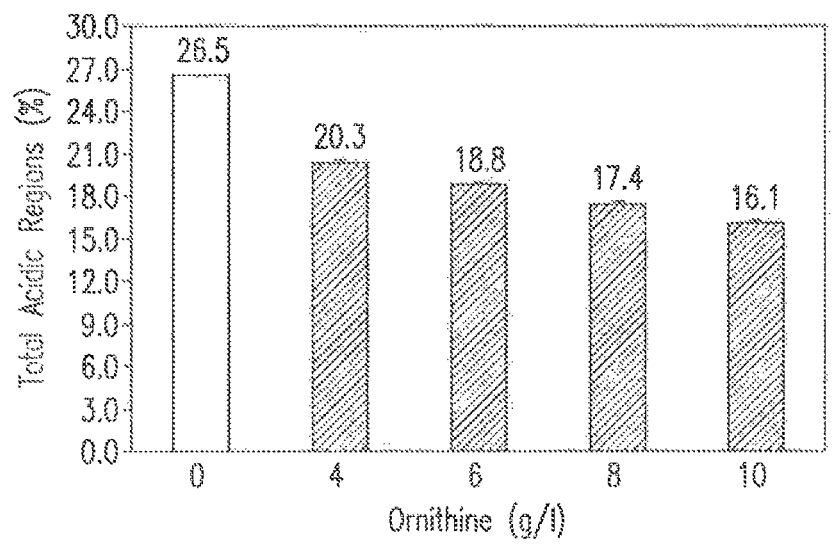

FIG. 50 depicts the effect of total ornithine concentration in adalimumab producing cell line 2, media 1 on WCX 10 profile total acidic regions.

Figure 51:
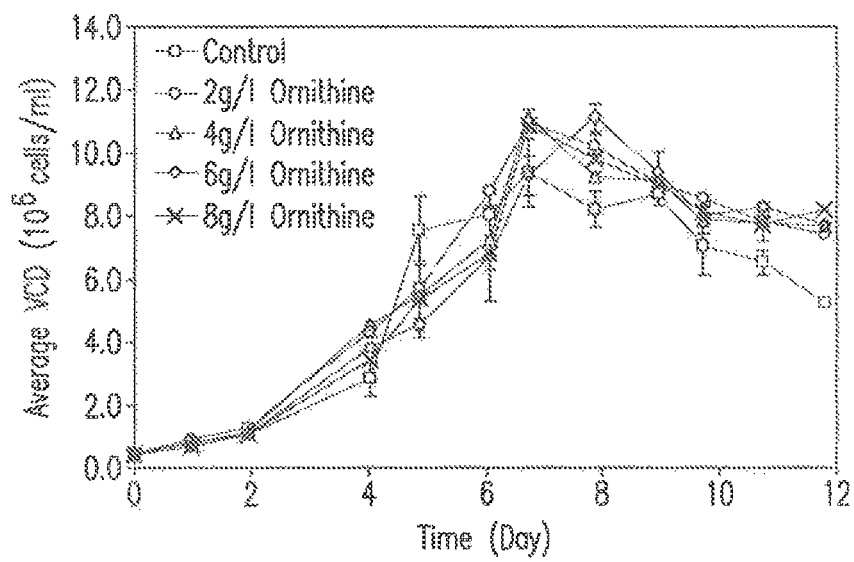

FIG. 51 depicts the effect of total ornithine concentration in adalimumab producing cell line 3, media 1 on viable cell density (n=2).

Figure 52:
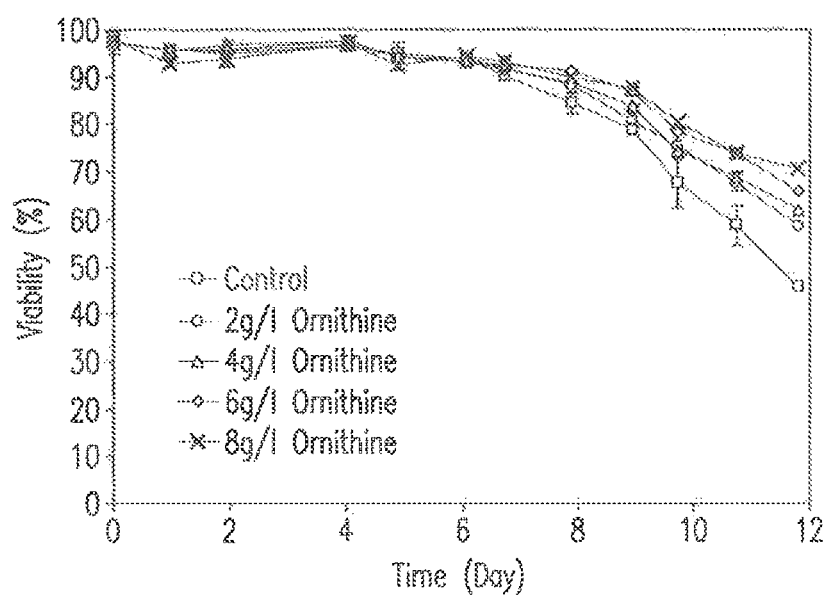

FIG. 52 depicts the effect of total ornithine concentration in adalimumab producing cell line 3, media 1 on viability (n=2).

Figure 53:
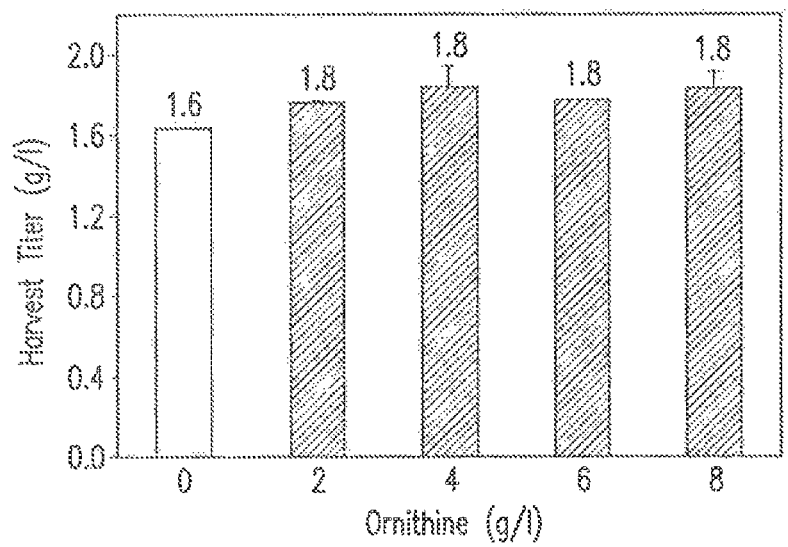

FIG. 53 depicts the effect of total ornithine concentration in adalimumab producing cell line 3, media 1 on harvest titer (n=2).

Figure 54:
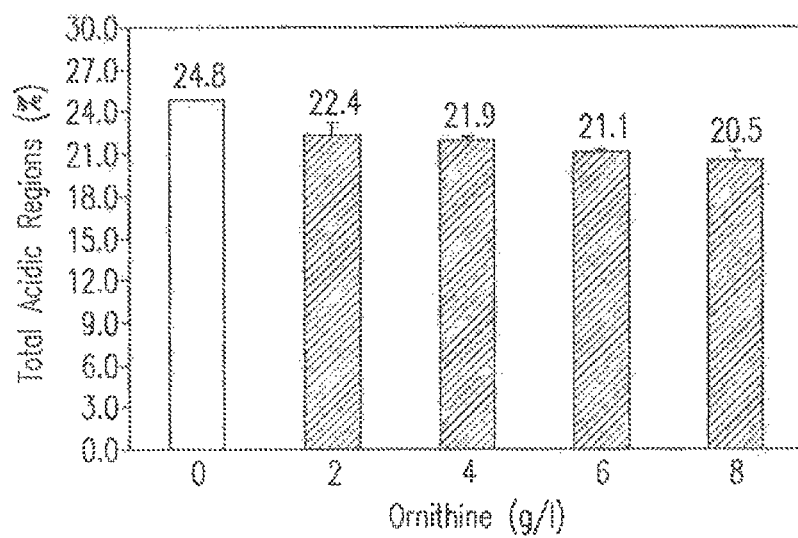

FIG. 54 depicts the effect of total ornithine concentration in adalimumab producing cell line 3, media 1 on WCX 10 profile total acidic regions (n=2).

Figure 55:
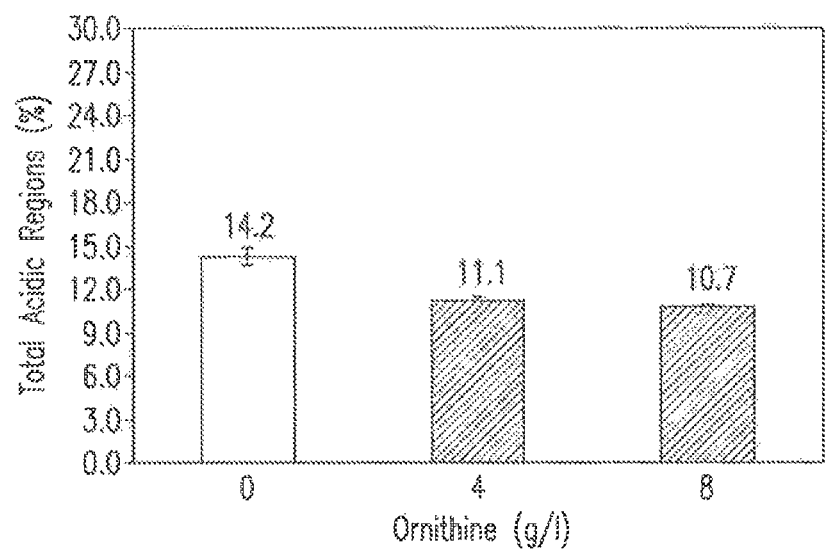

FIG. 55 depicts the effect of total ornithine concentration in adalimumab producing cell line 1, media 1 on WCX 10 profile total acidic regions (n=2).

Figure 56:
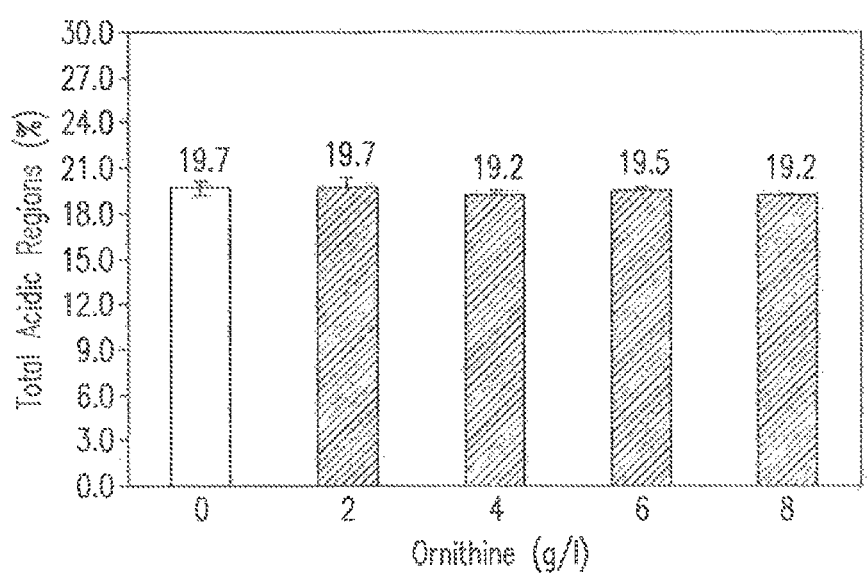

FIG. 56 depicts the effect of ornithine addition to adalimumab producing cell line 1, media 2 on WCX-10 profile total acidic regions (n=2).

Figure 57:
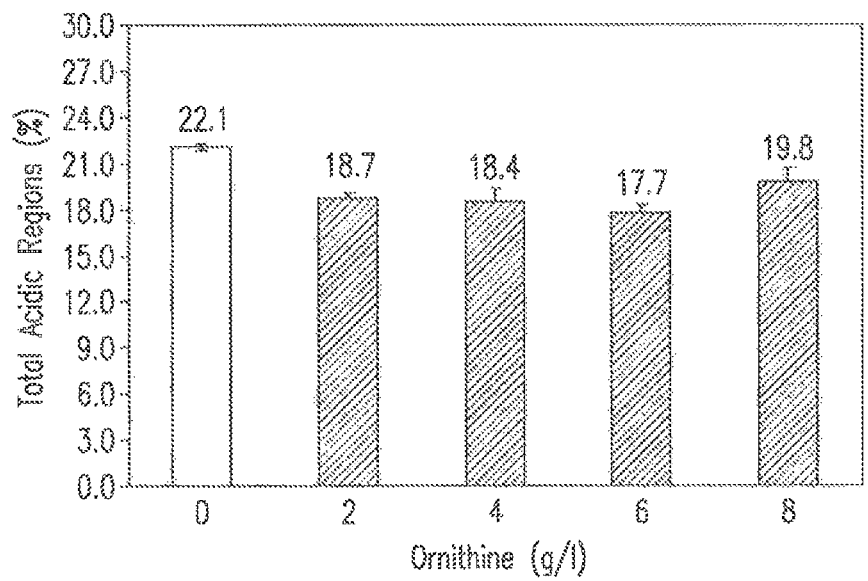

FIG. 57 depicts the effect of ornithine addition to adalimumab producing cell line 2, media 3 on WCX-10 profile total acidic regions (n=2).

Figure 58:
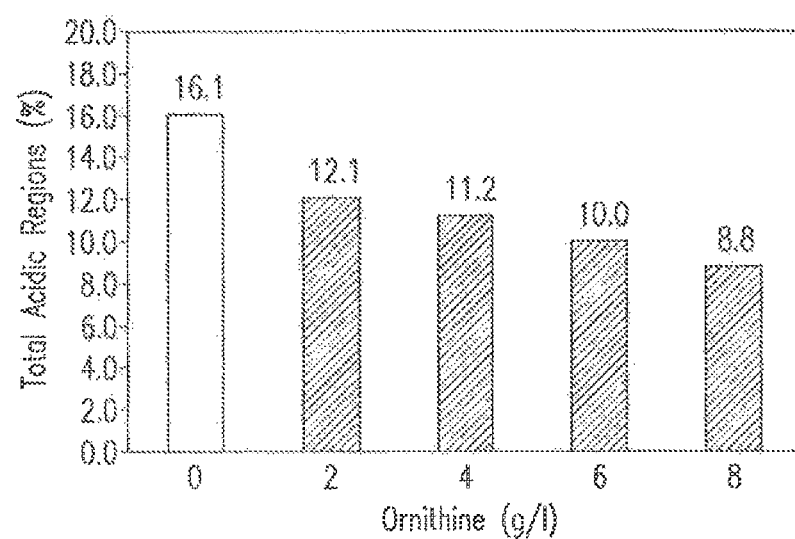

FIG. 58 depicts the effect of total ornithine concentration in mAB1 producing cell line on WCX-10 profile total acidic regions (n=1).

Figure 59:
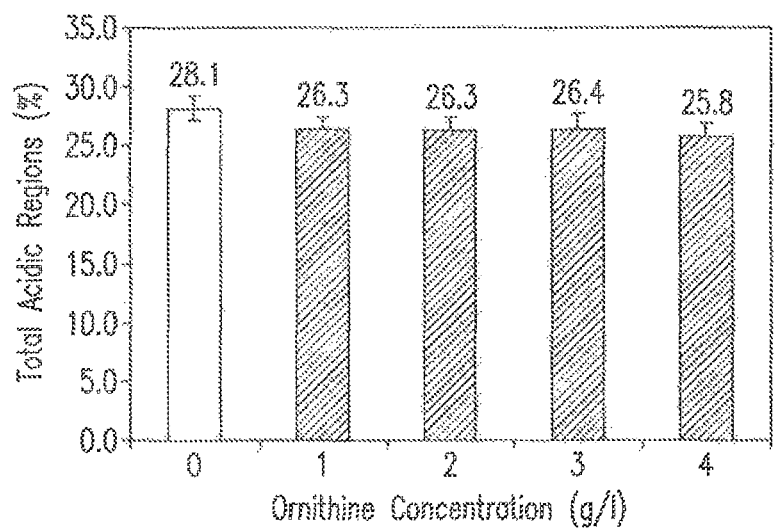

FIG. 59 depicts the effect of total ornithine concentration in mAB2 producing cell line on WCX-10 profile total acidic regions (n=2).

Figure 60:
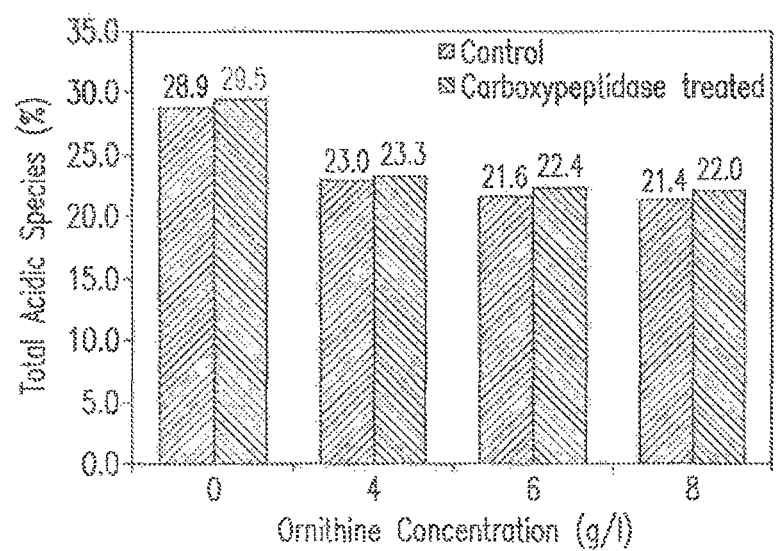

FIG. 60 depicts the effect of carboxypeptidase digestion of product from cell line 3, media 1 experiment on WCX-10 profile total acidic regions (n=1).

Figure 61:
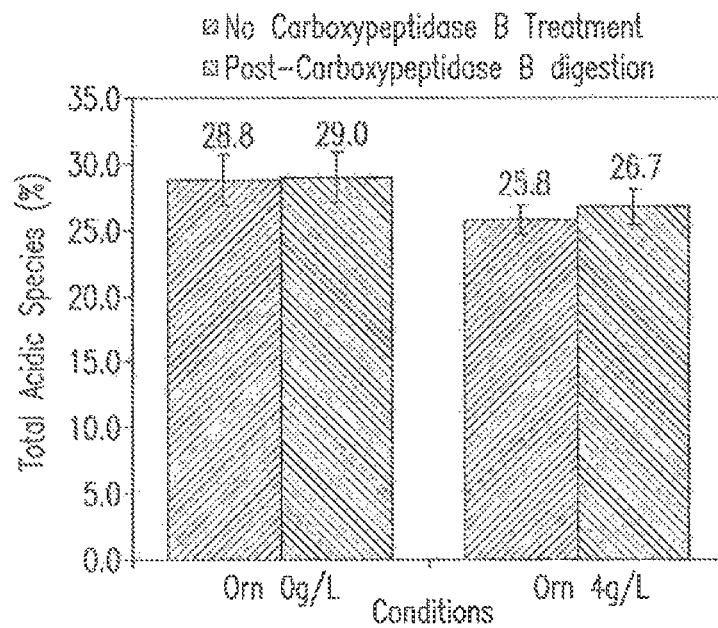

FIG. 61 depicts the effect of carboxypeptidase digestions of product from mAB2 producing cell line on WCX-10 profile total acidic regions (n=2).

Figure 62:
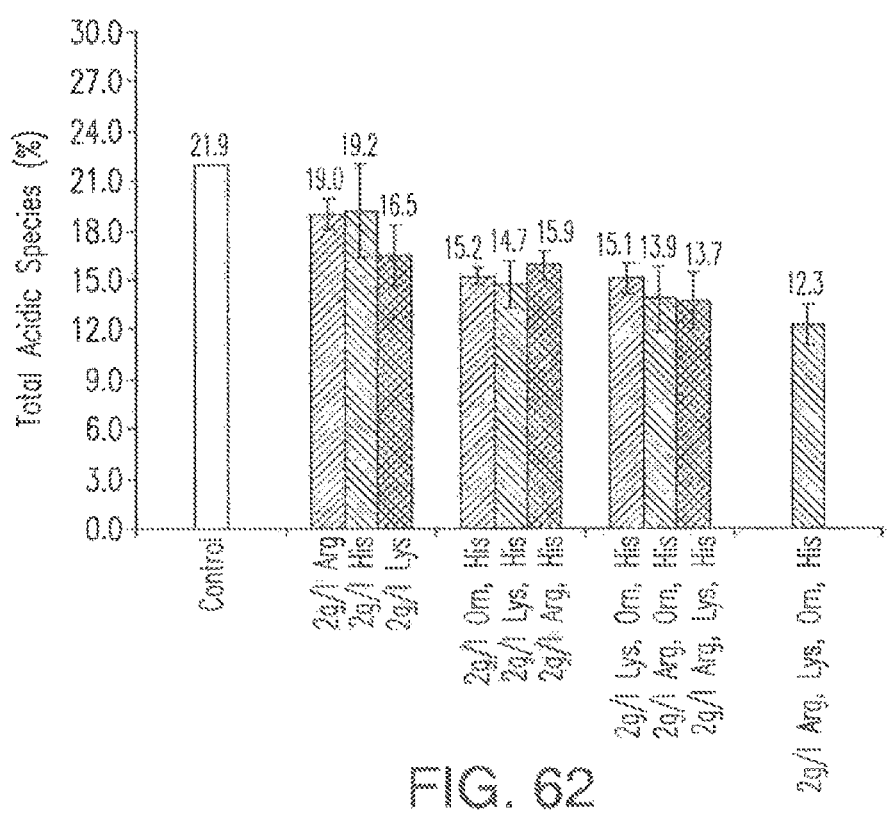

FIG. 62 depicts the effect of multiple amino acid additions to adalimumab producing cell line 2, media 1 on WCX 10 profile total acidic regions (n=2).

Figure 63:
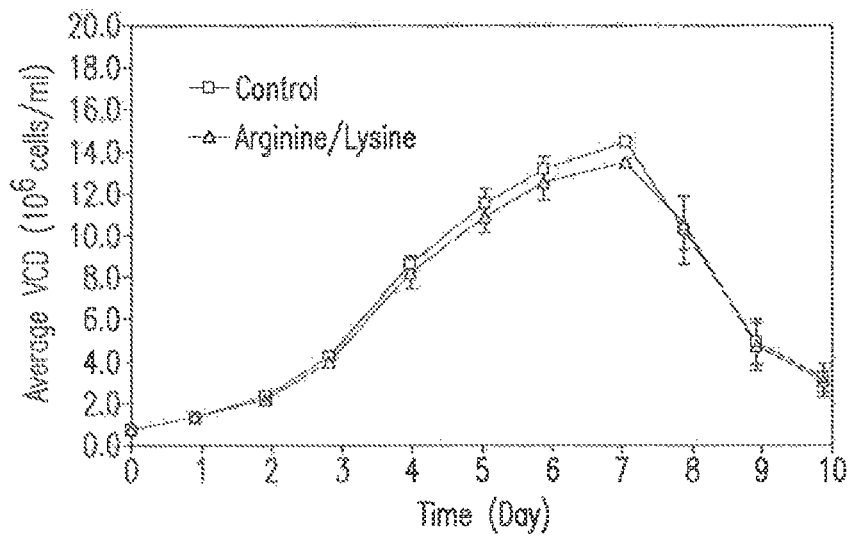

FIG. 63 depicts the effect of increased arginine and lysine concentration in adalimumab producing cell line 1, media 1 on viable cell density (n=3).

Figure 64:
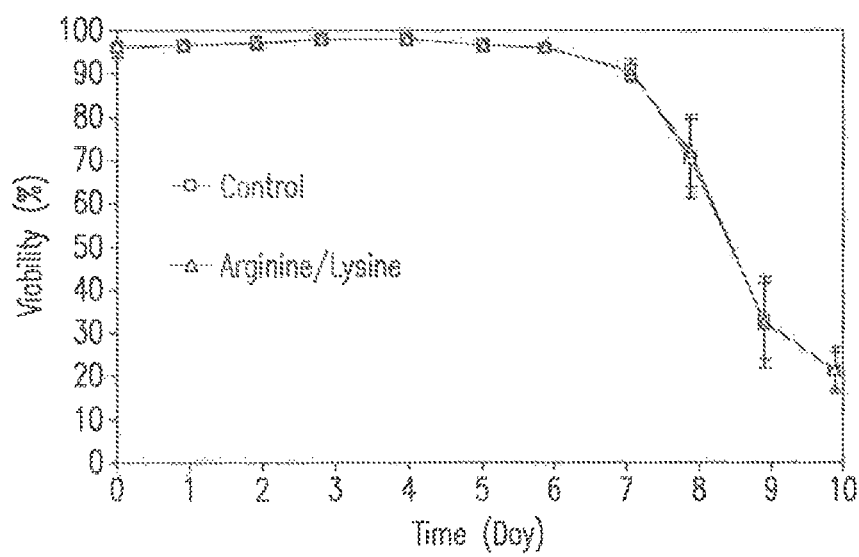

FIG. 64 depicts the effect of increased arginine and lysine concentration in adalimumab producing cell line 3, media 1 on viability (n=3).

Figure 65:
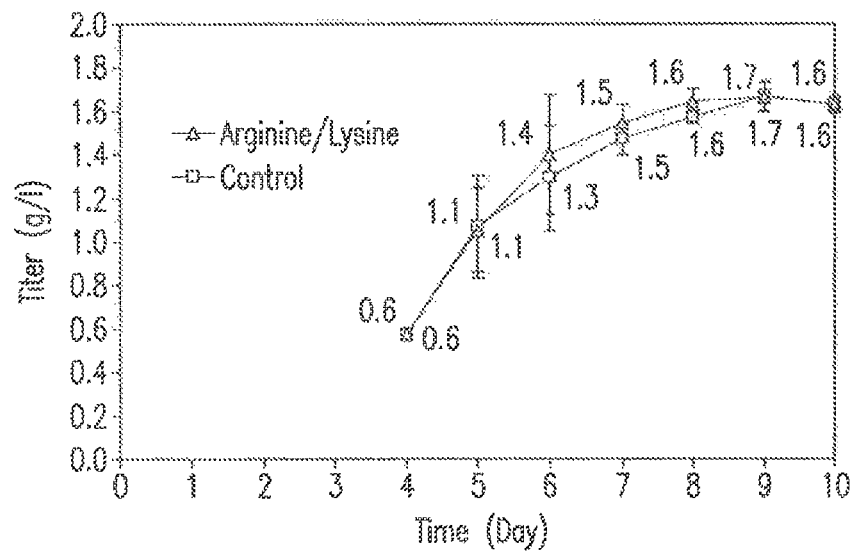

FIG. 65 depicts the effect of increased arginine and lysine concentration in adalimumab producing cell line 3, media 1 on culture titer (n=3).

Figure 66:
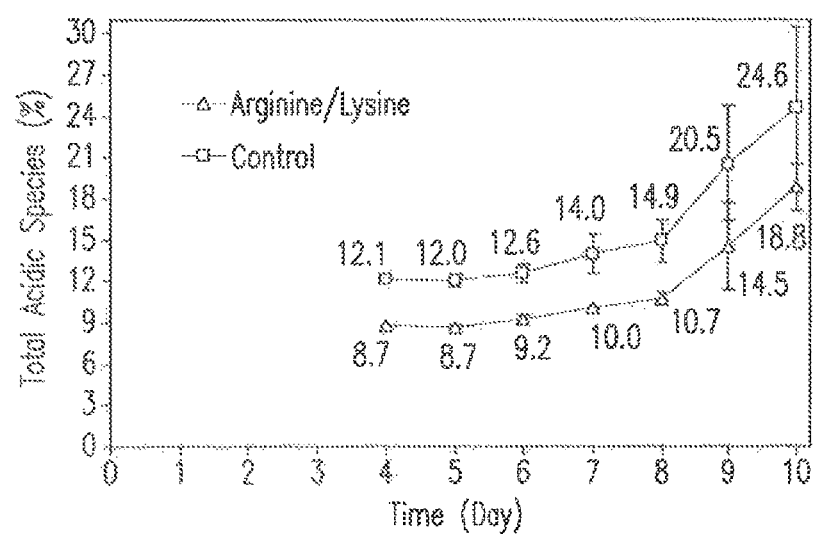

FIG. 66 depicts the effect of increased arginine and lysine concentration in adalimumab producing cell line 1, media 1 on WCX 10 profile total acidic regions (n=2).

Figure 67:
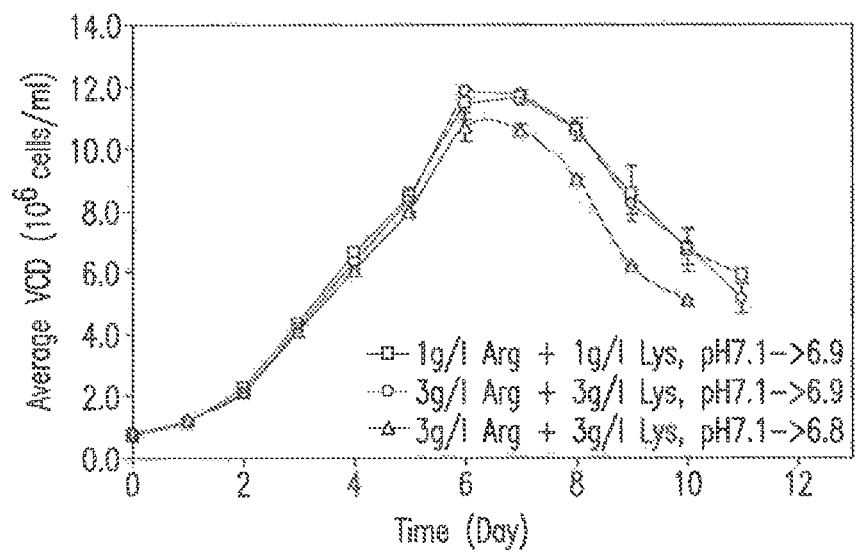

FIG. 67 depicts the effect of arginine, lysine and pH modulation to adalimumab producing cell line 1, media 1 on viable cell density (n=2).

Figure 68:
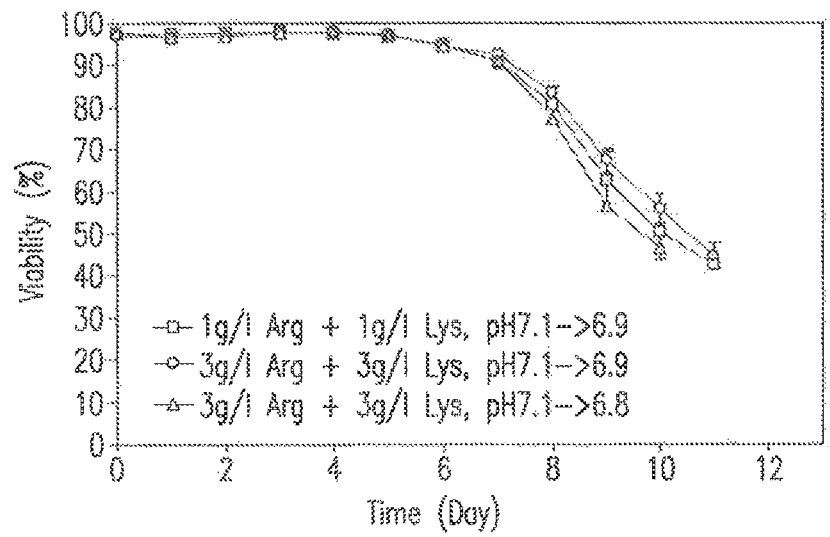

FIG. 68 depicts the effect of arginine, lysine and pH modulation to adalimumab producing cell line 3, media 1 on viability (n=2).

Figure 69:
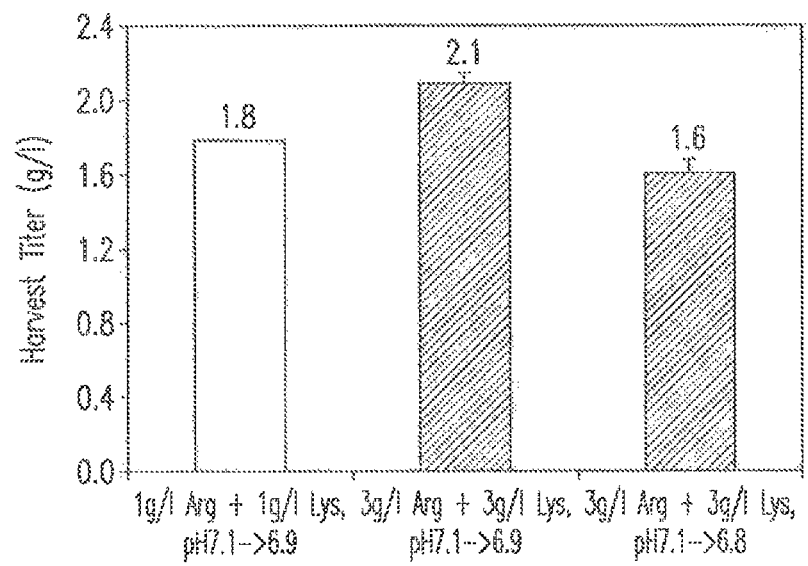

FIG. 69 depicts the effect of arginine, lysine and pH modulation to adalimumab producing cell line 3, media 1 on culture titer (n=2).

Figure 70:
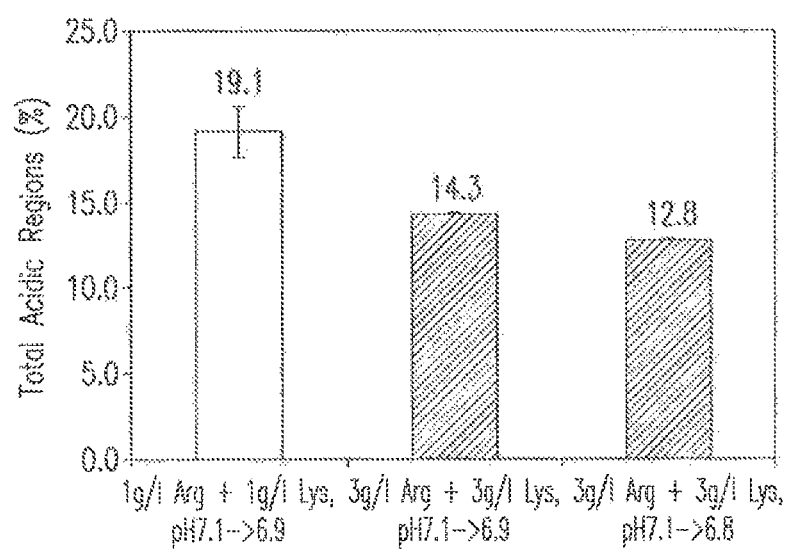

FIG. 70 depicts the effect of arginine, lysine and pH modulation to adalimumab producing cell line 1, media 1 on WCX 10 profile total acidic regions (n=2).

Figure 71:
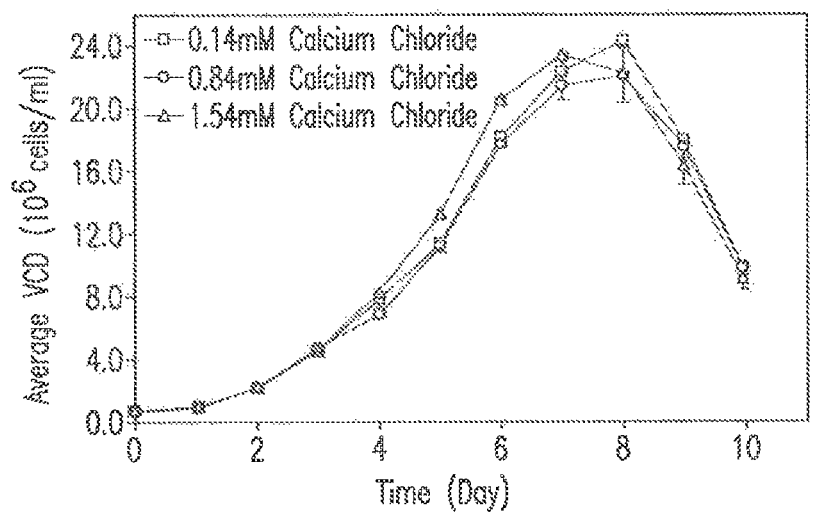

FIG. 71 depicts the effect of total calcium concentration in adalimumab producing cell line 2, media 1 on viable cell density (n=2).

Figure 72:
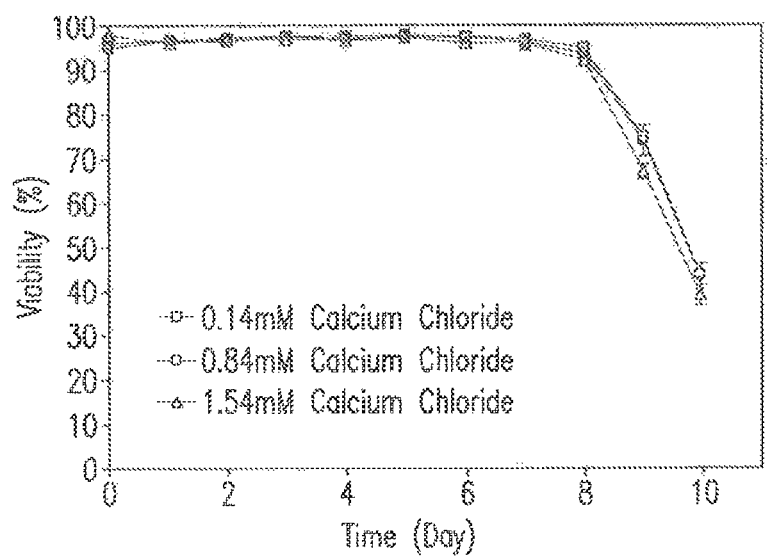

FIG. 72 depicts the effect of total calcium concentration in adalimumab producing cell line 2, media 1 on viability (n=2).

Figure 73:
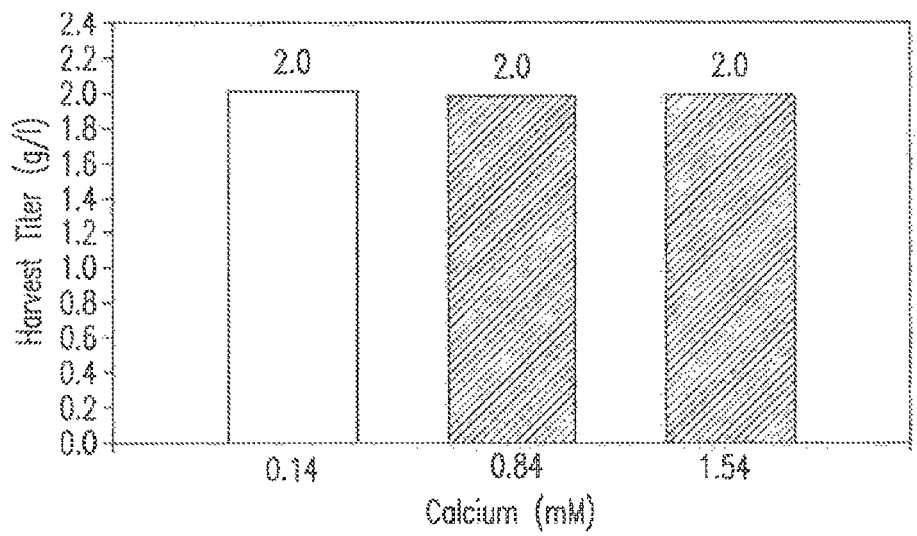

FIG. 73 depicts the effect of total calcium concentration in adalimumab producing cell line 2, media 1 on harvest titer (n=2).

Figure 74:
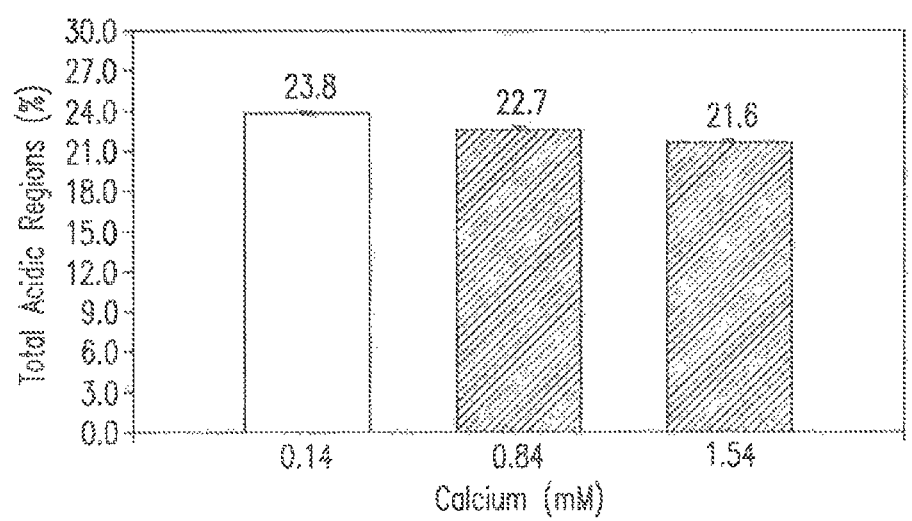

FIG. 74 depicts the effect of total calcium concentration in adalimumab producing cell line 2, media 1 on WCX 10 profile total acidic regions (n=2).

Figure 75:
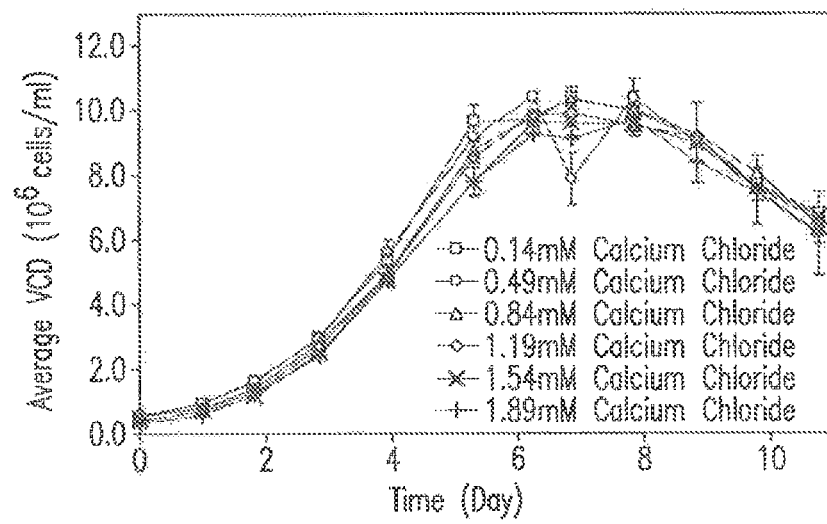

FIG. 75 depicts the effect of total calcium concentration in adalimumab producing cell line 3, media 1 on viable cell density (n=2).

Figure 76:
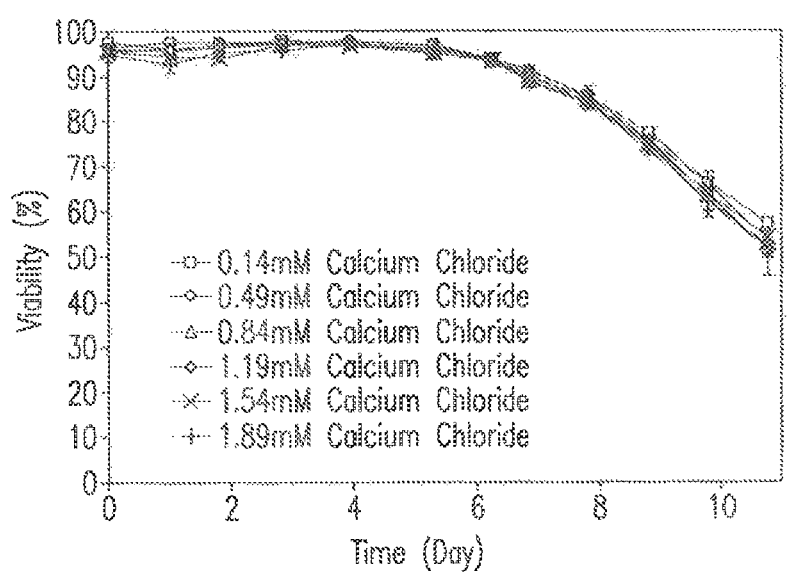

FIG. 76 depicts the effect of total calcium concentration in adalimumab producing cell line 3, media 1 on viability (n=2).

Figure 77:
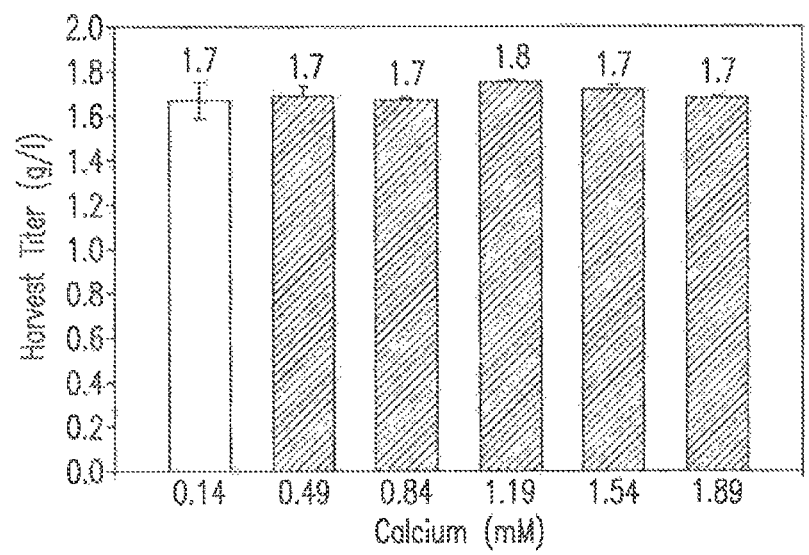

FIG. 77 depicts the effect of total calcium concentration in adalimumab producing cell line 3, media 1 on harvest titer (n=2)

Figure 78:
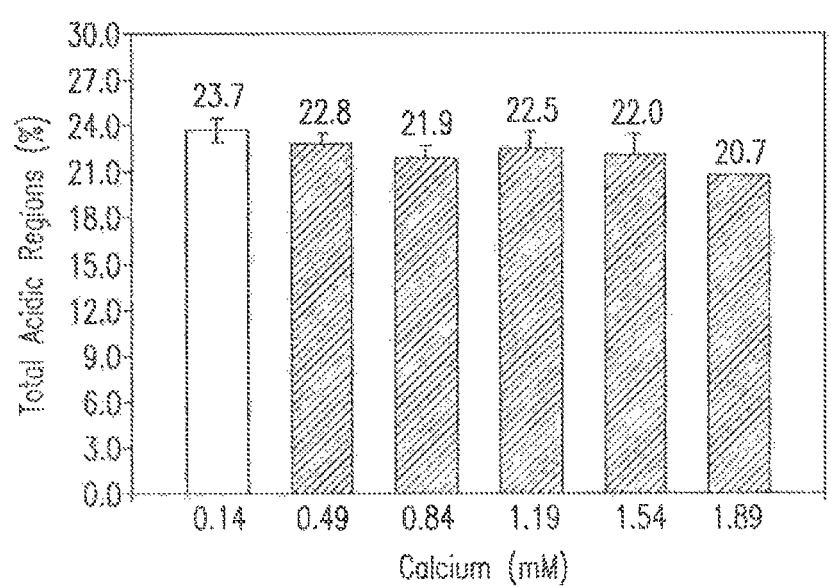

FIG. 78 depicts the effect of total calcium concentration in adalimumab producing cell line 3, media 1 on WCX 10 profile total acidic regions (n=2).

Figure 79:
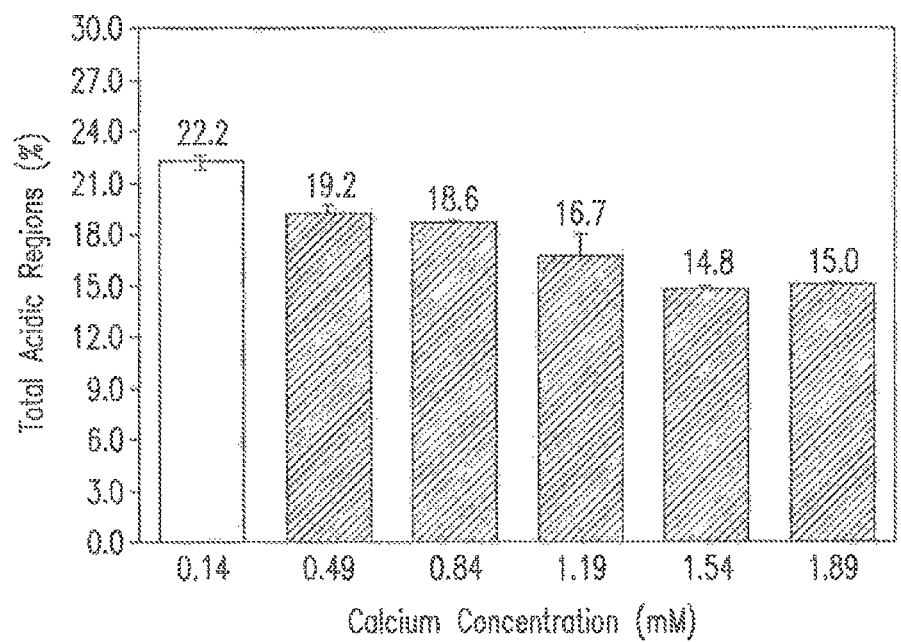

FIG. 79 depicts the effect of total calcium concentration in adalimumab producing cell line 1, media 1 on WCX 10 profile total acidic regions (n=2).

Figure 80:
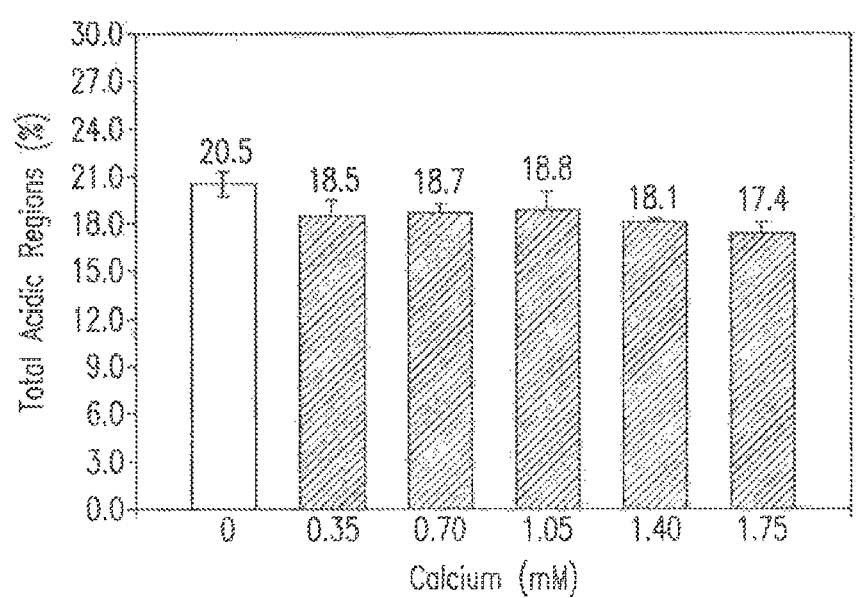

FIG. 80 depicts the effect of calcium addition to adalimumab producing cell line 1, media 2 on WCX-10 profile total acidic regions (n=2).

Figure 81:
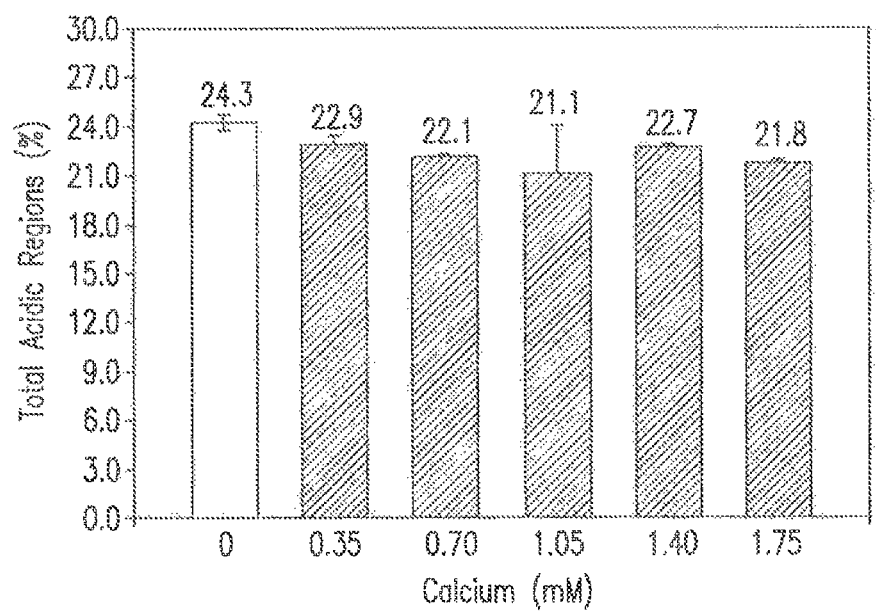

FIG. 81 depicts the effect of calcium addition to adalimumab producing cell line 2, media 3 on WCX-10 profile total acidic regions (n=2).

Figure 82:
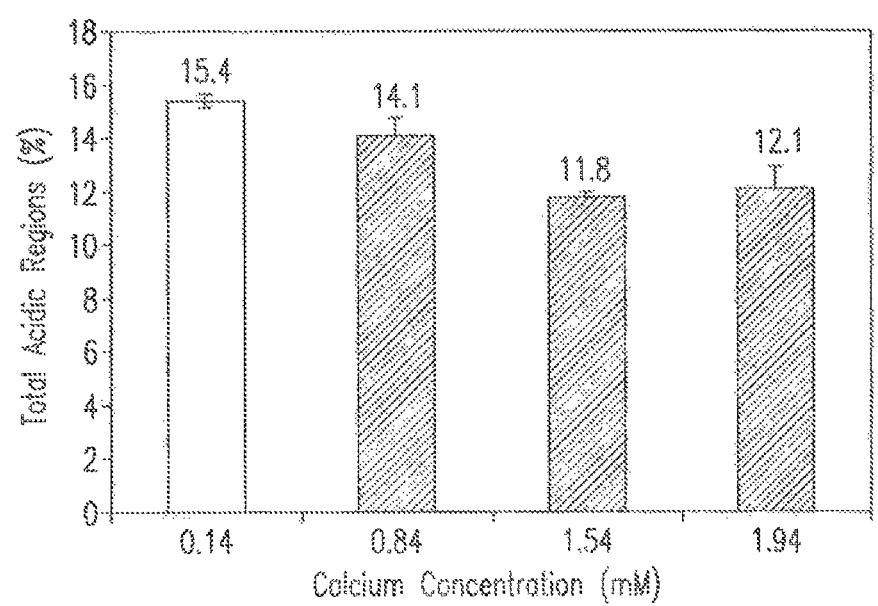

FIG. 82 depicts the effect of total calcium concentration in mAB1 producing cell line on WCX-10 profile total acidic regions (n=2).

Figure 83:
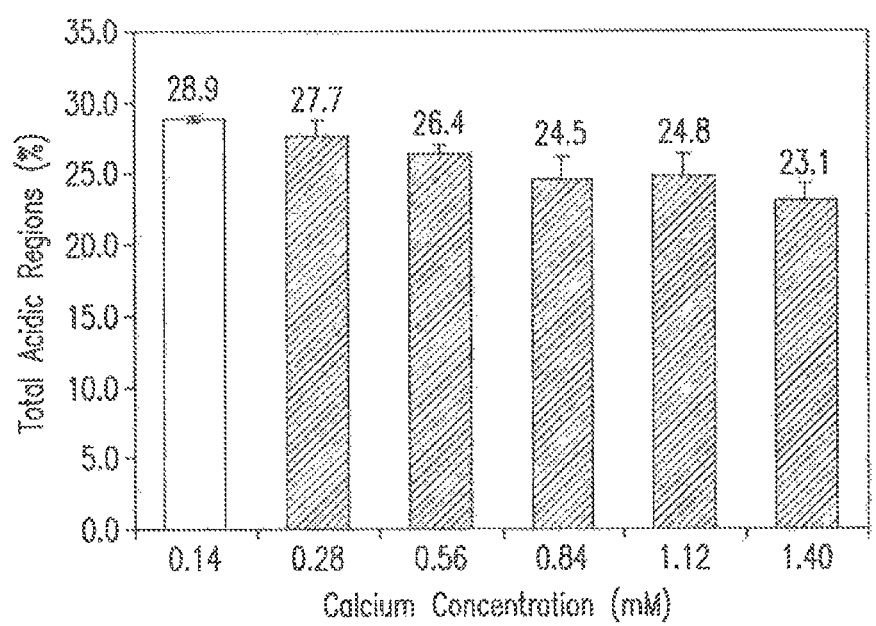

FIG. 83 depicts the effect of total calcium concentration in mAB2 producing cell line on WCX-10 profile total acidic regions (n=2).

Figure 84:
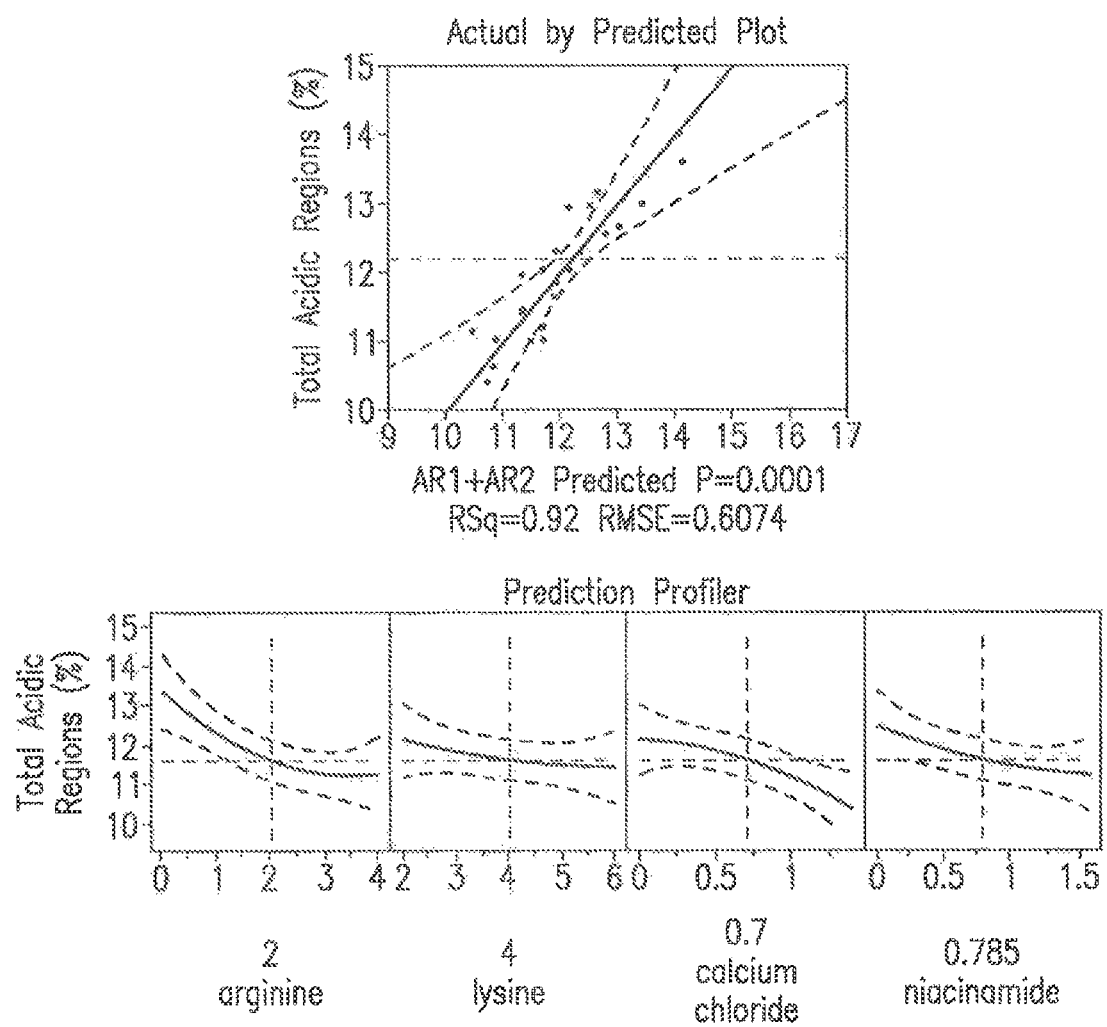

FIG. 84 depicts the effect of multiple amino acid additions to cell line 1, media 1 on WCX 10 profile total acidic regions a) overall prediction plot, b) prediction plots for each additive (n=2).

Figure 85:
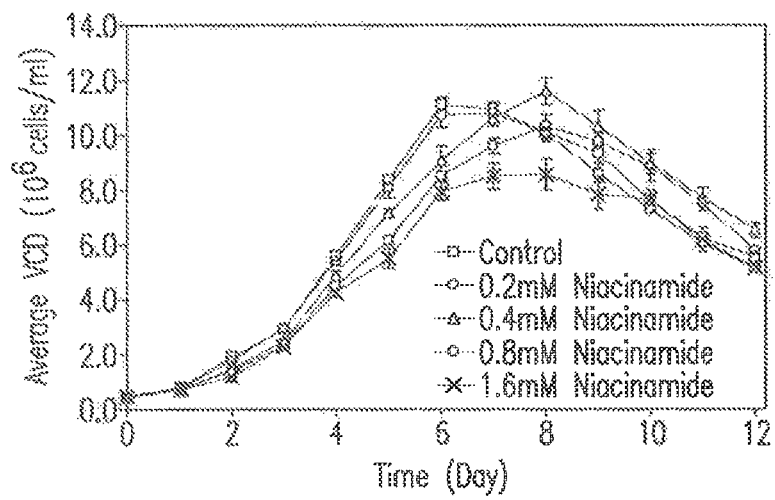

FIG. 85 depicts the effect of niacinamide addition to adalimumab producing cell line 1, media 1 on viable cell density (n=2).

Figure 86:
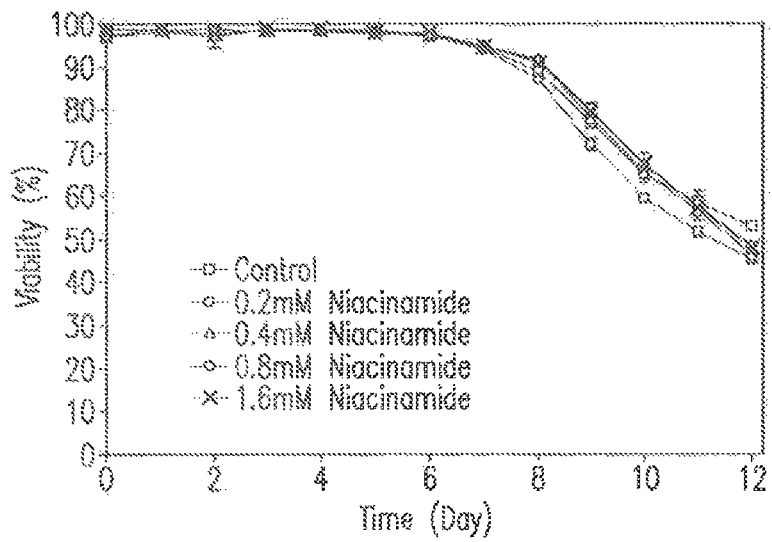

FIG. 86 depicts the effect of niacinamide addition to adalimumab producing cell line 1, media 1 on viability (n=2).

Figure 87:
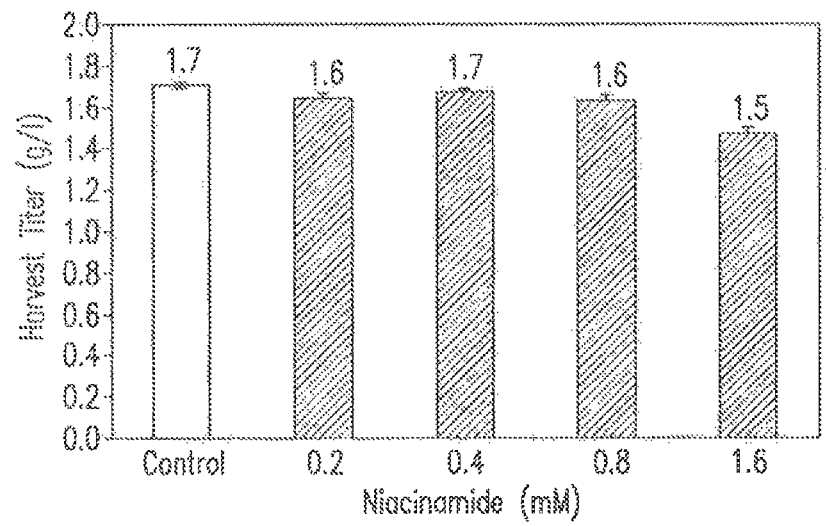

FIG. 87 depicts the effect of niacinamide addition to adalimumab producing cell line 1, media 1 on harvest titer (n=2).

Figure 88:
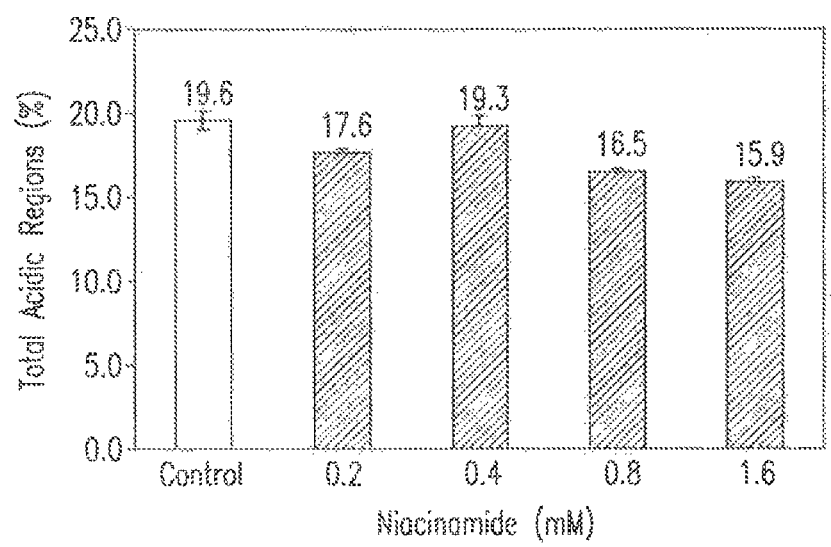

FIG. 88 depicts the effect of niacinamide addition to adalimumab producing cell line 1, media 1 on Day 11 WCX 10 profile total acidic regions (n=2).

Figure 89:
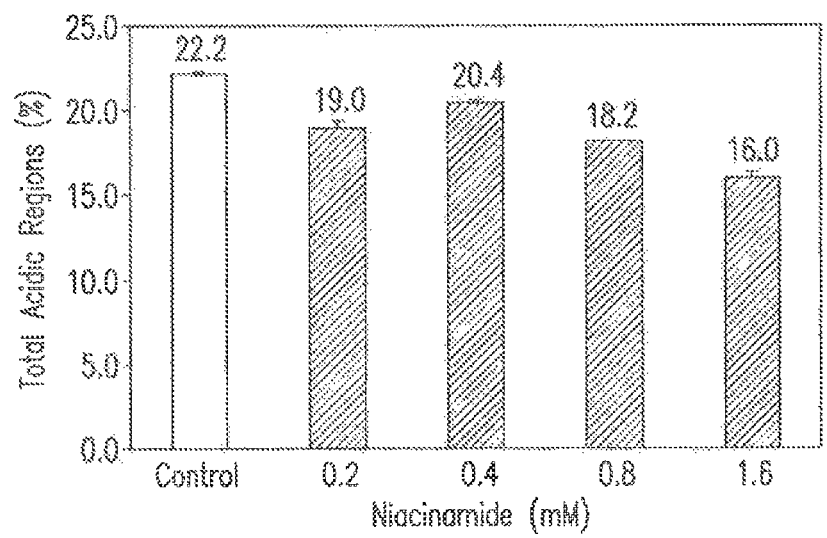

FIG. 89 depicts the effect of niacinamide addition to adalimumab producing cell line 1, media 1 on Day 12 WCX-10 profile total acidic regions (n=2).

Figure 90:
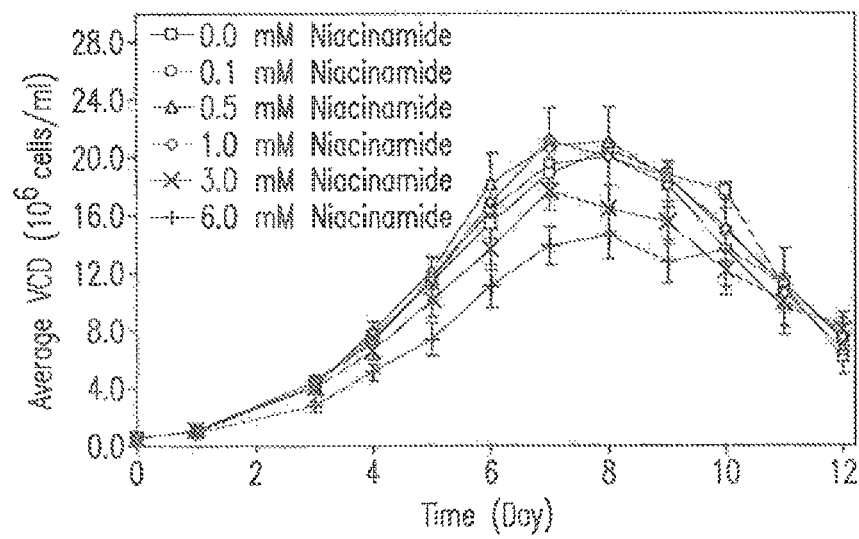

FIG. 90 depicts the effect of niacinamide addition to mAB2 producing cell line, media 1 on viable cell density (n=2).

Figure 91:
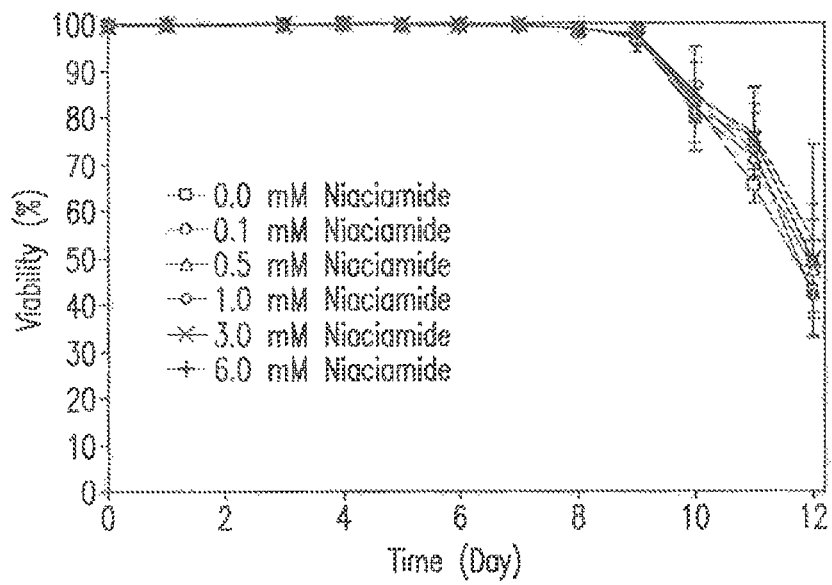

FIG. 91 depicts the effect of niacinamide addition to mAB2 producing cell line, media 1 on viability (n=2).

Figure 92:
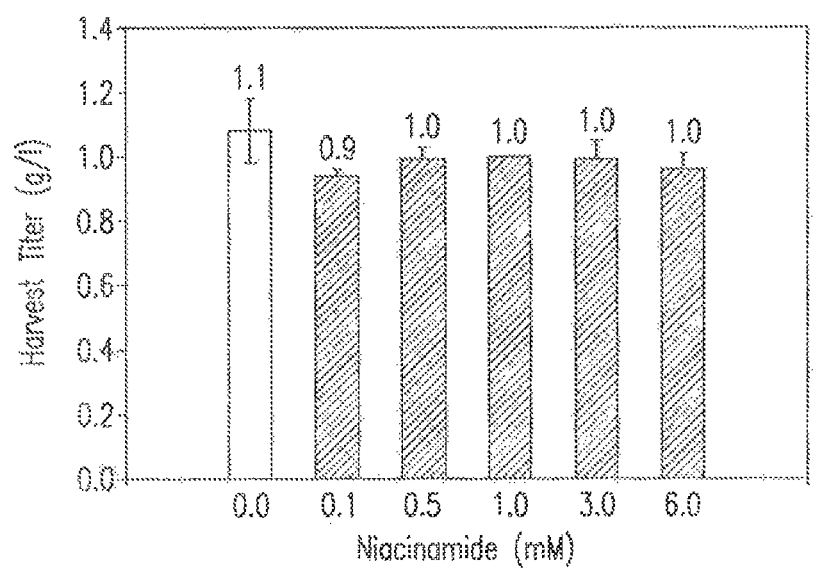

FIG. 92 depicts the effect of niacinamide addition to mAB2 producing cell line, media 1 on harvest titer (n=2).

Figure 93:
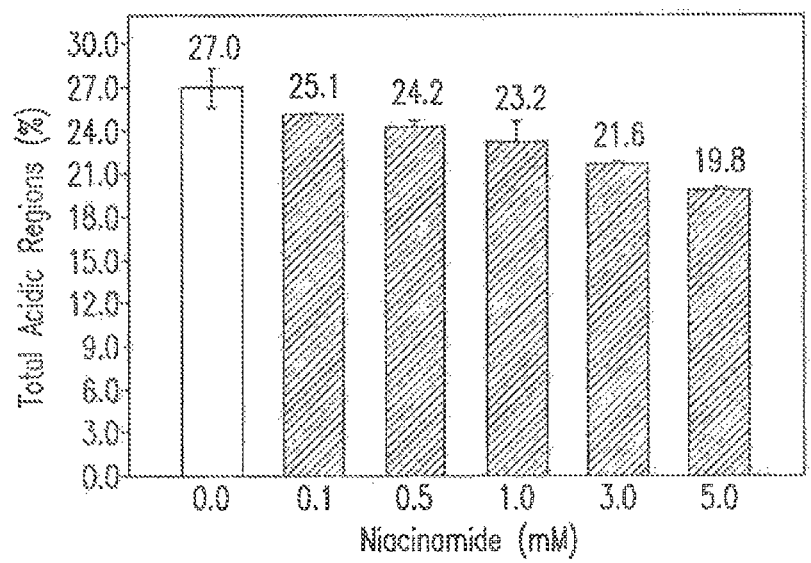

FIG. 93 depicts the effect of niacinamide addition to mAB2 producing cell line, media 1 on WCX 10 profile total acidic regions (n=2).

Figure 94:
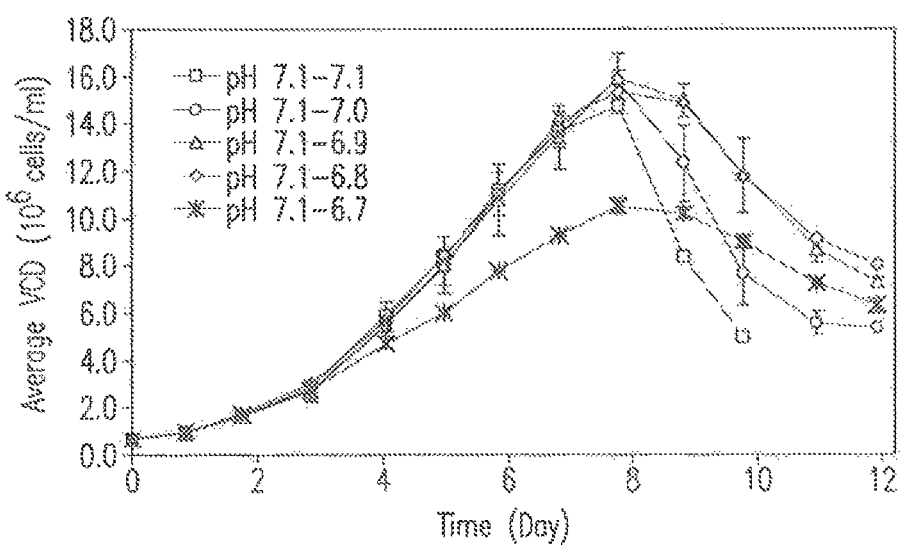

FIG. 94 depicts the effect of pH modulation of adalimumab producing cell line 1, media 1 on viable cell density (n=2).

Figure 95:
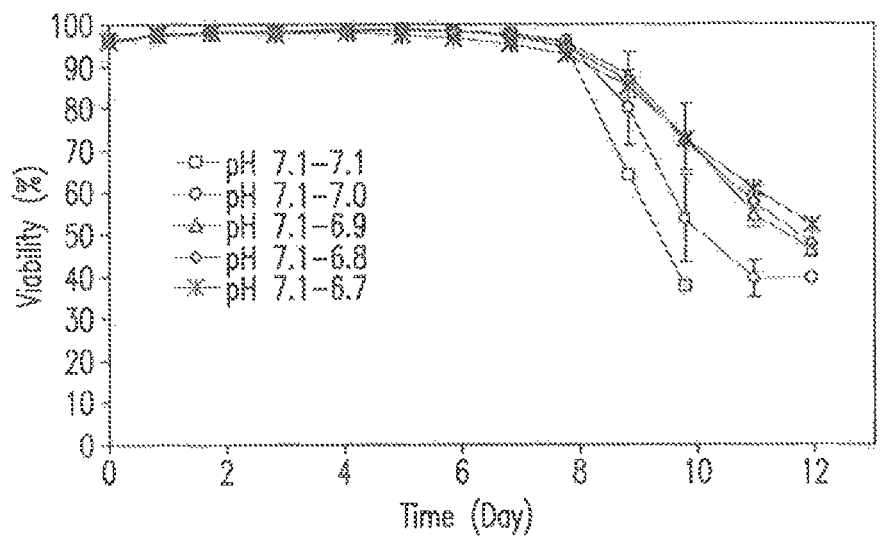

FIG. 95 depicts the effect of pH modulation adalimumab producing cell line 1, media 1 on viability (n=2).

Figure 96:
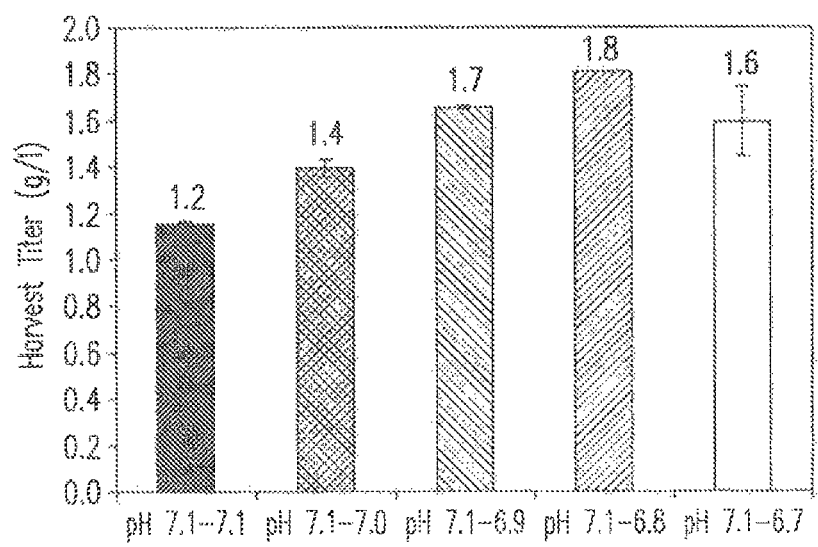

FIG. 96 depicts the effect of pH modulation of adalimumab producing cell line 1, media 1 on harvest titer (n=2).

Figure 97:
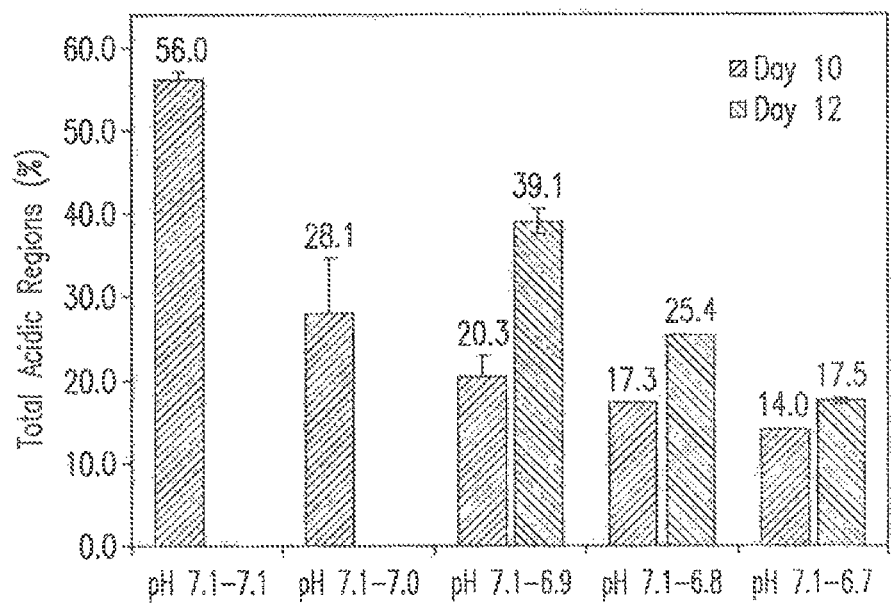

FIG. 97 depicts the effect of pH modulation of adalimumab producing cell line 1, media 1 on WCX 10 profile total acidic regions (n=2).

Figure 98:
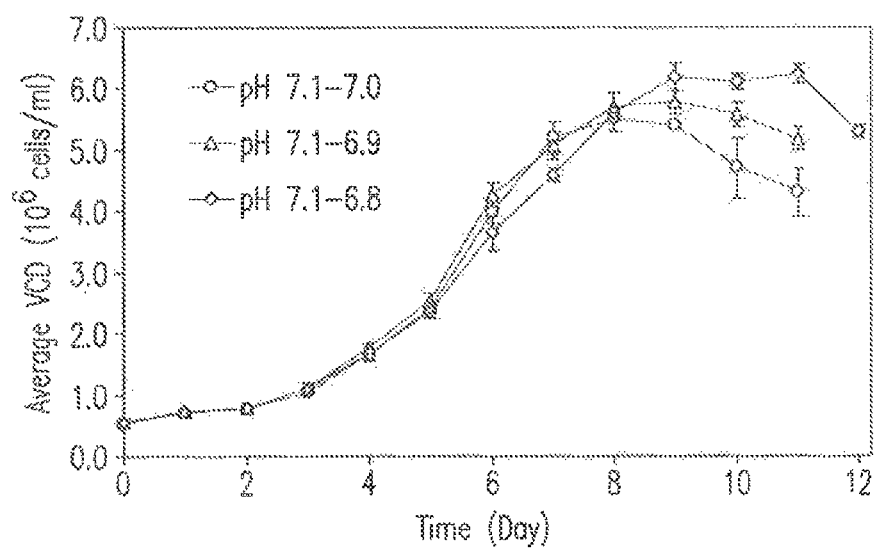

FIG. 98 depicts the effect of pH modulation of adalimumab producing cell line 1, media 2 on viable cell density (n=2).

Figure 99:
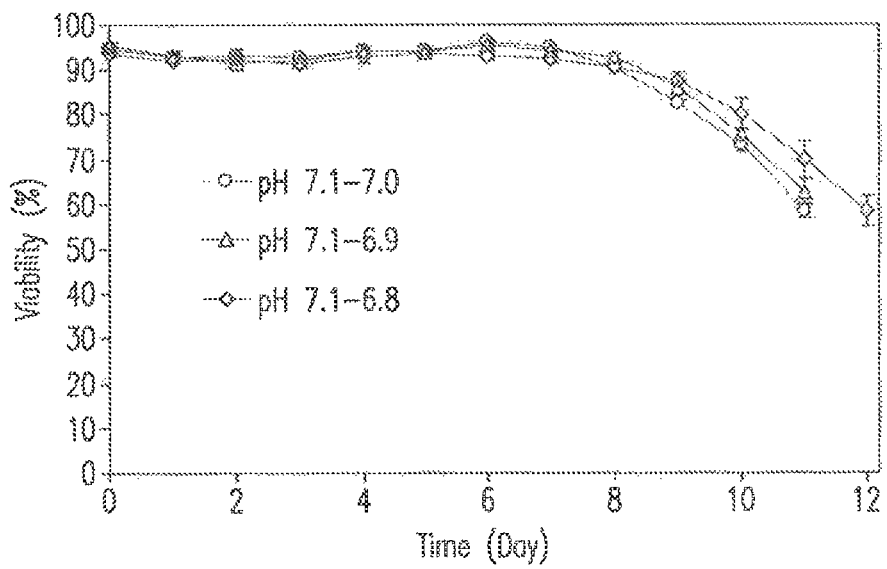

FIG. 99 depicts the effect of pH modulation addition of adalimumab producing adalimumab producing cell line 1, media 2 on viability (n=2).

Figure 100:
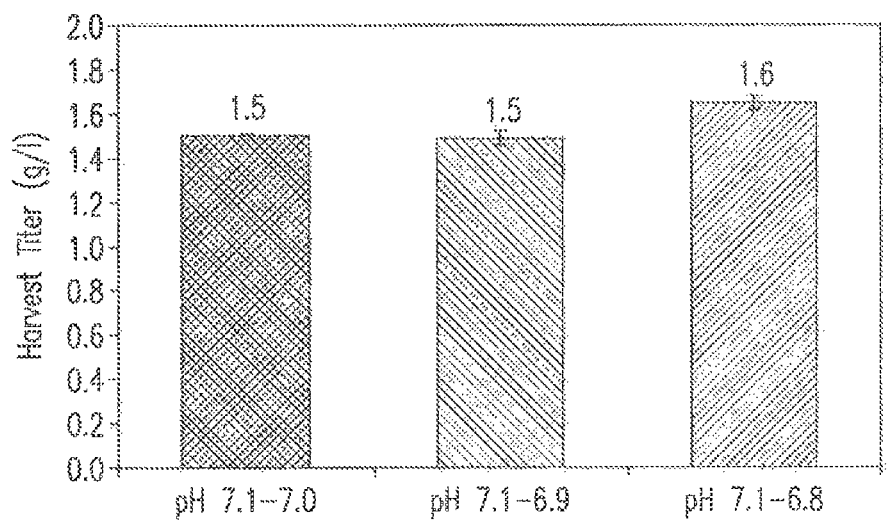

FIG. 100 depicts the effect of pH modulation of adalimumab producing cell line 1, media 2 on harvest titer (n=2).

Figure 101:
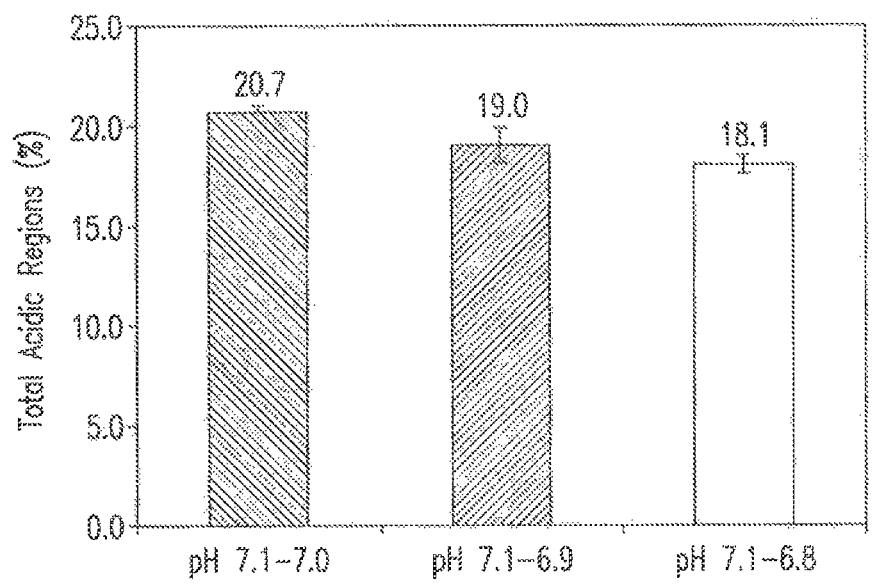

FIG. 101 depicts the effect of pH modulation of adalimumab producing cell line 1, media 2 on WCX 10 profile total acidic regions (n=2).

Figure 102:
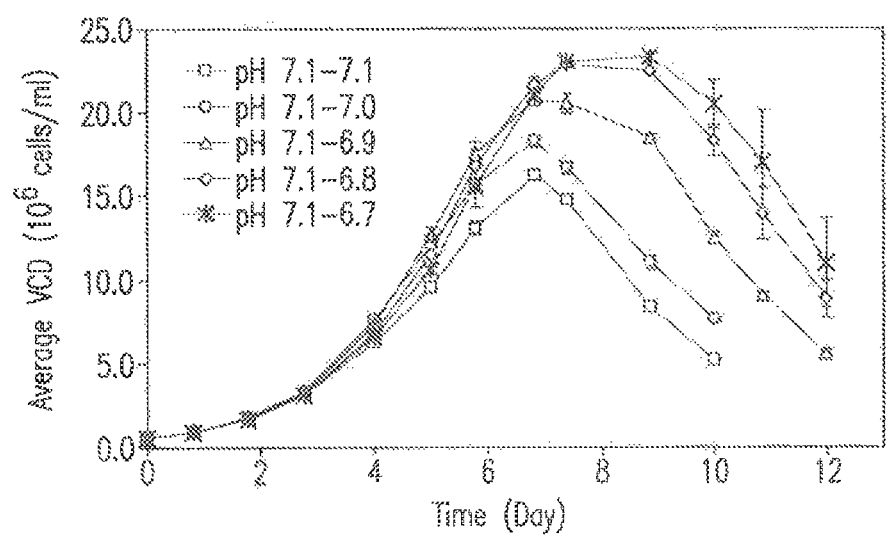

FIG. 102 depicts the effect of pH modulation of adalimumab producing cell line 3, media 1 on viable cell density (n=2).

Figure 103:
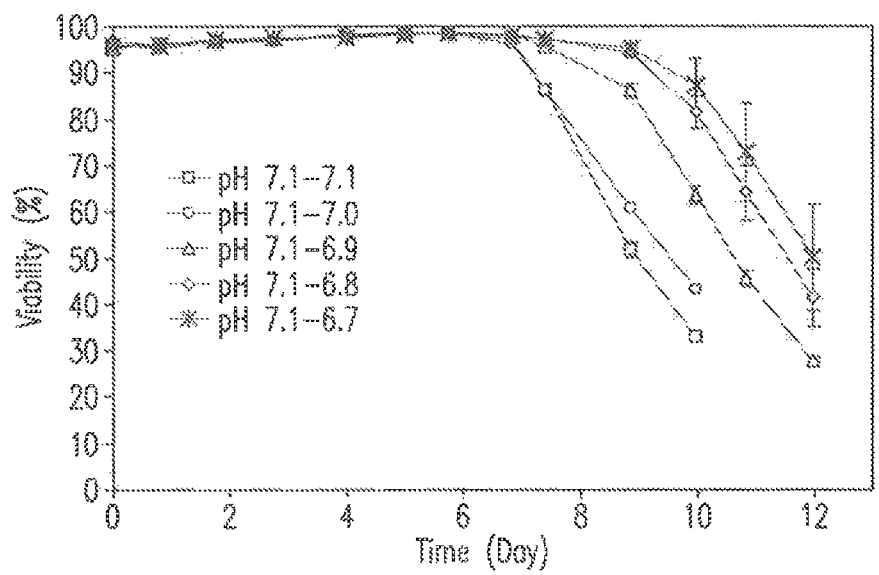

FIG. 103 depicts the effect of pH modulation adalimumab producing cell line 3, media 1 on viability (n=2).

Figure 104:
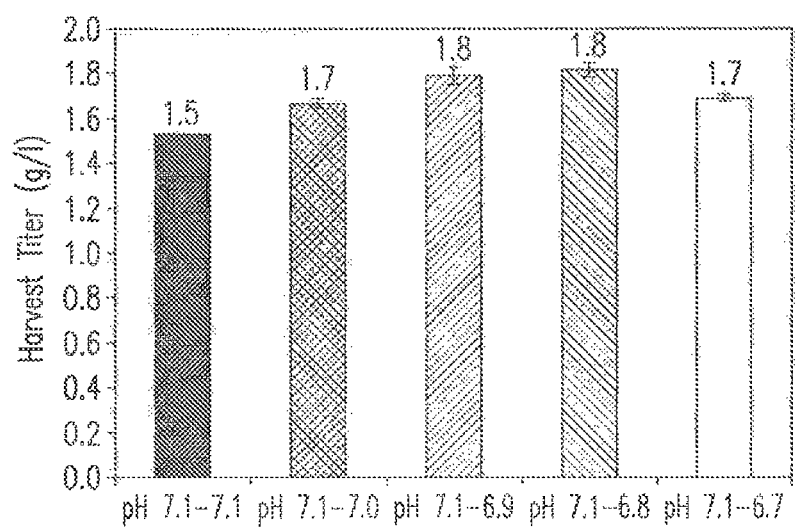

FIG. 104 depicts the effect of pH modulation of adalimumab producing cell line 3, media 1 on harvest titer (n=2).

Figure 105:
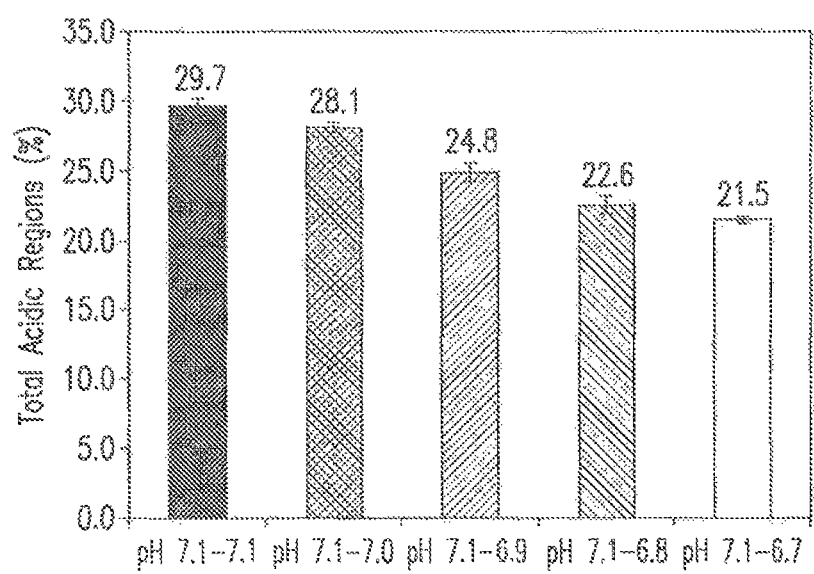

FIG. 105 depicts the effect of pH modulation of adalimumab producing cell line 3, media 1 on WCX 10 profile total acidic regions (n=2).

Figure 106:
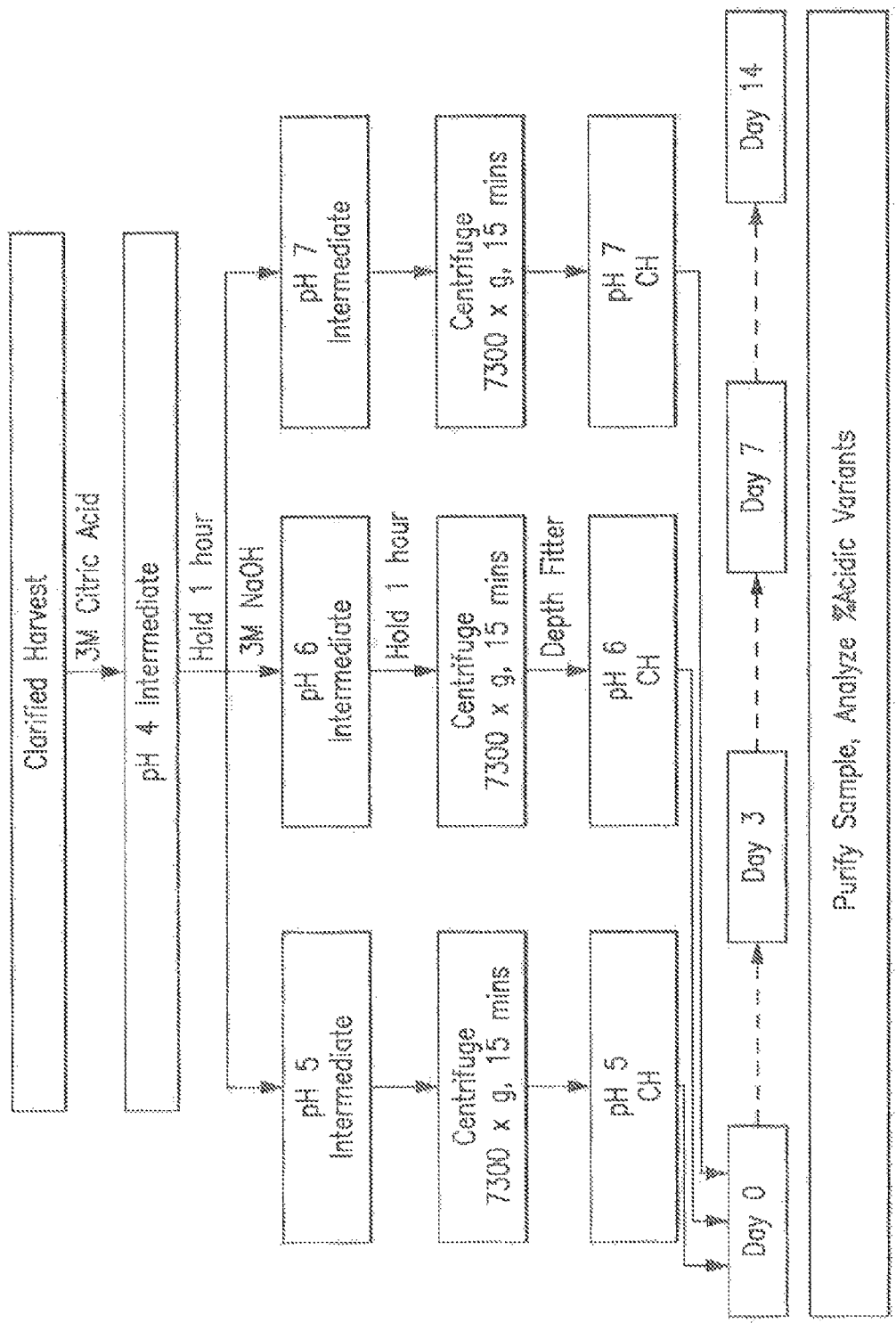

FIG. 106 depicts an acidification sample preparation scheme.

Figure 107:
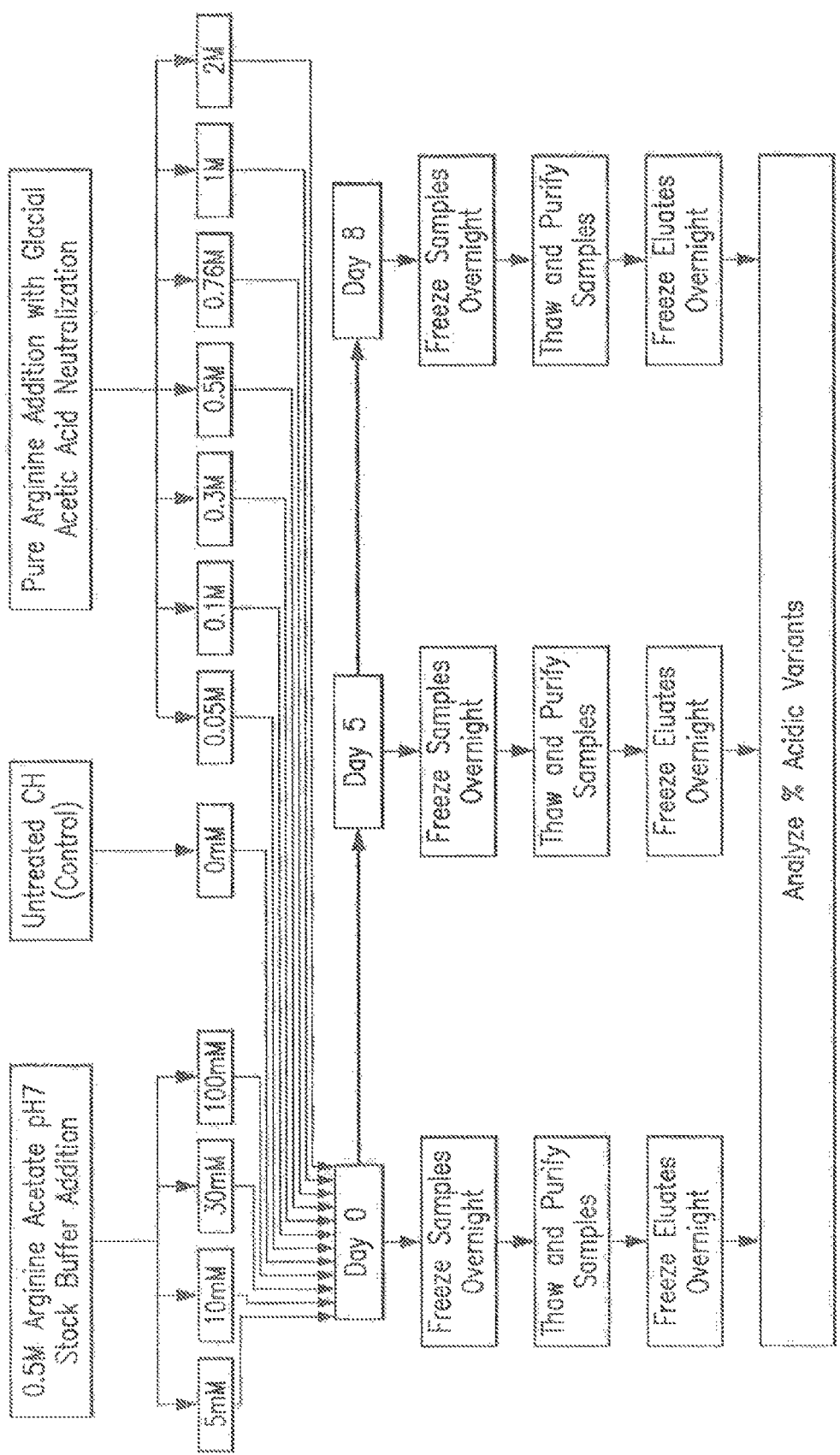

FIG. 107 depicts an arginine sample preparation scheme.

Figure 108:
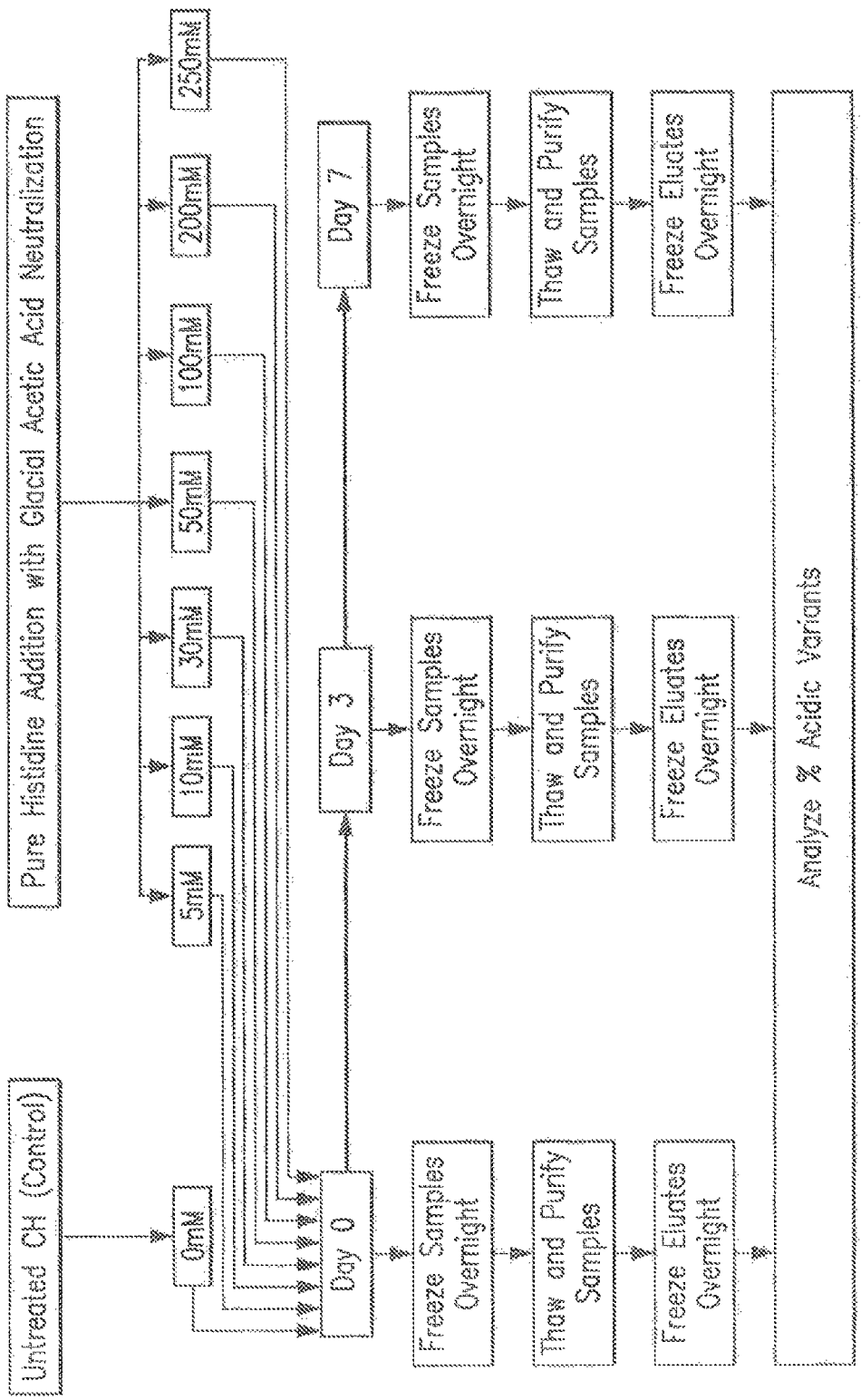

FIG. 108 depicts a histidine sample preparation scheme.

Figure 109:
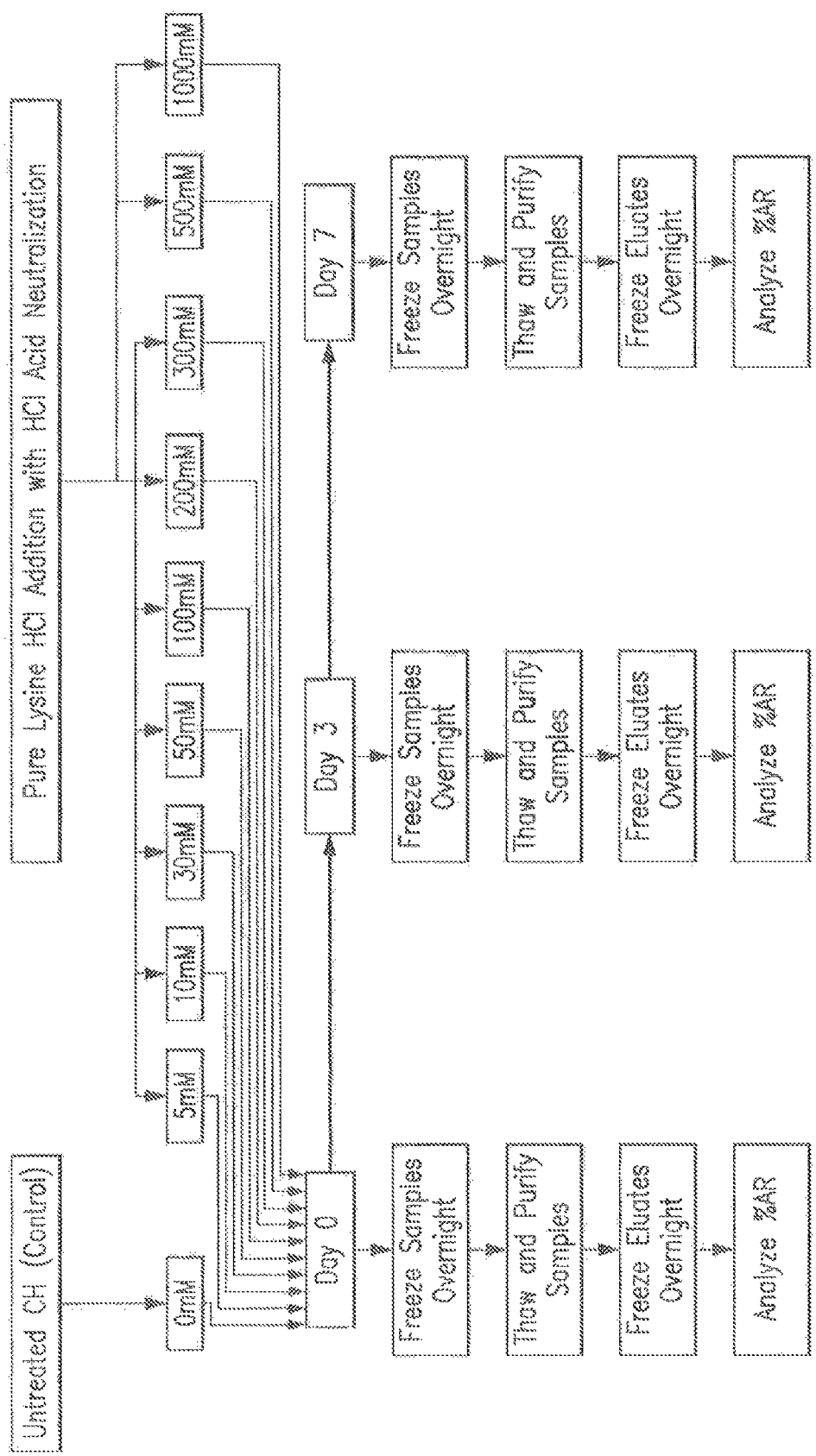

FIG. 109 depicts a lysine sample preparation scheme.

Figure 110:
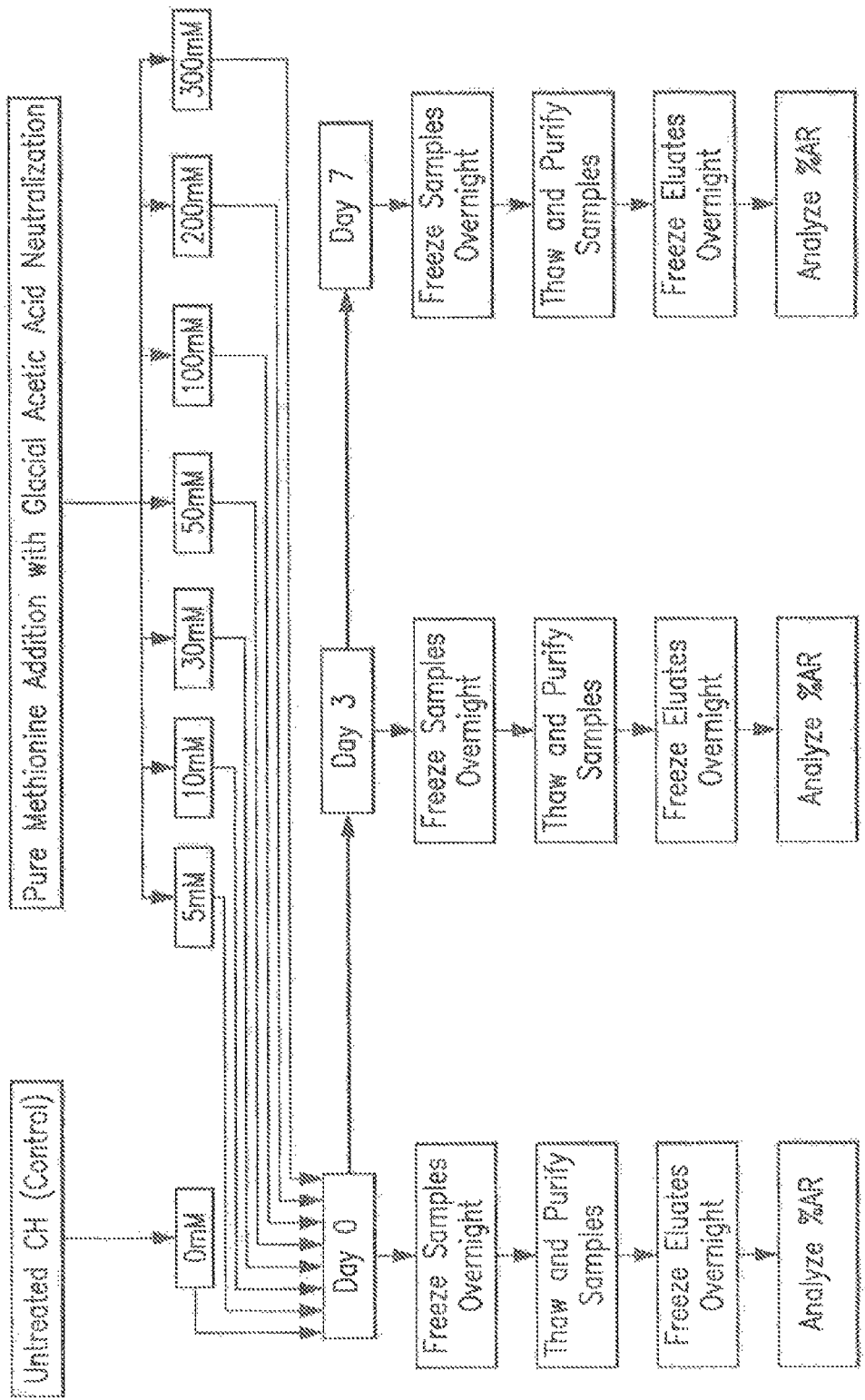

FIG. 110 depicts a methionine sample preparation scheme.

Figure 111:
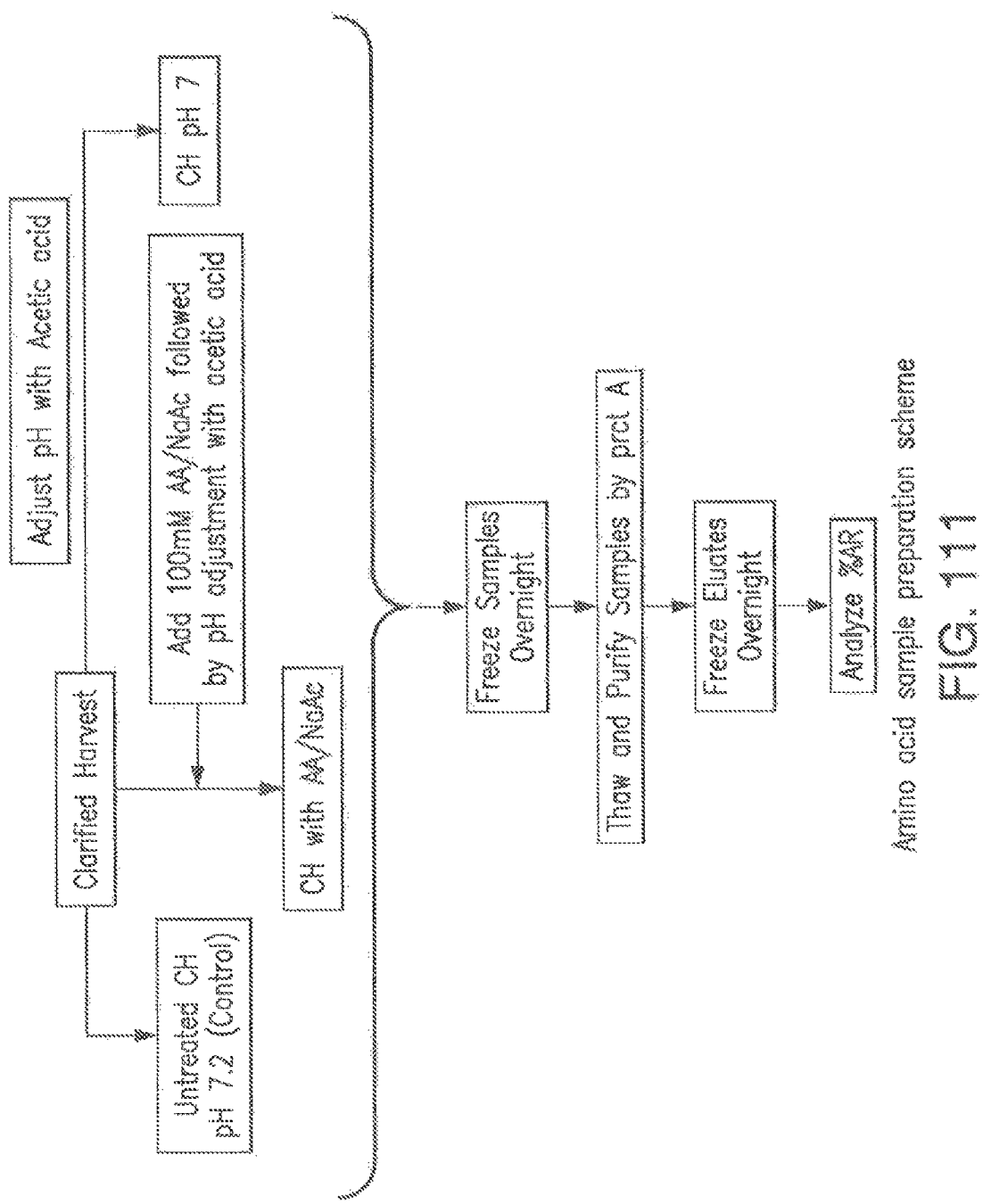

FIG. 111 depicts an amino acid sample preparation scheme.

Figure 112:
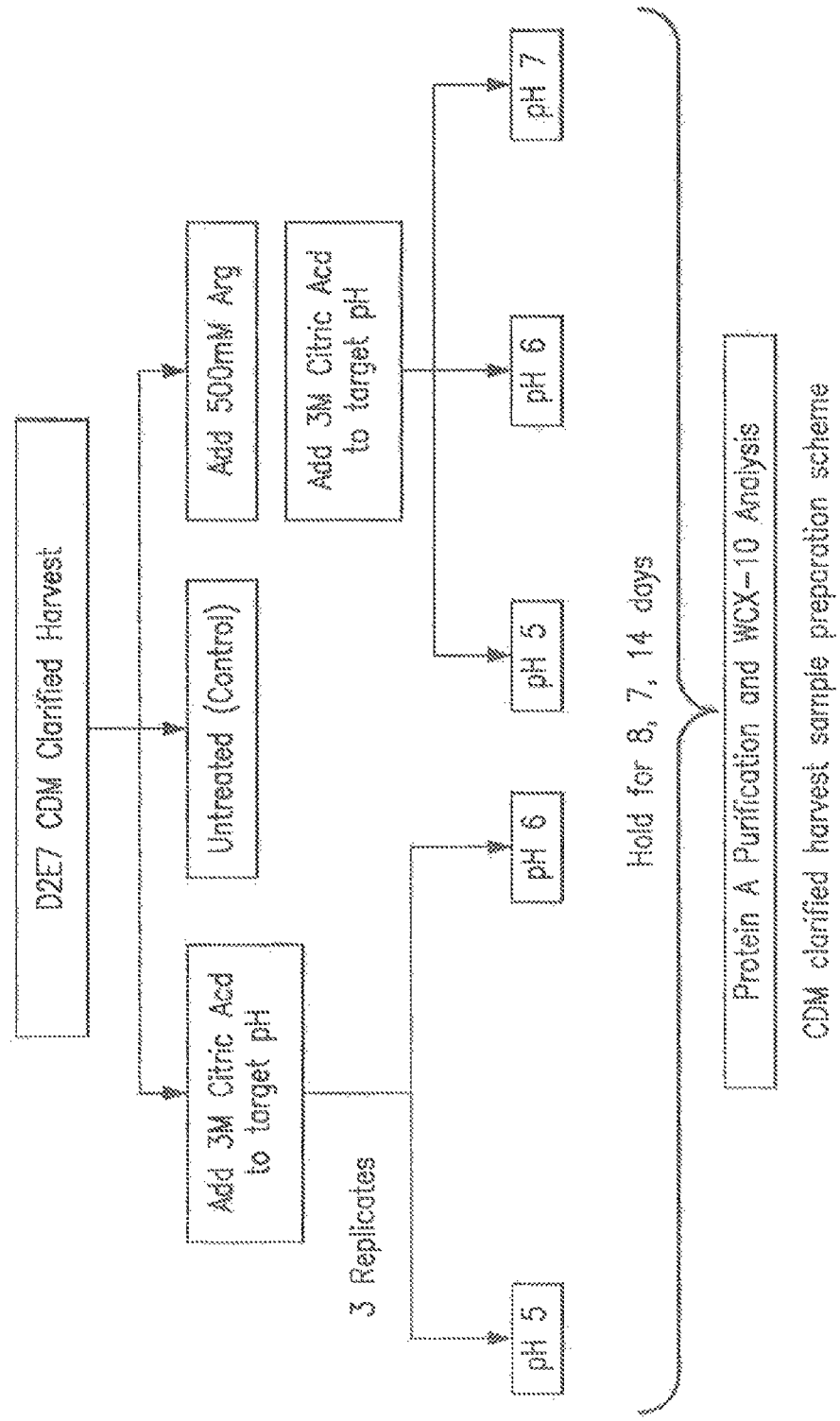

FIG. 112 depicts a CDM clarified harvest sample preparation scheme.

Figure 113:
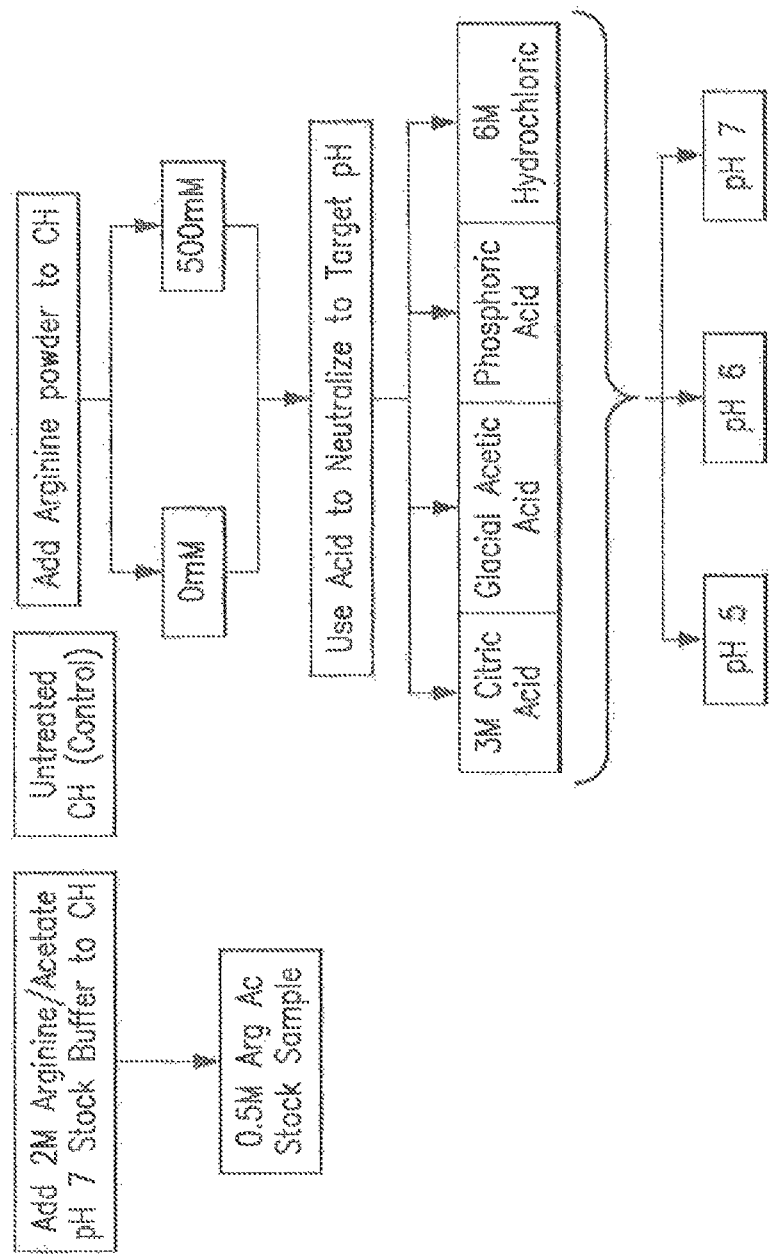

FIG. 113 depicts an acid-type pH study sample preparation scheme.

Figure 114:
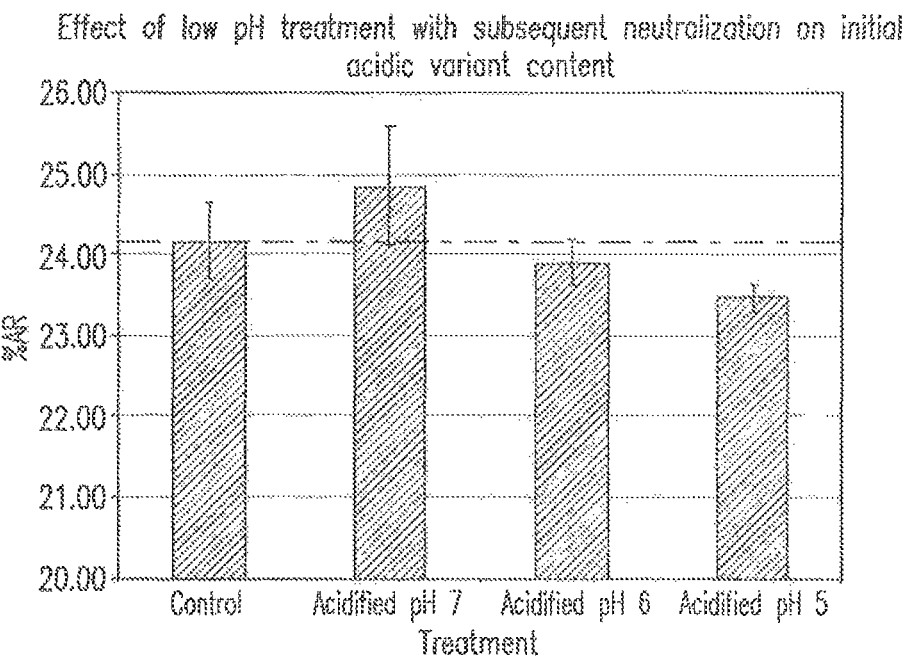

FIG. 114 depicts the effect of low pH treatment with subsequent neutralization on initial acidic variant content.

Figure 115:
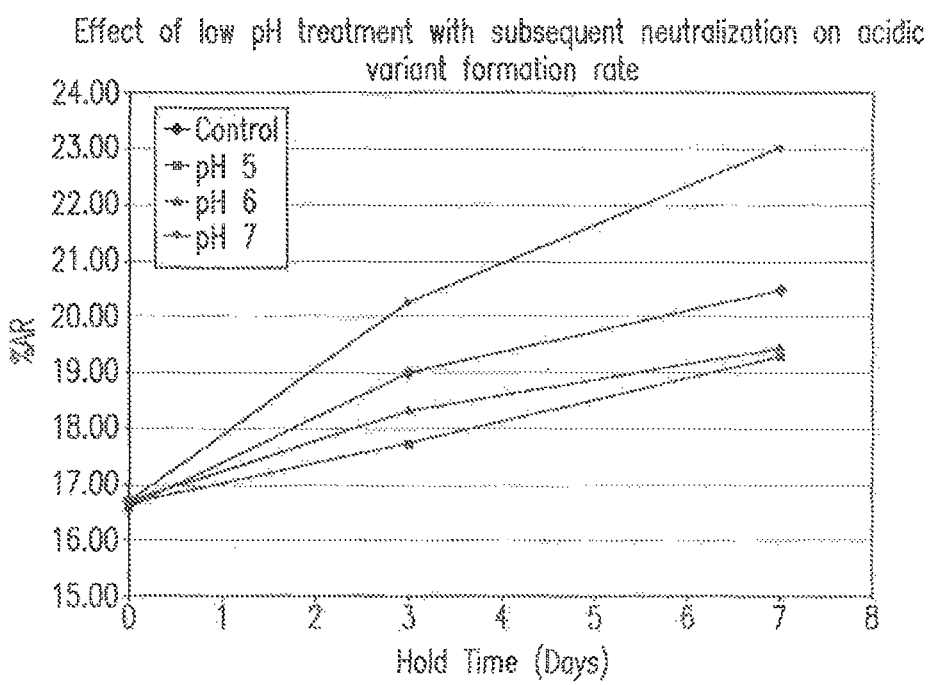

FIG. 115 depicts the effect of low pH treatment with subsequent neutralization on acidic variant formation rate.

Figure 116:
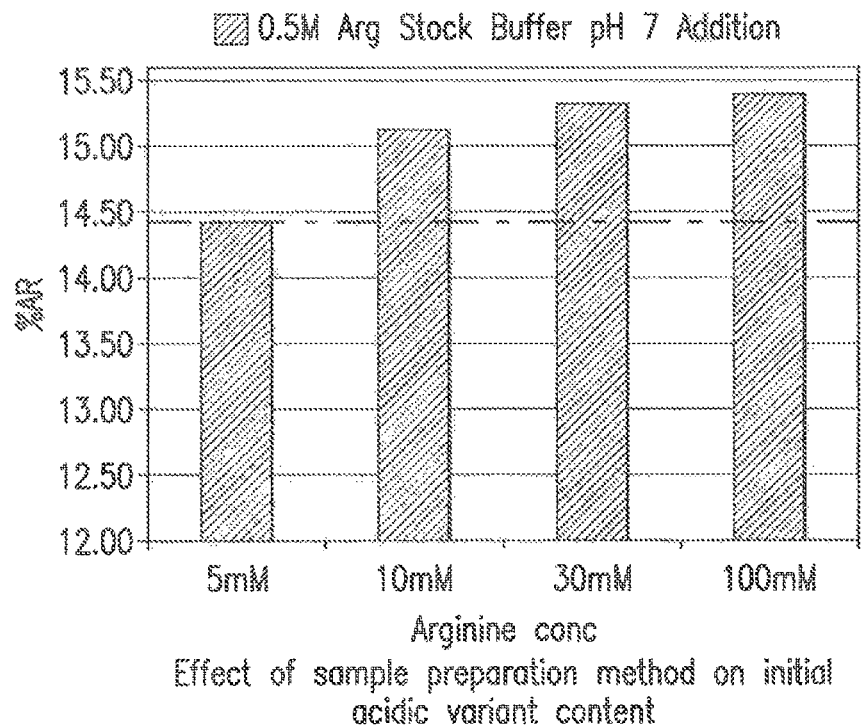

FIG. 116 depicts the effect of sample preparation method on initial acidic variant content.

Figure 117:
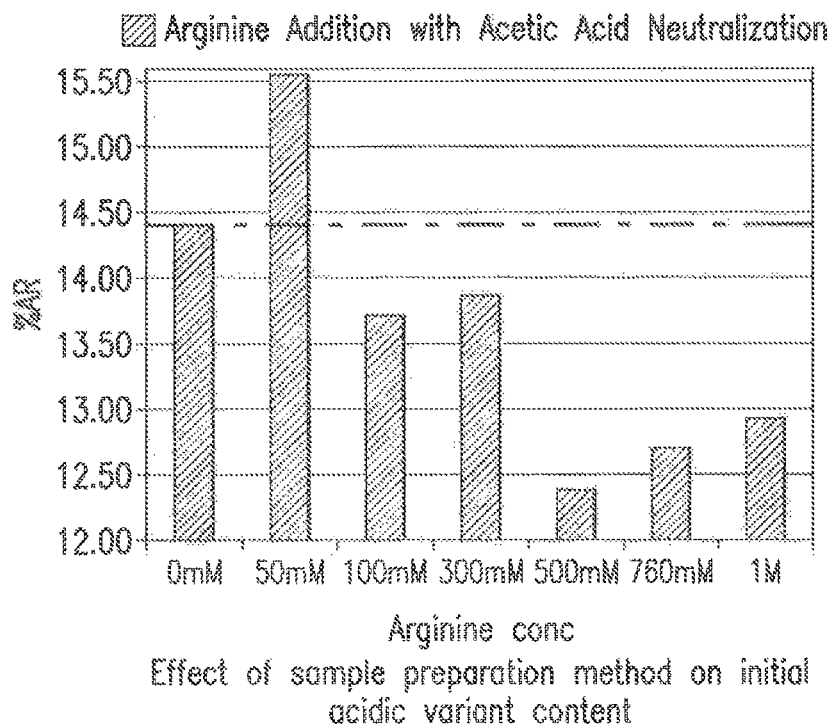

FIG. 117 depicts the effect of sample preparation method on initial acidic variant content.

Figure 118:
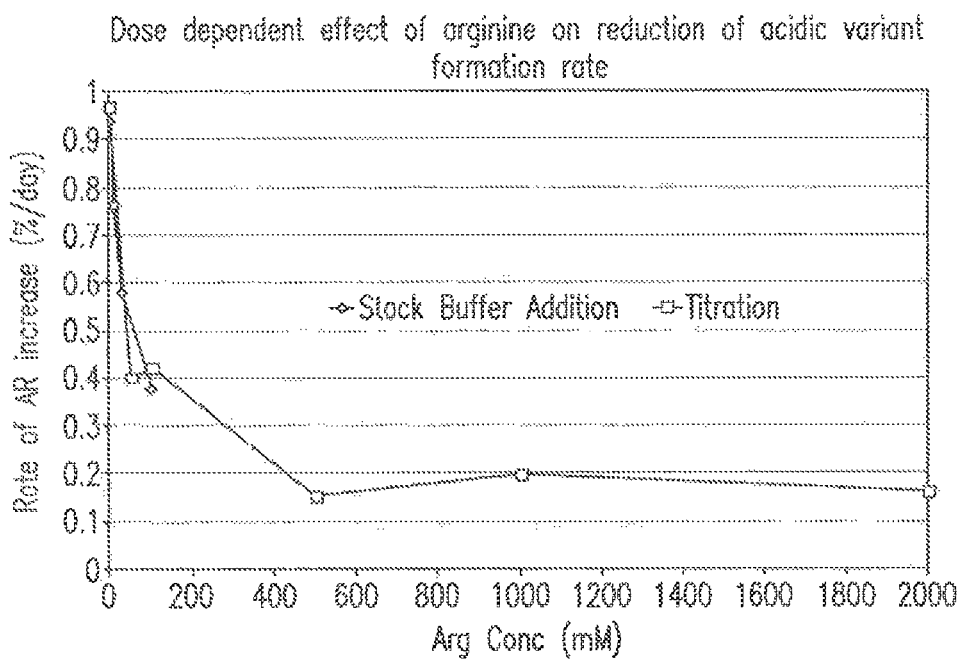

FIG. 118 depicts the dose dependent effect of arginine on reduction of acidic variant formation rate.

Figure 119:
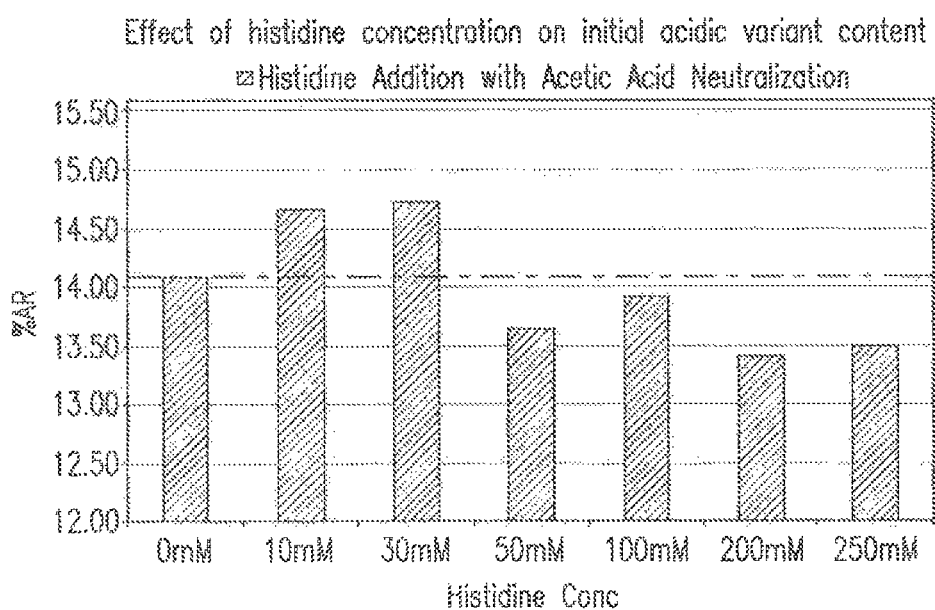

FIG. 119 depicts the effect of histidine concentration on initial acidic variant content.

Figure 120:
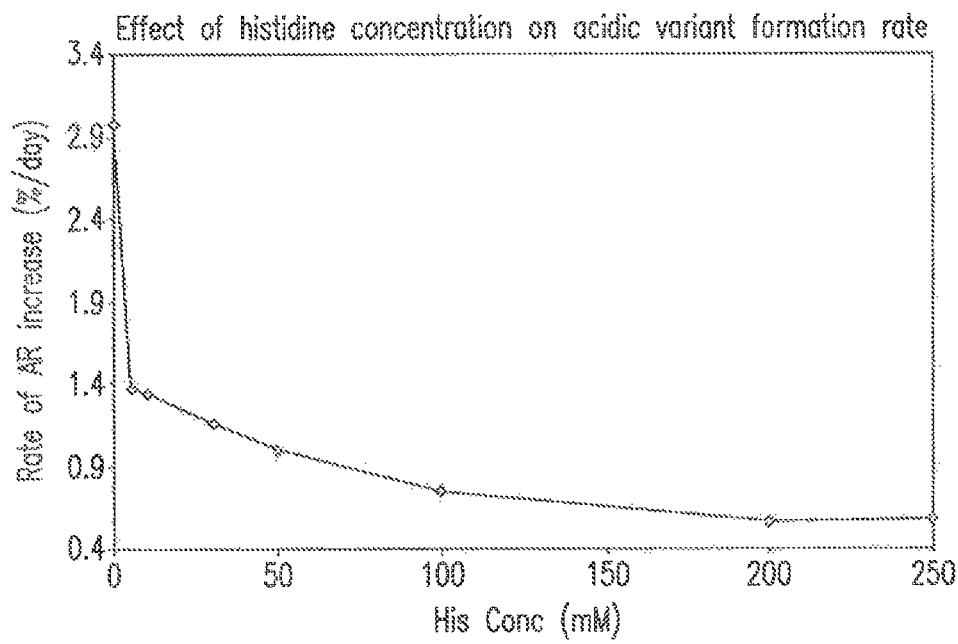

FIG. 120 depicts the effect of histidine concentration on acidic variant formation rate.

Figure 121:
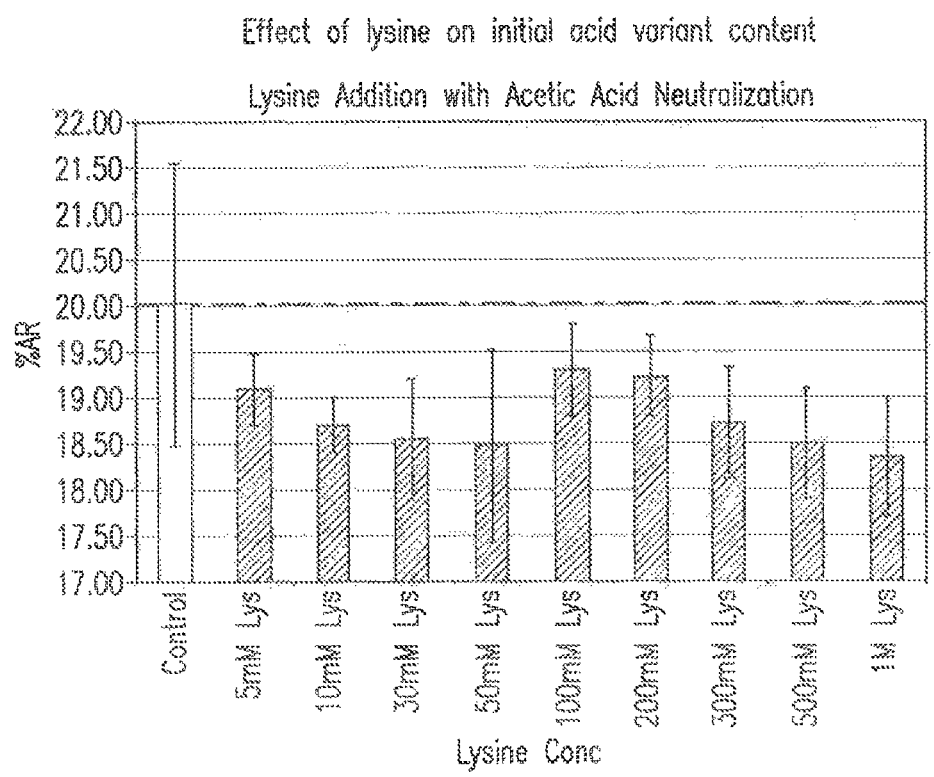

FIG. 121 depicts the effect of lysine on initial acid variant content.

Figure 122:
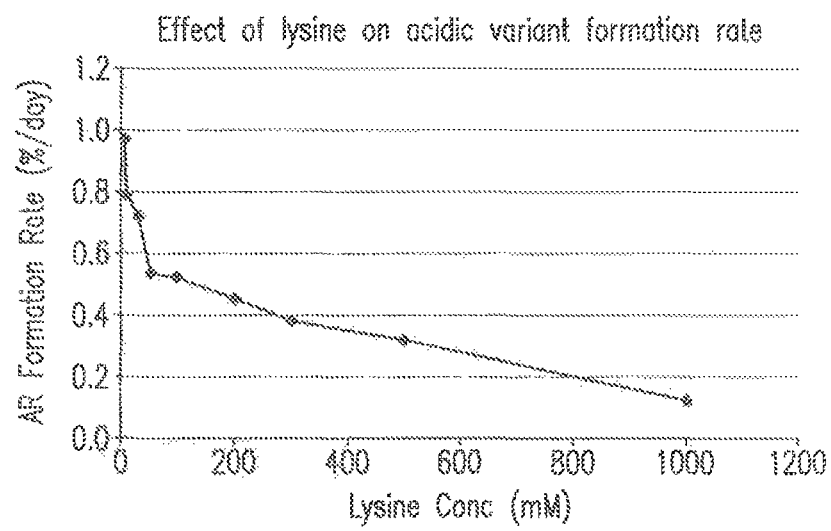

FIG. 122 depicts the effect of lysine on acidic variant formation rate.

Figure 123:
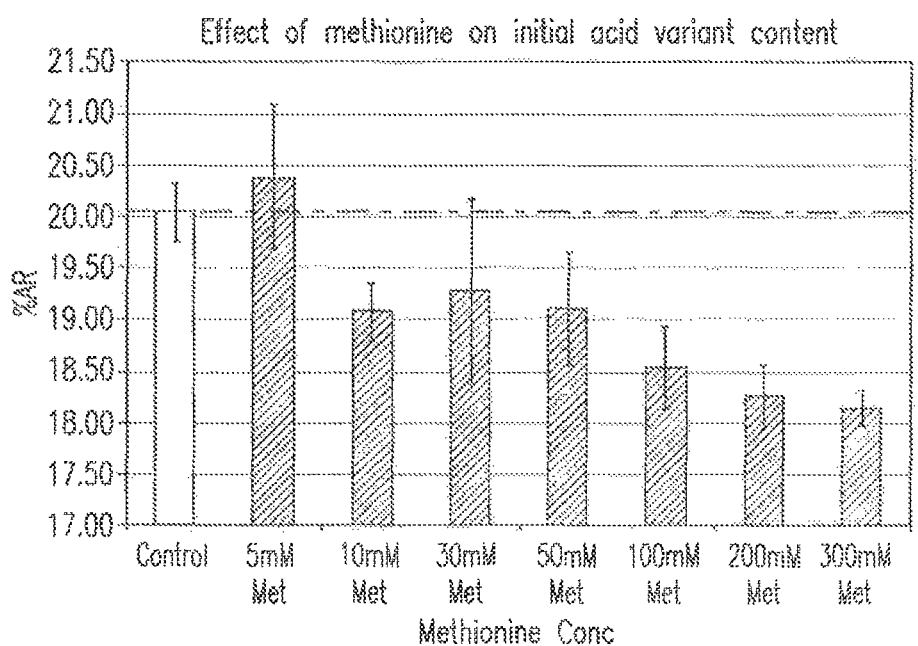

FIG. 123 depicts the effect of methionine on initial acid variant content.

Figure 124:
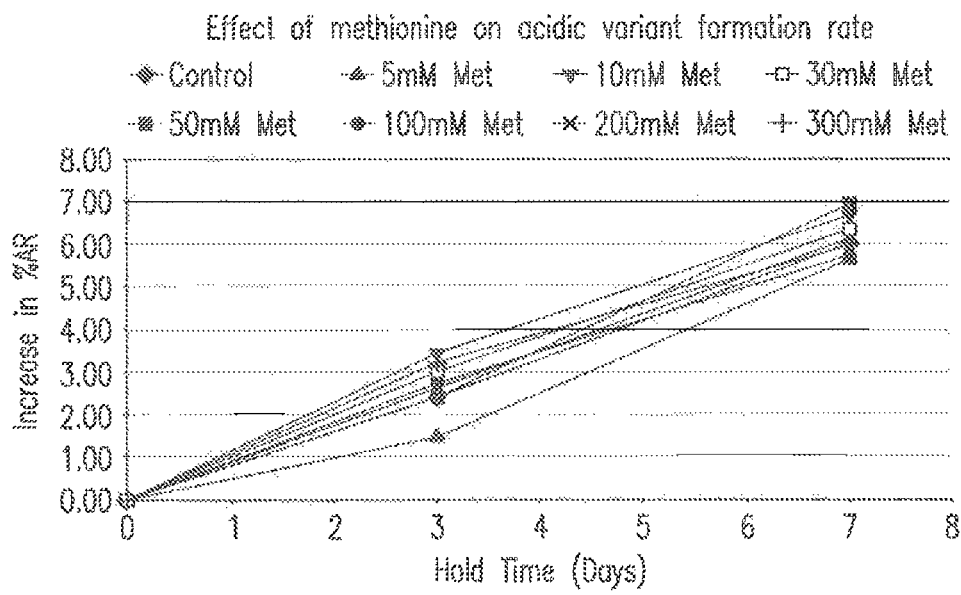

FIG. 124 depicts the effect of methionine on acidic variant formation rate.

Figure 125:
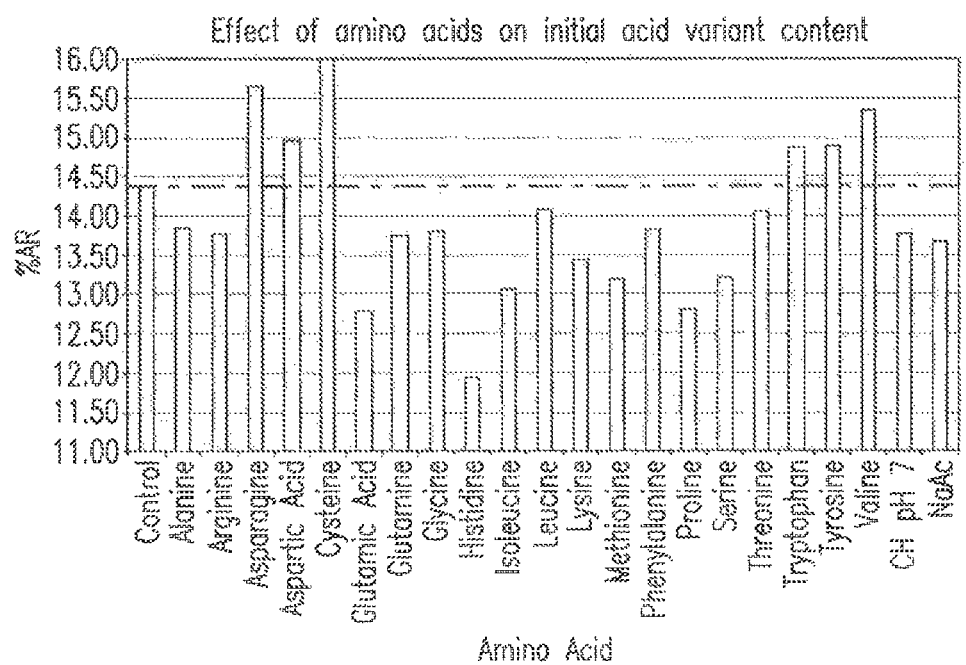

FIG. 125 depicts the effect of amino acids on initial acid variant content.

Figure 126:
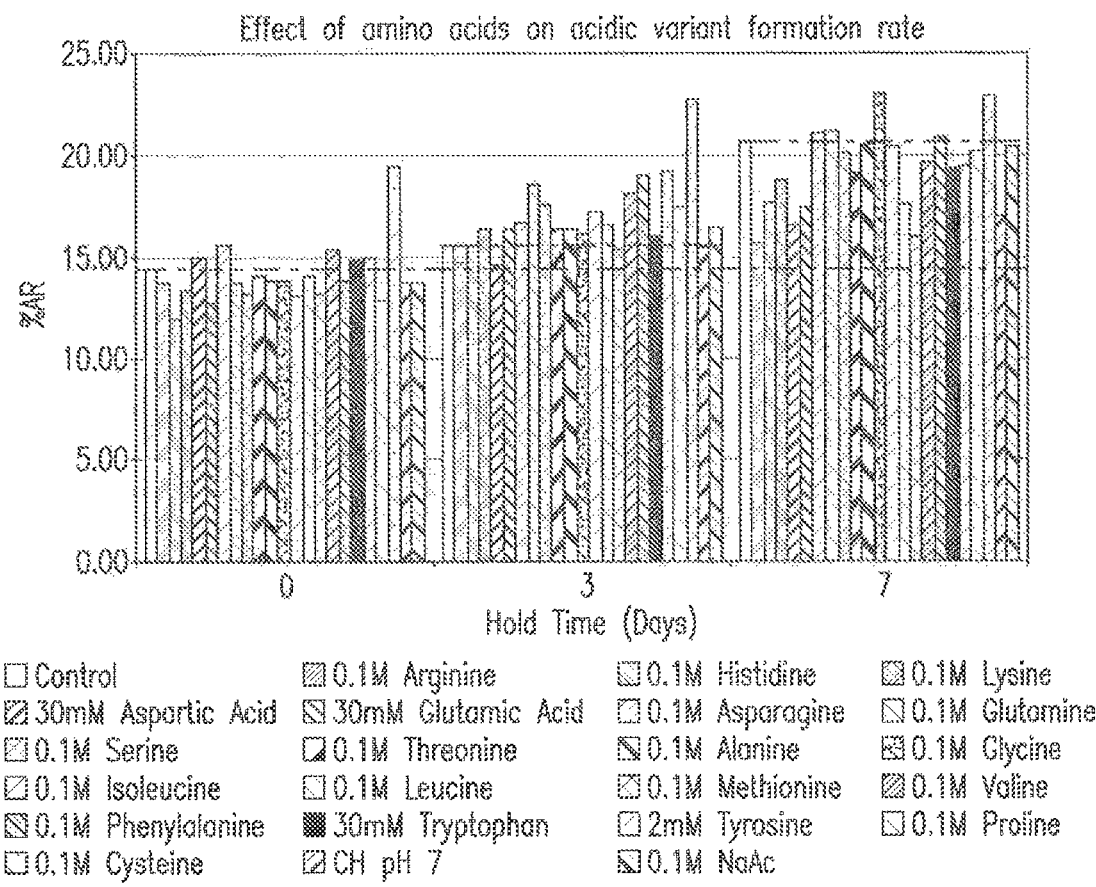

FIG. 126 depicts the effect of amino acids on acidic variant formation rate.

Figure 127:
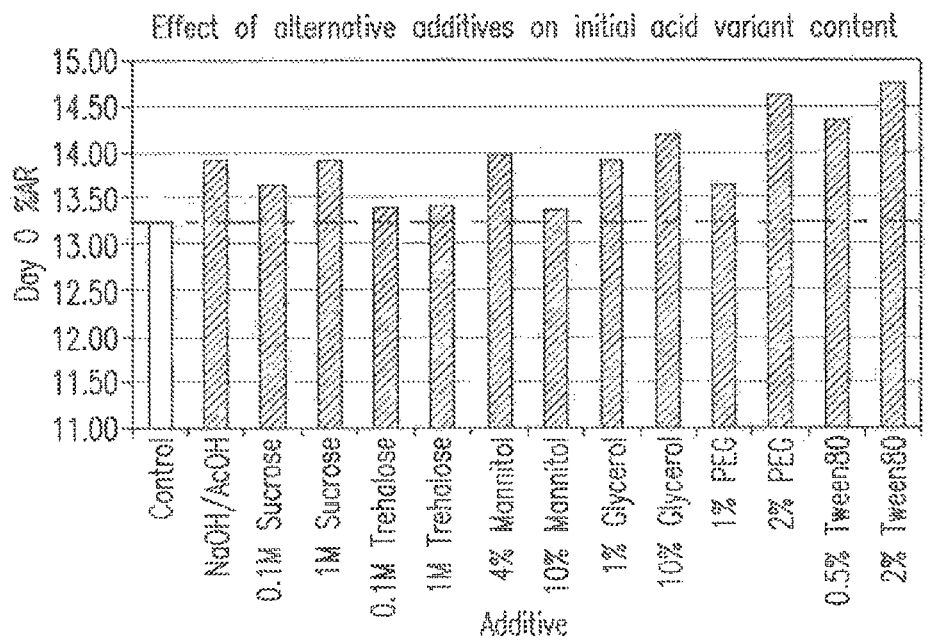

FIG. 127 depicts the effect of alternative additives on initial acid variant content.

Figure 128:
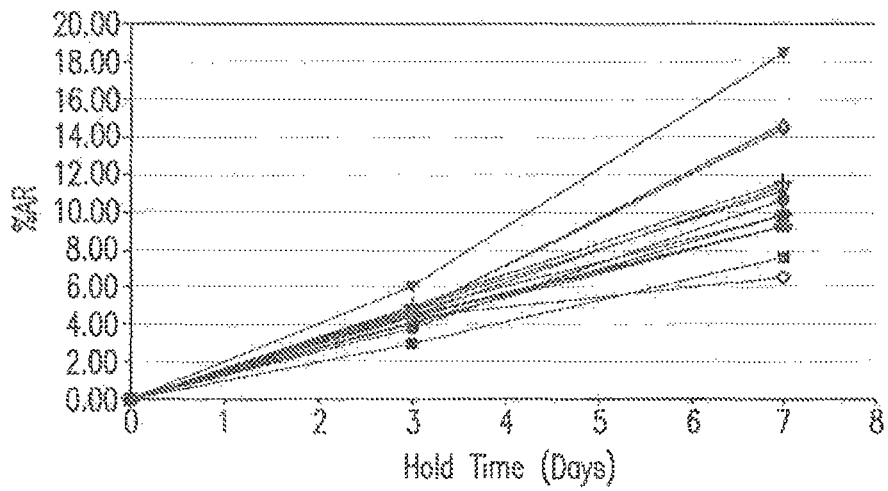

FIG. 128 depicts the effect of alternative additives on acidic variant formation rate.

Figure 129:
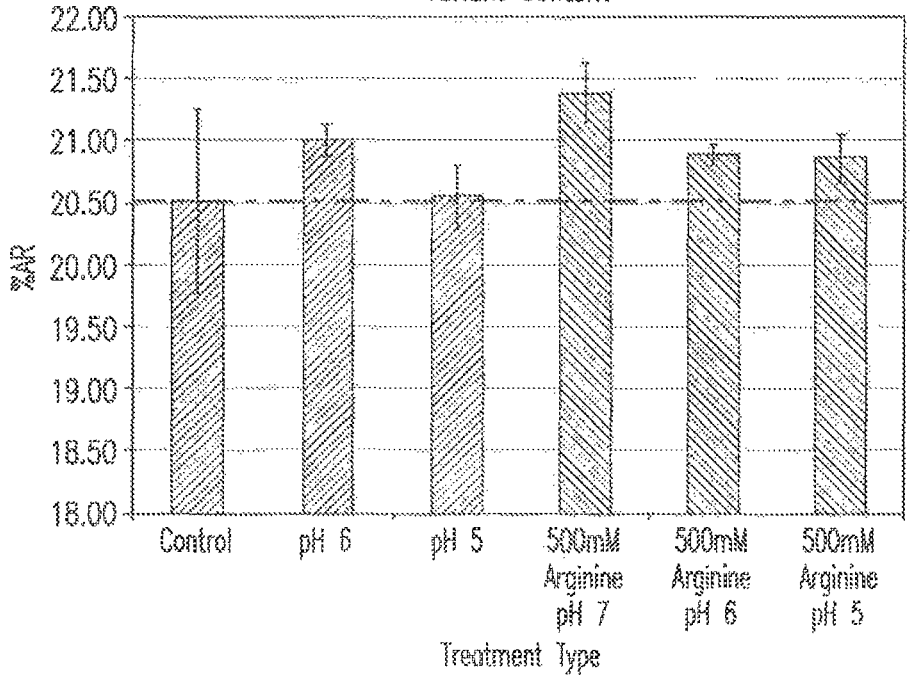

FIG. 129 depicts the effect of low pH/arginine treatment on D2E7 CDM initial acid variant content.

Figure 130:
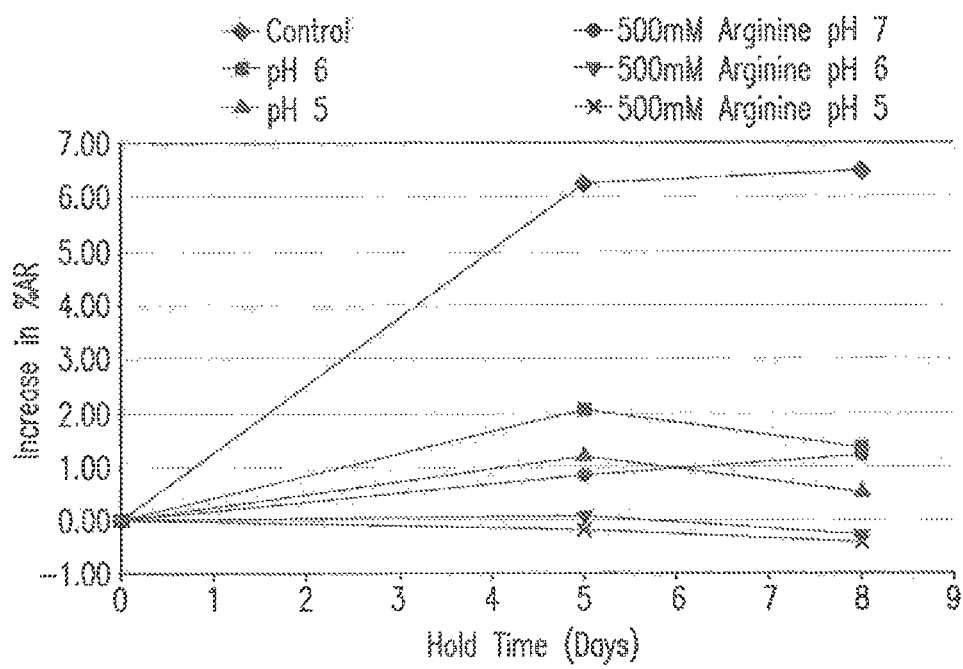

FIG. 130 depicts the effect of low pH/arginine treatment on D2E7 CDM acidic variant formation rate.

Figure 131:
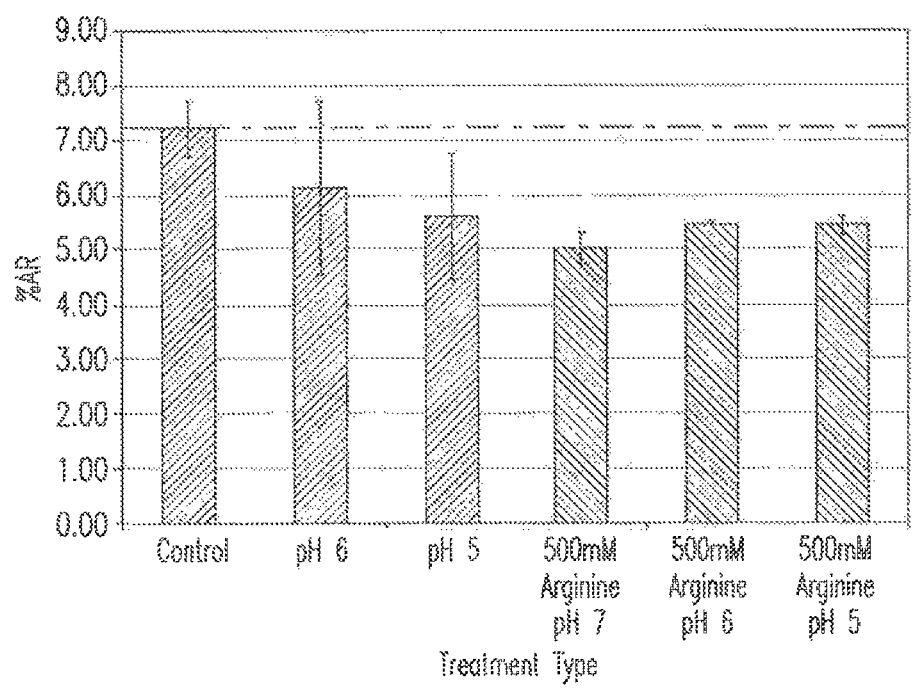

FIG. 131 depicts the effect of low pH/arginine treatment on mAb B hydrolysate initial acid variant content.

Figure 132:
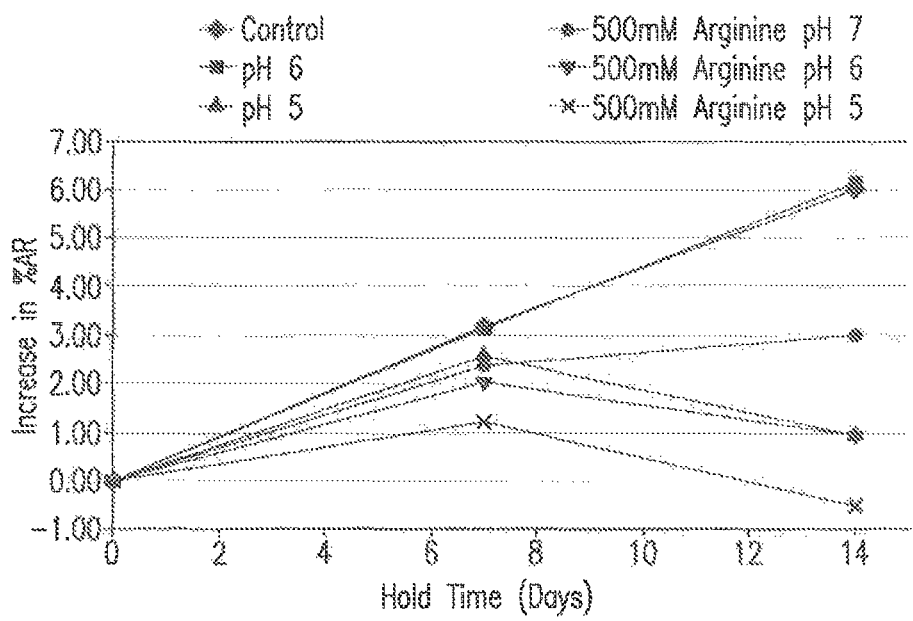

FIG. 132 depicts the effect of low pH/arginine treatment on mAb B hydrolysate acidic variant formation rate.

Figure 133:
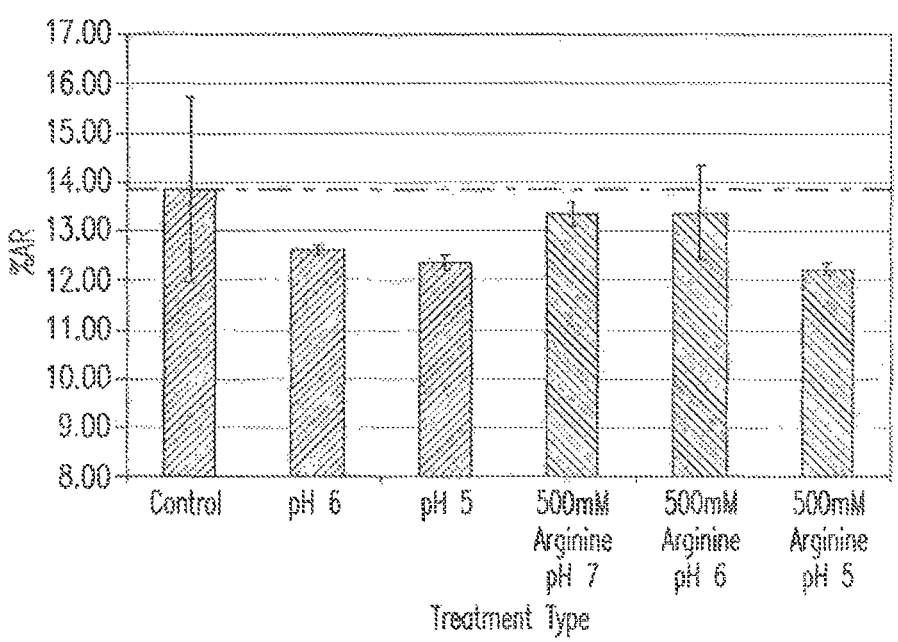

FIG. 133 depicts the effect of low pH/arginine treatment on mAb C hydrolysate initial acid variant content.

Figure 134:
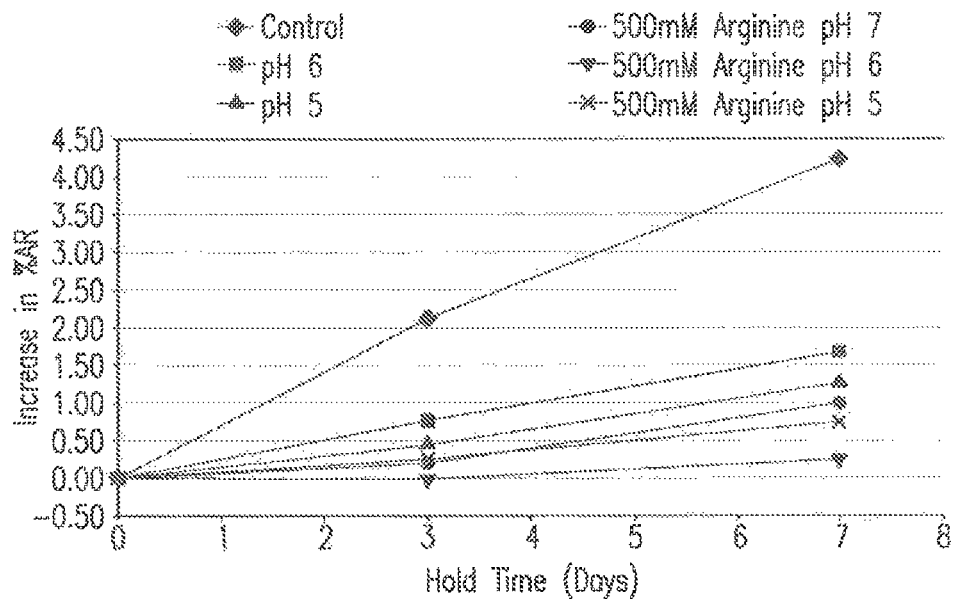

FIG. 134 depicts the effect of low pH/arginine treatment on mAb C hydrolysate acidic variant formation rate.

Figure 135:
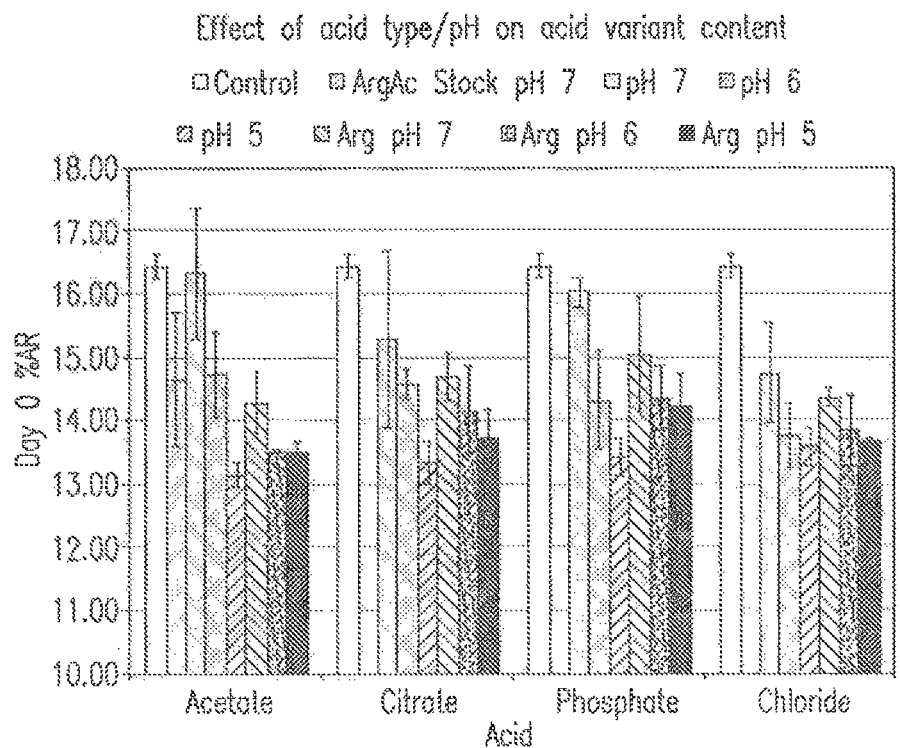

FIG. 135 depicts the effect of acid type/pH on acid variant content.

Figure 136:
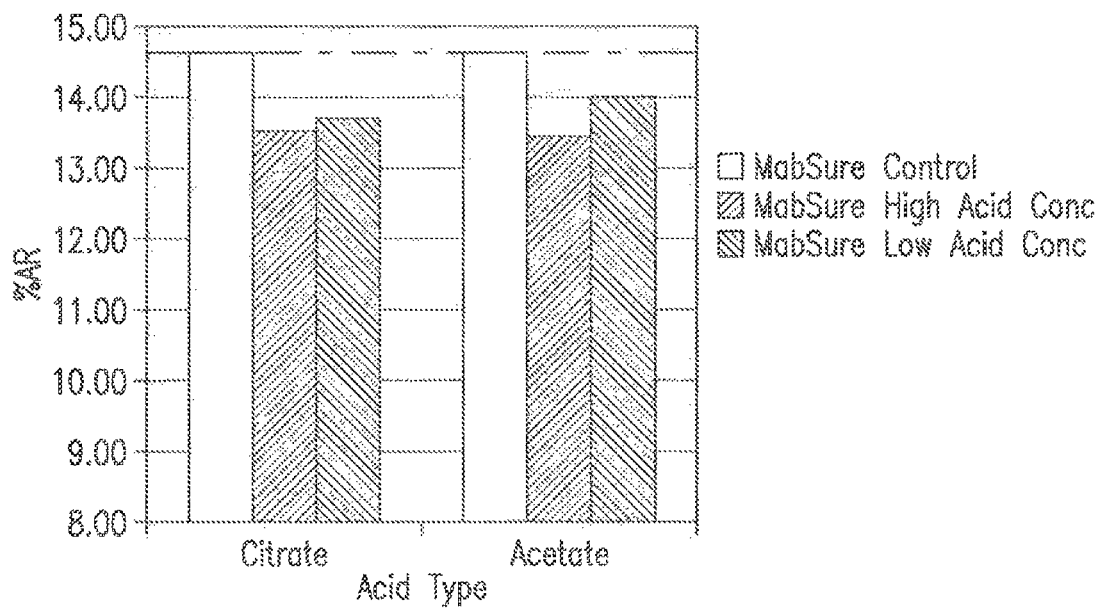

FIG. 136 depicts the effect of acid concentration on acid variant content.

Figure 137:
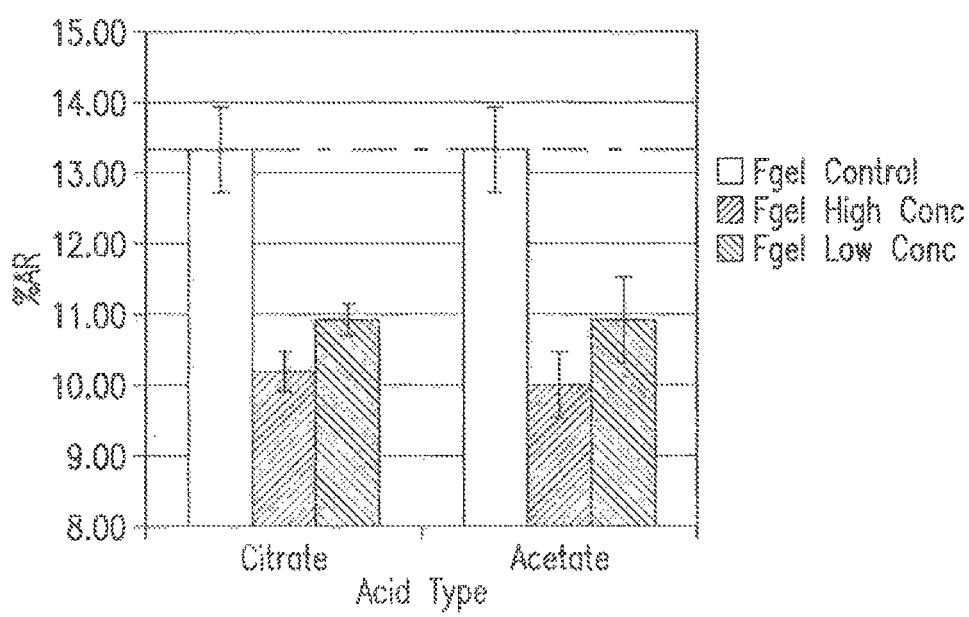

FIG. 137 depicts the effect of acid concentration on acid variant content.

Figure 138:
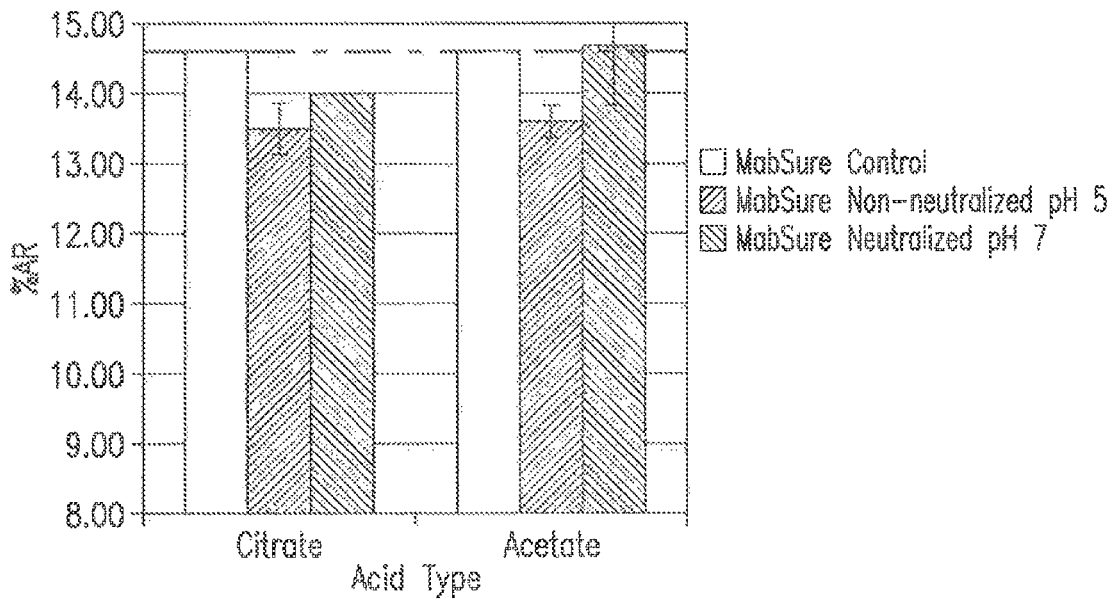

FIG. 138 depicts the effect of neutralization on acid variant content.

Figure 139:
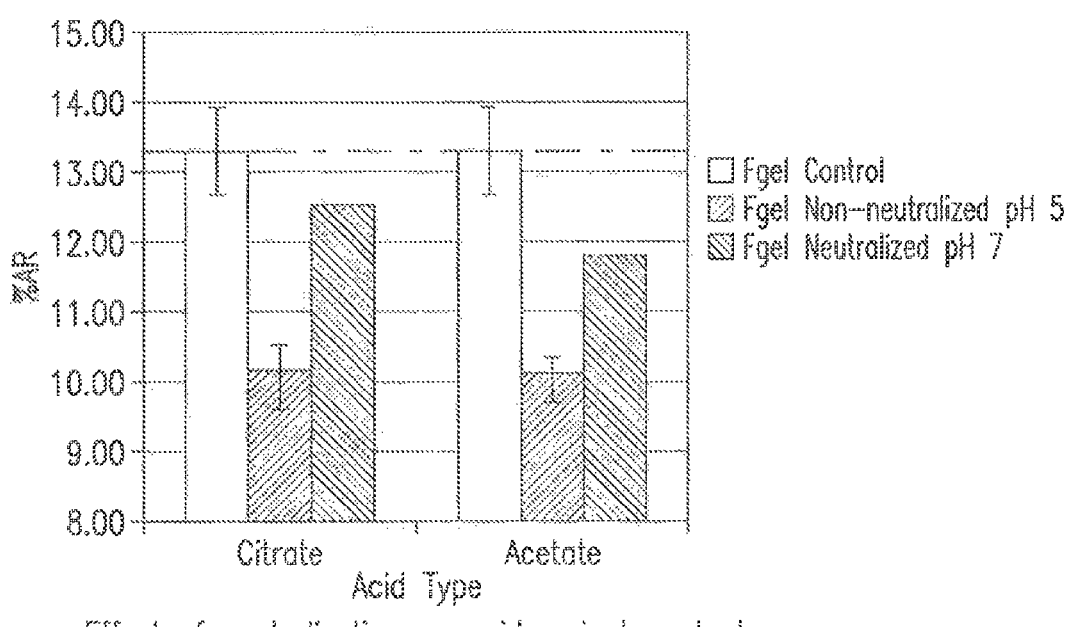

FIG. 139 depicts the effect of neutralization on acid variant content.

Figure 140:
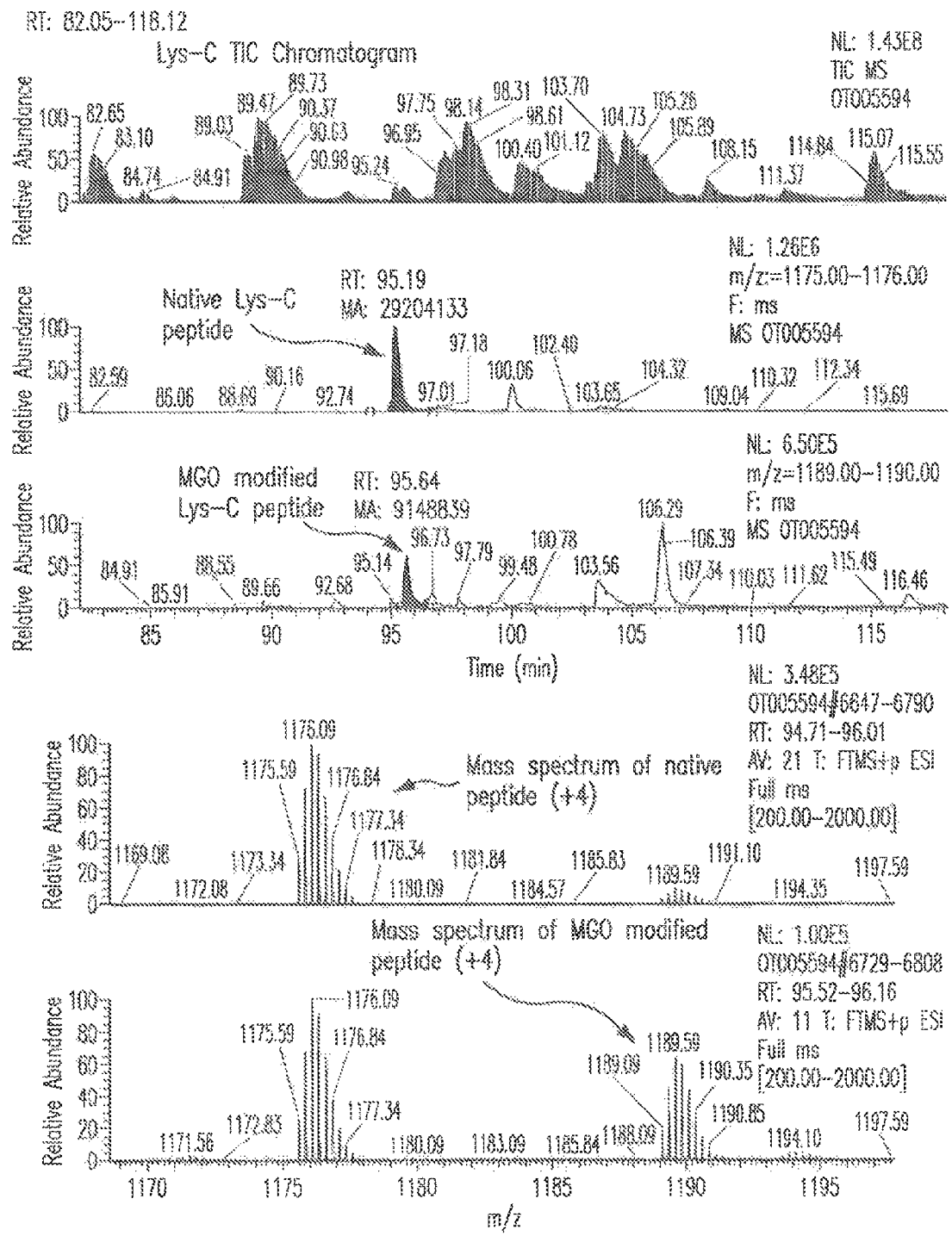

FIG. 140 depicts LC/MS peptide mapping analysis of exemplary antibodies expressed in the context of the cell culture conditions of the instant invention, including preparation of specific mass traces for both modified and non-modified peptides in order to accurately quantify the total amount of MGO modification. Mass spectra are also analyzed for the specific region of the chromatogram to confirm the peptide identity.

Figure 141:
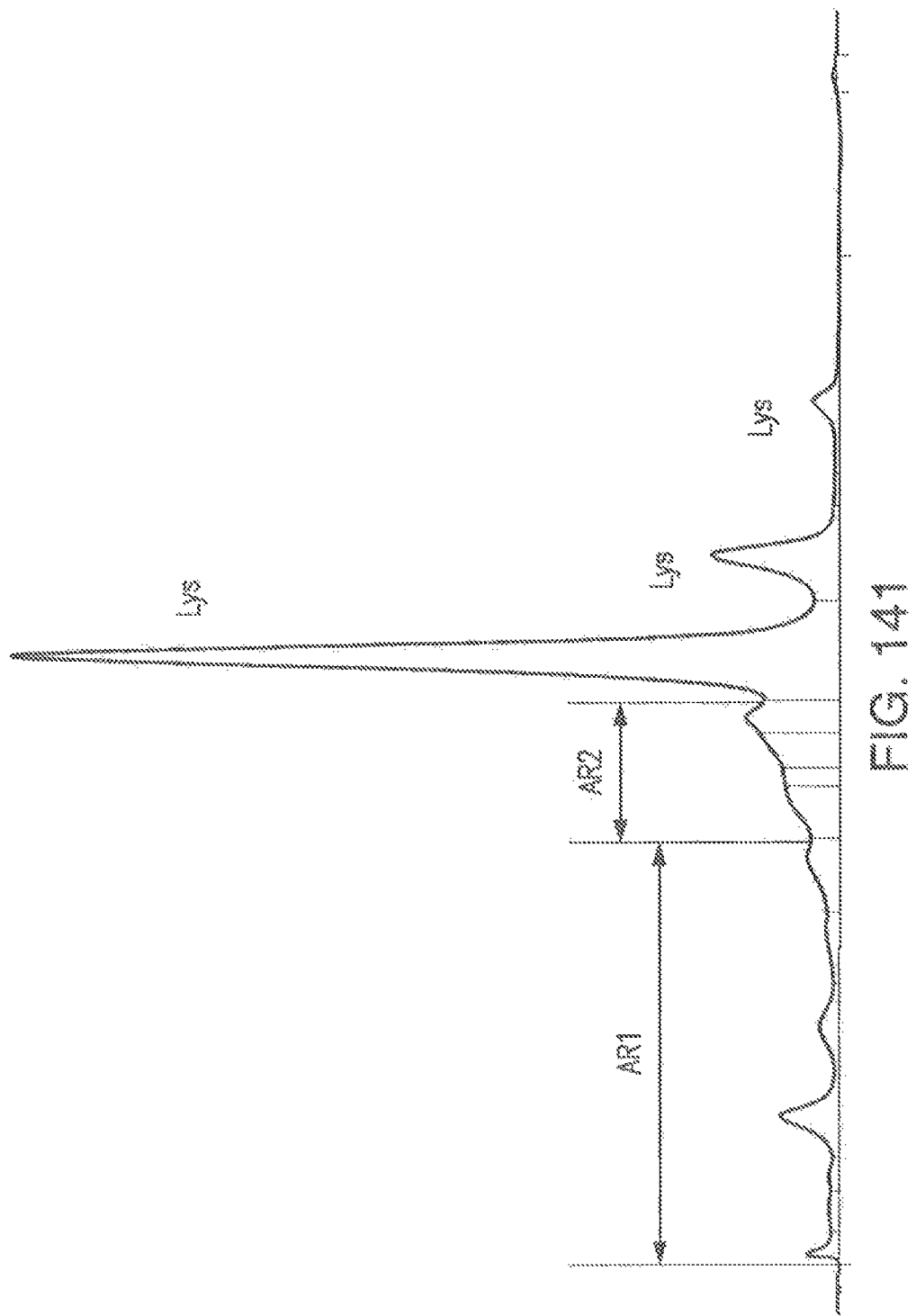

FIG. 141 depicts a chromatogram wherein the total acidic species associated with the expression of Adalimiumab is divided into a first acidic species region (AR1) and a second acidic species region (AR2).

Figure 142:
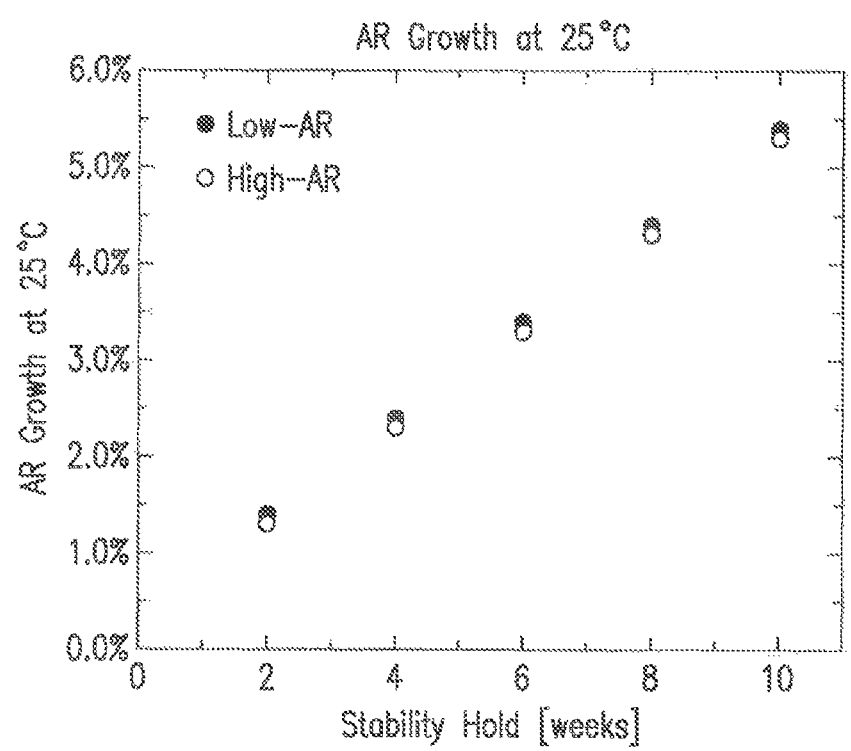

FIG. 142 depicts the AR Growth at 25° C. of low and high AR containing samples.

5. DETAILED DESCRIPTION OF THE INVENTION

The instant invention relates to the field of protein production. In particular, the instant invention relates to compositions and processes for controlling the amount of acidic species expressed by host cells when used to produce a protein of interest. Certain embodiments of the invention relate to culturing said cells to express said proteins under conditions that limit the amount of acidic species that are expressed by the cells. In certain embodiments, the methods described herein employ culturing said cells in media supplemented with one or more amino acids and/or calcium (e.g., as calcium chloride dihydrate) and/or niacinamide. In certain embodiments, the methods described herein employ culturing said cells in a culture with appropriate control of process parameters, such as pH. In certain embodiments, methods described herein employ culturing cells at a lower process pH. In certain embodiments of the instant invention, control of acidic species heterogeneity can be attained by the choice of cell culture methodology. In certain embodiments, use of a continuous or perfusion technology may be utilized to achieve the desired control over acidic species heterogeneity. In certain embodiments, this may be attained through choice of medium exchange rate. In certain embodiments, the present invention is directed toward pharmaceutical compositions comprising one or more proteins, such as, but not limited to an antibody or antigen-binding portion thereof, purified by a method described herein.

For clarity and not by way of limitation, this detailed description is divided into the following sub-portions:
(i) Definitions;
(ii) Antibody Generation;
(iii) Protein Production;
(iv) Protein Purification;
(v) Pharmaceutical Compositions

5.1 Definitions

In order that the present invention may be more readily understood, certain terms are first defined.

As used herein, the terms "acidic species" and "acidic species heterogeneity" refer to a characteristic of a population of proteins wherein the population includes a distribution of product-related impurities identifiable by the presence of charge heterogeneities. For example, in monoclonal antibody (mAb) preparations, such acidic species heterogeneities can be detected by various methods, such as, for example, WCX-10 HPLC (a weak cation exchange chromatography), or IEF (isoelectric focusing). In certain embodiments, the acidic species identified using such techniques comprise a mixture of product-related impurities containing antibody product fragments (e.g., Fc and Fab fragments), chemical modifications (e.g., methylglyoxal modified species (as described in U.S. patent application Ser. No. 14/078,181), glycated species) and/or post-translation modifications of the antibody product, such as, deamidated and/or glycosylated antibodies.

In certain embodiments, the acidic species heterogeneity comprises a difference in the type of acidic species present in the population of proteins. For example, the population of proteins may comprise more than one acidic species variant. For example, but not by way of limitation, the total acidic species can be divided based on chromatographic residence time. FIG. 141 depicts a non-limiting example of such a division wherein the total acidic species associated with the expression of Adalimiumab is divided into a first acidic species region (AR1) and a second acidic species region (AR2). The compositions of particular acidic species regions may differ depending on the particular antibody of interest, as well as the particular cell culture, purification, and/or chromatographic conditions employed.

In certain embodiments, the heterogeneity of the distribution of acidic species comprises a difference in the amount of acidic species in the population of proteins. For example, the population of proteins may comprise more than one acidic species variant, and each of the variants may be present in different amounts.

The term "antibody" includes an immunoglobulin molecule comprised of four polypeptide chains, two heavy (H) chains and two light (L) chains inter-connected by disulfide bonds. Each heavy chain is comprised of a heavy chain variable region (abbreviated herein as HCVR or VH) and a heavy chain constant region (CH). The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The term "antigen-binding portion" of an antibody (or "antibody portion") includes fragments of an antibody that retain the ability to specifically bind to an antigen (e.g., in the case of Adalimumab, hTNFα). It has been shown that the antigen-binding function of an antibody can be performed by fragments of a full-length antibody. Examples of binding fragments encompassed within the term "antigen-binding portion" of an antibody include (i) a Fab fragment, a monovalent fragment comprising the VL, VH, CL and CH1 domains; (ii) a F(ab')2 fragment, a bivalent fragment comprising two Fab fragments linked by a disulfide bridge at the hinge region; (iii) a Fd fragment comprising the VH and CH1 domains; (iv) a Fv fragment comprising the VL and VH domains of a single arm of an antibody, (v) a dAb fragment (Ward et al., (1989) Nature 341:544-546, the entire teaching of which is incorporated herein by reference), which comprises a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see, e.g., Bird et al. (1988) Science 242:423-426; and Huston et al. (1988) Proc. Natl. Acad. Sci. USA 85:5879-5883, the entire teachings of which are incorporated herein by reference). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, e.g., Holliger, P., et al. (1993) Proc. Natl. Acad. Sci. USA 90:6444-6448; Poljak, R. J., et al. (1994) Structure 2:1121-1123, the entire teachings of which are incorporated herein by reference). Still further, an antibody or antigen-binding portion thereof may be part of a larger immunoadhesion molecule, formed by covalent or non-covalent association of the antibody or antibody portion with one or more other proteins or peptides. Examples of such immunoadhesion molecules include use of the streptavidin core region to make a tetrameric scFv molecule (Kipriyanov, S. M., et al. (1995) Human Antibodies and Hybridomas 6:93-101, the entire teaching of which is incorporated herein by reference) and use of a cysteine residue, a marker peptide and a C-terminal polyhistidine tag to make bivalent and biotinylated scFv molecules (Kipriyanov, S. M., et al. (1994) Mol. Immunol. 31:1047-1058, the entire teaching of which is incorporated herein by reference). Antibody portions, such as Fab and F(ab')2 fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein. In one aspect, the antigen binding portions are complete domains or pairs of complete domains.

The phrase "clarified harvest" refers to a liquid material containing a protein of interest, for example, an antibody of interest such as a monoclonal or polyclonal antibody of interest, that has been extracted from cell culture, for example, a fermentation bioreactor, after undergoing centrifugation to remove large solid particles and subsequent filtration to remove finer solid particles and impurities from the material.

The term "human antibody" includes antibodies having variable and constant regions corresponding to human germline immunoglobulin sequences as described by Kabat et al. (See Kabat, et al. (1991) Sequences of proteins of Immunological Interest, Fifth Edition, U.S. Department of Health and Human Services, NIH Publication No. 91-3242). The human antibodies of the invention may include amino acid residues not encoded by human germline immunoglobulin sequences (e.g., mutations introduced by random or site-specific mutagenesis in vitro or by somatic mutation in vivo), e.g., in the CDRs and in particular CDR3. The mutations can be introduced using the "selective mutagenesis approach." The human antibody can have at least one position replaced with an amino acid residue, e.g., an activity enhancing amino acid residue which is not encoded by the human germline immunoglobulin sequence. The human antibody can have up to twenty positions replaced with amino acid residues which are not part of the human germline immunoglobulin sequence. In other embodiments, up to ten, up to five, up to three or up to two positions are replaced. In one embodiment, these replacements are within the CDR regions. However, the term "human antibody", as used herein, is not intended to include antibodies in which CDR sequences derived from the germline of another mammalian species, such as a mouse, have been grafted onto human framework sequences.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse) that is transgenic for human immunoglobulin genes (see, e.g., Taylor, L. D., et al. (1992) Nucl. Acids Res. 20:6287-6295, the entire teaching of which is incorporated herein by reference) or antibodies prepared, expressed, created or isolated by any other means that involves splicing of human immunoglobulin gene sequences to other DNA sequences. Such recombinant human antibodies have variable and constant regions derived from human germline immunoglobulin sequences (see, Kabat, E. A., et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. In certain embodiments, however, such recombinant antibodies are the result of selective mutagenesis approach or back-mutation or both.

An "isolated antibody" includes an antibody that is substantially free of other antibodies having different antigenic specificities (e.g., an isolated antibody that specifically binds hTNFα is substantially free of antibodies that specifically bind antigens other than hTNFα). An isolated antibody that specifically binds hTNFα may bind TNFα molecules from other species. Moreover, an isolated antibody may be substantially free of other cellular material and/or chemicals. A suitable anti-TNFα antibody is Adalimumab (Abbott Laboratories).

Figure 1:
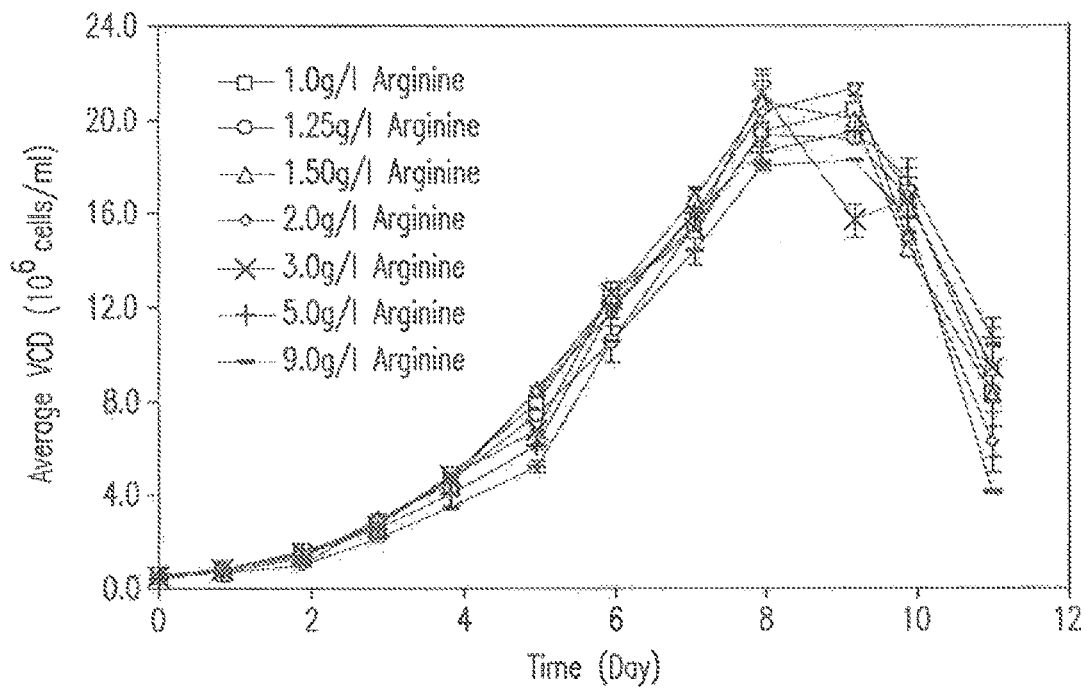
FIG. 1 depicts the effect of total arginine concentration in adalimumab producing cell line 2, media 1 on viable cell density (n=2).

As used herein, the term "adalimumab", also known by its trade name Humira® (AbbVie) refers to a human IgG antibody that binds the human form of tumor necrosis factor alpha. In general, the heavy chain constant domain 2 (CH2) of the adalimumab IgG-Fc region is glycosylated through covalent attachment of oligosaccharide at asparagine 297 (Asn-297). Weak cation-exchange chromatography (WCX) analysis of the antibody has shown that it has three main charged-variants (i.e. Lys 0, Lys 1, and Lys 2). These variants, or charged isomers, are the result of incomplete posttranslational cleavage of the C-terminal lysine residues. In addition to the lysine variants, the WCX-10 analysis measures the presence acidic species. These acidic regions (i.e., acidic species) are classified as product-related impurities that are relatively acidic when compared to the lysine variants and elute before the Lys 0 peak in the chromatogram (FIG. 1).

The term "activity" includes activities such as the binding specificity/affinity of an antibody for an antigen, and includes activities such as the binding specificity/affinity of an anti-TNFα antibody for its antigen, e.g., an anti-TNFα antibody that binds to a TNFα antigen and/or the neutralizing potency of an antibody, e.g., an anti-TNFα antibody whose binding to hTNFα inhibits the biological activity of hTNFα.

The phrase "nucleic acid molecule" includes DNA molecules and RNA molecules. A nucleic acid molecule may be single-stranded or double-stranded, but in one aspect is double-stranded DNA.

The phrase "isolated nucleic acid molecule," as used herein in reference to nucleic acids encoding antibodies or antibody portions (e.g., VH, VL, CDR3), e.g. those that bind hTNFα, and includes a nucleic acid molecule in which the nucleotide sequences encoding the antibody or antibody portion are free of other nucleotide sequences encoding antibodies or antibody portions that bind antigens other than hTNFα, which other sequences may naturally flank the nucleic acid in human genomic DNA. Thus, e.g., an isolated nucleic acid of the invention encoding a VH region of an anti-TNFα antibody contains no other sequences encoding other VH regions that bind antigens other than, for example, hTNFα. The phrase "isolated nucleic acid molecule" is also intended to include sequences encoding bivalent, bispecific antibodies, such as diabodies in which VH and VL regions contain no other sequences other than the sequences of the diabody.

The phrase "recombinant host cell" (or simply "host cell") includes a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "recombinant protein" refers to a protein produced as the result of the transcription and translation of a gene carried on a recombinant expression vector that has been introduced into a host cell. In certain embodiments the recombinant protein is an antibody, preferably a chimeric, humanized, or fully human antibody. In certain embodiments the recombinant protein is an antibody of an isotype selected from group consisting of: IgG (e.g., IgG1, IgG2, IgG3, IgG4), IgM, IgA1, IgA2, IgD, or IgE. In certain embodiments the antibody molecule is a full-length antibody (e.g., an IgG1 or IgG4 immunoglobulin) or alternatively the antibody can be a fragment (e.g., an Fc fragment or a Fab fragment).

As used herein, the term "cell culture" refers to methods and techniques employed to generate and maintain a population of host cells capable of producing a recombinant protein of interest, as well as the methods and techniques for optimizing the production and collection of the protein of interest. For example, once an expression vector has been incorporated into an appropriate host, the host can be maintained under conditions suitable for high level expression of the relevant nucleotide coding sequences, and the collection and purification of the desired recombinant protein. Mammalian cells are preferred for expression and production of the recombinant protein of the present invention, however other eukaryotic cell types can also be employed in the context of the instant invention. See, e.g., Winnacker, From Genes to Clones, VCH Publishers, N.Y., N.Y. (1987). Suitable mammalian host cells for expressing recombinant proteins according to the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159: 601-621, the entire teachings of which are incorporated herein by reference), NS0 myeloma cells, COS cells and SP2 cells. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

When using the cell culture techniques of the instant invention, the protein of interest can be produced intracellularly, in the periplasmic space, or directly secreted into the medium. In embodiments where the protein of interest is produced intracellularly, the particulate debris, either host cells or lysed cells (e.g., resulting from homogenization), can be removed by a variety of means, including but not limited to, by centrifugation or ultrafiltration. Where the protein of interest is secreted into the medium, supernatants from such expression systems can be first concentrated using a commercially available protein concentration filter, e.g., an Amicon™ or Millipore Pellicon™ ultrafiltration unit, which can then be subjected to one or more additional purification techniques, including but not limited to affinity chromatography, including protein A affinity chromatography, ion exchange chromatography, such as anion or cation exchange chromatography, and hydrophobic interaction chromatography.

As used herein the term "on-line" refers to processes that are accomplished in the context of an on-going cell culture run. For example, the administration of a particular nutrient or changes in temperature, pH, or dissolved oxygen level occur on-line when such administrations or changes are implemented in an existing cell culture run. Similarly, measurements of certain data are considered on-line if that data is being collected in the context of a particular cell culture run. For example, on-line gas analysis refers to the measurement of gases introduced into or released from a particular cell culture run. In contrast, the term "off-line", as used herein, refers to actions taken outside the context of a particular cell culture run. For example, the production of cell culture media comprising specific concentrations of particular components is an example of an off-line activity.

The term "modifying", as used herein, is intended to refer to changing one or more amino acids in the antibodies or antigen-binding portions thereof. The change can be produced by adding, substituting or deleting an amino acid at one or more positions. The change can be produced using known techniques, such as PCR mutagenesis.

The term "about", as used herein, is intended to refer to ranges of approximately 10-20% greater than or less than the referenced value. In certain circumstances, one of skill in the art will recognize that, due to the nature of the referenced value, the term "about" can mean more or less than a 10-20% deviation from that value.

The term "control", as used herein, is intended to refer to both limitation as well as to modulation. For example, in certain embodiments, the instant invention provides methods for controlling diversity that decrease the diversity of certain characteristics of protein populations, including, but not limited to, the presence of acidic species. Such decreases in diversity can occur by: (1) promotion of a desired characteristic; (2) inhibition of an unwanted characteristic; or (3) a combination of the foregoing. As used herein, the term "control" also embraces contexts where heterogeneity is modulated, i.e., shifted, from one diverse population to a second population of equal, or even greater diversity, where the second population exhibits a distinct profile of the characteristic of interest.

5.2 Antibody Generation

The term "antibody" as used in this section refers to an intact antibody or an antigen binding fragment thereof.

The antibodies of the present disclosure can be generated by a variety of techniques, including immunization of an animal with the antigen of interest followed by conventional monoclonal antibody methodologies e.g., the standard somatic cell hybridization technique of Kohler and Milstein (1975) Nature 256: 495. Although somatic cell hybridization procedures are preferred, in principle, other techniques for producing monoclonal antibody can be employed e.g., viral or oncogenic transformation of B lymphocytes.

One preferred animal system for preparing hybridomas is the murine system. Hybridoma production is a very well-established procedure. Immunization protocols and techniques for isolation of immunized splenocytes for fusion are known in the art. Fusion partners (e.g., murine myeloma cells) and fusion procedures are also known.

An antibody preferably can be a human, a chimeric, or a humanized antibody. Chimeric or humanized antibodies of the present disclosure can be prepared based on the sequence of a non-human monoclonal antibody prepared as described above. DNA encoding the heavy and light chain immunoglobulins can be obtained from the non-human hybridoma of interest and engineered to contain non-murine (e.g., human) immunoglobulin sequences using standard molecular biology techniques. For example, to create a chimeric antibody, murine variable regions can be linked to human constant regions using methods known in the art (see e.g., U.S. Pat. No. 4,816,567 to Cabilly et al.). To create a humanized antibody, murine CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al.).

In one non-limiting embodiment, the antibodies of this disclosure are human monoclonal antibodies. Such human monoclonal antibodies can be generated using transgenic or transchromosomic mice carrying parts of the human immune system rather than the mouse system. These transgenic and transchromosomic mice include mice referred to herein as the HuMAb Mouse® (Medarex, Inc.), KM Mouse® (Medarex, Inc.), and XenoMouse® (Amgen).

Moreover, alternative transchromosomic animal systems expressing human immunoglobulin genes are available in the art and can be used to raise antibodies of the disclosure. For example, mice carrying both a human heavy chain transchromosome and a human light chain transchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (e.g., Kuroiwa et al. (2002) Nature Biotechnology 20:889-894 and PCT application No. WO 2002/092812) and can be used to raise antibodies of this disclosure.

Recombinant human antibodies of the invention can be isolated by screening of a recombinant combinatorial antibody library, e.g., a scFv phage display library, prepared using human VL and VH cDNAs prepared from mRNA derived from human lymphocytes. Methodologies for preparing and screening such libraries are known in the art. In addition to commercially available kits for generating phage display libraries (e.g., the Pharmacia Recombinant Phage Antibody System, catalog no. 27-9400-01; and the Stratagene SurfZAP™ phage display kit, catalog no. 240612, the entire teachings of which are incorporated herein), examples of methods and reagents particularly amenable for use in generating and screening antibody display libraries can be found in, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) Bio/Technology 9:1370-1372; Hay et al. (1992) Hum Antibod Hybridomas 3:81-85; Huse et al. (1989) Science 246:1275-1281; McCafferty et al., Nature (1990) 348:552-554; Griffiths et al. (1993) EMBO J 12:725-734; Hawkins et al. (1992) J Mol Biol 226:889-896; Clackson et al. (1991) Nature 352:624-628; Gram et al. (1992) PNAS 89:3576-3580; Garrard et al. (1991) Bio/Technology 9:1373-1377; Hoogenboom et al. (1991) Nuc Acid Res 19:4133-4137; and Barbas et al. (1991) PNAS 88:7978-7982; the entire teachings of which are incorporated herein.

Human monoclonal antibodies of this disclosure can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

In certain embodiments, the methods of the invention include anti-TNFα antibodies and antibody portions, anti-TNFα-related antibodies and antibody portions, and human antibodies and antibody portions with equivalent properties to anti-TNFα, such as high affinity binding to hTNFα with low dissociation kinetics and high neutralizing capacity. In one aspect, the invention provides treatment with an isolated human antibody, or an antigen-binding portion thereof, that dissociates from hTNFα with a Kd of about $1\times10^{-8}$ M or less and a Koff rate constant of $1\times10^{-3}$ s$^{-1}$ or less, both determined by surface plasmon resonance. In specific non-limiting embodiments, an anti-TNFα antibody purified according to the invention competitively inhibits binding of Adalimumab to TNFα under physiological conditions.

Antibodies or fragments thereof, can be altered wherein the constant region of the antibody is modified to reduce at least one constant region-mediated biological effector function relative to an unmodified antibody. To modify an antibody of the invention such that it exhibits reduced binding to the Fc receptor, the immunoglobulin constant region segment of the antibody can be mutated at particular regions necessary for Fc receptor (FcR) interactions (see, e.g., Canfield and Morrison (1991) J. Exp. Med. 173:1483-1491; and Lund et al. (1991) J. of Immunol. 147:2657-2662, the entire teachings of which are incorporated herein). Reduction in FcR binding ability of the antibody may also reduce other effector functions which rely on FcR interactions, such as opsonization and phagocytosis and antigen-dependent cellular cytotoxicity.

5.3 Protein Production

To express a protein of the invention, such as an antibody or antigen-binding fragment thereof, DNAs encoding the protein, such as DNAs encoding partial or full-length light and heavy chains in the case of antibodies, are inserted into one or more expression vector such that the genes are operatively linked to transcriptional and translational control sequences. (See, e.g., U.S. Pat. No. 6,914,128, the entire teaching of which is incorporated herein by reference.) In this context, the term "operatively linked" is intended to mean that a gene encoding the protein of interest is ligated into a vector such that transcriptional and translational control sequences within the vector serve their intended function of regulating the transcription and translation of the gene. The expression vector and expression control sequences are chosen to be compatible with the expression host cell used. In certain embodiments, the protein of interest will comprising multiple polypeptides, such as the heavy and light chains of an antibody. Thus, in certain embodiments, genes encoding multiple polypeptides, such as antibody light chain genes and antibody heavy chain genes, can be inserted into a separate vector or, more typically, the genes are inserted into the same expression vector. Genes are inserted into expression vectors by standard methods (e.g., ligation of complementary restriction sites on the gene fragment and vector, or blunt end ligation if no restriction sites are present). Prior to insertion of the gene or genes, the expression vector may already carry additional polypeptide sequences, such as, but no limited to, antibody constant region sequences. For example, one approach to converting the anti-TNFα antibody or anti-TNFα antibody-related VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the protein from a host cell. The gene can be cloned into the vector such that the signal peptide is linked in-frame to the amino terminus of the gene. The signal peptide can be an immunoglobulin signal peptide or a heterologous signal peptide (i.e., a signal peptide from a non-immunoglobulin protein).

In addition to protein coding genes, a recombinant expression vector of the invention can carry one or more regulatory sequence that controls the expression of the protein coding genes in a host cell. The term "regulatory sequence" is intended to include promoters, enhancers and other expression control elements (e.g., polyadenylation signals) that control the transcription or translation of the protein coding genes. Such regulatory sequences are described, e.g., in Goeddel; Gene Expression Technology: Methods in Enzymology 185, Academic Press, San Diego, Calif. (1990), the entire teaching of which is incorporated herein by reference. It will be appreciated by those skilled in the art that the design of the expression vector, including the selection of regulatory sequences may depend on such factors as the choice of the host cell to be transformed, the level of expression of protein desired, etc. Suitable regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see, e.g., U.S. Pat. No. 5,168,062 by Stinski, U.S. Pat. No. 4,510,245 by Bell et al. and U.S. Pat. No. 4,968,615 by Schaffner et al., the entire teachings of which are incorporated herein by reference.

In addition to the protein coding genes and regulatory sequences, a recombinant expression vector of the invention may carry one or more additional sequences, such as a sequence that regulates replication of the vector in host cells (e.g., origins of replication) and/or a selectable marker gene. The selectable marker gene facilitates selection of host cells into which the vector has been introduced (see e.g., U.S. Pat. Nos. 4,399,216, 4,634,665 and 5,179,017, all by Axel et al., the entire teachings of which are incorporated herein by reference). For example, typically the selectable marker gene confers resistance to drugs, such as G418, hygromycin or methotrexate, on a host cell into which the vector has been introduced. Suitable selectable marker genes include the dihydrofolate reductase (DHFR) gene (for use in dhfr-host cells with methotrexate selection/amplification) and the neo gene (for G418 selection).

An antibody, or antibody portion, of the invention can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel et al. (eds.) Current Protocols in Molecular Biology, Greene Publishing Associates, (1989) and in U.S. Pat. Nos. 4,816,397 & 6,914,128, the entire teachings of which are incorporated herein.

For expression of protein, for example, the light and heavy chains of an antibody, the expression vector(s) encoding the protein is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the proteins of the invention in either prokaryotic or eukaryotic host cells, expression of antibodies in eukaryotic cells, such as mammalian host cells, is suitable because such eukaryotic cells, and in particular mammalian cells, are more likely than prokaryotic cells to assemble and secrete a properly folded and immunologically active protein. Prokaryotic expression of protein genes has been reported to be ineffective for production of high yields of active protein (Boss and Wood (1985) Immunology Today 6:12-13, the entire teaching of which is incorporated herein by reference).

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, e.g., Enterobacteriaceae such as *Escherichia*, e.g., *E. coli*, *Enterobacter*, *Erwinia*, *Klebsiella*, *Proteus*, *Salmonella*, e.g., *Salmonella typhimurium*, *Serratia*, e.g., *Serratia marcescans*, and *Shigella*, as well as *Bacilli* such as *B. subtilis* and *B. licheniformis* (e.g., *B. licheniformis* 41P disclosed in DD 266,710 published Apr. 12, 1989), *Pseudomonas* such as *P. aeruginosa*, and *Streptomyces*. One suitable *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for polypeptide encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*; *Kluyveromyces* hosts such as, e.g., *K. lactis*, *K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastoris* (EP 183,070); *Candida*; *Trichoderma reesia* (EP 244,234); *Neurospora crassa*; *Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger*.

Suitable host cells for the expression of glycosylated proteins, for example, glycosylated antibodies, are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells. Plant cell cultures of cotton, corn, potato, soybean, petunia, tomato, and tobacco can also be utilized as hosts.

Suitable mammalian host cells for expressing the recombinant proteins of the invention include Chinese Hamster Ovary (CHO cells) (including dhfr-CHO cells, described in Urlaub and Chasin, (1980) PNAS USA 77:4216-4220, used with a DHFR selectable marker, e.g., as described in Kaufman and Sharp (1982) Mol. Biol. 159:601-621, the entire teachings of which are incorporated herein by reference), NS0 myeloma cells, COS cells and SP2 cells. When recombinant expression vectors encoding protein genes are introduced into mammalian host cells, the antibodies are produced by culturing the host cells for a period of time sufficient to allow for expression of the antibody in the host cells or secretion of the antibody into the culture medium in which the host cells are grown. Other examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; and a human hepatoma line (Hep G2), the entire teachings of which are incorporated herein by reference.

Host cells are transformed with the above-described expression or cloning vectors for protein production and cultured in conventional nutrient media modified as appropriate for inducing promoters, selecting transformants, or amplifying the genes encoding the desired sequences.

The host cells used to produce a protein may be cultured in a variety of media. Commercially available media such as Ham's F10™ (Sigma), Minimal Essential Medium™ (MEM), (Sigma), RPMI-1640 (Sigma), and Dulbecco's Modified Eagle's Medium™ (DMEM), (Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. No. Re. 30,985 may be used as culture media for the host cells, the entire teachings of which are incorporated herein by reference. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamycin drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Host cells can also be used to produce portions of intact proteins, for example, antibodies, including Fab fragments or scFv molecules. It is understood that variations on the above procedure are within the scope of the present invention. For example, in certain embodiments it may be desirable to transfect a host cell with DNA encoding either the light chain or the heavy chain (but not both) of an antibody. Recombinant DNA technology may also be used to remove some or all of the DNA encoding either or both of the light and heavy chains that is not necessary for binding to an antigen. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the target antibody, depending on the specificity of the antibody of the invention, by crosslinking an antibody of the invention to a second antibody by standard chemical crosslinking methods.

In a suitable system for recombinant expression of a protein, for example, an antibody, or antigen-binding portion thereof, a recombinant expression vector encoding the protein, for example, both an antibody heavy chain and an antibody light chain, is introduced into dhfr-CHO cells by calcium phosphate-mediated transfection. Within the recombinant expression vector, the protein gene(s) are each operatively linked to CMV enhancer/AdMLP promoter regulatory elements to drive high levels of transcription of the gene(s). The recombinant expression vector also carries a DHFR gene, which allows for selection of CHO cells that have been transfected with the vector using methotrexate selection/amplification. The selected transformant host cells are cultured to allow for expression of the protein, for example, the antibody heavy and light chains, and intact protein, for example, an antibody, is recovered from the culture medium. Standard molecular biology techniques are used to prepare the recombinant expression vector, transfect the host cells, select for transformants, culture the host cells and recover the protein from the culture medium.

When using recombinant techniques, the protein, for example, antibodies or antigen binding fragments thereof, can be produced intracellularly, in the periplasmic space, or directly secreted into the medium. In one aspect, if the protein is produced intracellularly, as a first step, the particulate debris, either host cells or lysed cells (e.g., resulting from homogenization), can be removed, e.g., by centrifugation or ultrafiltration. Where the protein is secreted into the medium, supernatants from such expression systems can be first concentrated using a commercially available protein concentration filter, e.g., an Amicon™ or Millipore Pellicon™ ultrafiltration unit.

Numerous populations of proteins expressed by host cells, including, but not limited to, host cells expressing antibodies, such as adalimumab, may comprise a number of acidic species, and are therefore amenable to the instant invention's methods for control of acidic species heterogeneity. For example, weak cation-exchange chromatography (WCX) analysis of adalimumab has shown the presence of acidic regions. These acidic species are classified as product-related impurities that are relatively acidic when compared to the adalimumab protein population. The presence of these acidic species provides an exemplary system to identify those cell culture conditions that allow for control over acidic species heterogeneity.

5.3.1 Adjusting Amino Acid Concentration to Control Acidic Species

The variation in raw materials used in cell culture, particularly in the context of media preparation, can vary product quality significantly.

In certain embodiments of the instant invention, control of acidic species heterogeneity can be attained by adjustment of the media composition of the cell culture run. In certain embodiments, such adjustment will be to increase the amount of one or more amino acids in the media, while in other embodiments the necessary adjustment to achieve the desired control over acidic species heterogeneity will involve a decrease in the amount of one or more amino acids in the media. Such increases or decreases in the amount of the one or more amino acids can be of a magnitude of 1%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, of the original amount.

In certain embodiments, a cell culture media will include one or more of the amino acids, or other compositions, described herein as facilitating a reduction in acidic species. In certain embodiments the amount of the amino acid, or other composition, that is necessary to be supplemented may be adjusted to account for the amount present in the media prior to supplementation.

In certain embodiments, the cell culture media is supplemented with one or more amino acids wherein each of the one or more amino acids is supplemented in an amount of between about 0.025 and 20 g/L, or between about 0.05 and 15 g/L, or between about 0.1 and 14 g/L, or between about 0.2 and 13 g/L, or between about 0.25 and 12 g/L, or between about 0.5 and 11 g/L, or between about 1 and 10 g/L, or between about 1.5 and 9.5 g/L, or between about 2 and 9 g/L, or between about 2.5 and 8.5 g/L, or between about 3 and 8 g/L, or between about 3.5 and 7.5 g/L, or between about 4 and 7 g/L, or between about 4.5 and 6.5 g/L, or between about 5 and 6 g/L. In certain embodiments, the cell culture media is supplemented with one or more amino acids wherein each of the one or more amino acids is supplemented in an amount of about 0.25 g/L, or about 0.5 g/L, or about 1 g/L, or about 2 g/L, or about 4 g/L, or about 8 g/L.

In certain embodiments, the cell culture media is supplemented with one or more amino acids wherein each of the one or more amino acids is supplemented in an amount effective to reduce the amount of acidic species heterogeneity in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

In certain embodiments, the one or more amino acids used to supplement the cell culture media is a basic amino acid. In certain embodiments the one or more amino acids is arginine, lysine, histidine, ornithine, or certain combinations of arginine or lysine with ornithine or of all four amino acids. In certain embodiments, the amino acids are provided as single peptides, as dipeptides, as tripeptides or as longer oligopeptides. In certain embodiments, the di-, tri-, and/or oligopeptides are individually composed of a single amino acid, while in alternative embodiments, the di-, tri-, and/or oligopeptides are individually composed of two or more particular amino acids. In certain embodiments, the amount of amino acid supplemented to the cell culture to achieve concentrations of about 0 to about 9 g/l for arginine, about 0 to about 11 g/l for lysine, about 0 to about 11 g/l histidine, and about 0 to about 11 g/l ornithine. Although wider ranges are also within the scope of the instant invention, including, but not limited to: about 0 to about 30 g/l for arginine, about 0 to about 30 g/l for lysine, about 0 to about 30 g/l histidine, and about 0 to about 30 g/l ornithine.

For example, and not by way of limitation, as detailed in Example 6.1, below, when the production medium employed in the example was supplemented with arginine to achieve a total concentration of 9 g/L arginine, the total amount of acidic species of adalimumab present in a cell culture sample after purification was reduced from 19.7% of a control sample to 12.2% of the sample purified from the cells cultured with the arginine supplemented media. Similarly, when the production medium employed in the example was supplemented with lysine, or histidine, or ornithine to achieve total concentrations of 11 g/L lysine, 10 g/L ornithine or 10 g/L histidine, respectively, the total amount of acidic species of adalimumab present in a cell culture sample after purification was reduced by 11.5%, 10.4% and 10.9%, respectively, compared to a control sample.

In certain embodiments, control over the amount of acidic species of protein produced by cell culture is exerted by supplementing the media of cells expressing the protein of interest medium supplements described herein such that they can be included in the medium at the start of culture, or can be added in a fed-batch or in a continuous manner. The feed amounts may be calculated to achieve a certain concentration based on offline or online measurements. The supplements may be added as multimers, e.g., arg-arg, his-his, arg-his-orn, etc., and/or as chemical variants, e.g., of amino acids or analogs of amino acids, salt forms of amino acids, controlled release of amino acids by immobilizing in gels, etc, and/or in fully or partially dissolved form. The addition of one or more supplement may be based on measured amount of acidic species. The resulting media can be used in various cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired cell line. In addition, the harvest criterion for these cultures may be chosen, for example based on choice of harvest viability or culture duration, to further optimize a certain targeted acidic species profile.

5.3.1 Adjusting $CaCl_2$ and/or Niacinamide Concentration to Control Acidic Species In certain embodiments, the cell culture media is supplemented with calcium (e.g., as calcium chloride dihydrate), wherein the calcium is supplemented to achieve a calcium concentration of between about 0.05 and 2.5 mM, or between about 0.05 and 1 mM, or between about 0.1 and 0.8 mM, or between about 0.15 and 0.7 mM, or between about 0.2 and 0.6 mM, or between about 0.25 and 0.5 mM, or between about 0.3 and 0.4 mM.

In certain embodiments, the cell culture media is supplemented with calcium (e.g., as calcium chloride dihydrate) wherein the calcium is supplemented in an amount effective to reduce the amount of acidic species heterogeneity in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

For example, and not by way of limitation, as detailed in Example 6.3, below, when the production medium employed in the example was supplemented with calcium (e.g., as calcium chloride dihydrate) at a concentration of 1.05 mM, the total amount of acidic species of adalimumab present in a cell culture sample after purification was reduced from 23.2% of a control sample to 16.5% of the sample purified from the cells cultured with the calcium supplemented media.

In certain embodiments, the cell culture can be supplemented with a combination of calcium, e.g., $CaCl_2$, and one or more a basic amino acids. In certain embodiments the one or more basic amino acids is arginine, lysine, histidine, ornithine, or combinations of arginine or lysine with ornithine or of all four amino acids. In certain embodiments, the amino acids are provided as single peptides, as dipeptides, as tripeptides or as longer oligopeptides. In certain embodiments, the di-, tri-, and/or oligopeptides are individually composed of a single amino acid, while in alternative embodiments, the di-, tri-, and/or oligopeptides are individually composed of two or more particular amino acids. In certain embodiments, the amount of basic amino acid concentrations in combination with calcium in the cell culture is between about 0 to about 9 g/l for arginine, about 0 to about 11 g/l for lysine, about 0 to about 11 g/l histidine, and about 0 to about 11 g/l ornithine. Although wider ranges are also within the scope of the instant invention, including, but not limited to: about 0 to about 30 g/l for arginine, about 0 to about 30 g/l for lysine, about 0 to about 30 g/l histidine, and about 0 to about 30 g/l ornithine.

In certain embodiments, the cell culture media is supplemented with niacinamide, wherein the niacinamide is supplemented to achieve a niacinamide concentration of between about 0.2 and 3.0 mM, or between about 0.4 and 3.0 mM, or between about 0.8 and 3.0 mM.

In certain embodiments, the cell culture media is supplemented with niacinamide wherein the niacinamide is supplemented in an amount effective to reduce the amount of acidic species heterogeneity in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

For example, and not by way of limitation, as detailed in Example 6.3, below, when the production medium employed in the example was supplemented with niacinamide at a concentration of 1.6 mM, the total amount of acidic species of adalimumab present in a cell culture sample after purification was reduced from 19.9% of a control sample to 15.9% of the sample purified from the cells cultured with the niacinamide supplemented media. In a separate example, where the media was supplemented with 3 mM niacinamide, the total amount of acidic species of adalimumab present in a cell culture sample after purification was reduced from 27.0% of a control sample to 19.8% of the sample purified from the cells cultured with the niacinamide supplemented media.

In certain embodiments, the cell culture can be supplemented with a combination of niacinamide, calcium, e.g., $CaCl_2$, and/or one or more a basic amino acids. In certain embodiments the one or more basic amino acids is arginine, lysine, histidine, ornithine, or combinations of arginine or lysine with ornithine or of all four amino acids. In certain embodiments, the amino acids are provided as single peptides, as dipeptides, as tripeptides or as longer oligopeptides. In certain embodiments, the di-, tri-, and/or oligopeptides are individually composed of a single amino acid, while in alternative embodiments, the di-, tri-, and/or oligopeptides are individually composed of two or more particular amino acids. In certain embodiments, the amount of basic amino acid concentrations (after supplementation) in combination with calcium in the cell culture is between about 0 to about 9 g/l for arginine, about 0 to about 11 g/l for lysine, about 0 to about 11 g/l histidine, and about 0 to about 11 g/l ornithine. Although wider ranges are also within the scope of the instant invention, including, but not limited to: about 0 to about 30 g/l for arginine, about 0 to about 30 g/l for lysine, about 0 to about 30 g/l histidine, and about 0 to about 30 g/l ornithine.

In certain embodiments, control over the amount of acidic species of protein produced by cell culture is exerted by supplementing the media of cells expressing the protein of interest medium supplements described herein such that they can be included in the medium at the start of culture, or can be added in a fed-batch or in a continuous manner. The feed amounts may be calculated to achieve a certain concentration based on offline or online measurements. The addition of the supplement may be based on measured amount of acidic species. Other salts of particular supplements, e.g., calcium, may also be used, for example Calcium Nitrate. The resulting media can be used in various cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired cell line.

In certain embodiments, control over amount and/or rate of formation of acidic species is achieved by supplementing a clarified harvest. For example, but not by way of limitation, such clarified harvests can be supplemented as described above (e.g., with calcium, niacinamide, and/or basic amino acids) to achieve a reduction the amount of acidic species and/or a reduction in the rate such acidic species form.

5.3.3 Adjusting Process Parameters to Control Acidic Species

In certain embodiments of the instant invention, control of acidic species heterogeneity can be attained by adjustment of pH of the cell culture run. In certain embodiments, such adjustment will be to decrease in the pH of the cell culture. Such decreases in the pH, can be of a magnitude of 1%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, of the original amount.

In certain embodiments, pH is either increased or decreased in order to increase or decrease the amount of acidic species and/or the rate at which such acidic species form. For example, but not by way of limitation, a reduction in pH to 6.7 from a control pH of 7.1 can be employed to decrease the acidic species during cell culture and the rate of acidic species formation in the context of a clarified harvest.

In certain embodiments, the pH is maintained in such a manner as to reduce the amount of acidic species in a protein or antibody sample by about 1%, 1.2%, 1.5%, 2%, 2.2%, 2.5%, 3%, 3.2%, 3.5%, 4%, 4.2%, 4.5%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding.

In certain embodiments, control over the amount of acidic species of protein produced by cell culture can be exerted by maintaining the pH of the cell culture expressing the protein of interest as described herein along with choice of suitable temperature or temperature shift strategies, for example, but not limited to, lower process temperature of operation, temperature shift to a lower temperature or a temperature shift at an earlier culture time point. These culture conditions can be used in various cultivation methods including, but not limited to, batch, fed-batch, chemostat and perfusion, and with various cell culture equipment including, but not limited to, shake flasks with or without suitable agitation, spinner flasks, stirred bioreactors, airlift bioreactors, membrane bioreactors, reactors with cells retained on a solid support or immobilized/entrapped as in microporous beads, and any other configuration appropriate for optimal growth and productivity of the desired cell line. These may also be used in combination with supplementation of culture media with amino acids, niacinamide, and/or calcium salt, as described above.

5.3.4 Continuous/Perfusion Cell Culture Technology to Control Acidic Species In certain embodiments of the instant invention, control of acidic species heterogeneity can be attained by the choice of cell culture methodology. In certain embodiments, use of a continuous or perfusion technology may be utilized to achieve the desired control over acidic species heterogeneity. In certain embodiments, this may be attained through choice of medium exchange rate (where the exchange rate is the rate of exchange of medium in/out of a reactor). Such increases or decreases in medium exchange rates may be of magnitude of 1%, 5%, 10%, 15%, 20%, 25%, 30%, 35%, 40%, 45%, 50%, 55%, 60%, 65%, 70%, 75%, 80%, 85%, 90%, 95%, 100%, and ranges within one or more of the preceding, of the original amount.

In certain, non-limiting, embodiments, maintenance of the medium exchange rates (working volumes/day) of a cell culture run between 0 and 20, or between 0.5 and 12 or between 1 and 8 or between 1.5 and 6 can be used to achieve the desired reduction in acidic species.

For example, and not by way of limitation, as detailed in Example 6.4, below, when the medium exchange rate was chosen to be 1.5, the acidic species was 8.1%. With further increase in exchange rates to 6, a further reduction in acidic species to 6% was obtained.

In certain embodiments, the choice of cell culture methodology that allows for control of acidic species heterogeneity can also include, for example, but not by way of limitation, employment of an intermittent harvest strategy or through use of cell retention device technology.

5.4 Protein Purification

5.4.1 Protein Purification Generally

In certain embodiments, the methods of the present invention can be used in combination with techniques for protein purification to provide for the production of a purified protein preparation, for example, a preparation comprising an antibody or an antigen binding fragment thereof, from a mixture comprising a protein and at least one process-related impurity or product-related substance.

For example, but not by way of limitation, once a clarified solution or mixture comprising the protein of interest, for example, an antibody or antigen binding fragment thereof, has been obtained, separation of the protein of interest from the process-related impurities and/or product-related substances can be performed using a combination of different purification techniques, including, but not limited to, affinity separation steps, ion exchange separation steps, mixed mode separation steps, and hydrophobic interaction separation steps. The separation steps separate mixtures of proteins on the basis of their charge, degree of hydrophobicity, or size. In one aspect of the invention, separation is performed using chromatography, including cationic, anionic, and hydrophobic interaction. Several different chromatography resins are available for each of these techniques, allowing accurate tailoring of the purification scheme to the particular protein involved. The essence of each of the separation methods is that proteins can be caused either to traverse at different rates down a column, achieving a physical separation that increases as they pass further down the column, or to adhere selectively to the separation medium, being then differentially eluted by different solvents. In some cases, the antibody is separated from impurities when the impurities specifically adhere to the column and the antibody does not, i.e., the antibody is present in the flow through.

As noted above, accurate tailoring of a purification scheme relies on consideration of the protein to be purified. In certain embodiments, the separation steps of employed in connection with the cell culture methods of the instant invention facilitate the separation of an antibody from one or more process-related impurity and/or product-related substance. Antibodies that can be successfully purified using the methods described herein include, but are not limited to, human IgA1, IgA2, IgD, IgE, IgG1, IgG2, IgG3, IgG4, and IgM antibodies. In certain embodiments, Protein A affinity chromatography can be useful, however, in certain embodiments, the use of Protein A affinity chromatography would prove useful, for example in the context of the purification of IgG3 antibodies, as IgG3 antibodies bind to Protein A inefficiently. Other factors that allow for specific tailoring of a purification scheme include, but are not limited to: the presence or absence of an Fc region (e.g., in the context of full length antibody as compared to an Fab fragment thereof) because Protein A binds to the Fc region; the particular germline sequences employed in generating to antibody of interest; and the amino acid composition of the antibody (e.g., the primary sequence of the antibody as well as the overall charge/hydrophobicity of the molecule). Antibodies sharing one or more characteristic can be purified using purification strategies tailored to take advantage of that characteristic.

5.4.2 Primary Recovery and Virus Inactivation

In certain embodiments, it will be advantageous to subject a sample produced by the techniques of the instant invention to at least a first phase of clarification and primary recovery. In addition, the primary recovery process can also be a point at which to reduce or inactivate viruses that can be present in the sample mixture. For example, any one or more of a variety of methods of viral reduction/inactivation can be used during the primary recovery phase of purification including heat inactivation (pasteurization), pH inactivation, solvent/detergent treatment, UV and γ-ray irradiation and the addition of certain chemical inactivating agents such as β-propiolactone or e.g., copper phenanthroline as in U.S. Pat. No. 4,534,972, the entire teaching of which is incorporated herein by reference.

The primary recovery may also include one or more centrifugation steps to further clarify the sample mixture and thereby aid in purifying the protein of interest. Centrifugation of the sample can be run at, for example, but not by way of limitation, 7,000×g to approximately 12,750×g. In the context of large scale purification, such centrifugation can occur on-line with a flow rate set to achieve, for example, but not by way of limitation, a turbidity level of 150 NTU in the resulting supernatant. Such supernatant can then be collected for further purification.

In certain embodiments, the primary recovery may also include the use of one or more depth filtration steps to further clarify the sample matrix and thereby aid in purifying the antibodies produced using the cell culture techniques of the present invention. Depth filters contain filtration media having a graded density. Such graded density allows larger particles to be trapped near the surface of the filter while smaller particles penetrate the larger open areas at the surface of the filter, only to be trapped in the smaller openings nearer to the center of the filter. In certain embodiments, the depth filtration step can be a delipid depth filtration step. Although certain embodiments employ depth filtration steps only during the primary recovery phase, other embodiments employ depth filters, including delipid depth filters, during one or more additional phases of purification. Non-limiting examples of depth filters that can be used in the context of the instant invention include the Cuno™ model 30/60ZA depth filters (3M Corp.), and 0.45/0.2 µm Sartopore™ bi-layer filter cartridges.

5.4.3 Affinity Chromatography

In certain embodiments, it will be advantageous to subject a sample produced by the techniques of the instant invention to affinity chromatography to further purify the protein of interest away from process-related impurities and/or product-related substances. In certain embodiments the chromatographic material is capable of selectively or specifically binding to the protein of interest. Non-limiting examples of such chromatographic material include: Protein A, Protein G, chromatographic material comprising, for example, an antigen bound by an antibody of interest, and chromatographic material comprising an Fc binding protein. In specific embodiments, the affinity chromatography step involves subjecting the primary recovery sample to a column comprising a suitable Protein A resin. In certain embodiments, Protein A resin is useful for affinity purification and isolation of a variety of antibody isotypes, particularly IgG1, IgG2, and IgG4. Protein A is a bacterial cell wall protein that binds to mammalian IgGs primarily through their Fc regions. In its native state, Protein A has five IgG binding domains as well as other domains of unknown function.

There are several commercial sources for Protein A resin. One suitable resin is MabSelect™ from GE Healthcare. A non-limiting example of a suitable column packed with MabSelect™ is an about 1.0 cm diameter×about 21.6 cm long column (~17 mL bed volume). This size column can be used for small scale purifications and can be compared with other columns used for scale ups. For example, a 20 cm×21 cm column whose bed volume is about 6.6 L can be used for larger purifications. Regardless of the column, the column can be packed using a suitable resin such as MabSelect™.

5.4.4 Ion Exchange Chromatography

In certain embodiments, it will be advantageous to subject a sample produced by the techniques of the instant invention to ion exchange chromatography in order to purify the protein of interest away from process-related impurities and/or product-related substances. Ion exchange separation includes any method by which two substances are separated based on the difference in their respective ionic charges, and can employ either cationic exchange material or anionic exchange material. For example, the use of a cationic exchange material versus an anionic exchange material is based on the localized charges of the protein. Therefore, it is within the scope of this invention to employ an anionic exchange step prior to the use of a cationic exchange step, or a cationic exchange step prior to the use of an anionic exchange step. Furthermore, it is within the scope of this invention to employ only a cationic exchange step, only an anionic exchange step, or any serial combination of the two.

In performing the separation, the initial protein mixture can be contacted with the ion exchange material by using any of a variety of techniques, e.g., using a batch purification technique or a chromatographic technique.

Anionic or cationic substituents may be attached to matrices in order to form anionic or cationic supports for chromatography. Non-limiting examples of anionic exchange substituents include diethylaminoethyl (DEAE), quaternary aminoethyl (QAE) and quaternary amine(Q) groups. Cationic substituents include carboxymethyl (CM), sulfoethyl (SE), sulfopropyl (SP), phosphate (P) and sulfonate (S). Cellulose ion exchange resins such as DE23™, DE32™, DE52™, CM-23™, CM-32™, and CM-52™ are available from Whatman Ltd. Maidstone, Kent, U.K. SEPHADEX®-based and -locross-linked ion exchangers are also known. For example, DEAE-, QAE-, CM-, and SP-SEPHADEX® and DEAE-, Q-, CM- and S-SEPHAROSE® and SEPHAROSE® Fast Flow are all available from Pharmacia AB. Further, both DEAE and CM derivitized ethylene glycol-methacrylate copolymer such as TOYOPEARL™ DEAE-6505 or M and TOYOPEARL™ CM-650S or M are available from Toso Haas Co., Philadelphia, Pa.

5.4.5 Ultrafiltration/Diafiltration

In certain embodiments, it will be advantageous to subject a sample produced by the techniques of the instant invention to ultrafiltration and/or diafiltration in order to purify the protein of interest away from process-related impurities and/or product-related substances. Ultrafiltration is described in detail in: Microfiltration and Ultrafiltration: Principles and Applications, L. Zeman and A. Zydney (Marcel Dekker, Inc., New York, N.Y., 1996); and in: Ultrafiltration Handbook, Munir Cheryan (Technomic Publishing, 1986; ISBN No. 87762-456-9). A preferred filtration process is Tangential Flow Filtration as described in the Millipore catalogue entitled "Pharmaceutical Process Filtration Catalogue" pp. 177-202 (Bedford, Mass., 1995/96). Ultrafiltration is generally considered to mean filtration using filters with a pore size of smaller than 0.1 µm. By employing filters having such small pore size, the volume of the sample can be reduced through permeation of the sample buffer through the filter while antibodies are retained behind the filter.

Diafiltration is a method of using ultrafilters to remove and exchange salts, sugars, and non-aqueous solvents, to separate free from bound species, to remove low molecular-weight material, and/or to cause the rapid change of ionic and/or pH environments. Microsolutes are removed most efficiently by adding solvent to the solution being ultrafiltered at a rate approximately equal to the ultratfiltration rate. This washes microspecies from the solution at a constant volume, effectively purifying the retained protein. In certain embodiments of the present invention, a diafiltration step is employed to exchange the various buffers used in connection with the instant invention, optionally prior to further chromatography or other purification steps, as well as to remove impurities from the protein preparations.

5.4.6 Hydrophobic Interaction Chromatography

In certain embodiments, it will be advantageous to subject a sample produced by the techniques of the instant invention to hydrophobic interaction chromatography in order to purify the protein of interest away from process-related impurities and/or product-related substances. For example, a first eluate obtained from an ion exchange column can be subjected to a hydrophobic interaction material such that a second eluate having a reduced level of impurity is obtained. Hydrophobic interaction chromatography (HIC) steps, such as those disclosed herein, are generally performed to remove protein aggregates, such as antibody aggregates, and process-related impurities.

In performing an HIC-based separation, the sample mixture is contacted with the HIC material, e.g., using a batch purification technique or using a column. Prior to HIC purification it may be desirable to remove any chaotropic agents or very hydrophobic substances, e.g., by passing the mixture through a pre-column.

Whereas ion exchange chromatography relies on the charges of the protein to isolate them, hydrophobic interaction chromatography uses the hydrophobic properties of the protein. Hydrophobic groups on the protein interact with hydrophobic groups on the column. The more hydrophobic a protein is the stronger it will interact with the column. Thus the HIC step removes host cell derived impurities (e.g., DNA and other high and low molecular weight product-related species).

Hydrophobic interactions are strongest at high ionic strength, therefore, this form of separation is conveniently performed following salt precipitations or ion exchange procedures. Adsorption of the protein of interest to a HIC column is favored by high salt concentrations, but the actual concentrations can vary over a wide range depending on the nature of the protein and the particular HIC ligand chosen. Various ions can be arranged in a so-called soluphobic series depending on whether they promote hydrophobic interactions (salting-out effects) or disrupt the structure of water (chaotropic effect) and lead to the weakening of the hydrophobic interaction. Cations are ranked in terms of increasing salting out effect as $Ba^{++}$; $Ca^{++}$; $Mg^{++}$; $Li^+$; $Cs^+$; $Na^+$; $K^+$; $Rb^+$; $NH4^+$, while anions may be ranked in terms of increasing chaotropic effect as $PO^-$; $SO_4^-$; $CH_3CO_3^-$; $Cl^-$; $Br^-$; $NO_3^-$; $ClO_4^-$; $I^-$; $SCN^-$.

In general, Na, K or $NH_4$ sulfates effectively promote ligand-protein interaction in HIC. Salts may be formulated that influence the strength of the interaction as given by the following relationship: $(NH_4)_2SO_4$>$Na_2SO_4$>NaCl>$NH_4Cl$>NaBr>NaSCN. In general, salt concentrations of between about 0.75 and about 2 M ammonium sulfate or between about 1 and 4 M NaCl are useful.

HIC columns normally comprise a base matrix (e.g., cross-linked agarose or synthetic copolymer material) to which hydrophobic ligands (e.g., alkyl or aryl groups) are coupled. A suitable HIC column comprises an agarose resin substituted with phenyl groups (e.g., a Phenyl Sepharose™ column). Many HIC columns are available commercially. Examples include, but are not limited to, Phenyl Sepharose™ 6 Fast Flow column with low or high substitution (Pharmacia LKB Biotechnology, AB, Sweden); Phenyl Sepharose™ High Performance column (Pharmacia LKB Biotechnology, AB, Sweden); Octyl Sepharose™ High Performance column (Pharmacia LKB Biotechnology, AB, Sweden); Fractogel™ EMD Propyl or Fractogel™ EMD Phenyl columns (E. Merck, Germany); Macro-Prep™ Mehyl or Macro-Prep™ t-Butyl Supports (Bio-Rad, California); WP HI-Propyl (C3)™ column (J. T. Baker, New Jersey); and Toyopearl™ ether, phenyl or butyl columns (TosoHaas, PA).

5.4.7 Multimodal Chromatography

In certain embodiments, it will be advantageous to subject a sample produced by the techniques of the instant invention to multimodal chromatography in order to purify the protein of interest away from process-related impurities and/or product-related substances. Multimodal chromatography is chromatography that utilizes a multimodal media resin. Such a resin comprises a multimodal chromatography ligand. In certain embodiments, such a ligand refers to a ligand that is capable of providing at least two different, but co-operative, sites which interact with the substance to be bound. One of these sites gives an attractive type of charge-charge interaction between the ligand and the substance of interest. The other site typically gives electron acceptordonor interaction and/or hydrophobic and/or hydrophilic interactions. Electron donor-acceptor interactions include interactions such as hydrogen-bonding, π-π, cation-π, charge transfer, dipole-dipole, induced dipole etc. Multimodal chromatography ligands are also known as "mixed mode" chromatography ligands.

In certain embodiments, the multimodal chromatography resin is comprised of multimodal ligands coupled to an organic or inorganic support, sometimes denoted a base matrix, directly or via a spacer. The support may be in the form of particles, such as essentially spherical particles, a monolith, filter, membrane, surface, capillaries, etc. In certain embodiments, the support is prepared from a native polymer, such as cross-linked carbohydrate material, such as agarose, agar, cellulose, dextran, chitosan, konjac, carrageenan, gellan, alginate etc. To obtain high adsorption capacities, the support can be porous, and ligands are then coupled to the external surfaces as well as to the pore surfaces. Such native polymer supports can be prepared according to standard methods, such as inverse suspension gelation (S Hjerten: Biochim Biophys Acta 79(2), 393-398 (1964). Alternatively, the support can be prepared from a synthetic polymer, such as cross-linked synthetic polymers, e.g. styrene or styrene derivatives, divinylbenzene, acrylamides, acrylate esters, methacrylate esters, vinyl esters, vinyl amides etc. Such synthetic polymers can be produced according to standard methods, see e.g. "Styrene based polymer supports developed by suspension polymerization" (R Arshady: Chimica e L'Industria 70(9), 70-75 (1988)). Porous native or synthetic polymer supports are also available from commercial sources, such as Amersham Biosciences, Uppsala, Sweden.

5.5 Pharmaceutical Compositions

The proteins, for example, antibodies and antibody-portions, produced using the cell culture techniques of the instant invention can be incorporated into pharmaceutical compositions suitable for administration to a subject. Typically, the pharmaceutical composition comprises a protein of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it is desirable to include isotonic agents, e.g., sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

The protein compositions of the invention can be incorporated into a pharmaceutical composition suitable for parenteral administration. The protein can be prepared as an injectable solution containing, e.g., 0.1-250 mg/mL antibody. The injectable solution can be composed of either a liquid or lyophilized dosage form in a flint or amber vial, ampule or pre-filled syringe. The buffer can be L-histidine approximately 1-50 mM, (optimally 5-10 mM), at pH 5.0 to 7.0 (optimally pH 6.0). Other suitable buffers include but are not limited to sodium succinate, sodium citrate, sodium phosphate or potassium phosphate. Sodium chloride can be used to modify the toxicity of the solution at a concentration of 0-300 mM (optimally 150 mM for a liquid dosage form).

Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 24%). Stabilizers can be used in both liquid and lyophilized dosage forms, principally 1-50 mM L-methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants.

In one aspect, the pharmaceutical composition includes the protein at a dosage of about 0.01 mg/kg-10 mg/kg. In another aspect, the dosages of the protein include approximately 1 mg/kg administered every other week, or approximately 0.3 mg/kg administered weekly. A skilled practitioner can ascertain the proper dosage and regime for administering to a subject.

The compositions of this invention may be in a variety of forms. These include, e.g., liquid, semi-solid and solid dosage forms, such as liquid solutions (e.g., injectable and infusible solutions), dispersions or suspensions, tablets, pills, powders, liposomes and suppositories. The form depends on, e.g., the intended mode of administration and therapeutic application. Typical compositions are in the form of injectable or infusible solutions, such as compositions similar to those used for passive immunization of humans with other antibodies. One mode of administration is parenteral (e.g., intravenous, subcutaneous, intraperitoneal, intramuscular). In one aspect, the protein is administered by intravenous infusion or injection. In another aspect, the protein is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., protein, antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the methods of preparation are vacuum drying and spray-drying that yields a powder of the active ingredient plus any additional desired ingredient from a previously sterile-filtered solution thereof. The proper fluidity of a solution can be maintained, e.g., by the use of a coating such as lecithin, by the maintenance of the required particle size in the case of dispersion and by the use of surfactants. Prolonged absorption of injectable compositions can be brought about by including in the composition an agent that delays absorption, e.g., monostearate salts and gelatin.

The protein of the present invention can be administered by a variety of methods known in the art, one route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978, the entire teaching of which is incorporated herein by reference.

In certain aspects, a protein of the invention may be orally administered, e.g., with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain aspects, a protein of the invention is co-formulated with and/or co-administered with one or more additional therapeutic agents that are useful for treating disorders. For example, an antibody or antibody portion of the invention may be co-formulated and/or co-administered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies. It will be appreciated by the skilled practitioner that when the protein of the invention are used as part of a combination therapy, a lower dosage of protein may be desirable than when the protein alone is administered to a subject (e.g., a synergistic therapeutic effect may be achieved through the use of combination therapy which, in turn, permits use of a lower dose of the protein to achieve the desired therapeutic effect).

It should be understood that the protein of the invention can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the protein of the present invention. The additional agent also can be an agent which imparts a beneficial attribute to the therapeutic composition, e.g., an agent which effects the viscosity of the composition.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. In certain embodiments it is especially advantageous to formulate parenteral compositions in dosage unit form for ease of administration and uniformity of dosage. Dosage unit form as used herein refers to physically discrete units suited as unitary dosages for the mammalian subjects to be treated; each unit comprising a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of a protein of the invention is 0.01-20 mg/kg, or 1-10 mg/kg, or 0.3-1 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

6. EXAMPLES 6.1 Method for Reducing the Extent of Acidic Species in Cell Culture by the Addition of Medium Components Production of recombinant proteins by host cells can result in product-related charge heterogeneities present in the population of proteins produced by the cells. The presence of acidic species in the population of proteins is an example of a product-related charge heterogeneity. Control of the amount of acidic species present in the population of proteins produced by the host cells can be accomplished by modifying the culture conditions of the host cells.

6.1.1 Materials and Methods

Cell Source and Adaptation Cultures

Three adalimumab producing cell lines, one mAb1 producing cell line and one mAb2 producing were employed in the studies covered here. For adalimumab producing cell lines, cells were cultured in their respective growth media (chemically defined media (media 1) or a hydrolysate based media (media 2 or media 3)) in a combination of vented non-baffled shake flasks (Corning) on a shaker platform at 110 RPM (cell line 1), 180 RPM (cell line 2), 140 RPM (cell line 3) and 10 L or 20 L wave bags (GE). For experiments with cells in the hydrolysate based media (media 3), cells were thawed in media 1 and then adapted to media 3 over a few passages. Cultures were propagated in a 35° C., 5% $CO_2$ incubator for cell line 1 and 2 and in a 36° C., 5% $CO_2$ incubator for cell line 3 in order to obtain the required number of cells to be able to initiate production stage cultures.

For the mAb1 producing cell line, cells were cultured in chemically defined growth media (media 1) in a combination of vented non-baffled shake flasks (Corning) on a shaker platform at 130 RPM and 20 L wave bags (GE). Cultures were propagated in a 36° C., 5% $CO_2$ incubator to obtain the required number of cells to be able to initiate production stage cultures.

For the mAb2 producing cell line, cells were cultured in chemically defined growth media (media 1) in a combination of vented non-baffled shake flasks (Corning) on a shaker platform at 140 RPM and 20 L wave bags (GE). Cultures were propagated in a 35° C., 5% $CO_2$ incubator to obtain the required number of cells to be able to initiate production stage cultures.

Cell Culture Media

Growth and production media were prepared from either a chemically defined media formulation (media 1) or hydrolysate-based medium formulations (media 2 and media 3). For preparation of the media 1, the media (IVGN GIA-1, a proprietary basal media formulation from Invitrogen) was supplemented with L-glutamine, sodium bicarbonate, sodium chloride, and methotrexate solution. Production media consisted of all the components in the growth medium, excluding methotrexate. For cell line 1, both growth and production medium were also supplemented with insulin. For mAB1 and mAB2 producing cell lines, the growth medium were also supplemented with insulin.

For the hydrolysate-based formulation (media 2), the growth media was composed of PFCHO (proprietary chemically defined formulation from SAFC), Dextrose, L-Glutamine, L-Asparagine, HEPES, Poloxamer 188, Ferric Citrate, Recombinant Human Insulin, Yeastolate (BD), Phytone Peptone (BD), Mono- and Di-basic Sodium Phosphate, Sodium Bicarbonate, Sodium Chloride and methotrexate. Production media consisted of all the components listed in the growth medium, excluding methotrexate.

For the hydrolysate-based formulation (media 3), the growth media was composed of OptiCHO (Invitrogen), L-Glutamine, Yeastolate (BD), Phytone Peptone (BD) and methotrexate. Production media consisted of all the components listed in the growth medium, excluding methotrexate.

Amino acids used for the experiments were reconstituted in Milli-Q water to make a 100 g/L stock solution, which was subsequently supplemented to both growth and production basal media. After addition of amino acids, media was brought to a pH similar to unsupplemented (control) media using 5N hydrochloric acid/5N NaOH, and it was brought to an osmolality similar to unsupplemented (control) media by adjusting the concentration of sodium chloride.

Calcium Chloride Dihydrate (Sigma or Fluka) used for the experiments were reconstituted in Milli-Q water to make a stock solution, which was subsequently supplemented to the production basal media. After addition of calcium chloride, media was brought to a pH similar to non-supplemented (control) media using 6N hydrochloric acid/5N NaOH, and it was brought to an osmolality similar to non-supplemented (control) media by adjusting the concentration of sodium chloride.

Niacinamide (Sigma or Calbiochem) used for the experiments were reconstituted in Milli-Q water to make a stock solution, which was subsequently supplemented to the production basal media. After addition of niacinamide, media was brought to a pH similar to non-supplemented (control) media using 6N hydrochloric acid/5N NaOH, and it was brought to an osmolality similar to non-supplemented (control) media by adjusting the concentration of sodium chloride.

All media was filtered through Corning 1 L filter systems (0.22 µm PES) and stored at 4° C. until usage.

TABLE 2

List of medium additives supplemented to culture media

| Medium additive | Catalog No./Source of medium supplements |
|---|---|
| Arginine | Sigma, A8094 |
| Lysine | Calbiochem, 4400 |
| Histidine | Sigma, H5659 |
| Ornithine | Sigma, 06503 |

TABLE 2-continued

List of medium additives supplemented to culture media

| Medium additive | Catalog No./Source of medium supplements |
|---|---|
| Calcium Chloride | Fulka, 21097 Sigma, C8106 |
| Niacinamide | Calbiochem, 481907 Sigma, N0636 |

Production Cultures

Production cultures were initiated either in 500 ml shake flasks (Corning) or in 3 L Bioreactors (Applikon). For shake flask experiments, duplicate 500 mL Corning vented non-baffled shake flasks (200 mL working volume) were used for each condition. The shake flasks were kept in incubators either maintained at 35° C. or 36° C. and 5% $CO_2$ on shaker platforms that were either set at 110 rpm for adalimumab producing cell line 1, 180 rpm for adalimumab producing cell line 2, 140 rpm for adalimumab producing cell line 3, for 130 rpm for mAB1 producing cell line, or 140 rpm for mAB2 producing cell line. For the bioreactor experiments, 3 L bioreactors (1.5 L working volume) were run at 35° C., 30% DO, 200 rpm, pH profile from 7.1 to 6.9 in three days and pH 6.9 thereafter. In all experiments, the cells were transferred from the seed train to the production stage at a split ratio of 1:5.

Cultures were run in either batch or fed-batch mode. In the batch mode, cells were cultured in the respective production medium. 1.25% (v/v) of 40% glucose stock solution was fed when the media glucose concentration reduced to less than 3 g/L. In the fed-batch mode, cultures were run with either the IVGN feed (proprietary chemically defined feed formulation from Invitrogen) as per the following feed schedule—(4% (v/v)—day 6, day 7, and day 8, respectively) along with 10× Ex-Cell PFCHO feed (proprietary chemically defined formulation)—3% (v/v) on day 3. The cultures were also fed with 1.25% (v/v) of 40% glucose stock solution when the glucose concentration was below 3.0 g/l.

Retention samples for titer analysis, of 2×1.5 mL, were collected daily for the bioreactor experiments (section 2.2.4) beginning on Day 8, and frozen at −80° C. The samples taken from each were later submitted for titer analysis.

The harvest procedure of the shake flasks and reactors involved centrifugation of the culture sample at 3,000 RPM for 30 min and storage of supernatant in PETG bottles at −80° C. before submission for protein A purification and WCX-10 analysis.

WCX-10 Assay

This method is employed towards the quantification of the acidic species and other charge variants present in cell culture harvest samples. Cation exchange chromatography was performed on a Dionex ProPac WCX-10, Analytical column (Dionex, CA).

For adalimumab and mAB1 samples, the mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

For mAb2 samples, the mobile phases used were 20 mM (4-Morpholino) ethanesulfonic Acid Monohydrate (MES) pH 6.5 (Mobile phase A) and 20 mM MES, 500 mM Sodium Chloride pH 6.5 (Mobile phase B). An optimized gradient (minute/% B): 0/3, 1/3, 46/21, 47/100, 52/100, 53/3, 58/3 was used with detection at 280 nm.

Quantitation is based on the relative area percent of detected peaks. The peaks that elute at relative residence time earlier than the main peak corresponding to the drug product are together represented as the acidic peaks (FIG. 1).

Lysine-C Peptide Mapping for MGO Quantification

Typical trypsin digestion employed almost universally for peptide mapping cuts a denatured, reduced and alkylated protein at the carboxyl side of the two basic amino acids, lysine and arginine. Methylglyoxal is a small molecule metabolite derived as a glycolysis byproduct which can modify arginine residues. A modification of an arginine prevents trypsin from cutting this site and results in a mis-cleavage. The challenge of quantifying the amount of MGO modified peptide is that it is not compared to an equivalent non-modified peptide but rather two parental cleaved peptides which will likely have different ionization potential than the modified peptide. In order to determine a truly accurate direct measurement of an MGO-modified peptide, it must be compared to its non-modified counterpart and expressed as a percent. Using endoproteinase Lysine-C as an alternative enzyme, cleavages only occur at lysine residues. The result is a direct comparison of the same peptide with and without an MGO modification which provides a high degree of accuracy in quantifying even trace levels of the modified species.

Procedure: Samples are diluted to a nominal concentration of 4 mg/mL. 8 M guanidine-HCl is added to the sample in a 3:1 ratio resulting in a 1 mg/mL concentration in 6M guanidine-HCl. The samples are reduced with 10 mM final conc. DTT for 30 minutes at 37° C. followed by an alkylation with 25 mM final conc. iodoacetic acid for 30 minutes at 37° C. in the dark. The samples are then buffer exchanged into 10 mM Tris pH 8.0 using NAP-5 columns. The samples are then digested for 4 hours at 37° C. using endoproteinase Lys-C at an enzyme to protein ratio of 1:20. The digest is quenched by adding 5 μL of formic acid to each sample. Samples are analyzed by LC/MS peptide mapping. Briefly, 50 μL of sample is loaded onto a Waters BEH C18 1.7μ 1.0×150 mm UPLC column with 98% 0.08% formic acid, 0.02% TFA in water and 2% 0.08% formic acid, 0.02% TFA in acetonitrile. The composition is changed to 65% 0.08% formic acid, 0.02% TFA in water and 35% 0.08% formic acid, 0.02% TFA in acetonitrile in 135 minutes using a Waters Acquity UPLC system. Eluting peaks are monitored using a Thermo Scientific LTQ-Orbitrap Mass Spectrometer. Specific mass traces are extracted for both modified and non-modified peptides in order to accurately quantify the total amount of MGO modification at each site. Mass spectra are also analyzed for the specific region of the chromatogram to confirm the peptide identity. An example data set is shown in FIG. 140.

6.1.2 Results

Effect of Arginine Supplementation to Cell Culture Media

The addition of arginine was tested in several experimental systems covering multiple cell lines, media and monoclonal antibodies. Following is a detailed description of two representative experiments where two different adalimumab producing cell lines were cultured in a chemically defined media (media 1).

Figure 2:
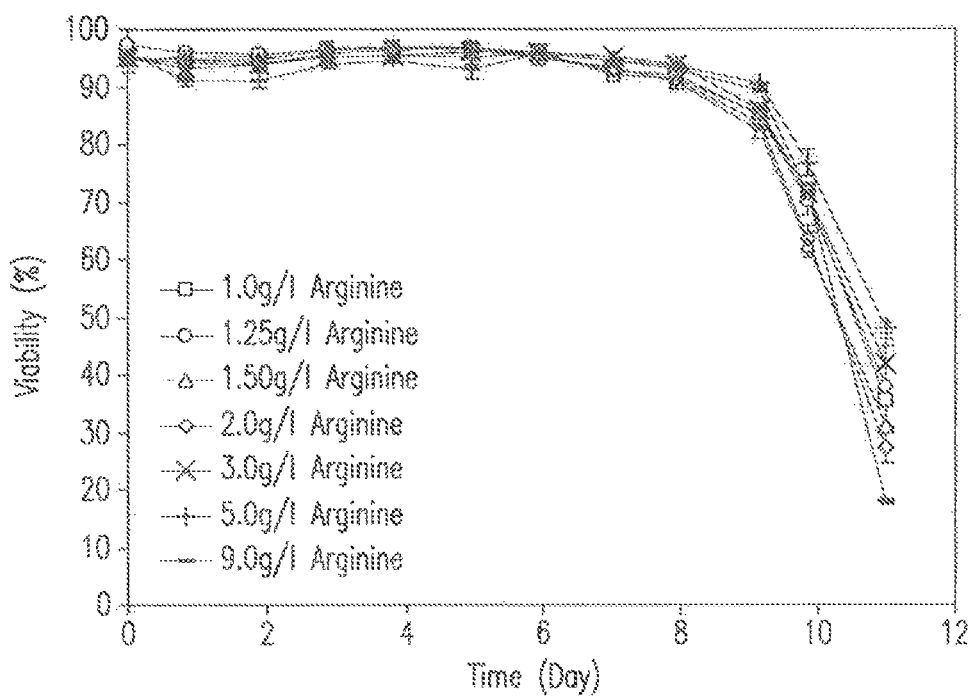
FIG. 2 depicts the effect of total arginine concentration in adalimumab producing cell line 2, media 1 on viability (n=2).
Figure 3:
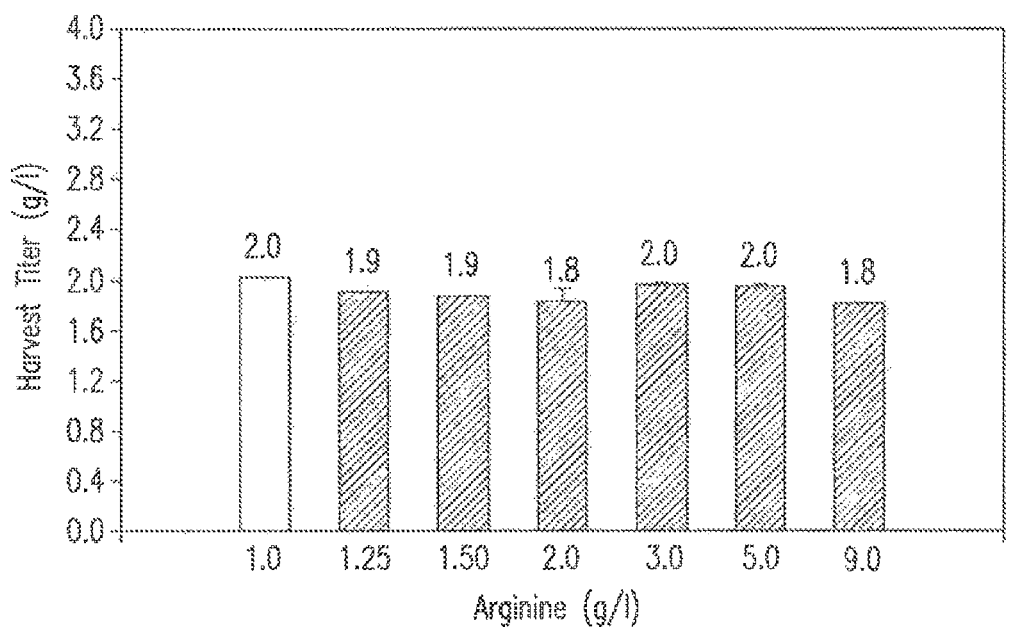
FIG. 3 depicts the effect of total arginine concentration in adalimumab producing cell line 2, media 1 on harvest titer (n=2).

Cell line 2 was cultured in media 1 with different total amounts of arginine (1 (control), 1.25, 1.5, 2, 3, 5, 9 g/l). The cultures were performed in shake flasks in batch format with only glucose feed as described in the materials and methods. The cells grew to maximum viable cell densities (VCD) in the range of 18-22×10$^6$ cells/ml for the different conditions tested. The growth and viability profiles were comparable between the different test conditions, although a slight decrease in viable cell density profile was observed in samples with the 9 g/l arginine test condition (FIGS. 1, 2). The harvest titers were comparable between the conditions (FIG. 3). On Day 10 and Day 12 of culture, duplicate shake flasks for each of the conditions were harvested and then subsequently analyzed using WCX-10 post protein A purification and the percentages of total peak(s) area corresponding to the acidic species were quantified (FIG. 4, 5). The percentage of acidic species in the control sample was as high as 19.7% on day 10. In the sample with the highest total concentration of arginine in this experiment (9 g/l), the percentage of acidic species was reduced to 12.2%. A dose dependent decrease in acidic species was observed in test conditions with arginine concentrations beyond 2 g/l (FIG. 4). A similar trend in reduction of acidic species with arginine increase was also observed in the day 12 harvest samples (FIG. 5). Further, while the extent of acidic species in the 1 g/l arginine samples increased from 19.7% (day 10 harvest) to 25.5% (day 12 harvest), this increase in the 9 g/l arginine test condition was significantly smaller from 12.2% (day 10 harvest) to 13.9% (day 12 harvest). Thus, the increase of total arginine led to a reduction in the extent of total acidic species at a particular time point in culture as well the rate of increase of acidic species with time of culture.

Cell line 3 was cultured in media 1 with different total amounts of arginine (1 (control), 3, 5, 7, 9 g/l). The cultures were performed in shake flasks in batch format with only glucose feed as described in the materials and methods. The cells grew to maximum viable cell densities (VCD) in the range of 7-10×10$^6$ cells/ml for the different conditions tested. The growth and viability profiles were comparable between the different test conditions, although a slight decrease in viable cell density and viability profiles was observed in samples with the 9 g/l arginine condition (FIG. 6, 7). The product titer was also comparable between all conditions (FIG. 8). On Day 10 of culture, duplicate shake flasks for each of the conditions were harvested and then subsequently analyzed using WCX-10 post protein A purification and the percentages of total peak(s) area corresponding to the acidic species were quantified (FIG. 9). The percentage of acidic species in the control sample was as high as 23.3% on day 10. In the sample with the highest total concentration of arginine in this experiment (9 g/l), the percentage of acidic species was reduced to 17.0%. A dose dependent decrease in acidic species was observed in conditions with higher concentrations of arginine.

Additional experiments were performed with multiple cell lines in chemically defined or hydrolysate based media to demonstrate the wide range of applicability of this method. The experimental setup for each of these experiments was similar to that described above. The summaries of results of the different experiments performed for adalimumab are summarized in FIGS. 10, 11, 12. A reduction in acidic species with increased arginine concentration was also observed in each case.

In addition to adalimumab, the utility of this method for acidic species reduction was also demonstrated for processes involving two other mAB producing cell lines. The experimental setup for each of these experiments was similar to that described in section above and in the materials and methods. The reduction of acidic species with increased arginine concentration for experiments corresponding to each mAB is summarized in FIG. 13, 14. For mAB2, a significant reduction in acidic species was only observed at arginine concentration of 9 g/l.

In U.S. patent application Ser. No. 13/830,976 we describe the utility of arginine supplementation to culture media towards modulation of the lysine variant distribution. It is possible that a fraction of acidic species also shifted along with shift in lysine variants (from Lys 0 to Lys1 and Lys2), in addition to the fraction of acidic species that is completely removed from the entire protein population. To estimate the acidic species reduction that is independent of this redistribution of lysine variants, protein A eluate samples from a representative set of arginine supplementation experiments were pre-treated with the enzyme carboxypeptidase before WCX-10. One set of samples from adalimumab experiment and another set of samples from a mAB2 experiment were used for this analysis. The carboxypeptidase treatment of the samples resulted in the cleavage of the C-terminal lysine residues as demonstrated by the complete conversion of Lys1/Lys2 to Lys 0 in each of these samples (data not shown here). As a result of this conversion, the acidic species quantified in these samples corresponded to an aggregate sum of acidic species that would be expected to also include those species that may have previously shifted corresponding to the lysine variant shift and perhaps gone unaccounted for in the samples that were not treated with carboxypeptidase prior to WCX-10. A dose dependent reduction in acidic species was observed in the carboxypeptidase treated samples with increasing concentration arginine (FIG. 15, 16). This suggests that the acidic species reduction described here is not completely attributed to a probable shift of the acidic species corresponding to the lysine variant redistribution.

Effect of Lysine Supplementation to Cell Culture Media

The addition of lysine was tested in several experimental systems covering multiple cell lines, media and monoclonal antibodies. Following is a detailed description of two representative experiments where two different cell lines were cultured in a chemically defined media (media 1) for the production of adalimumab.

Cell line 2 was cultured in media 1 with different total concentrations of lysine (1 (control), 5, 7, 9, 11 g/l). The cultures were performed in shake flasks in batch format with only glucose feed as described in the materials and methods. The cells grew to maximum viable cell densities (VCD) in the range of $17\text{-}23\times10^6$ cells/ml for the different conditions tested. A slight dose dependent decrease in viable cell density profile was observed in all samples with respect to the control sample (FIG. 17). The viability profiles were comparable between the conditions (FIG. 18). On Days 10 and 11 of culture samples were collected for titer analysis (FIG. 19). The titers for all conditions were comparable. On Day 11 of culture, duplicate shake flasks for each of the conditions were harvested and then subsequently analyzed using WCX-10 post protein A purification and the percentages of total peak(s) area corresponding to the acidic species were quantified (FIG. 20). The percentage of acidic species in the control was as high as 26.5%. In the sample with the highest tested concentration of lysine in this experiment (11 g/l), the percentage of acidic species was reduced to 15.0%. A dose dependent decrease in acidic species was observed in test conditions with higher total concentrations of lysine.

Cell line 3 was cultured in media 1 with different total concentrations of lysine (1 (control), 3, 5, 7, 9, 11 g/l). The cultures were performed in shake flasks in batch format with only glucose feed as described in the materials and methods. The cells grew to maximum viable cell densities (VCD) in the range of $9.5\text{-}11.5\times10^6$ cells/ml for the different conditions tested. The growth and viability profiles were comparable between the different test conditions, although a slight decrease in viable cell density and viability profiles was observed in samples with higher lysine concentrations than that in the control sample (FIG. 21, 22). On Days 10, 11 and 12 of culture samples were collected for titer analysis (FIG. 23). The titers for all conditions were comparable. On Day 12 of culture, duplicate shake flasks for each of the conditions were harvested and then subsequently analyzed using WCX-10 post protein A purification and the percentages of total peak(s) area corresponding to the acidic species were quantified (FIG. 24). The percentage of acidic species in the control sample was as high as 26.6%. In the sample with the highest tested concentration of lysine in this experiment (11 g/l) the percentage of acidic species was reduced to 18.1%. A dose dependent decrease in acidic species was observed in test conditions with higher total concentrations of lysine.

Additional experiments were performed with multiple cell lines in chemically defined or hydrolysate based media to demonstrate the wide range of applicability of this method. The experimental setup for each of these experiments was similar to that described above and in materials and methods section. The summaries of results of the different experiments performed for adalimumab are summarized in FIGS. 25, 26, 27. A reduction in acidic species with increased lysine concentration was also observed in each case.

In addition to adalimumab, the utility of this method for acidic species reduction was also demonstrated for processes involving two other mABs. The experimental setup for each of these experiments was similar to that described above and in the materials and methods section. The reduction of acidic species with lysine addition for experiments corresponding to each mAB is summarized in FIGS. 28, 29. For mAB2, a significant reduction in acidic species was only observed at lysine concentration of 11 g/l.

In U.S. patent application Ser. No. 13/830,976 we describe the utility of lysine supplementation to culture media towards modulation of the lysine variant distribution. To estimate the acidic species reduction that is independent of this redistribution of lysine variants, protein A eluate samples from a representative set of lysine supplementation experiments were pre-treated with the enzyme carboxypeptidase before WCX-10. One set of samples from adalimumab experiment and another set of samples from a mAB2 experiment were used for this analysis. The carboxypeptidase treatment of the samples resulted in the cleavage of the C-terminal lysine residues as demonstrated by the conversion of Lys1/Lys2 to Lys 0 in each of these samples (data not shown here). As a result of this conversion, the acidic species quantified in these samples corresponded to an aggregate sum of acidic species that would be expected to also include those species that may have previously shifted corresponding to the lysine variant shift and perhaps gone unaccounted for in the samples that were not treated with carboxypeptidase prior to WCX-10. A dose dependent reduction in acidic species was observed in the carboxypeptidase treated samples with increasing concentration of lysine for the adalimumab samples from 26.8% in the non-supplemented sample to 21.1% in the 10 g/l Lysine supplemented sample, a reduction of 5.7% in total acidic species (FIG. 30). Similar results were also observed for the mA2 samples (FIG. 31). This suggests that the acidic species reduction described here is not completely attributed to a probable shift of the acidic species corresponding to the lysine redistribution.

Effect of Histidine Supplementation to Cell Culture Media

The addition of histidine was tested in several experimental systems covering multiple cell lines, media and monoclonal antibodies. Following is a detailed description of two representative experiments where two different cell lines were cultured in a chemically defined media (media 1) for the production of adalimumab.

Cell line 2 was cultured in media 1 with different total concentrations of histidine (0 (control), 4, 6, 8, 10 g/l). The cultures were performed in shake flasks in batch format with only glucose feed as described in the materials and methods. The cells grew to maximum viable cell densities (VCD) in the range of 12-22×10$^6$ cells/ml for the different conditions tested. A dose dependent decrease in viable cell density profile was observed with the 10 g/l histidine condition having significant reduction in growth (FIG. 32). A corresponding effect on viability was also observed (FIG. 33). On Days 10, 11 and 12 of culture samples were collected for titer analysis and reported for the harvest day for each sample (FIG. 34). There was a small dose dependent decrease in titers for conditions with histidine supplementation. On Days 11-12, duplicate shake flasks were harvested and then subsequently analyzed using WCX-10 post protein A purification and the percentages of total peak(s) area corresponding to the acidic species were quantified (FIG. 35). The percentage of acidic species in the control sample was as high as 26.5%. In the sample with the highest tested concentration of histidine in this experiment (10 g/l), the percentage of acidic species was reduced to 15.6%. A dose dependent decrease in acidic species was observed in test conditions with increased histidine concentrations.

Cell line 3 was cultured in media 1 with different total concentrations of histidine (0 (control), 2, 4, 6, 8 g/l). The cultures were performed in shake flasks in batch format with only glucose feed as described in the materials and methods. The cells grew to maximum viable cell densities (VCD) in the range of 6-10×10$^6$ cells/ml for the different conditions tested. A dose dependent decrease in viable cell density profile was observed in all conditions with histidine concentrations higher than that in the control (FIG. 36). The viability profiles were more comparable between conditions with this cell line (FIG. 37). On Day 12 of culture, samples were collected for titer analysis (FIG. 38). The titers for all conditions were comparable. On Day 12 of culture, duplicate shake flasks for each of the conditions were harvested and then subsequently analyzed using WCX-10 post protein A purification and the percentages of total peak(s) area corresponding to the acidic species were quantified (FIG. 39). The percentage of acidic species in the control sample was 26.2%. In the sample with the highest tested concentration of histidine in this experiment (8 g/l), the percentage of acidic species was reduced to 20.0%. A dose dependent decrease in acidic species was observed in test conditions with increased histidine concentration.

Additional experiments were performed with multiple cell lines in chemically defined or hydrolysate based media to evaluate the wide range of applicability of this method. The experimental setup for each of these experiments was similar to that described above and in the materials and methods section. The summaries of results of the different experiments performed for adalimumab are summarized in FIGS. 40, 41, 42. A reduction in acidic species with increased histidine concentration was observed with cell line 1 in media 1 (FIG. 40) and with cell line 2 in media 3 (FIG. 42). For cell line 2 in media 3, a dose dependent reduction in acidic species was observed upto 4 g/l histidine, with no further significant reduction at higher concentrations of histidine (FIG. 42). For cell line 1, media 2, no significant reduction of acidic species was observed within the histidine concentration range (0-4 g/l) (FIG. 41).

In addition to adalimumab, the utility of this method for acidic species reduction was also demonstrated for processes involving two other mABs. The experimental setup for each of these experiments was similar to that described above and in the materials and methods section. The reduction of acidic species with increased histidine concentration for experiments corresponding to each mAB is summarized in FIGS. 43, 44. For mAB2, in contrast with the results reported with arginine and lysine supplementation shown previously, a clear significant dose dependent reduction in total acidic species from 28.1% in the control to 21.5% in 4 g/l histidine sample was observed.

In U.S. patent application Ser. No. 13/830,976 we also describe the utility of increased histidine to culture media towards modulation of the lysine variant distribution. To estimate the acidic species reduction that is independent of this redistribution of lysine variants, protein A eluate samples from a representative set of histidine supplementation experiments were also pre-treated with the enzyme carboxypeptidase before WCX-10. One set of samples from adalimumab experiment and another set of samples from a mAB2 experiment were used for this analysis. The carboxypeptidase treatment of the samples resulted in the cleavage of the C-terminal lysine residues as demonstrated by the complete conversion of Lys1/Lys2 to Lys 0 in each of these samples (data not shown here). A dose dependent reduction in acidic species was observed in the carboxypeptidase treated samples with increasing concentration of histidine (FIG. 45, 46). This suggests that the acidic species reduction described here is not completely attributed to a probable shift of the acidic species corresponding to the lysine redistribution.

Effect of Ornithine Supplementation to Cell Culture Media

The addition of ornithine was tested in several experimental systems covering multiple cell lines, media and monoclonal antibodies. Following is a detailed description of two representative experiments where two different cell lines were employed in a chemically defined media (media 1) for the production of adalimumab.

Cell line 2 was cultured in media 1 with different total concentrations of ornithine (0 (control), 4, 6, 8, 10 g/l). The cultures were performed in shake flasks in batch format with only glucose feed as described in the materials and methods. The cells grew to maximum viable cell densities (VCD) in the range of 15-22×10$^6$ cells/ml for the different conditions tested. A slight decrease in viable cell density with ornithine supplementation was observed (FIG. 47). Corresponding differences in the viability profiles were also observed (FIG. 48). On Day 11 of culture, samples were collected for titer analysis (FIG. 49). The titers for all conditions were comparable. On Day 11, duplicate shake flasks were harvested for each condition and then subsequently analyzed using WCX-10 post protein A purification and the percentages of total peak(s) area corresponding to the acidic species were quantified (FIG. 50). The percentage of acidic species in the control sample was 26.5%. In the sample with the highest tested concentration of ornithine in this experiment (10 g/l), the percentage of acidic species was reduced to 16.1%. A dose dependent decrease in acidic species was observed in test conditions with increased ornithine concentration.

Cell line 3 was cultured in media 1 supplemented with different total concentrations of ornithine (0 (control), 2, 4, 6, 8 g/l). The cultures were performed in shake flasks in batch format with only glucose feed as described in the materials and methods. The cells grew to maximum viable cell densities (VCD) in the range of 9.5-11.5×10$^6$ cells/ml for the different conditions tested. The viable cell density and viability profiles were comparable (FIG. 51, 52). On Day 12 of culture, samples were collected for titer analysis (FIG. 53). The titers for all conditions were comparable. On Day 12 of culture, duplicate shake flasks for each of the conditions were harvested and then subsequently analyzed using WCX-10 post protein A purification and the percentages of total peak(s) area corresponding to the acidic species were quantified (FIG. 54). The percentage of acidic species in the control sample was 24.8%. In the sample with the highest tested concentration of ornithine in this experiment (8 g/l), the percentage of acidic species was reduced to 20.5%. A dose dependent decrease in acidic species was observed in test conditions with increased ornithine concentration.

Additional experiments were performed with multiple cell lines in chemically defined or hydrolysate based media to evaluate the wide range of applicability of this method. The experimental setup for each of these experiments was similar to that described above and in the materials and methods section. The summaries of results of the different experiments performed for adalimumab are summarized in FIGS. 55, 56 and 57. For cell line 1 in media 1, a dose dependent reduction was observed (FIG. 55). However, for cell line 1 in media 2, a hydrolysate media, no significant reduction in acidic species was observed across the conditions (FIG. 56). For cell line 2 in media 3, a reduction in acidic species from 22.1% in the control sample to 18.7% in the 2 g/l ornithine sample with no further reduction at higher ornithine concentrations was observed (FIG. 57).

In addition to adalimumab, the utility of this method for acidic species reduction was also demonstrated for processes involving two other mABs. The experimental setup for each of these experiments was similar to that described in section above and in the materials and method section. The reduction of acidic species with ornithine addition for experiments corresponding to each mAB is summarized in FIG. 58, 59. In the case of mAB1, a 7.3% dose dependent reduction in total acidic species was observed within the concentration range tested. For mAB2, about 2% reduction was observed in the 1 g/l ornithine concentration sample with minimum further reduction at higher ornithine concentrations.

Similar to the analysis conducted with the other amino acids, protein A eluate samples from a representative set of ornithine experiments were also pre-treated with the enzyme carboxypeptidase before WCX-10. One set of samples from adalimumab experiment and another set of samples from a mAB2 experiment were used for this analysis. A dose dependent reduction in acidic species was observed in the carboxypeptidase treated samples with increasing concentration of ornithine (FIG. 60, 61). The percentage of acidic species was also comparable between an untreated and a carboxypeptidase treated sample for a particular concentration of ornithine. This suggests that the acidic species reduction is independent of any probable shift of the acidic species that may be corresponding to any lysine redistribution.

Effect of Increasing a Combination of Arginine, Lysine, Histidine, Ornithine to Cell Culture Media In this experiment, the combined use of the four amino acids arginine, lysine, histidine and ornithine for acidic species reduction is demonstrated. The experiment described here was performed using adalimumab producing cell line 2 in chemically defined media (media 1). The concentration range for arginine and lysine in this experiment was 1-3 g/l while the concentration range for histidine and ornithine in this experiment was between 0-2 g/l. In comparison to the lower concentrations, or conditions where a single amino acid concentration was increased, a further reduction in total acidic species was observed in conditions where combinations of amino acids were increased in the media (FIG. 62). A progressive decrease was observed in total acidic species when more amino acids were increased in combination. The percentage of acidic species was reduced from 21.9% in the lowest concentration sample to 12.3% in the sample with high concentrations of all four amino acids.

Control of Acidic Species Through Cell Culture with Increased Arginine and Lysine and Choice of Harvest Criterion and/or Modulation of pH The increase of the amino acid (arginine, lysine) concentration in basal media may also be combined with choice of when to harvest a culture to achieve optimal reduction in total acidic species. In this example, a study was carried out in 3 L bioreactors with cell line 1 (producing adalimumab) in media 1. Two sets of conditions were tested: Control condition (Arginine 1 g/l, Lysine 1 g/l); Test condition 1 (Arginine 3 g/l, Lysine 5 g/l). Cell growth, viability and titer profiles were comparable between the conditions (FIG. 63, 64, 65). A small amount of cell culture harvests were collected every day from day 4 to day 10 from each of the reactors and submitted for protein A purification and WCX-10 analysis. The percentage of acidic species in the control condition increased from 12.1% (on day 4) to 24.6% (on day 10) (FIG. 66). The percentage of acidic species in the test condition 1 was lower than that observed in the control condition at each corresponding culture day. The percentage of acidic species in the test condition also increased from 8.7% (day 4) to 18.8% (day 10). The rate of increase in acidic species with culture duration also correlated with the drop in viability for both conditions, with a sharp increase on day 8. Thus, along with increasing arginine and lysine concentrations in culture media, choice of harvest day/harvest viability can be used in combination to achieve a desired acidic species reduction.

The increase of the amino acid (arginine, lysine) concentration in basal media may be combined with process pH modulation to achieve further reduction in total acidic species. In this example, a study was carried out in 3 L bioreactors with cell line 1 (producing adalimumab) in media 1. Three sets of conditions were tested in duplicates: Control condition (Arginine (1 g/l), Lysine (1 g/l), pH 7.1→6.9 in 3 days, pH 6.9 thereafter); Test condition 1 (Arginine (3 g/l), Lysine (3 g/l), pH 7.1→6.9 in 3 days, pH 6.9 thereafter); Test condition 2 (Arginine (3 g/l), Lysine (3 g/l), pH 7.1→6.8 in 3 days, pH 6.8 thereafter). In comparison to the control, a slight decrease in VCD profile and harvest titer was observed for condition 2 (FIG. 67, 68, 69). The cultures were harvested when the viability was less than 50% and the culture harvests were submitted for protein A and WCX-10 analysis. The percentage of acidic species in the control sample was 19.1%. The percentage of acidic species was reduced to 14.3% in test condition 1 and to 12.8% in test condition 2 (FIG. 70). Thus, this demonstrates that the increase of amino acid concentration along with choice of lower final process pH can be used in combination for further reducing the extent of acidic species.

Effect of Supplementation of $CaCl_2$ to Cell Culture Media

The addition of calcium chloride was tested in several experimental systems covering multiple cell lines, media and monoclonal antibodies. Following is a detailed description of two representative experiments where two different cell lines were cultured in a chemically defined media (media 1) for the production of adalimumab.

Cell line 2 was cultured in media 1 with different concentrations of calcium (0.14, 0.84 and 1.54 mM). The cultures were performed in shake flasks in batch format with only glucose feed as described in the materials and methods. The cells grew to maximum viable cell densities (VCD) in the range of 22-24.5×10$^6$ cells/ml for the different conditions tested. The viable cell density and viability profiles for all test conditions were comparable (FIG. 71, 72). On Day 10 of culture samples were collected for titer analysis (FIG. 73). The titers for all conditions were comparable. On Day 10 duplicate shake flasks were harvested for each condition and then subsequently analyzed using WCX-10 post protein A purification and the percentages of total peak(s) area corresponding to the acidic species were quantified (FIG. 74). The percentage of acidic species in the 0.14 mM calcium condition was 23.8%. In the sample with the highest tested concentration of calcium in this experiment (1.54 mM), the percentage of acidic species was reduced to 21.6%. A dose dependent decrease in acidic species was observed in test conditions with increased calcium concentration.

Cell line 3 was cultured in media 1 with different total concentrations of calcium (0.14, 0.49, 0.84, 1.19, 1.54, 1.89 g/l). The cultures were performed in shake flasks in batch format with only glucose feed as described in the materials and methods. The cells grew to maximum viable cell densities (VCD) in the range of 9.5-10.5×10$^6$ cells/ml for the different conditions tested. The viable cell density and viability profiles for all test conditions were comparable (FIG. 75, 76). On Day 11 of culture, samples were collected for titer analysis. The harvest titers for all conditions were comparable (FIG. 77). On Day 11 of culture, duplicate shake flasks for each of the conditions were harvested and then subsequently analyzed using WCX-10 post protein A purification and the percentages of total peak(s) area corresponding to the acidic species were quantified (FIG. 78). The percentage of acidic species in the 0.14 mM calcium condition was 23.7%. In the sample with the highest tested concentration of calcium in this experiment (1.89 mM), the percentage of acidic species was reduced to 20.7%. A dose dependent decrease in acidic species was observed in test conditions with increased calcium concentration.

Additional experiments were performed with multiple cell lines in chemically defined or hydrolysate based media to evaluate the wide range of applicability of this method. The experimental setup for each of these experiments was similar to that described in section above and in the materials and methods section. The summaries of results of the different experiments performed for adalimumab are summarized in FIGS. 79, 80 and 81. A reduction in acidic species with increased calcium concentration was also observed in each case.

In addition to adalimumab, the utility of this method for acidic species reduction was also demonstrated for processes involving two other mABs. The experimental setup for each of these experiments was similar to that described in section above. The dose dependent reduction of acidic species with ornithine addition for experiments corresponding to each mAB is summarized in FIGS. 82, 83. For mAB1, a small yet significant acidic species reduction from 15.4% (0.14 mM calcium sample) to 11.8% (1.54 mM calcium chloride supplemented sample) was observed. For mAB2, a larger dose dependent reduction from 28.9% (0.14 mM calcium sample) to 23.1% (1.40 mM calcium chloride supplemented sample) was observed.

Effect of Increased Concentration of Arginine, Lysine, Calcium Chloride, Niacinamide in Combination In this experiment, the effect of the combined use of the amino acids arginine, lysine, inorganic salt calcium chloride and vitamin niacinamide for acidic species reduction was evaluated. The experiment described here was performed using cell line 2 (producing adalimumab) in chemically defined media (media 1) supplemented with 3% (v/v) PFCHO (proprietary chemically defined medium formulation from SAFC). A central composite DOE experimental design was used in this experiment. The basal media for each condition was supplemented with different concentrations of the four supplements. Cell cultures were carried out in duplicates for each condition. Upon harvest, WCX-10 analysis was performed post protein A purification. In Table 3, the experimental conditions from DOE design, including the concentration of each component supplemented, and the % total acidic species (or AR) obtained for each condition is summarized. Reduction of acidic species through the increased concentration of these components in combination was observed. For instance, condition (#24), where all four components were at their maximum concentration, the % total AR was reported to be reduced to 9.7%. Using the data from the experiment, a model predicting the effects of addition of these components to media for AR reduction ($R^2$: 0.92, P<0.0001) is described in FIG. 84. The model predicted a contribution from each of the four components towards acidic species reduction. It may be also possible to utilize this model to predict the choice of concentrations of these different components to the media, in order to achieve a target reduction in total AR.

TABLE 3

Experimental design and summary for the combined addition of arginine, lysine, calcium chloride and niacinamide

| Conditions | Arginine (g/l) | Lysine (g/l) | Calcium Chloride (mM) | Niacinamide (mM) | % Total AR |
|---|---|---|---|---|---|
| 1 | 0.0 | 4.0 | 0.7 | 0.8 | 13.0 |
| 2 | 0.0 | 6.0 | 1.4 | 0.0 | 12.6 |
| 3 | 4.0 | 2.0 | 0 | 1.6 | 12.3 |
| 4 | 4.0 | 6.0 | 0 | 1.6 | 11.6 |
| 5 | 2.0 | 4.0 | 0.7 | 0.8 | 11.2 |
| 6 | 0.0 | 6.0 | 0 | 0.0 | 15.0 |
| 7 | 0.0 | 6.0 | 1.4 | 1.6 | 10.7 |
| 8 | 0.0 | 2.0 | 0 | 0.0 | 16.7 |
| 9 | 2.0 | 4.0 | 0.7 | 0.8 | 11.0 |
| 10 | 4.0 | 6.0 | 1.4 | 1.6 | 11.0 |
| 11 | 2.0 | 2.0 | 0.7 | 0.8 | 12.9 |
| 12 | 2.0 | 4.0 | 1.4 | 0.8 | 11.1 |
| 13 | 0.0 | 6.0 | 0 | 1.6 | 13.2 |
| 14 | 4.0 | 2.0 | 0 | 0.0 | 12.3 |
| 15 | 2.0 | 4.0 | 0.7 | 0.0 | 13.0 |
| 16 | 2.0 | 4.0 | 0.7 | 1.6 | 11.4 |
| 17 | 0.0 | 2.0 | 1.4 | 1.6 | 12.0 |
| 18 | 2.0 | 4.0 | 0 | 0.8 | 12.0 |
| 19 | 4.0 | 4.0 | 0.7 | 0.8 | 12.0 |
| 20 | 0.0 | 2.0 | 1.4 | 0.0 | 14.0 |
| 21 | 4.0 | 6.0 | 1.4 | 0.0 | 11.0 |
| 22 | 0.0 | 2.0 | 0 | 1.6 | 13.6 |
| 23 | 2.0 | 6.0 | 0.7 | 0.8 | 11.0 |
| 24 | 4.0 | 2.0 | 1.4 | 1.6 | 9.7 |
| 25 | 4.0 | 6.0 | 0 | 0.0 | 11.8 |
| 26 | 4.0 | 2.0 | 1.4 | 0.0 | 10.4 |
| 27 | 2.0 | 4.0 | 0 | 0.0 | 12.7 |

Use of Niacinamide Supplementation to Cell Culture Media for Acidic Species Reduction In addition to the use of niacinamide in combination with other supplements described in the previous section, niacinamide addition may also be used independent of the other supplements as demonstrated in the experiments below for two mAbs: adalimumab and mAb1.

For the experiment corresponding to adalimumab, Cell line 1 was cultured in media 1 supplemented with different amounts of niacinamide (0, 0.2, 0.4, 0.8 and 1.6 mM). The cultures were performed in shake flasks in batch format with only glucose feed as described in the materials and methods. The cells grew to maximum viable cell densities (VCD) in the range of 8.5-11×10$^6$ cells/ml for the different conditions tested. A slight decrease in the viable cell density profile was observed with the maximum niacinamide supplementation (1.6 mM for this experiment) (FIG. 85). The viability profile for the test conditions were comparable (FIG. 86). On Day 12 of culture, samples were collected for titer analysis. The titers for all conditions were comparable (FIG. 87). On Day 11 and day 12, duplicate shake flasks were harvested for each condition and then subsequently analyzed using WCX-10 post protein A purification and the percentages of total peak(s) area corresponding to the acidic species were quantified (FIG. 88, 89). The percentage of acidic species in the day 10 control sample (without niacinamide supplementation) was 19.6%. In the day 10 sample with the highest tested concentration of niacinamide in this experiment (1.6 mM), the percentage of acidic species was reduced to 15.9%. Similar acidic species reduction with niacinamide supplementation was also observed in the day 12 samples.

For the experiment corresponding to mAb2, a mAB2 producing cell line was cultured in media 1 supplemented with different amounts of niacinamide (0, 0.1, 0.5, 1.0, 3.0 and 6.0 mM). The cultures were performed in shake flasks in batch format with only glucose feed as described in the materials and methods. The cells grew to maximum viable cell densities (VCD) in the range of 14-21.5×10$^6$ cells/ml for the different conditions tested. A slight decrease in the viable cell density profile was observed for the conditions with 3.0 mM and 6.0 mM niacinamide concentrations (FIG. 90). The viability profiles for all test conditions were comparable (FIG. 91). On Day 12 of culture samples were collected for titer analysis (FIG. 92). The titers for all conditions were comparable. On Day 12 duplicate shake flasks were harvested for each condition and then subsequently analyzed using WCX-10 post protein A purification and the percentages of total peak(s) area corresponding to the acidic species were quantified (FIG. 93). The percentage of acidic species in the control sample (without niacinamide supplementation) was 27.0%. In the sample with the highest tested concentration of niacinamide in this experiment (6.0 mM), the percentage of acidic species was reduced to 19.8%. A dose dependent decrease in acidic species was observed in test conditions with niacinamide supplementation.

Types of Acidic Species Variants Reduced by Supplementation of Culture Medium with Additives The addition of medium additives may be used to specifically reduce particular acidic variants within the larger fraction of total acidic species. In Table 4, a summary of the extent of some of the sub-species of the acidic species fraction have been presented for a representative set of experiments for adalimumab. Along with the reduction in total acidic species, the methods presented in this section may also be used for reduction of sub-species that include, but not limited to, AR1, AR2 and MGO (methylglyoxal) modified product variants.

TABLE 4

Summary of types of acidic species variants reduced in cultures supplemented with medium additives

| | | | | % MGO modified species | | | | | | |
|---|---|---|---|---|---|---|---|---|---|---|
| | | | | LIGHT CHAIN | | | HEAVY CHAIN | | | |
| Sample | % AR | % AR1 | % AR2 | Arg 30 | Arg 93 | Arg 108 | Arg 16 (19) | Arg 259 | Arg 359 | Arg 420 | TOTAL |
| Control | 26.9 | 9.7 | 17.3 | 1.63 | 1.21 | 0.33 | 0.6 | 0.06 | 3.96 | 3.31 | 11.1 |
| Lysine (10 g/l) | 15.0 | 4.5 | 10.4 | 1.29 | 0.91 | 0 | 0.46 | 0.04 | 1.77 | 2.09 | 6.56 |
| Histidine (10 g/l) | 14.7 | 5.3 | 9.4 | 1.21 | 0.61 | 0 | 0.49 | 0.02 | 1.42 | 1.47 | 5.22 |
| Ornithine (10 g/l) | 16.5 | 4.4 | 12.1 | 1.17 | 0.71 | 0 | 0.37 | 0.03 | 1.11 | 1.29 | 4.68 |
| Control | 22.5 | 7.5 | 15.0 | 1.13 | 0.69 | 0 | 0.17 | 0.02 | 0.03 | 0 | 2.04 |
| Arginine (8 g/l) | 17.1 | 4.6 | 12.5 | 1.05 | 0.63 | 0 | 0.16 | 0.04 | 0.04 | 0 | 1.92 |
| Control | 23.1 | 6.6 | 16.6 | 1.43 | 0.82 | 0 | 0.38 | 0.05 | 1 | 1.35 | 5.03 |
| Calcium Chloride (1.75 mM) | 20.8 | 5.9 | 14.9 | 1.28 | 0.83 | 0 | 0.2 | 0.04 | 1.07 | 1.52 | 4.94 |

6.1.3 Conclusion

The different experiments above demonstrate that supplementation of cell culture medium with supplemental amounts of amino acids, calcium chloride and niacinamide enhances product quality by decreasing the amount of acidic species in the culture harvest. The amino acids included in the study were arginine, lysine, ornithine and histidine and belong to group of amino acids that are basic. The study covered examples from multiple cell lines/molecules, in shake flasks and bioreactors and in batch and fed-batch culture formats. A dose dependent effect in the extent of reduction of acidic species with increasing concentrations of the supplements was observed. In addition, the possibility to supplement these medium additives individually or in suitable combinations for acidic species reduction was also demonstrated.

6.2 Method for Reducing the Extent of Acidic Species in Cell Culture by Adjusting Process Parameters 6.2.1 Materials and Methods Cell Source and Adaptation Cultures Two adalimumab producing CHO cell lines and a mAB2 producing cell line were employed in the studies covered here. Upon thaw, adalimumab producing cell line 3 was cultured in chemically defined growth media (media 1) in a combination of vented shake flasks on a shaker platform @ 140 rpm and 20 L wave bags. Cultures were propagated in a 36° C., 5% CO$_2$ incubator to obtain the required number of cells to be able to initiate production stage cultures.

Upon thaw, adalimumab producing cell line 1 was cultured in a hydrolysate based growth media (media 2) in a combination of vented shake flasks on a shaker platform @ 110 rpm and 20 L wavebags in a 35° C., 5% CO$_2$ incubator. In some cases, the culture might be transferred into a seed reactor with pH 7.1, 35° C. and 30% DO. The culture would be adapted to either media for media 2 by propagated in a 10 L or 20 L wavebag for 7-13 days with one or two passages before initiating production stage cultures.

Upon thaw, mAb2 producing cells were cultured in media 1 in a combination of vented non-baffled shake flasks (Corning) on a shaker platform at 140 RPM and 20 L wave bags (GE). Cultures were propagated in a 35° C., 5% $CO_2$ incubator to obtain the required number of cells to be able to initiate production stage cultures.

Cell Culture Media

Media 1, the chemical defined growth or production media, was prepared from basal IVGN CD media (proprietary formulation). For preparation of the IVGN CD media formulation, the proprietary media was supplemented with L-glutamine, sodium bicarbonate, sodium chloride, and methotrexate solution. Production media consisted of all the components in the growth medium, excluding methotrexate. For cell line 1 and mAb2, the medium was also supplemented with insulin. In addition, 10 mM or 5 mM of Galactose (Sigma, G5388) and 0.2 µM or 10 µM of Manganese (Sigma, M1787) were supplemented into production medium for cell line 3 or 1, respectively. Osmolality was adjusted by the concentration of sodium chloride. All media was filtered through filter systems (0.22 µm PES) and stored at 4° C. until usage.

Media 2 is the hydrolysate based media, which contains basal proprietary media, Bacto TC Yeastolate and Phytone Peptone.

Production Cultures

Production cultures were initiated in 3 L Bioreactors (Applikon). The bioreactors (1.5-2.0 L working volume) were run at the following conditions (except for the different experimental conditions): 35° C., 30% DO (dissolved oxygen), 200 rpm, pH profile from 7.1 to 6.9 in three days and pH 6.9 thereafter. In all experiments, the cells were transferred from the wavebag to the production stage at a split ratio of 1:5.6 (except mAb2 with a ratio of 1:5). When the media glucose concentration reduced to less than 3 g/L, approximately 1.25% (v/v) of 40% glucose stock solution was fed.

The harvest procedure of reactors involved centrifugation of the culture sample at 3,000 RPM for 30 min and storage of supernatant in PETG bottles at −80° C. before submission for protein A purification and WCX-10 analysis.

WCX-10 Assay

The acidic species and other charge variants present in cell culture harvest samples were quantified. Cation exchange chromatography was performed on a Dionex ProPac WCX-10, Analytical column (Dionex, CA). For adalimumab producing cell lines, a Shimadzu LC10A HPLC system was used as the HPLC. The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm. The WCX-10 method used for mAb B used different buffers. The mobile phases used were 20 mM (4-Morpholino) ethanesulfonic Acid Monohydrate (MES) pH 6.5 (Mobile phase A) and 20 mM MES, 500 mM Sodium Chloride pH 6.5 (Mobile phase B). An optimized gradient (minute/% B): 0/3, 1/3, 46/21, 47/100, 52/100, 53/3, 58/3 was used with detection at 280 nm.

Quantitation is based on the relative area percent of detected peaks. The peaks that elute at relative residence time earlier than the main peak corresponding to the drug product are together represented as the acidic peaks.

6.2.2 Results

Effect of Process pH in Media 1 with Cell Line 1

Five different pH conditions were assessed in this study: 7.1, 7.0, 6.9, 6.8 and 6.7. The cultures were started at pH set point of 7.1; then were ramped down to the target pH set points within 4 days. All cultures reached the same maximum viable cell density on day 8, except for the culture at pH 6.7 condition, in which the maximum cell density was much lower than the other cultures (FIG. 94). In addition, the viability of the culture at pH 7.1 and pH 7.0 dropped much earlier than the other cultures. The viability of cultures at pH 7.1 and pH 7.0 were 38% and 54% on day 10, respectively; while the viability of the cultures at lower pH (including pH 6.9, 6.8 and 6.7) was above 70% on the same day (FIG. 95). Samples taken in the last three days of the cultures were measured for IgG concentration. The titer of each tested condition increased corresponding to the decrease in pH, from 1.2 g/L in the pH 7.1 condition to 1.8 g/L in the pH 6.8 condition; however, product titer was not continued to increase at pH 6.7 (1.6 g/L) (FIG. 96). The cultures were harvested either on day 10 or on day 12. The harvest was protein A purified, then analyzed using WCX-10. The resulting peak areas from WCX-10 analysis were quantified (FIG. 97). The percentage of acidic species decreased corresponding to the decrease in pH, from 56.0% in the pH 7.1 condition to 14.0% in the pH 6.7 condition. Since the cultures at pH 6.9, 6.8 and 6.7 were at 70% viability on day 10, additional samples were taken on day 12 for these cultures, when viability reached ~50%. WCX-10 analysis was also performed for these samples. The percentage of acidic species on day 12 was increased for these three conditions (i.e., pH 6.9, 6.8 and 6.7) comparing to day 10; however, the increase in the percentage of acidic species was smaller at lower pH. The percentage of acidic species increased 18.8% (pH 6.9), 8.1% (pH6.8) and 3.5% (pH6.7), respectively from day 10 (70% viability) to day 12 (50% viability). Therefore, the percentage of acidic species was lower at lower pH on day 12 too. The percent acidic species decreased with decrease in pH from 39.1% in the pH 6.9 condition to 17.5% in the pH6.7 condition, for a total reduction of 21.6%.

The effect of process pH to specifically reduce particular acidic variants within the larger fraction of total acidic species was also evaluated. In Table 5, a summary of the extent of some of the sub-species of the acidic species fraction have been presented. Along with the reduction in total acidic species, the methods presented in this section may also be used for reduction of sub-species that include, but not limited to, AR1, AR2 and MGO (methylglyoxal) modified product variants.

TABLE 5

Effect of process pH on reduction of sub-species of acidic variants

| Sample | | | | % MGO modified species | | | | | | |
|---|---|---|---|---|---|---|---|---|---|---|
| | | | | LIGHT CHAIN | | | HEAVY CHAIN | | | |
| Final pH | % AR | % AR1 | % AR2 | Arg 30 | Arg 93 | Arg 108 | Arg 16 (19) | Arg 259 | Arg 359 | Arg 420 | TOTAL |
| 7.1 | 56.0 | 32.8 | 23.3 | 26.1 | 10.6 | 0.2 | 6.1 | 2.7 | 3.5 | 0.5 | 49.7 |
| 6.9 | 39.1 | 18.9 | 20.2 | 9.5 | 3.8 | 0.0 | 2.2 | 0.9 | 1.2 | 0.2 | 18.8 |
| 6.7 | 17.5 | 5.2 | 12.2 | 1.2 | 0.5 | 0.0 | 0.2 | 0.1 | 0.1 | 0.0 | 2.0 |

Effect of Process pH in Media 2 with Cell Line 1

Three different pH conditions were assessed in this study: 7.0, 6.9, and 6.8. The cultures were started at pH of 7.1; then were ramped down to the target pH set points within 3 days of culture. The viable cell density and viability were comparable across the different pH set points until day 8. After day 8, the viable cell density and viability were slightly higher with lower pH set points (FIGS. 98 and 99). The cultures were harvested on ~50% viability. The product titer was slightly higher at pH 6.8 comparing to pH 6.9 and 7.0 (FIG. 100). The resulting peak areas from WCX-10 analysis were quantified (FIG. 101). The percentage of acidic species decreased with decrease in pH from 20.7% in the pH 7.0 condition to 18.0% in the pH6.8 condition, for a total reduction of 2.7%.

Effect of Process pH in Media 1 with Cell Line 3

Five different pH conditions were assessed in this study: 7.1 7.0, 6.9, 6.8, and 6.7. The cultures were started at pH set point of 7.1; then were ramped down to the target pH set points within 4 days of culture. The pH set points showed significant effect on the cell growth and viability with this cell line and media. Cell density was lower at higher pH and viability also dropped earlier at higher pH (FIGS. 102 and 103). The cells were harvested either on day 10 or when viability dropped to equal or less than 50%. The titer was slightly increased as the pH was reduced, reached the highest titer at pH 6.8 condition (FIG. 104). The resulting peak areas from WCX-10 analysis were quantified (FIG. 105). The percent acidic species decreased with decrease in pH from 29.7% in the pH 7.1 condition to 21.5% in the pH6.7 condition, for a total reduction of 8.2%.

6.2.3 Conclusion

The experiments described in the instant Example demonstrate that altering cell culture process parameters on-line can be used to modulate/reduce the acidic species of a protein of interest, e.g., the antibody adalimumab or mAB2. For example, a decrease in final pH set points can lead to reductions in Acidic Regions.

6.3 Method for Reducing Acidic Species in Cell Culture by the Addition of Amino Acids to Clarified Cell Culture Harvest and by Modifying the pH of the Clarified Harvest.

The present study describes a process for reducing and controlling levels of acidic species in antibody preparations. Specifically, the invention provides a method for reducing the acidic variant content in clarified harvest, as well as a method for reducing the formation rate of acidic species in clarified harvest. The method involves adding additives like various amino acids to clarified harvest or adjusting the pH of the clarified harvest using acidic substances.

6.3.1 Materials and Methods

Clarified Harvest Material

Different batches of adalimumab clarified harvest material were employed in the following experiments described below. Clarified harvest is liquid material containing a monoclonal antibody of interest that has been extracted from a fermentation bioreactor after undergoing centrifugation to remove large solid particles and subsequent filtration to remove finer solid particles and impurities from the material. Clarified harvest was used for low pH treatment studies described herein. Clarified harvest was also used for the experiments to study the effect of amino acid concentration on the presence of acidic species in clarified harvest, and for acid type-pH treatment studies described herein. Different batches of mAB-B and mAb-C clarified harvest material were employed for experiments to study the effect of amino acid and low pH treatment studies on the presence of acidic species described herein.

Preparation of Study Materials

The clarified harvest material was first adjusted to pH 4 using 3M citric acid. The material at pH 4 was then agitated for 60 minutes before adjusting the pH to a target pH of 5, 6 or 7 with 3M sodium hydroxide. The material was then agitated for a further 60 minutes. The samples were then subjected to centrifugation at 7300×g for 15 minutes in a Sorvall Evolution RC with an SLA-3000 centrifuge bowl. The supernatants obtained from the centrifuged material were then depth filtered using B1HC depth filters (Millipore) followed by 0.22 μm sterile filters. The filtrates of different pH were then subjected to holding for different period of time for evaluating the formation rate of acidic variants. After the holding, the material was purified with Protein A affinity column and the eluate was sampled and analyzed using the WCX 10 method. The preparation scheme is shown below in FIG. 106.

The material to study the effect of arginine on acidic species was prepared in two ways. For lower target arginine concentrations of 5 mM, 10 mM, 30 mM and 100 mM, they were made by adding the appropriate amount of 0.5M arginine stock buffer at pH 7 (pH adjusted with acetic acid) to attain the target arginine concentrations needed. For higher target arginine concentrations of 50 mM, 100 mM, 300 mM, 500 mM, 760 mM, 1M and 2M, they were made by adding the appropriate amount of arginine (solid) to the samples to attain the target arginine concentrations, with subsequent titration to a final pH of 7 using glacial acetic acid. Arginine was adjusted to a final concentration of 100 mM using the two methods to determine if the method of preparation would result in different effects. For all the experiments, following the arginine addition, treated clarified harvests were held at room temperature for the indicated duration followed by purification with Protein A column and analysis of charge variants. This study provided two results; (1) data of samples from Day 0 gave the effects of arginine on reducing acidic species in clarified harvest, (2) data of samples with different holding days gave effect of arginine on reducing the formation rate of acidic species. The preparation scheme is shown in FIG. 107.

The material to study the effect of histidine was prepared with target concentrations of 5 mM, 10 mM, 30 mM 50 mM, 100 mM, 200 mM and 250 mM. The samples were prepared by adding the appropriate amount of histidine (solid) to the samples to attain the target histidine concentrations, with subsequent titration to a final pH of 7 using glacial acetic acid. The sample preparation scheme is shown in FIG. 108.

The material to study the effect of Lysine was prepared with target concentrations of 5 mM, 10 mM, 30 mM 50 mM, 100 mM, 200 mM, 300 mM, 500 mM and 1000 mM. The samples were prepared by adding the appropriate amount of lysine hydrochloride (solid) to the samples to attain the target Lysine concentrations, with subsequent titration to a final pH of 7 using hydrochloric acid. The sample preparation scheme is shown below in FIG. 109.

The material to study the effect of methionine was prepared with target concentrations of 5 mM, 10 mM, 30 mM 50 mM, 100 mM, 200 mM and 300 mM. The samples were prepared by adding the appropriate amount of methionine (solid) to the samples to attain the target methionine concentrations, with subsequent titration to a final pH of 7 using glacial acetic acid. The sample preparation scheme is shown in FIG. 110.

The material to study the effect of different amino acids was prepared with different target concentrations for each of the 20 amino acids evaluated as well as two controls using sodium acetate in place of an amino acid, and the other simply bringing the pH of the clarified harvest down to pH 7 using glacial acetic acid. The target concentrations for the amino acids are shown below in Table 6.

TABLE 6

Amino Acid Target Concentrations

| Amino Acid | Concentration (mM) |
|---|---|
| Alanine | 100 |
| Arginine | 100 |
| Asparagine | 100 |
| Aspartic Acid | 30 |
| Cysteine | 100 |
| Glutamic Acid | 30 |
| Glutamine | 100 |
| Glycine | 100 |
| Histidine | 100 |
| Isoleucine | 100 |
| Leucine | 100 |
| Lysine | 100 |
| Methionine | 100 |
| Phenylalanine | 100 |
| Proline | 100 |
| Serine | 100 |
| Threonine | 100 |
| Tryptophan | 30 |
| Tyrosine | 2 |
| Valine | 100 |
| NaAc | 100 |

The samples were prepared by adding the appropriate amount of amino acid (solid) to the samples to attain the target amino acid concentrations as shown in Table 6, with subsequent titration to a final pH of 7 using glacial acetic acid. The sample preparation scheme is shown below in FIG. 111.

The material to study the effect of additives other than amino acids was prepared with different target concentrations for each of the additives evaluated as well as a control in which sodium hydroxide was used in place of arginine to bring the pH of the material to pH 10 before neutralizing it back to pH 7 with glacial acetic acid. The target concentrations for the additives are shown below in Table 7.

TABLE 7

Alternative Additive Target Concentrations

| Additive | Low Conc | High Conc |
|---|---|---|
| Sucrose | 0.1M | 1M |
| Trehalose | 0.1M | 1M |
| Mannitol | 4% w/v | 10% w/v |
| Glycerol | 1% v/v | 10% v/v |
| PEG | 1% w/v | 2% w/v |
| Tween80 | 0.5% v/v | 2% v/v |

The samples were prepared by adding the appropriate amount of additive to the samples to attain the target amino acid concentrations as shown in Table 2, with subsequent titration to a final pH of 7 using glacial acetic acid.

The material to study the effect of the aforementioned methods on CDM clarified harvest was prepared using the following scheme shown in FIG. 112.

The mAb B hydrolysate clarified harvest was used to study the effect of the aforementioned methods.

The mAb C hydrolysate clarified harvest was used to study the effect of the aforementioned methods.

Hold Studies for Treated Clarified Harvest

After the aforementioned sample preparations, the samples were placed in separate sterile stainless steel containers for the purpose of holding at either 4° C. or at room temperature. For each material, different containers were used for each day of holding evaluated. For the acidified samples, the acidic variant compositions of the samples were evaluated on days 0, 3, 7 and 14 of holding at either temperature. For the arginine containing materials, the acidic variant compositions of the samples were evaluated on days 0, 5 and 8 of holding at room temperature. For the histidine containing materials, the acidic variant compositions of the samples were evaluated on days 0, 3 and 7 of holding at room temperature.

Acid Type and pH Effects on Clarified Harvest

The effects of acid type, clarified harvest pH and arginine content on acidic variant reduction were evaluated in this study. The samples were prepared in triplicates on 3 consecutive days to target arginine concentrations of either 0 mM (no arginine added) or 500 mM, then titrated with either glacial acetic acid, phosphoric acid, 3M citric acid or 6M hydrochloric acid to target pH values of either 5, 6 or 7. One other sample was prepared by adding a 2M arginine acetate pH 7 stock buffer to clarified harvest to attain a target arginine concentration of 500 mM. The sample preparation scheme is shown in FIG. 113.

Protein A Purification

Protein A purification of the samples was performed using a 5 mL rProtein A FF Hitrap column (GE Healthcare) at 10 g D2E7/L resin loading and a operating flow rate of 3.4 mL/min. 5 column volumes (CVs) of equilibration (1×PBS pH 7.4) is followed by loading of the sample, then washing of the column with equilibration buffer to remove non-specifically bound impurities, followed by elution of the protein with 0.1M Acetic acid, 0.15M sodium chloride.

The eluate samples were collected and neutralized to pH 6.9-7.2 with 1M Tris pH 9.5 at 45-75 minutes after collection. The samples were then frozen at −80° C. for at least one day before thawing and subjecting to WCX-10 analysis.

Effects Purification Method, Acid Concentration and Neutralization on Clarified Harvest The effects of purification methods with different types of chromatography resins, acid concentration and pH neutralization on acidic variant reduction were evaluated in this study. The following samples were prepared, shown below in Table 8.

TABLE 8

Acid Concentration Sample Treatments

| Sample | Treatment |
|---|---|
| Control | None |
| 3M Citric Acid pH 6 | Titrate to pH 6 with 3M Citric Acid |
| 1M Citric Acid pH 6 | Titrate to pH 6 with 1M Citric Acid |
| Glacial Acetic Acid pH 6 | Titrate to pH 6 with Glacial Acetic Acid |
| 3M Acetic Acid pH 6 | Titrate to pH 6 with 3M Acetic Acid |
| 3M Citric Acid pH 5 | Titrate to pH 5 with 3M Citric Acid |
| 3M Acetic Acid pH 5 | Titrate to pH 5 with 3M Acetic Acid |
| 3M Citric Acid pH 5 to 7 | Titrate to pH 5 with 3M Citric Acid, then 3M Tris to pH 7 |
| 3M Acetic Acid pH 5 to 7 | Titrate to pH 5 with 3M Acetic Acid, then 3M Tris to pH 7 |

Each of the material made was then subjected to either Mabselect Sure or Fractogel S capture in duplicate. The eluate samples are collected and neutralized to pH 6.9-7.2 with 1M Tris pH 9.5 at 45-75 minutes after collection. The samples are then frozen at −80° C. for at least one day before thawing and subjecting to WCX-10 analysis.

Charge Variant Analysis (WCX-10 Assay)

Cation exchange chromatography was performed on a 4 mm×250 mm Dionex ProPac WCX-10 Analytical column (Dionex, CA). A Shimadzu LC10A HPLC system was used to perform the HPLC assay. The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm.

Quantitation is based on the relative area percent of detected peaks. The peaks that elute at relative residence time less than that of the dominant Lysine 0 peak are together represented as the acidic variant peaks (AR).

6.3.2 Results

Effect of Low pH Treatment with Subsequent Neutralization

The results of the low pH treatment with subsequent neutralization are shown below in FIGS. 114 and 115. FIG. 115 shows that the low pH treatment with subsequent neutralization to pH 5 or 6 reduces the rate of acidic variant formation over time. However, there is no significant reduction in initial acidic variant content as shown in FIG. 114.

Effect of Arginine Treatment

The results of the arginine treatment are shown in FIG. 116 and FIG. 117. FIG. 116, 117 shows that the sample preparation method resulted in different levels of acidic species in clarified harvest. Adding a 0.5M Arginine pH 7 stock buffer tends to increase acidic species, while adding pure arginine with subsequent acetic acid titration to pH 7 reduced acidic variants at arginine concentrations of greater than 100 mM. Moreover, the effect due to treatment method is demonstrated when comparing the two 100 mM arginine samples, which show an absolute difference of 1% in acidic variants between the two methods.

FIG. 118 shows that the rate of acidic variant formation decreases with increasing arginine concentration in clarified harvest, plateauing at around concentrations of 500 mM arginine and higher. However, the two methods of sample preparation does not result in significantly different formation rate of acidic variants.

Effect of Histidine Treatment

The results of the histidine treatment are shown in FIG. 119 and FIG. 120. Similar to arginine treatment effect, as shown in FIG. 128, when histidine was added to clarified harvest with subsequent pH neutralization with acetic acid, acidic variants were reduced at histidine concentrations higher than 50 mM. FIG. 120 shows that the rate of acidic variants formation decreases with increasing Histidine concentration in clarified harvest, plateauing at around concentrations of 200 mM Histidine and higher.

Effect of Lysine Treatment

The results of the lysine treatment are summarized in FIG. 121 and FIG. 122. Similar to arginine treatment effect, as shown in FIG. 128, when lysine was added to clarified harvest with subsequent pH neutralization with acetic acid, acidic variants were significantly reduced by ~1% or more. FIG. 132 shows that the rate of acidic variants formation decreases with increasing lysine concentration in clarified harvest.

Effect of Methionine Treatment

The results of the methionine treatment are summarized below in FIGS. 133 and 144. Similar to arginine treatment effect, as shown in FIG. 118, when methionine was added to clarified harvest with subsequent pH neutralization with acetic acid, acidic variants were significantly reduced by ~1% or more at concentrations of >10 mM. FIG. 124 shows that the rate of acidic variants formation is not affected significantly by methionine presence in clarified harvest.

Effect of Other Amino Acid Treatment

The results of the treatments with the various amino acids are summarized below in FIGS. 125 and 146. As shown in FIG. 125, the addition of 14 amino acids including arginine, histidine, lysine and methionine resulted in lower amounts of acidic variant content in clarified harvest. The addition of sodium acetate or the use of acetic acid also caused a reduction in acidic variant content as well. FIG. 126 shows that the rate of acidic variants formation is reduced by several amino acids including arginine, histidine, lysine, aspartic acid, glutamic acid, and leucine.

Effect of Alternative Additive Treatment

The results of the treatments with the other additives are summarized below in FIGS. 127 and 128. As shown in FIG. 127, the addition of any of the additives did not result in lower acidic variant content in D2E7 hydrolysate clarified harvest. However, FIG. 128 shows that the rate of acidic variants formation is reduced by most of the additives.

Effect of Low pH/Arginine Treatment on D2E7 CDM Clarified Harvest

The results of CDM clarified harvest study are summarized below in FIGS. 129 and 130. As shown in FIG. 129, low pH/arginine treatment did not result in lower acidic variant content in D2E7 CDM clarified harvest. However, FIG. 130 shows that the rate of acidic variants formation is reduced significantly by all the treatments.

Effect of Low pH/Arginine Treatment on mAb B Hydrolysate Clarified Harvest

The results of mAb B hydrolysate clarified harvest study are summarized below in FIGS. 131 and 132. As shown in FIGS. 131 and 132, low pH/arginine treatment results in both lower acidic variant content and slower rates of acidic variants formation in mAb B hydrolysate clarified harvest.

Effect of Low pH/Arginine Treatment on mAb C Hydrolysate Clarified Harvest

The results of mAb C hydrolysate clarified harvest study are summarized below in FIGS. 133 and 134. As shown in FIGS. 133 and 134, low pH/arginine treatment results in both lower acidic variant content and slower rates of acidic variants formation in mAb C hydrolysate clarified harvest.

Effect of Acid Type and pH

The results obtained from the acid type-pH study are summarized in FIG. 135. Greater acidic species reduction is obtained at lower pH. Arginine addition also reduces acidic species content further, but not to a significant extent when taking the high concentrations (500 mM) used into consideration. The results also show that acidic species reduction of ~1% can be achieved with the usage of an arginine acetate stock buffer, although using pure arginine powder with subsequent acid titration performs slightly better. With regard to acid type used for pH adjustment, there were no significant differences between different acids observed.

Effect of Purification Method, Acid Concentration and Neutralization

The results obtained from the study are summarized below in FIGS. 136, 137, 138, and 139. FIGS. 136, 137 indicate that when the acid used is of higher concentration, there is an decrease in acidic variant content in hydrolysate clarified harvest as compared to a lower concentration acid being used. FIGS. 138, 139 show that when the clarified harvest is subjected to base neutralization to pH 7 after being treated with low pH, there is an increase in acidic variant content. The figures also show that the Fractogel resin is better able to clear acidic variants than Mabselect Sure.

6.3.3 Conclusion

Antibody acidic species in clarified harvest can be reduced by adding additives such as arginine or histidine to clarified harvest at concentrations of more than 100 mM and 50 mM, respectively. It can also be achieved by pH adjustment of the clarified harvest to pH 6 or pH 5. In addition, the rate of acidic variant formation can be reduced through the use of arginine or histidine in a concentration dependent manner, or by low pH treatment of the clarified harvest.

6.4 Method for Reducing Acidic Species in Cell Culture Use of a Continuous Media Perfusion Technology.

As demonstrated in section 6.3, generation or formation of acidic species in the population of proteins may occur during the hold of the antibody in clarified harvest or spent media. Thus, the possibility of enhanced stability of the product antibody or a reduction in acidic species generation was explored using a continuous/perfusion based cell culture technology. Control or reduction in the amount of acidic species present in the population of proteins obtained at end of cell culture can be accomplished by modifying the exchange rate of fresh medium into the bioreactor (or removal of spent medium with product antibody out of the bioreactor).

6.4.1 Materials and Methods

Cell Source

One adalimumab producing CHO cell line was employed in the study covered here. Upon thaw, the vial was cultured in a chemically defined growth media (media 1) in a series of vented shake flasks on a shaker platform at 110 rpm in a 35° C., 5% $CO_2$ incubator. Cultures were propagated to obtain a sufficient number of cells for inoculation of the perfusion cultibag.

Cell Culture Media

A chemically defined growth or production media was used in this study. For preparation of the media formulation, the proprietary media (Invitrogen) was supplemented with L-glutamine, sodium bicarbonate, sodium chloride, recombinant human insulin and methotrexate solution. Perfusion stage media consisted of all the components in the growth medium, with the exception of a higher concentration of recombinant human insulin and the exclusion of methotrexate solution.

Perfusion Culture

The perfusion culture was carried out with the Sartorius BIOSTAT RM 20 optical perfusion system (SN#00582112) in a Sartorius Cultibag RM 10 L perfusion pro 1.2my (lot 1205-014) perfusion bag. The perfusion bag was run with a working culture volume of 1.5 L and operation conditions of; pH: 7.00, dissolved oxygen 30%, 25 rpm, 35° C., an air overlay of 0.3 slpm and a $CO_2$ overlay of 15 sccm. pH control was initiated on day three of the culture. pH was controlled with 0.5M sodium hydroxide and $CO_2$ additions.

Perfusion was carried out by 'harvesting' spent culture through an integrated 1.2 μm filter integrated into the perfusion cultibag. Fresh media was added to the culture through a feed line at the same rate as the harvest. Perfusion began on day four of the process at a rate of 1.0 exchanges per day (ex/day). The perfusion rate was adjusted throughout the run to accommodate glucose needs, lactate accumulation and sampling plans. Perfusion cell-free harvest samples were collected at perfusion rates of 1.5, 3.0 and 6.0 exchange volumes/day on day 5-6 of perfusion. A fresh harvest bag was used for each harvest sample. The samples were then purified using protein A and analyzed using WCX-10 assay.

The perfusion culture was ended on day 8 of the process.

WCX-10 Assay

The acidic species and other charge variants present in cell culture harvest samples were quantified. Cation exchange chromatography was performed on a Dionex ProPac WCX-10, Analytical column (Dionex, CA).

The mobile phases used were 10 mM Sodium Phosphate dibasic pH 7.5 (Mobile phase A) and 10 mM Sodium Phosphate dibasic, 500 mM Sodium Chloride pH 5.5 (Mobile phase B). A binary gradient (94% A, 6% B: 0-20 min; 84% A, 16% B: 20-22 min; 0% A, 100% B: 22-28 min; 94% A, 6% B: 28-34 min) was used with detection at 280 nm. The WCX-10 method used for mAb2 samples used different buffers. The mobile phases used were 20 mM (4-Morpholino) ethanesulfonic Acid Monohydrate (MES) pH 6.5 (Mobile phase A) and 20 mM MES, 500 mM Sodium Chloride pH 6.5 (Mobile phase B). An optimized gradient (minute/% B): 0/3, 1/3, 46/21, 47/100, 52/100, 53/3, 58/3 was used with detection at 280 nm. Quantitation is based on the relative area percent of detected peaks, as described above.

6.4.2 Results

Effect of Use of Perfusion Technology and Choice of Medium Exchange Rates on Acidic Species Adalimumab producing cell line 1 was cultured in media 1 and the cultures were carried out as described in the materials and methods. As described in table 9, the exchange rates were modified over a period of 24 hrs between day 5 and day 6 to explore the influence of medium exchange rates on the extent of acidic species. At a continuous medium exchange rate of 1.5 volumes/day, the product antibody in spent medium was collected in a harvest bag over a period of 17 hrs. The harvest bag was then exchanged with a new bag and the old bag was transferred to 4 C. Subsequently and in succession, the medium exchange rates were increased to 3 and 6 volumes/day and the product harvest was collected over a time period of 5 and 2 hrs, respectively. After an overnight hold at 4 C, the three harvest samples were processed through protein A and analyzed for acidic species using WCX-10. The percentage of acidic species in the sample with a medium exchange rate of 1.5 volumes/day was 8.1%. In the sample with the highest tested exchange rate in this experiment (6 volumes/day), the percentage of acidic species was reduced to 6%. An exchange rate dependent reduction in acidic species was observed in the three samples (Table 9). Reductions in different sub-species within the acidic variants (AR1 and AR2) were also noted. An increase in volumetric productivity, with exchange rate, was also observed.

TABLE 9

Effect of medium exchange rates in a perfusion bioreactor on acidic species

| Start Time (day, hrs:min) | Exchange rate (no. of working volumes/day) | Exchange time (for collection in harvest bag) (hrs) | Harvest bag Volumetric Productivity (mg/l-hr) | % Total AR | % AR1 | % AR2 |
|---|---|---|---|---|---|---|
| Day 5, 16:00 | 1.5 | 17 | 10.94 | 8.1 | 2.0 | 6.1 |
| Day 6, 10:25 | 3 | 5 | 39.80 | 6.9 | 1.7 | 5.2 |
| Day 6, 15:25 | 6 | 2 | 69.50 | 6.0 | 1.3 | 4.7 |

6.5. Utility of AR Reduction

The current invention provides a method for reducing acidic species for a given protein of interest. In this example adalimumab was prepared using a combination of supplementation of arginine and lysine to cell culture as shown in this invention along with AEX and CEX purification technologies (described in U.S. patent application Ser. No. 13/829,989) to produce a Low-AR and High-AR sample with a final AR of 2.5% and 6.9%, respectively. Both samples were incubated in a controlled environment at 25° C. and 65% relative humidity for 10 weeks, and the AR measured every two weeks. FIG. 142 shows the growth of AR for each sample over the 10 week incubation. It is evident from FIG. 142 the growth rate of AR is linear and similar between both the Low-AR and High-AR samples. Based on these results the reduced AR material can be stored 3 fold longer before reaching the same AR level as the High-AR sample. This is a significant utility as this can be very beneficial in storage handling and use of the antibody or other proteins for therapeutic use.

6.6 Process Combinations to Achieve Target % AR or AR Reductions

Upstream and Downstream process technologies, e.g., cell culture and chromatographic separations, of the inventions disclosed in the following applications can be combined together or combined with methods in the art to provide a final target AR value or achieve a % AR reduction, as well as to, in certain embodiments, reduce product related substances and/or process related impurities. Upstream methods for AR reduction include, but are not limited to those described in the instant application. Downstream methods for AR reduction include, but are not limited to, those described in U.S. patent application Ser. No. 13/829, 989. Exemplary technologies disclosed in the referenced applications include, but are not limited to: cell culture additives & conditions; clarified harvest additives and pH/salt conditions; mixed mode media separations; anion exchange media separations; and cation Exchange media separations.

The instant example demonstrates the combined effect of one or more of these technologies in achieving a target AR value or AR reduction, thereby facilitating the preparation of an antibody material having a specific charge heterogeneity. Additional examples of combinations of downstream technologies and upstream technologies are provided in the referenced applications.

In this example, the combination of upstream and downstream methods involves the reduction of acidic species in 3 L bioreactor cell cultures supplemented with arginine (2 g/l) and lysine (4 g/l) as has been previously demonstrated in the instant application. The results of that strategy are summarized in Table 10. The total acidic species was reduced from 20.5% in the control sample to 10.2% in sample from cultures that were supplemented with the additives. In this study, Adalimumab producing cell line 1 was cultured in media 1 (chemically defined media) supplemented with amino acid arginine (2 g/l) and lysine (4 g/l) in a 300 L bioreactor. On Day 12 of culture, the culture was harvested and then subsequently analyzed using WCX-10 post protein A purification and the percentages of total peak(s) area corresponding to the acidic species were quantified. The percentage of acidic species was estimated to be 9.1% in the 300 L harvest sample

TABLE 10

| AR levels achieved with use of upstream technologies | | | | | | | | |
|---|---|---|---|---|---|---|---|---|
| 3 L Bioreactor | | | | | | 300 L Bioreactor | | |
| Control | | | Arginine (2 g/l) + Lysine (4 g/l) | | | Arginine (2 g/l) + Lysine (4 g/l) | | |
| AR1 (%) | AR2 (%) | Total AR (%) | AR1 (%) | AR2 (%) | Total AR (%) | AR1 (%) | AR2 (%) | Total AR (%) |
| 6.3 | 14.2 | 20.5 | 2.6 | 7.6 | 10.2 | 2.4 | 6.7 | 9.1 |

The material produced by the 300 L Bioreactor employing Arginine and Lysine additions, that effectively reduced the AR levels to 9.1% was purified using a downstream process employing Mixed Mode chromatography as the primary AR Reduction method.

Adalimumab was purified by a Protein A chromatography step followed with a low pH viral inactivation step. The filtered viral inactivated material was buffer exchanged and loaded onto a Capto Adhere column. The flowthrough of Capto Adhere material was then purified with a HIC column with bind/elute mode as well as Flow Through mode. As shown in Table 11, AR reduction was achieved primarily with MM step, with some contribution from other steps. The table also shows that additional product related substances such as aggregates and process related impurities such as HCP can be effectively reduced employing these combined technologies.

TABLE 11

| Complete Downstream Process Train with Protein A Capture - AR, HMW and HCP reduction | | | | |
|---|---|---|---|---|
| Process | Yield (%) | % AR reduction | % HMW reduction | HCP LRF |
| Clarified Harvest | 97.0% | n/a | n/a | n/a |
| Prt-A Eluate Pool | 89.6% | 0.06 | | 1.87 |
| Viral Inactivated Filtrate | 99.7% | No reduction | 0.07 | 0.39 |
| MM FT pool | 91.9% | 2.26 | 0.83 | 1.63 |
| HIC (B/E) Eluate | 90.1% | 0.40 | 0.22 | 1.41 |
| Nanofiltrate Filtrate | 90.7% | No reduction | No reduction | 0.15 |
| BDS (B/E) | 102.0% | No reduction | No reduction | 0.22 |
| HIC FT-pool | 98.5% | 0.16 | 0.23 | 0.46 |
| VF (FT) Filtrate | 96.1% | No reduction | No reduction | 0.10 |
| BDS (FT) | 103.8% | No reduction | No reduction | No reduction |

As is evident from the above example, the MM method further reduced the AR levels, by 2.26%. Therefore upstream technologies for reduction can be combined with downstream technologies to achieve AR levels/AR reduction.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Patents, patent applications, publications, product descriptions, GenBank Accession Numbers, and protocols that may be cited throughout this application, the disclosures of which are incorporated herein by reference in their entireties for all purposes. For example, but not by way of limitation, the following U.S. patent applications designated by the following numbers are incorporated herein by reference in their entireties for all purposes: U.S. patent application Ser. Nos. 13/803,808, 13/829,989, 13/830,976, 13/831,181, and 13/804,220.

What is claimed is:

1. A composition comprising adalimumab, wherein the composition comprises less than 10% total acidic species of adalimumab,
    wherein the acidic species of adalimumab are product-related impurities and do not include process-related impurities comprising host cells and lysed host cells, and
    wherein the acidic species of adalimumab correspond to the peaks that elute earlier than the main peak in a WCX-10 HPLC chromatogram of adalimumab as shown in FIG. 141.

2. The composition of claim 1, wherein the WCX-10 HPLC chromatogram is generated using a first mobile phase of 10 mM Sodium Phosphate dibasic (pH 7.5) and a second mobile phase of 10 mM Sodium Phosphate dibasic, 500 mM Sodium Chloride (pH 5.5), and wherein the WCX-10 HPLC chromatogram is generated using detection at 280 nm.

3. The composition of claim 1, wherein the acidic species of adalimumab comprise a first acidic region (AR1) and a second acidic region (AR2).

4. The composition of claim 1, wherein the composition comprises 9% or less acidic species of adalimumab.

5. The composition of claim 1, wherein the composition comprises 6%-8% acidic species of adalimumab.

6. The composition of claim 1, wherein the adalimumab is produced in a mammalian host cell grown in cell culture.

7. The composition of claim 6, wherein the mammalian host cell is selected from the group consisting of a CHO cell, an NSO cell, a COS cell, and an SP2 cell.

8. The composition of claim 7, wherein the mammalian host cell is a CHO cell.

9. The composition of claim 8, wherein the composition is lyophilized.

10. A pharmaceutical composition suitable for administration to a subject comprising the composition of claim 8 and a pharmaceutically acceptable carrier.

11. The pharmaceutical composition of claim 10, wherein adalimumab is present in the pharmaceutical composition at a concentration of 0.1-250 mg/ml.

12. The pharmaceutical composition of claim 10, wherein the pharmaceutical composition comprises one or more excipient.

13. The pharmaceutical composition of claim 12, wherein the one or more excipient is selected from the group consisting of a buffer, an isotonic agent, a surfactant or a combination thereof.

14. The pharmaceutical composition of claim 13, wherein the pharmaceutical composition comprises the surfactant polysorbate 80.

15. The pharmaceutical composition of claim 13, wherein the pharmaceutical composition comprises an amino acid buffer.

16. The pharmaceutical composition of claim 15, wherein the amino acid is histidine.

17. The pharmaceutical composition of claim 13, wherein the pharmaceutical composition comprises the isotonic agent mannitol.

18. A method for treating a subject in need thereof, comprising administering to the subject the pharmaceutical composition of claim 10, thereby treating the subject.

19. A composition comprising adalimumab, wherein the composition comprises less than 10% total acidic species of adalimumab,
    wherein the acidic species of adalimumab are product-related impurities and do not include process-related impurities comprising host cells and lysed host cells,
    wherein the acidic species of adalimumab correspond to the peaks that elute earlier than the main peak in a WCX-10 HPLC chromatogram of adalimumab, and wherein the WCX-10 HPLC chromatogram is generated using a first mobile phase of 10 mM Sodium Phosphate dibasic (pH 7.5) and a second mobile phase of 10 mM Sodium Phosphate dibasic, 500 mM Sodium Chloride (pH 5.5), and wherein the WCX-10 HPLC chromatogram is generated using detection at 280 nm.

20. The composition of claim 19, wherein the acidic species of adalimumab comprise a first acidic region (AR1) and a second acidic region (AR2).

21. The composition of claim 19, wherein the composition comprises 9% or less acidic species of adalimumab.

22. The composition of claim 19, wherein the composition comprises 6%-8% acidic species of adalimumab.

23. The composition of claim 19, wherein the adalimumab is produced in a mammalian host cell grown in cell culture.

24. The composition of claim 23, wherein the mammalian host cell is selected from the group consisting of a CHO cell, an NSO cell, a COS cell, and an SP2 cell.

25. The composition of claim 24, wherein the mammalian host cell is a CHO cell.

26. A pharmaceutical composition suitable for administration to a subject comprising the composition of claim 25 and a pharmaceutically acceptable carrier.

27. The pharmaceutical composition of claim 26, wherein adalimumab is present in the pharmaceutical composition at a concentration of 0.1-250 mg/ml.

28. The pharmaceutical composition of claim 26, wherein the pharmaceutical composition comprises one or more excipient.

29. The pharmaceutical composition of claim 28, wherein the one or more excipient is selected from the group consisting of a buffer, an isotonic agent, a surfactant or a combination thereof.

30. A method for treating a subject in need thereof, comprising administering to the subject the pharmaceutical composition of claim 26, thereby treating the subject.

* * * * *